(12) United States Patent
Kang et al.

(10) Patent No.: US 12,329,029 B2
(45) Date of Patent: Jun. 10, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Eun Jin Kang, Cheonan-si (KR); Hyun Ju Song, Cheonan-si (KR); Ji young Kim, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/950,455

(22) Filed: Nov. 18, 2024

(65) Prior Publication Data

US 2025/0089562 A1 Mar. 13, 2025

Related U.S. Application Data

(63) Continuation-in-part of application No. 18/180,625, filed on Mar. 8, 2023, which is a continuation-in-part (Continued)

(30) Foreign Application Priority Data

Oct. 26, 2020 (KR) .......... 10-2020-0139441

(51) Int. Cl.
*H10K 85/60* (2023.01)
*C07D 251/24* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02);
(Continued)

(58) Field of Classification Search
CPC .................................................. C07D 251/24
See application file for complete search history.

(56) References Cited

U.S. PATENT DOCUMENTS

2014/0367654 A1* 12/2014 Kim ............... H10K 85/654
257/40
2015/0303379 A1 10/2015 Lee et al.
(Continued)

FOREIGN PATENT DOCUMENTS

KR 10-2009-0079134 A 7/2009
KR 10-2016-0111780 A 9/2016
(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound of Formula 1 that can improve the luminous efficiency, stability, and lifespan of an organic electronic element employing the compound; a composition comprising the same; an organic electronic element using the same; and an electronic device thereof.

17 Claims, 3 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.

| | |
|---|---|
| *C09K 11/06* | (2006.01) |
| *H10K 50/11* | (2023.01) |
| *H10K 50/15* | (2023.01) |
| *H10K 50/16* | (2023.01) |
| *H10K 50/18* | (2023.01) |
| *H10K 101/00* | (2023.01) |
| *H10K 101/10* | (2023.01) |

(52) U.S. Cl.
CPC ...... *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

FOREIGN PATENT DOCUMENTS

| | | |
|---|---|---|
| WO | 2017/171420 A1 | 10/2017 |
| WO | 2019/124902 A1 | 6/2019 |

\* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to compounds for organic electronic elements, organic electronic elements using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer etc.

A material used as an organic material layer in an organic electronic element may be classified into a light emitting material and a charge transport material, such as a hole injection material, a hole transport material, an electron transport material, an electron injection material etc. depending on its function. And the light emitting material can be classified into a high molecular weight type and a low molecular weight type according to the molecular weight, and it can be classified into a fluorescent material derived from a singlet excited state of an electron and a phosphorescent material derived from a triplet excited state of an electron depending on the light emission mechanism. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. Here, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic element has not yet been sufficiently made. Therefore, the development of new materials is continuously required, and in particular, the development of a host material for the emitting layer is urgently needed.

DETAILED DESCRIPTION OF THE INVENTION

Summary

In order to solve the problems of the above-mentioned background technology, the present invention has discovered a compound with a novel structure, and also discovered that when the compound is applied to an organic electronic element, the luminous efficiency, stability, and lifespan of the element can be greatly improved.

Accordingly, the purpose of the present invention is to provide a novel compound, an organic electronic element using the same, and an electronic device thereof.

Technical Solution

The present invention provides a compound represented by Formula 1.

Formula 1

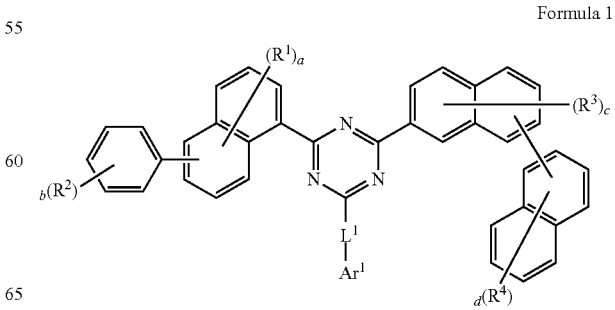

In another aspect, the present invention provides a composition for an organic electronic element comprising a mixture of a compound represented by Formula 1 and a compound represented by Formula 2 or Formula 3.

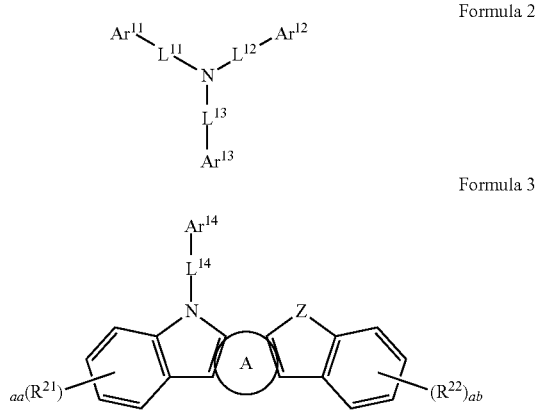

Formula 2

Formula 3

In another aspect, the present invention provides an organic electronic element comprising the compound represented by Formula 1 or the composition for the organic electronic element and an electronic device thereof.

Effects of the Invention

By using the compound according to the present invention, high luminous efficiency, low driving voltage and high heat resistance of the element can be achieved, and color purity and lifespan of the element can be greatly improved.

Figure 1:
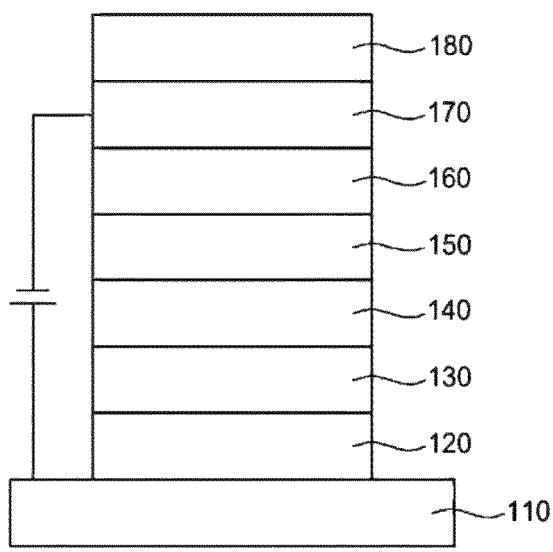
FIG. 1 to FIG. 3 are exemplary views of an organic electroluminescent device according to the present invention.

Description of the numerals:

| | | | |
|---|---|---|---|
| 100, 200, 300: | organic electronic element | 110: | the first electrode |
| 120: | hole injection layer | 130: | hole transport layer |
| 140: | emitting layer | 150: | electron transport layer |
| 160: | electron injection layer | 170: | second electrode |
| 180: | light efficiency enhancing Layer | 210: | buffer layer |
| 220: | emitting auxiliary layer | 320: | first hole injection layer |
| 330: | first hole transport layer | 340: | first emitting layer |
| 350: | first electron transport layer | 360: | first charge generation layer |
| 361: | second charge generation layer | 420: | second hole injection layer |
| 430: | second hole transport layer | 440: | second emitting layer |
| 450: | second electron transport layer | CGL: | charge generation layer |
| STI: | first stack | ST2: | second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, 1 to 30 carbon atoms, 1 to 25 carbon atoms, 1 to 18 carbon atoms, or 1 to 12 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, 2 to 30 carbon atoms, 2 to 25 carbon atoms, 2 to 18 carbon atoms, 2 to 12 carbon atoms, but is not limited thereto, and includes a linear or a branched chain group.

Unless otherwise stated, the term "cycloalkyl", as used herein, means alkyl forming a ring having 3 to 60 carbon atoms, 3 to 30 carbon atoms, 3 to 25 carbon atoms, 3 to 18 carbon atoms, 3 to 12 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms, 1 to 30 carbon atoms, 1 to 25 carbon atoms, 1 to 18 carbon atoms, or 1 to 12 carbon atoms.

Unless otherwise stated, the term "aryloxyl group" or "aryloxy group", as used herein, means an aryl group bonded to oxygen radical, but is not limited thereto, and has 6 to 60 carbon atoms, 6 to 30 carbon atoms, 6 to 25 carbon atoms, 6 to 18 carbon atoms, or 6 to 12 carbon atoms.

Unless otherwise specified, the terms "aryl group" and "arylene group" used in the present invention have 6 to 60 carbon atoms, 6 to 30 carbon atoms, 6 to 25 carbon atoms, 6 to 18 carbon atoms, or 6 to 12 carbon atoms, respectively, but are not limited thereto. In the present invention, an aryl group or arylene group refers to an aromatic group of a single ring or multiple rings, and includes an aromatic ring formed by combining adjacent substituents or participating in a reaction. For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, 2 to 30 carbon atoms, 2 to 25 carbon atoms, 2 to 18 carbon atoms, 2 to 12 carbon atoms, and includes any one of a single ring or multiple ring, and may include heteroaliphatic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, "heterocyclic group" refers to a single ring containing heteroatoms, a ring aggregate, multiple fused ring systems, spiro compounds, etc. Additionally, compounds containing heteroatom groups such as $SO_2$, $P=O$, etc., such as the compounds below, instead of carbon forming a ring, may also be included in the heterocyclic group. For example, "heterocyclic group" includes the following compound.

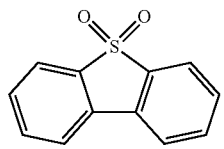 [SMILES: O=S1(=O)c2ccccc2-c2ccccc21]

The term "aliphatic ring group" used in the present invention refers to cyclic hydrocarbons excluding aromatic hydrocarbons, and includes single rings, ring aggregates, fused multiple ring systems, spiro compounds, etc., and means a ring having 3 to 60 carbon atoms, 3 to 30 carbon atoms, 3 to 25 carbon atoms, 3 to 18 carbon atoms, 3 to 12 carbon atoms, but is not limited thereto. For example, even when benzene, an aromatic ring, and cyclohexane, a non-aromatic ring, are fused, it is an aliphatic ring.

Unless otherwise stated, the term "fluorenyl group", "fluorenylene group" or "fluorentriyl group" as used herein, means a monovalent, divalent or trivalent functional group, in which R, R' and R" are all hydrogen in the following structures, and the term "substituted fluorenyl group", "substituted fluorenylene group" or "substituted fluorentriyl group" means that at least one of the substituents R, R' and R" is a substituent other than hydrogen, and include those in which R and R' are bonded to each other to form a spiro compound together with the carbon to which they are bonded. In this specification, fluorenyl group, fluorenylene group, and fluorenetriyl group may all be referred to as fluorene groups, regardless of valence.

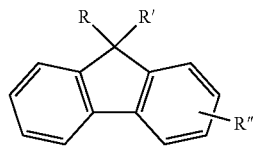

The term "spiro compound", as used herein, has a 'spiro union', and a spiro union means a connection formed by 2 rings sharing only one atom. Wherein, the atoms shared between the 2 rings are called 'spiro atoms', and depending on the number of spiro atoms contained in a compound, they are called 'monospiro-', 'dispiro-', and 'trispiro-' compounds, respectively.

Unless otherwise stated, the term "aliphatic" as used herein means an aliphatic hydrocarbon having 1 to 60 carbon atoms, 1 to 30 carbon atoms, 1 to 25 carbon atoms, 1 to 18 carbon atoms or 1 to 12 carbon atoms, and "aliphatic ring" means an aliphatic hydrocarbon ring having 3 to 60 carbon atoms, 3 to 30 carbon atoms, 3 to 25 carbon atoms, 3 to 18 carbon atoms or 3 to 12 carbon atoms.

Unless otherwise stated, the term "ring", as used herein, means an aliphatic ring having 3 to 60 carbon atoms, 3 to 30 carbon atoms, 3 to 25 carbon atoms, 3 to 18 carbon atoms or 3 to 12 carbon atoms; or an aromatic ring having 6 to 60 carbon atoms, 6 to 30 carbon atoms, 6 to 25 carbon atoms, 6 to 18 carbon atoms, or 6 to 12 carbon atoms; or a heterocyclic having 2 to 60 carbon atoms, 2 to 30 carbon atoms, 2 to 25 carbon atoms, 2 to 18 carbon atoms, 2 to 12 carbon atoms, or a fused ring formed by the combination thereof, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

In this specification, the 'group name' corresponding to the aryl group, arylene group, heterocyclic group, etc., as examples of each symbol and its substituent, may be written as the 'name of the group reflecting the valence', but is written as the 'parent compound name'. For example, in the case of 'phenanthrene', a type of aryl group, the name of the group may be written by distinguishing the valence, such as the monovalent 'group' is 'phenanthryl' and the divalent group is 'phenanthrylene', but may be written as 'phenanthrene', which is the name of the parent compound, regardless of the valence. Similarly, in the case of pyrimidine, it can be written as 'pyrimidine' regardless of the valence, or it can be written as the 'name of the group' of the valence, such as pyrimidineyl group in the case of monovalent group, pyrimidineylene in the case of divalent group, etc. Additionally, in this specification, when describing compound names or substituent names, numbers or alphabets indicating positions may be omitted. For example, pyrido[4,3-d]pyrimidine to pyridopyrimidine, benzofuro[2,3-d]pyrimidine to benzofuropyrimidine, 9,9-dimethyl-9H- fluorene can be described as dimethylfluorene, etc. Therefore, both benzo[g]quinoxaline and benzo[f]quinoxaline can be described as benzoquinoxaline.

Also, unless there is an explicit explanation, the formula used in the present invention is the same as the definition of the substituent by the exponent definition of the following formula.

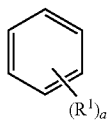

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

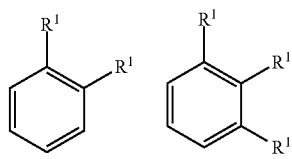

Unless otherwise expressly stated, the terms "ortho", "meta", and "para" used in the present invention refer to the substitution positions of all substituents, and the ortho position refers to a compound in which the position of the substituent is immediately adjacent, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

[Example of Ortho-Position]

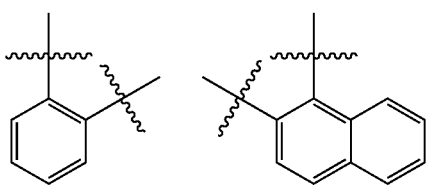

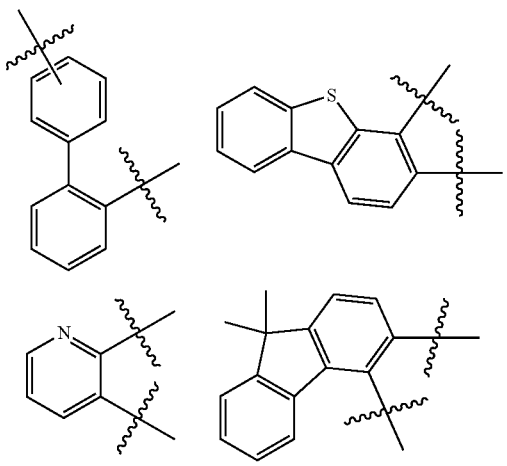

[Example of Meta-Position]

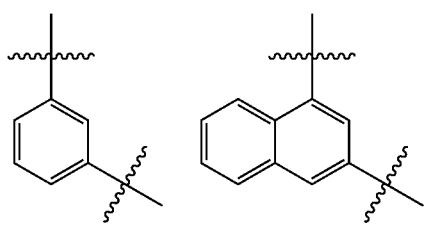

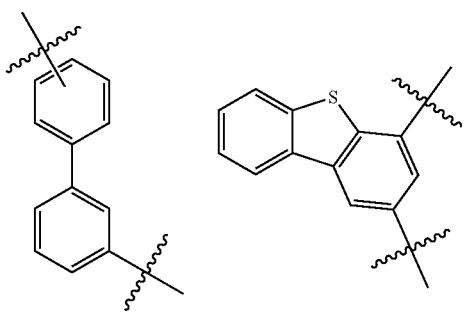

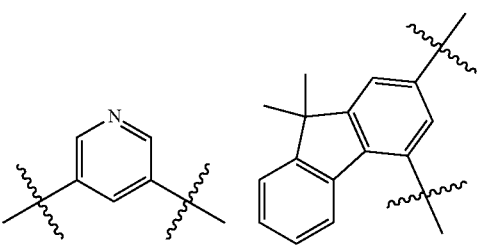

[Example of Para-Position]

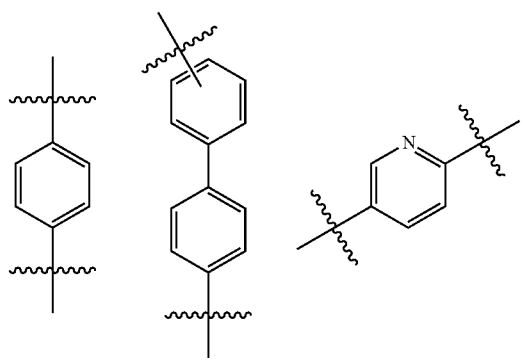

As used herein, the term "composition" is intended to be interpreted broadly, comprising compounds as well as solutions, dispersions, liquids and solid mixtures (mixture, admixture). The composition of the present invention may comprise the compound of the present invention alone, or the compounds are comprised in a combination of 2 or more different types, or the compounds may be comprised in combinations of 2 or more types with other compounds. In other words, the composition may comprise a compound corresponding to Formula 1 alone, a mixture of 2 or more compounds of Formula 1, or a mixture of a compound of Formula 1 and a compound not corresponding to the present invention. Wherein, the compound not corresponding to the present invention may be a single compound, and may be 2 or more types of compounds. Here, when the compound is comprised in a combination of 2 or more types of other compounds, the other compounds may be already known compounds of each organic material layer, or may be compounds to be developed in the future. Wherein, the compound contained in the organic material layer may consist of only the same type of compound, but may also be a mixture of 2 or more types of different compounds represented by Formula 1.

Hereinafter, a compound according to an aspect of the present invention, a composition for an organic electronic element and an organic electronic element comprising the same will be described.

The present invention provides a compound represented by Formula 1.

Formula 1

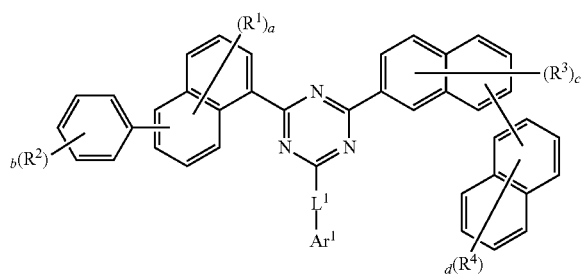

Wherein:

R$^1$, R$^2$, R$^3$ and R$^4$ are the same or different from each other and are independently selected from the group consisting of a hydrogen; or deuterium;

a and c are integers from 0 to 6, b is an integer from 0 to 5, and d is an integer from 0 to 7, L$^1$ is a single bond; or a C$_6$-C$_{12}$ arylene group;

Wherein L$^1$ is an arylene group, preferably an C$_6$-C$_{12}$ arylene group, such as phenylene, biphenylene, naphthylene, etc.

Ar$^1$ is an C$_6$-C$_{12}$ aryl group;

Wherein when Ar$^1$ is an aryl group, preferably an C$_6$-C$_{12}$ arylene group, such as phenyl, biphenyl, terphenyl, naphthalene, etc.

wherein the aryl group and arylene group may be substituted with one or more substituents selected from the group consisting of deuterium; C$_6$-C$_{20}$ aryl group; and C$_6$-C$_{20}$ aryl group substituted with deuterium; also the hydrogen of these substituents may be further substituted with one or more deuterium.

Also, the present invention provides a compound represented by any one of the Formulas 1-1 to 1-4.

Formula 1-1

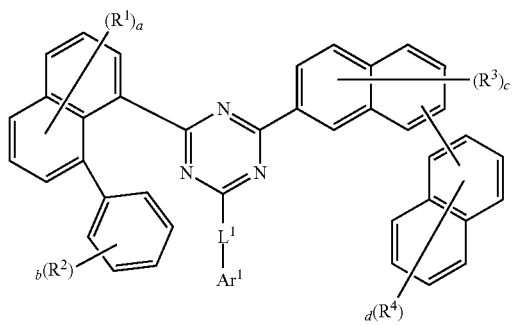

Formula 1-2

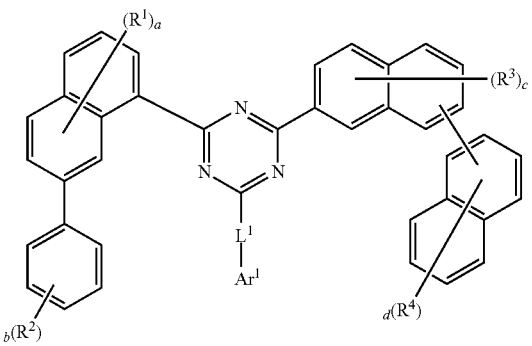

Formula 1-3

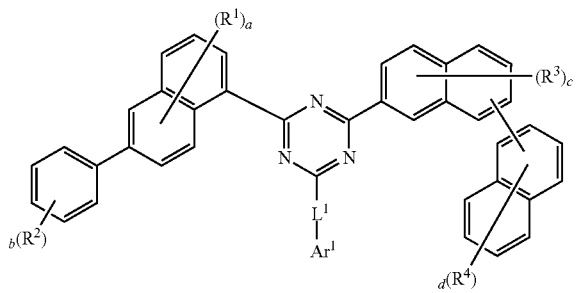

Formula 1-4

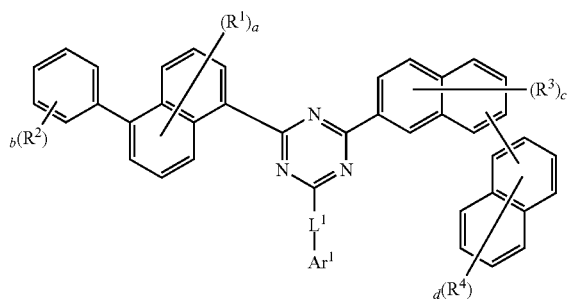

Wherein, $L^1$, $Ar^1$, $R^1$, $R^2$, $R^3$, $R^4$, a, b, c and d are the same as defined above.

Also, Formula 1 may preferably be any one of Formulas 2-1 to 2-2:

Formula 2-1

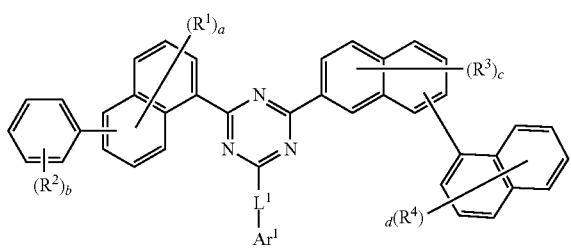

Formula 2-2

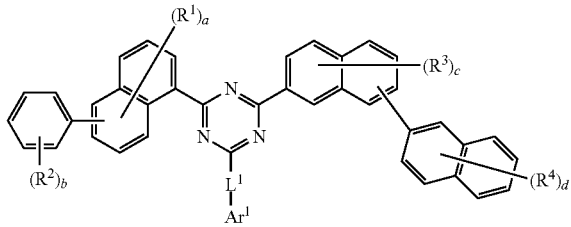

Wherein, $L^1$, $Ar^1$, $R^1$, $R^2$, $R^3$, $R^4$, a, b, c and d are the same as defined in Formula 1.

Formula 1 is any one of Formulas 2-3 to 2-6.

Formula 2-3

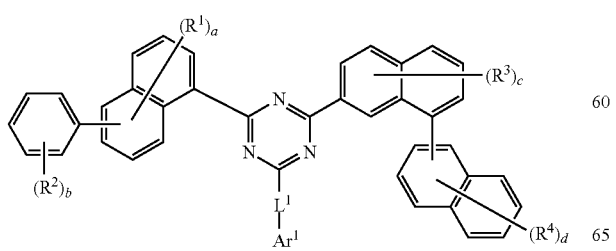

Formula 2-4

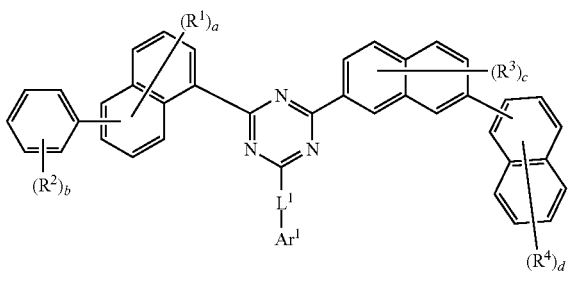

Formula 2-5

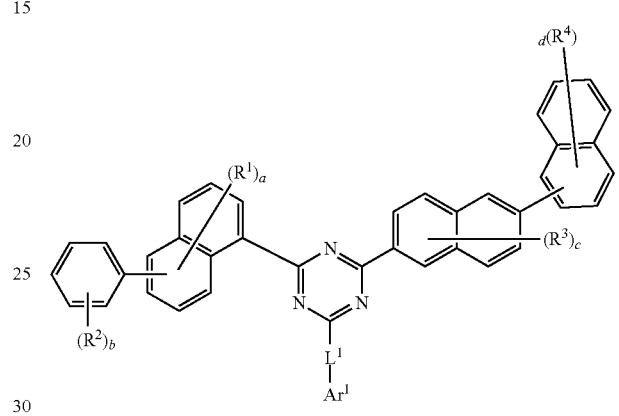

Formula 2-6

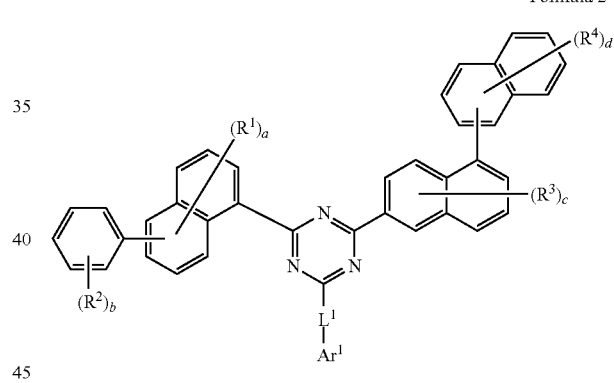

Wherein, $L^1$, $Ar^1$, $R^1$, $R^2$, $R^3$, $R^4$, a, b, c and d are the same as defined above.

Also, in Formula 1, $Ar^1$ is represented by any one of Formulas (A-1) to (A-6).

Formula (A-1)

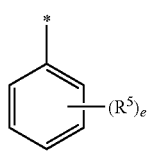

Formula (A-2)

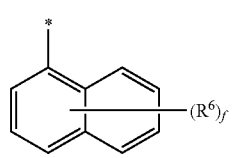

-continued
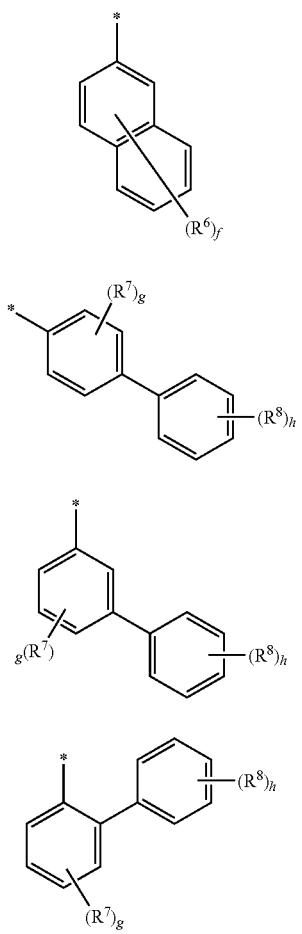
Formula (A-3)
Formula (A-4)
Formula (A-5)
Formula (A-6)
Wherein, $R^5$, $R^6$, $R^7$ and $R^8$ are each the same or different and independently hydrogen or deuterium, e is an integer from 0 to 5, f is an integer from 0 to 7, g is an integer from 0 to 4, h is an integer from 0 to 5, and * indicates a position to be bonded.
Also, in Formula 1, $L^1$ is represented by any one of Formulas <L-1> to <L-19>.
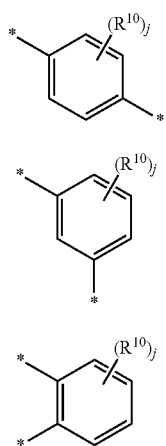
(L-1)
(L-2)
(L-3)
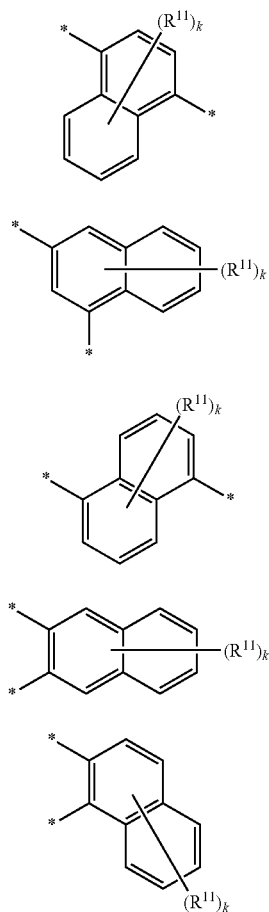
(L-4)
(L-5)
(L-6)
(L-7)
(L-8)
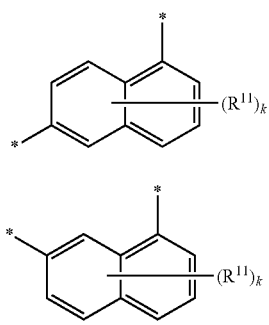
(L-9)
(L-10)
(L-11)
(L-12)
(L-13)

-continued

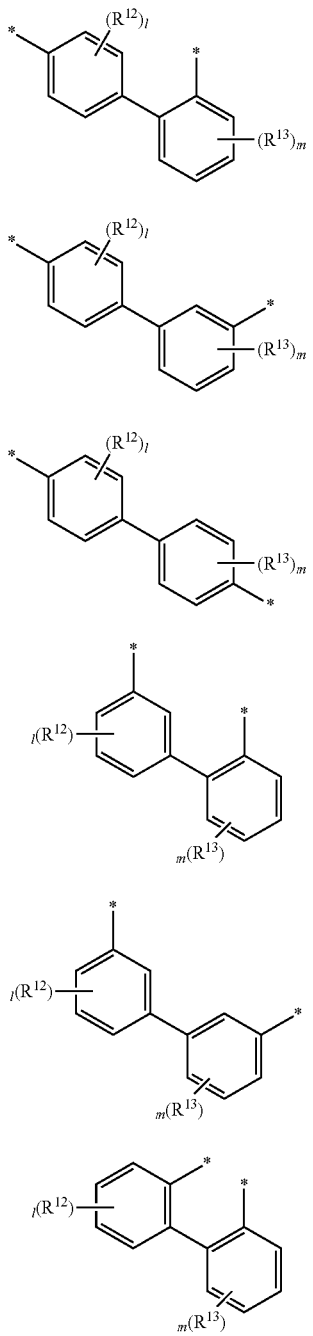

Wherein:

R[10], R[11], R[12] and R[13] are each the same or different from each other and are independently hydrogen; or deuterium; j, l and m are each independently an integer from 0 to 4, k is an integer from 0 to 6,

* indicates a position to be bonded.

Specifically, the compound represented by Formula 1 may be a compound represented by any one of the compounds P-1 to P-136, but is not limited thereto.

-continued
P-5
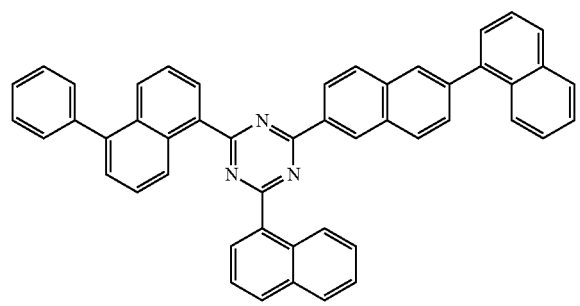
P-6
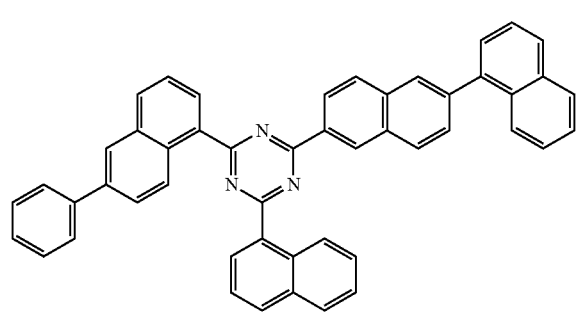
P-7
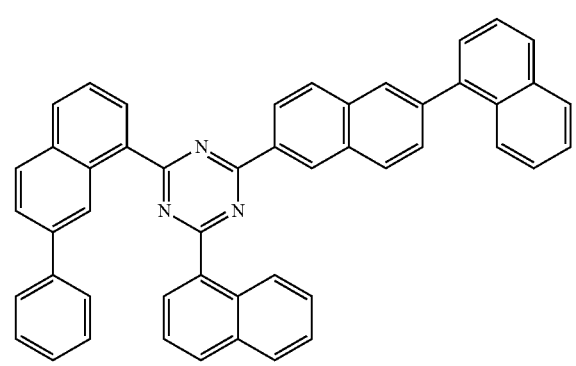
P-8
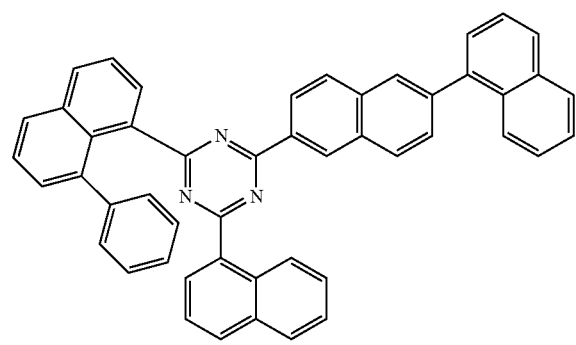
-continued
P-9
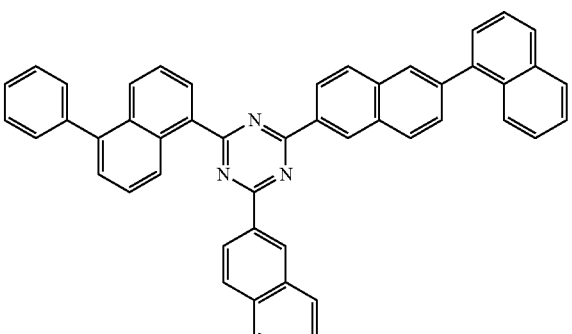
P-10
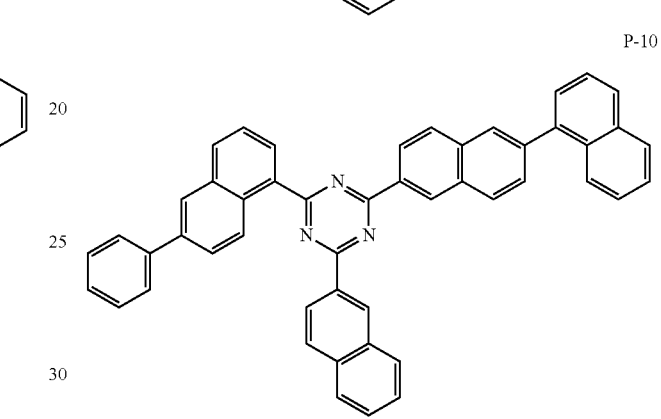
P-11
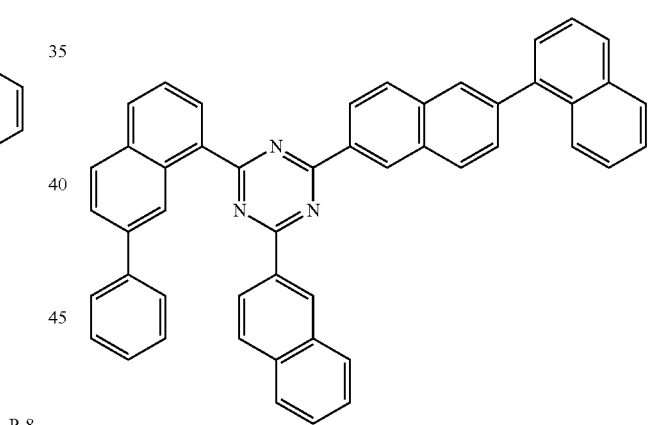
P-12
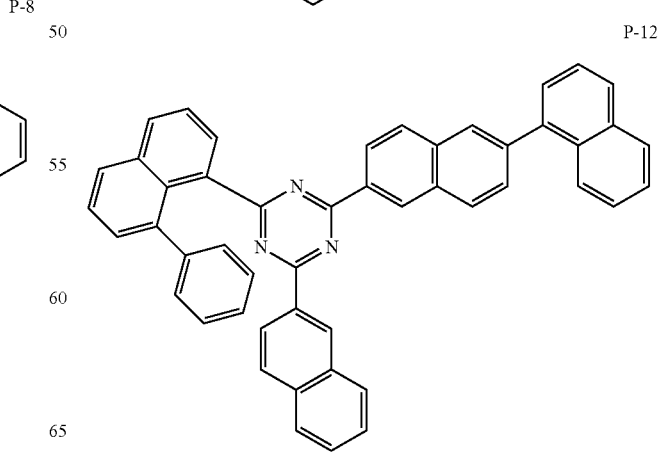

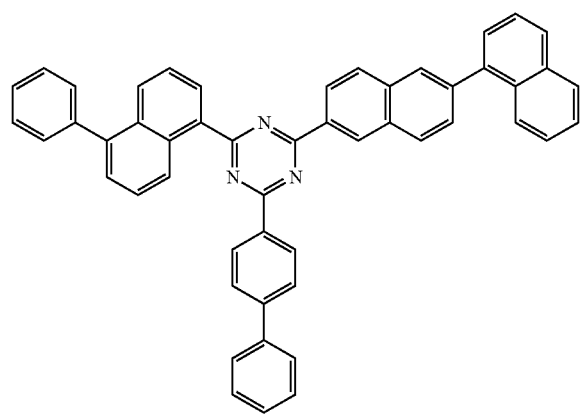
P-13
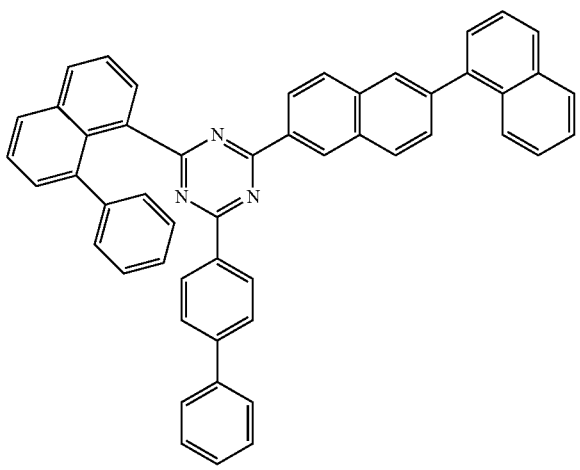
P-16
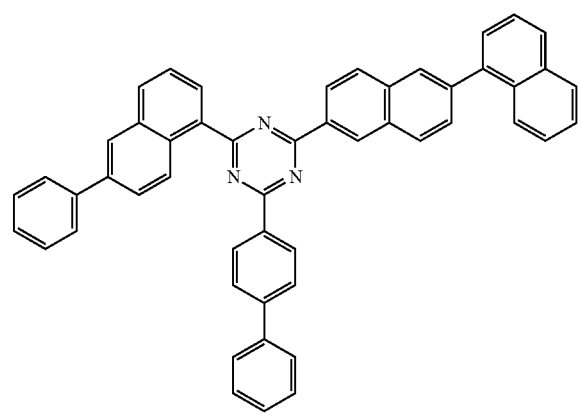
P-14
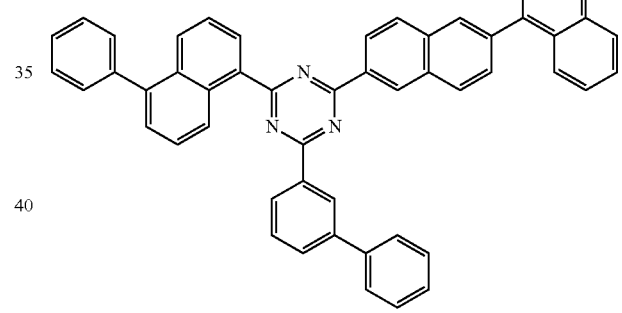
P-17
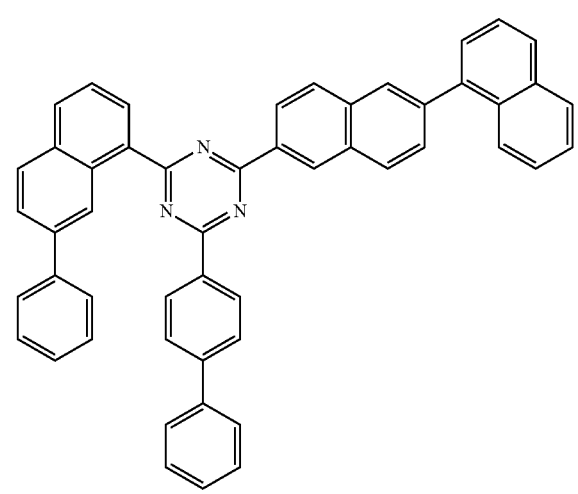
P-15
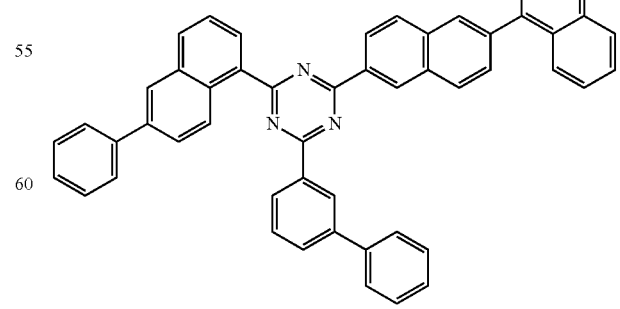
P-18

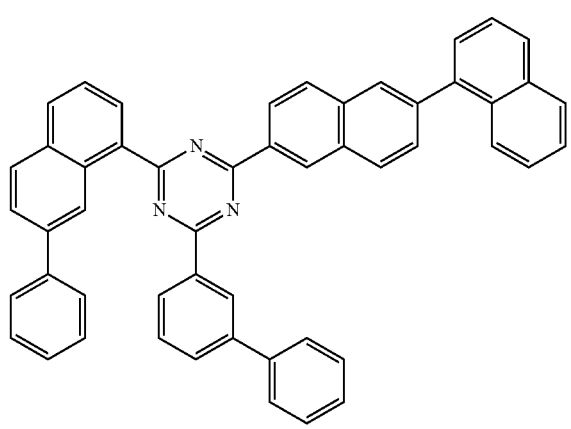
P-19
P-20
P-21
P-22
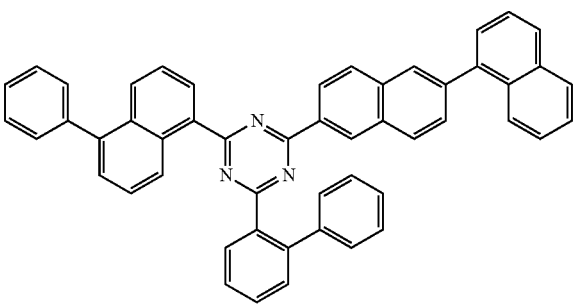
P-23
P-24
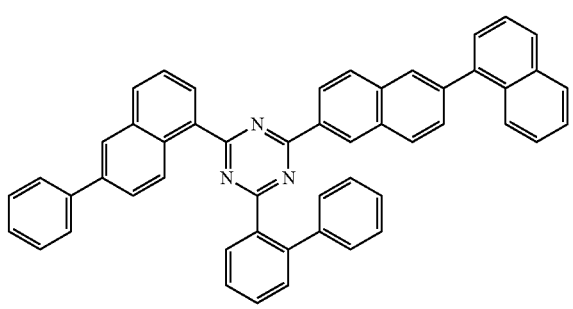
P-25
P-26

-continued
P-27
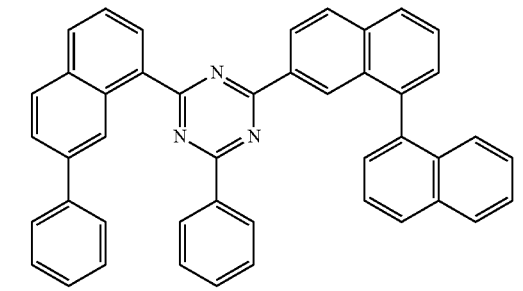
P-28
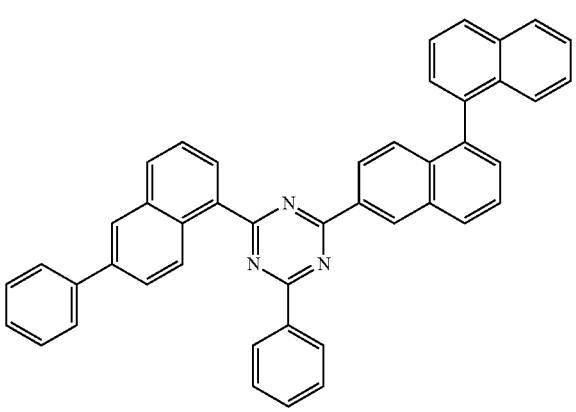
P-29
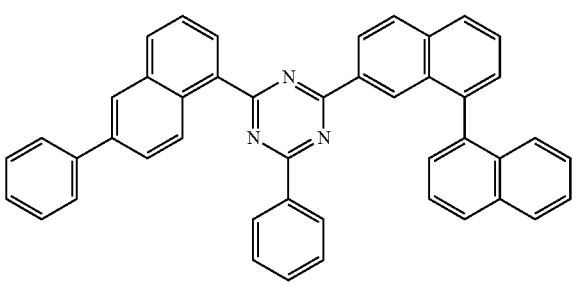
P-30
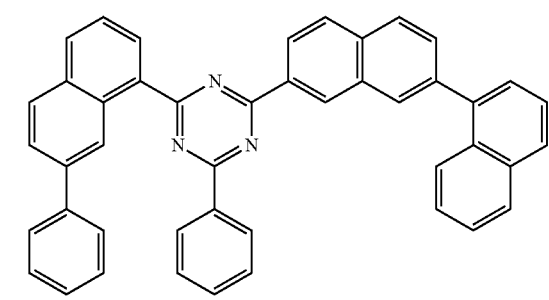
-continued
P-31
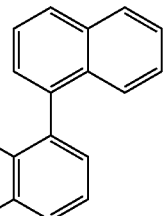
P-32
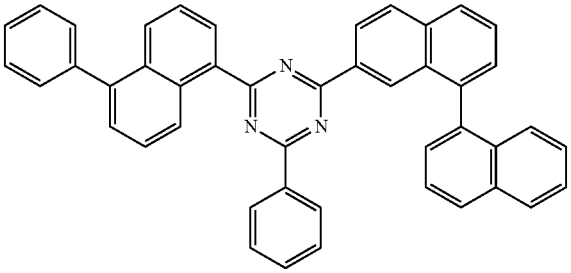
P-33
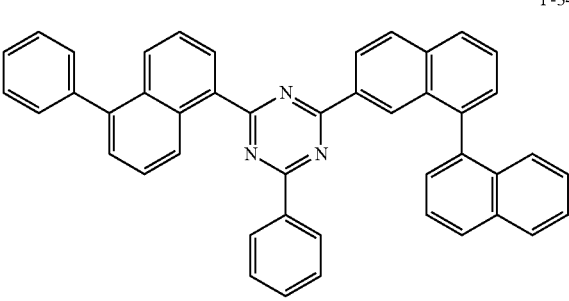
P-34
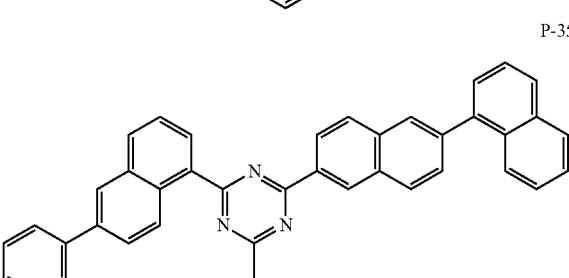
P-35

P-36
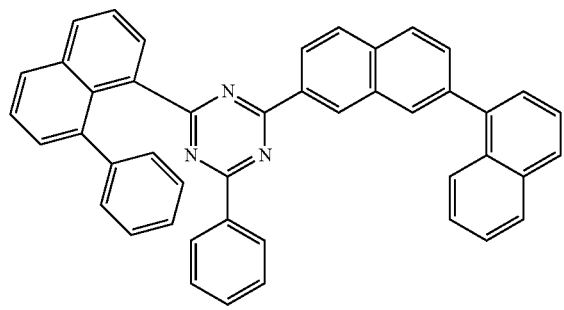
P-37
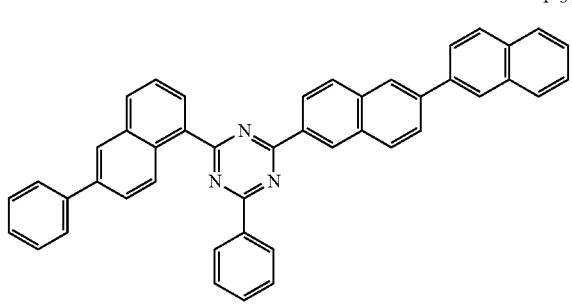
P-38
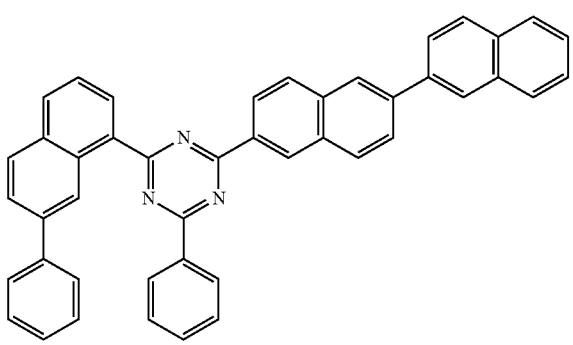
P-39
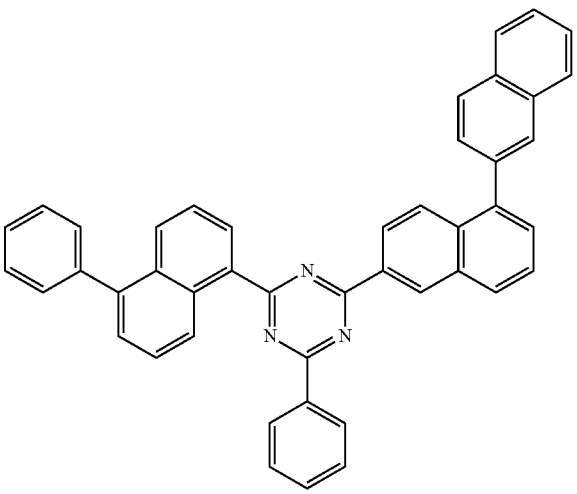
P-40
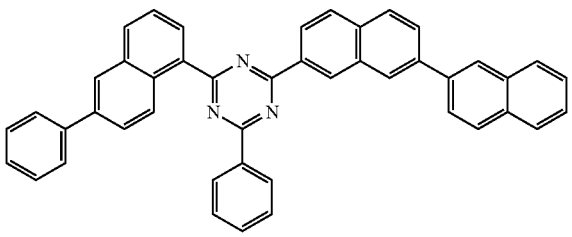
P-41
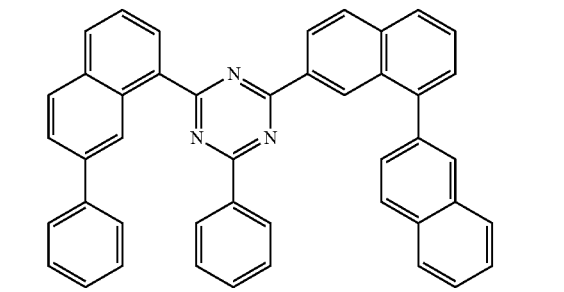
P-42
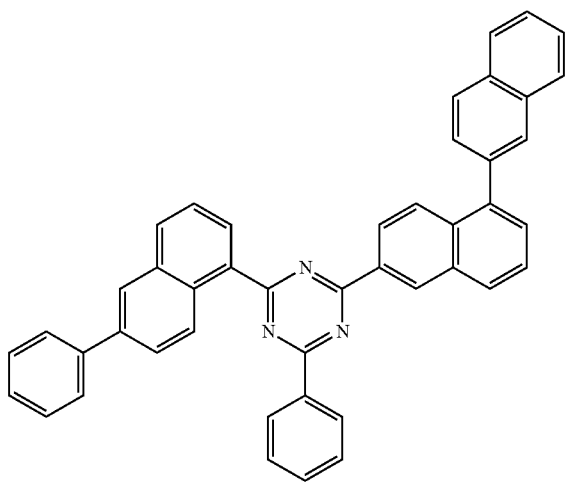
P-43

P-44
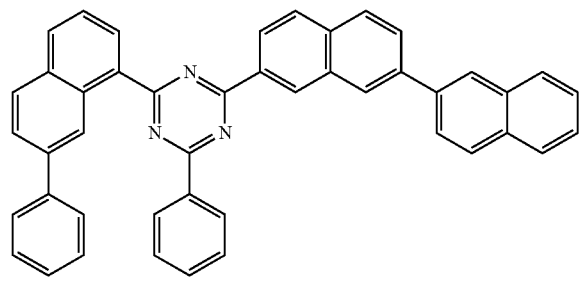
P-45
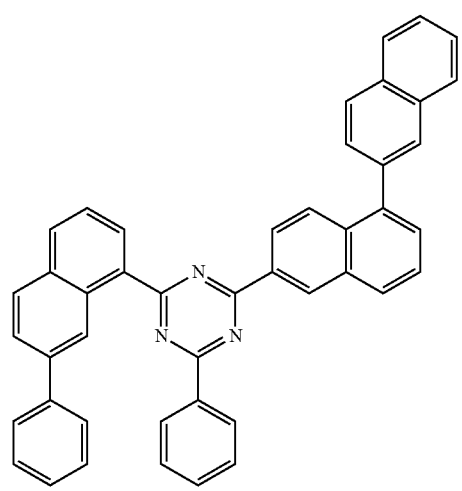
P-46
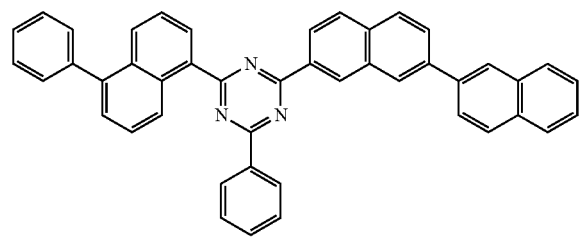
P-47
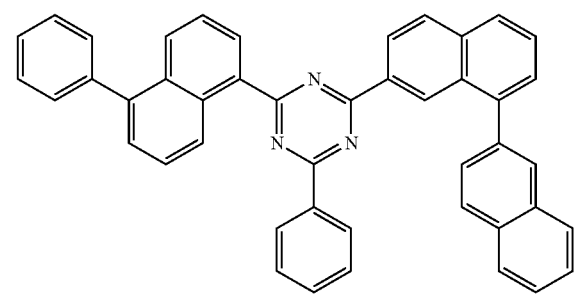
P-48
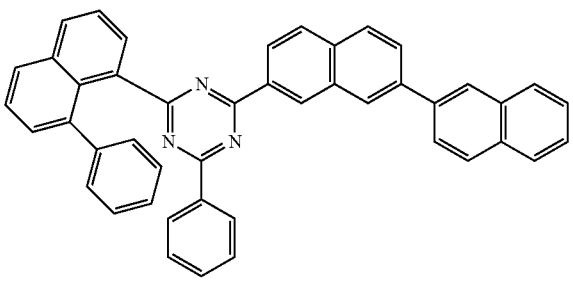
P-49
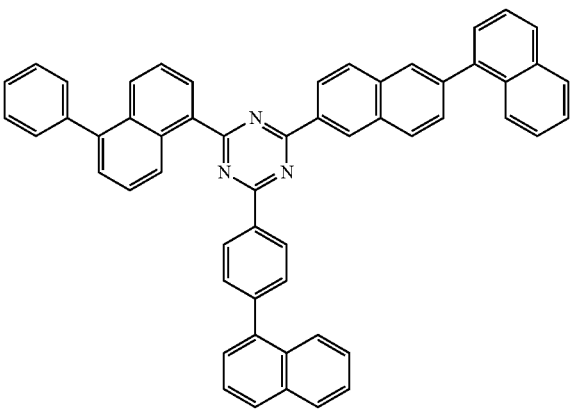
P-50
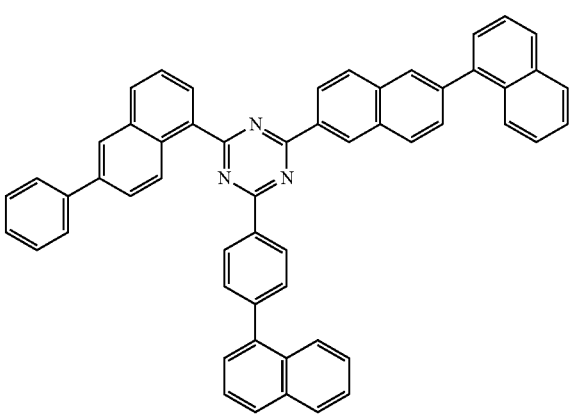

P-51
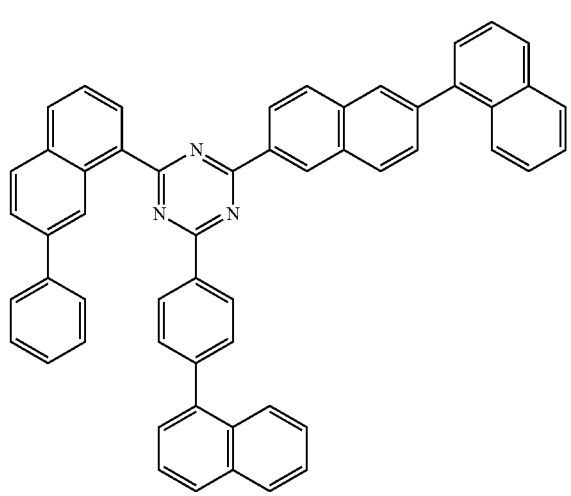
P-54
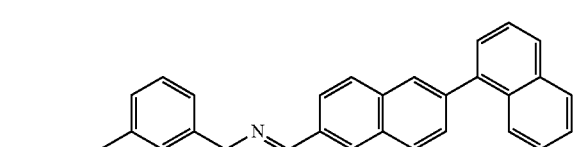
P-55
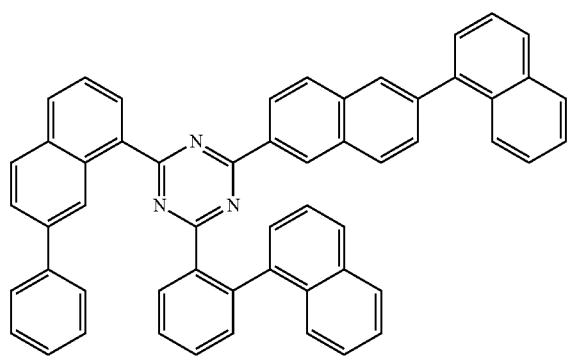
P-52
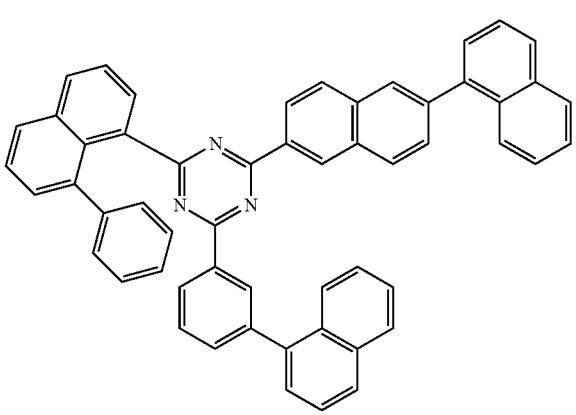
P-56
P-53
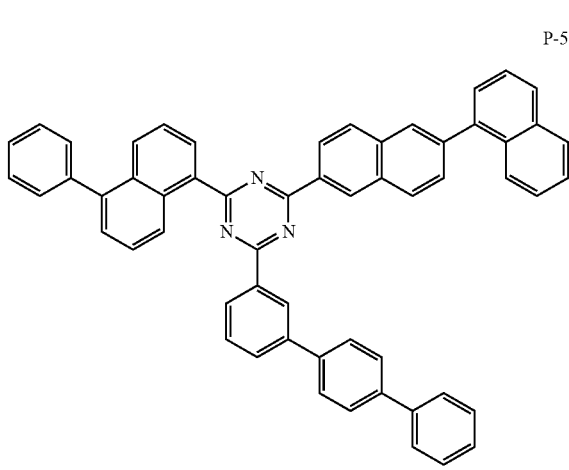
P-57
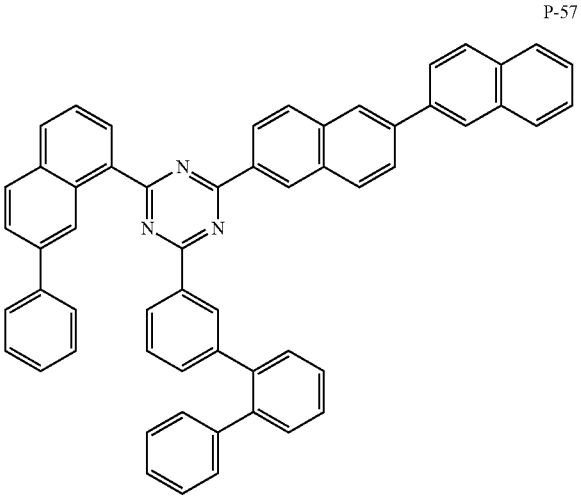

-continued
P-58
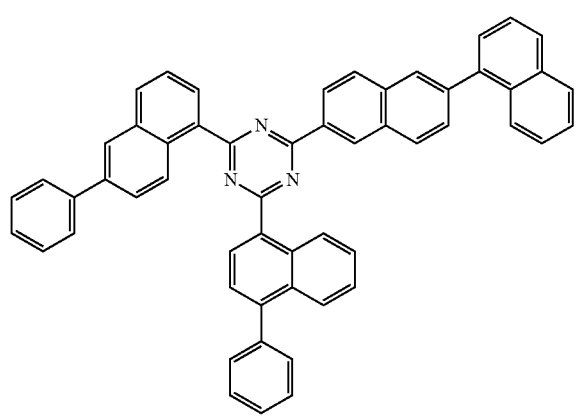
P-59
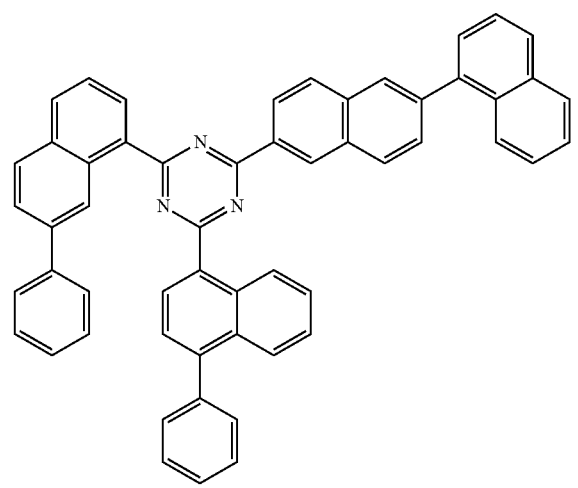
P-60
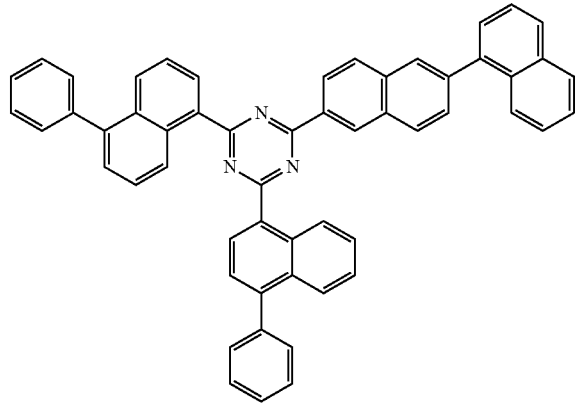
P-61
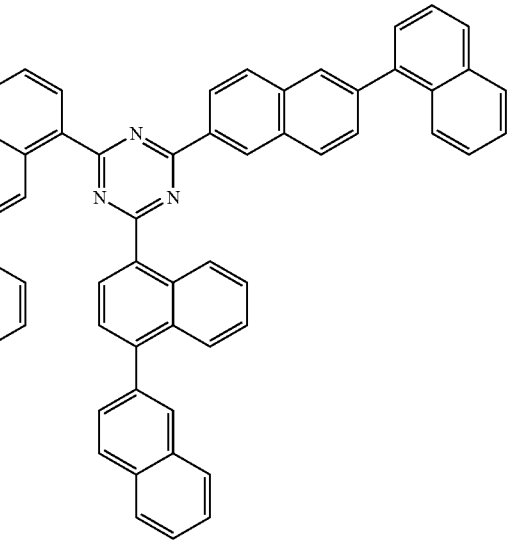
P-62
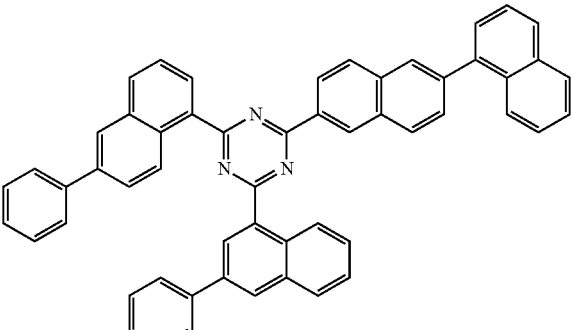
P-63
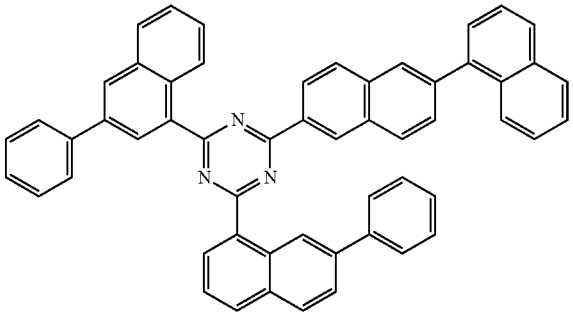
P-64
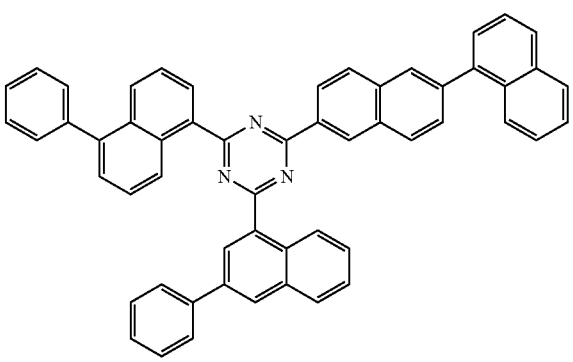

-continued
P-65
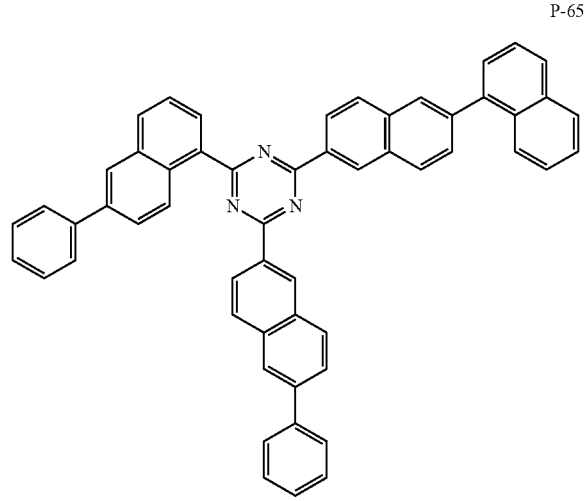
P-66
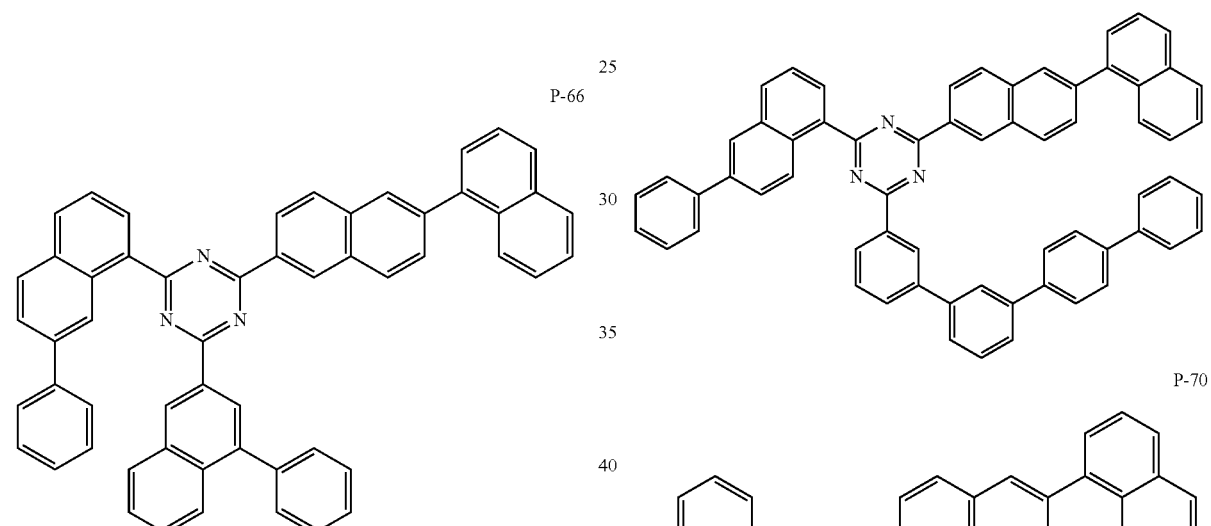
P-67
-continued
P-68
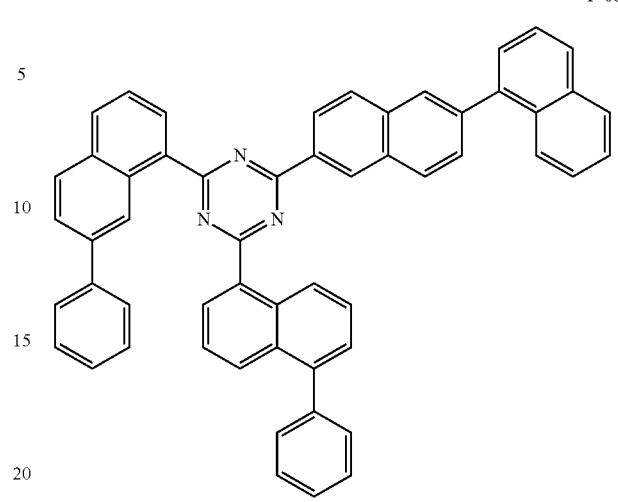
P-69
P-70
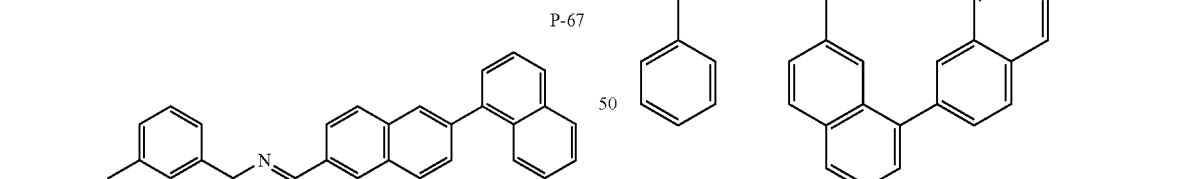
P-71
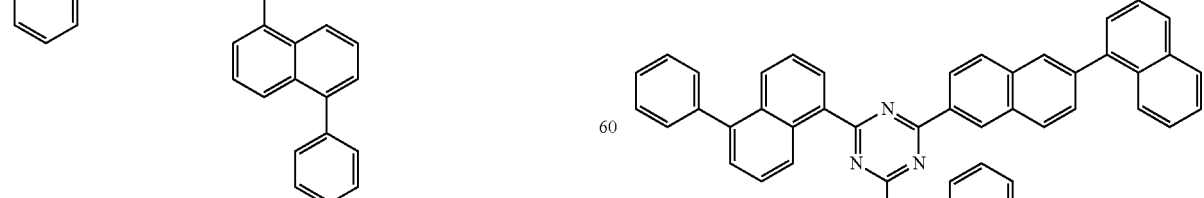

P-72
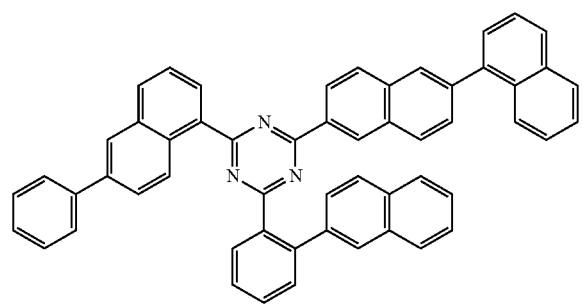
P-73
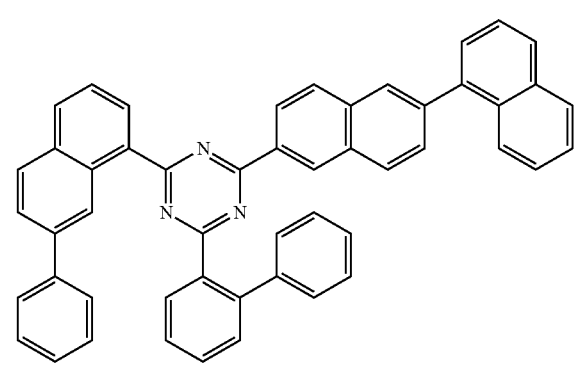
P-74
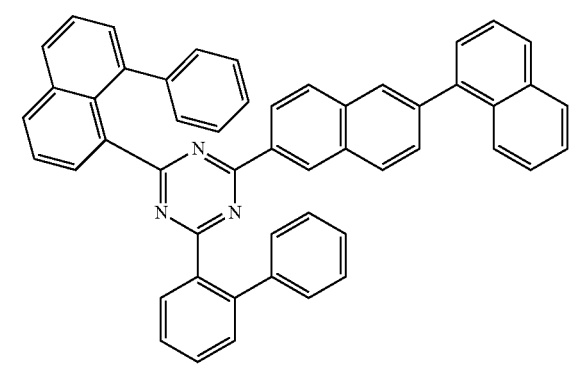
P-75
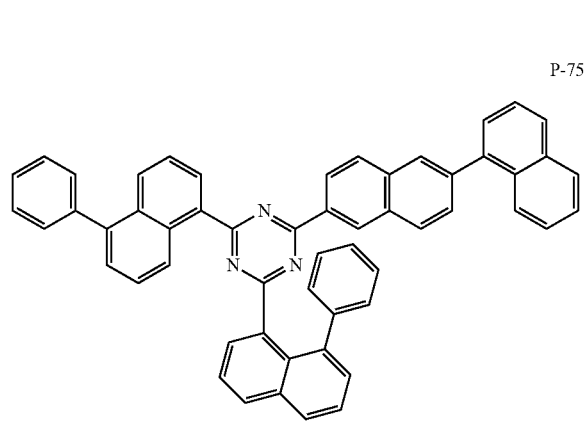
P-76
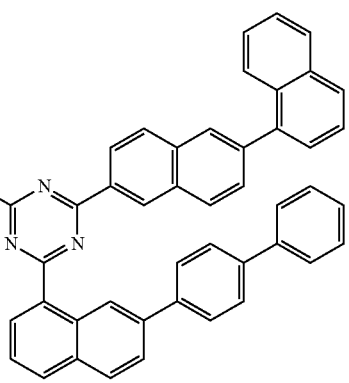
P-77
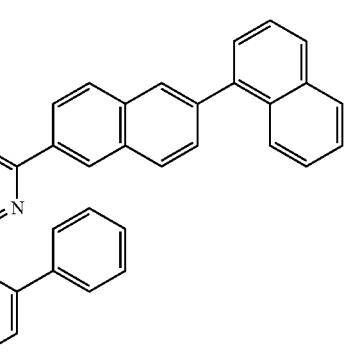
P-78
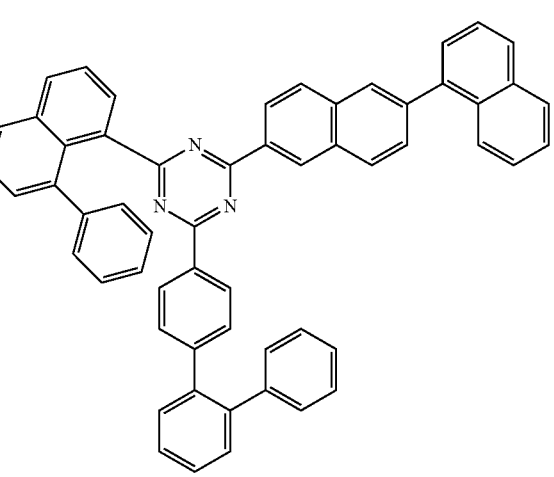

P-79
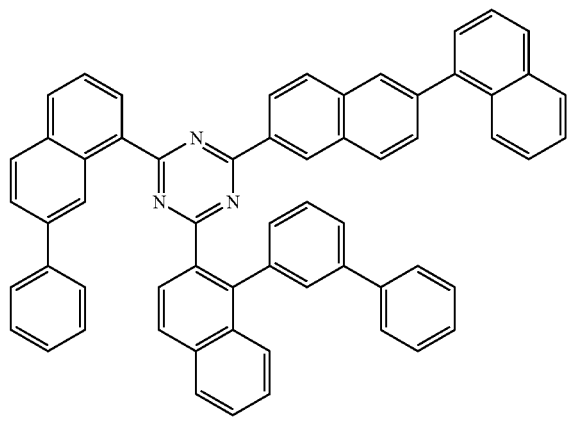
P-80
P-81
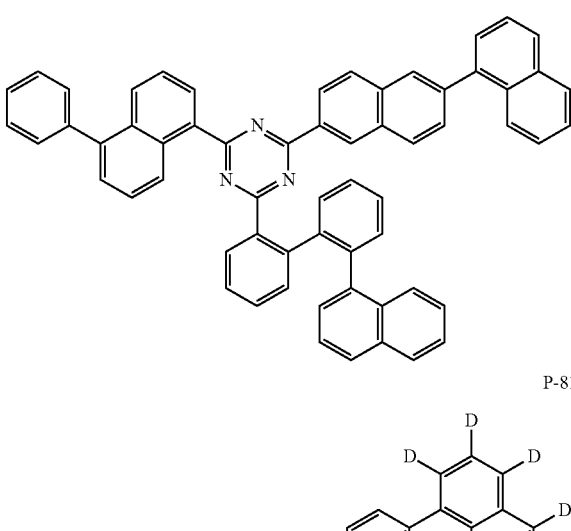
P-82
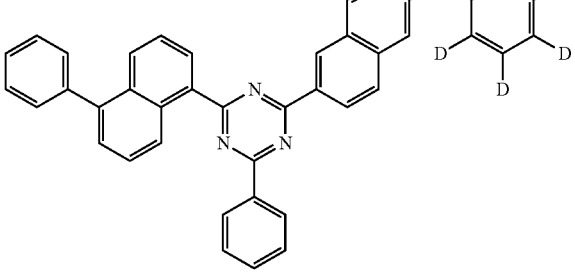
P-83

P-84
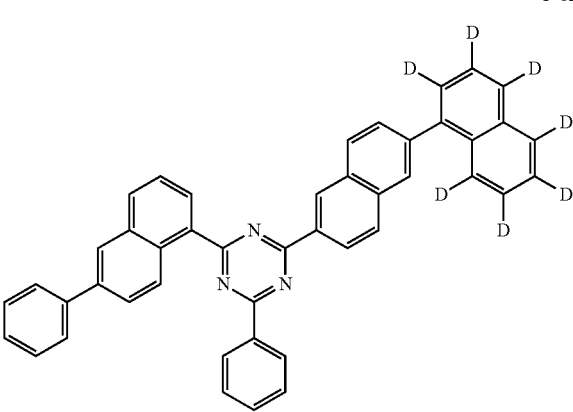
P-85
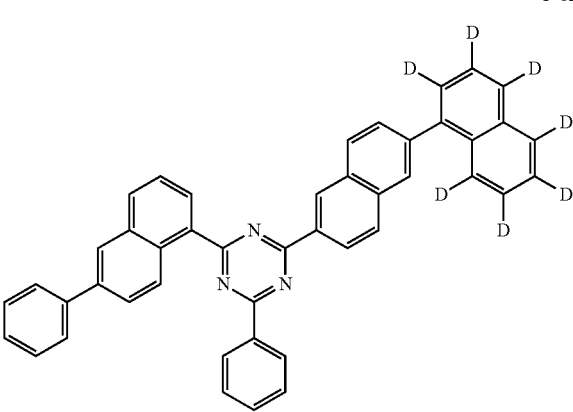

P-86
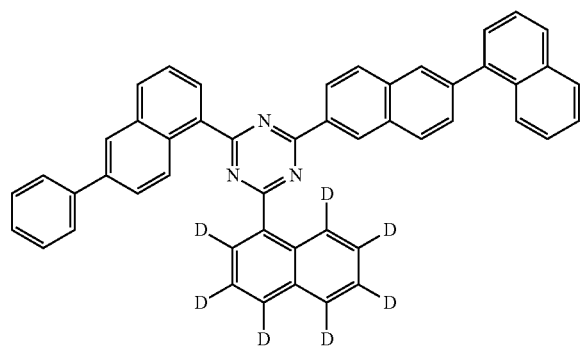
P-87
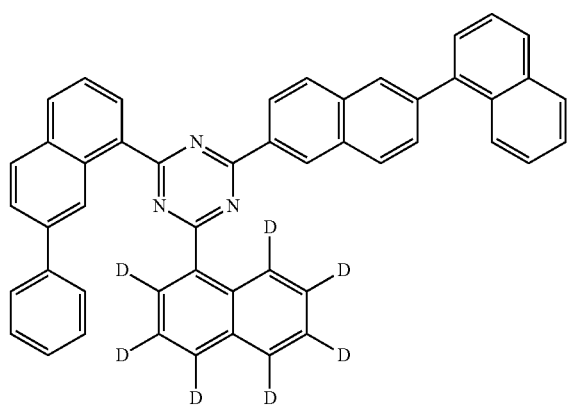
P-88
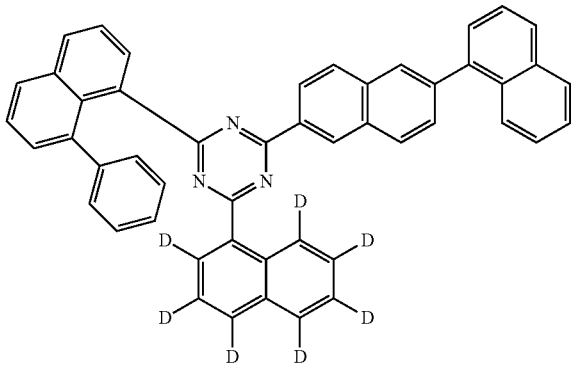
P-89
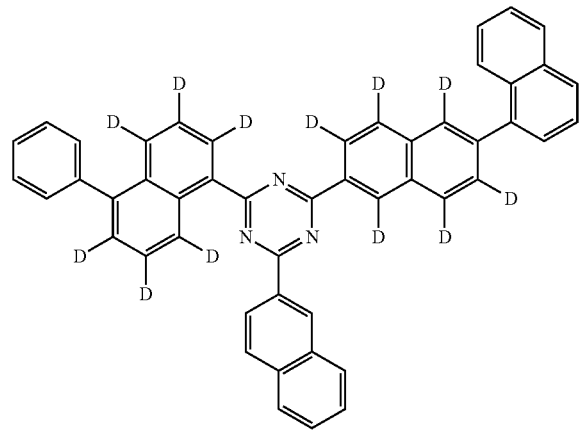
P-90
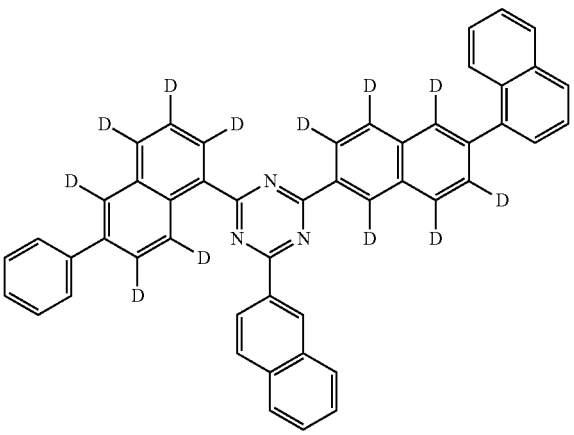
P-91
P-91
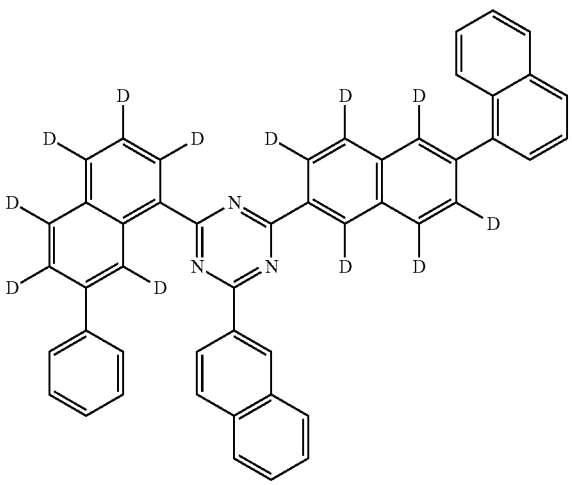

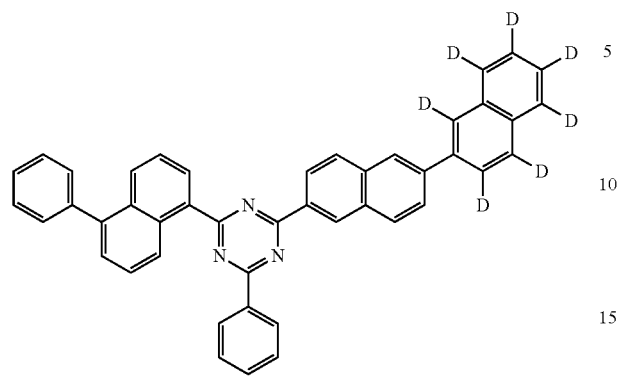
P-93
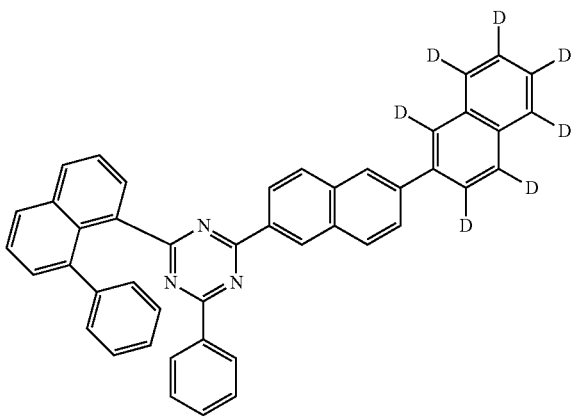
P-96
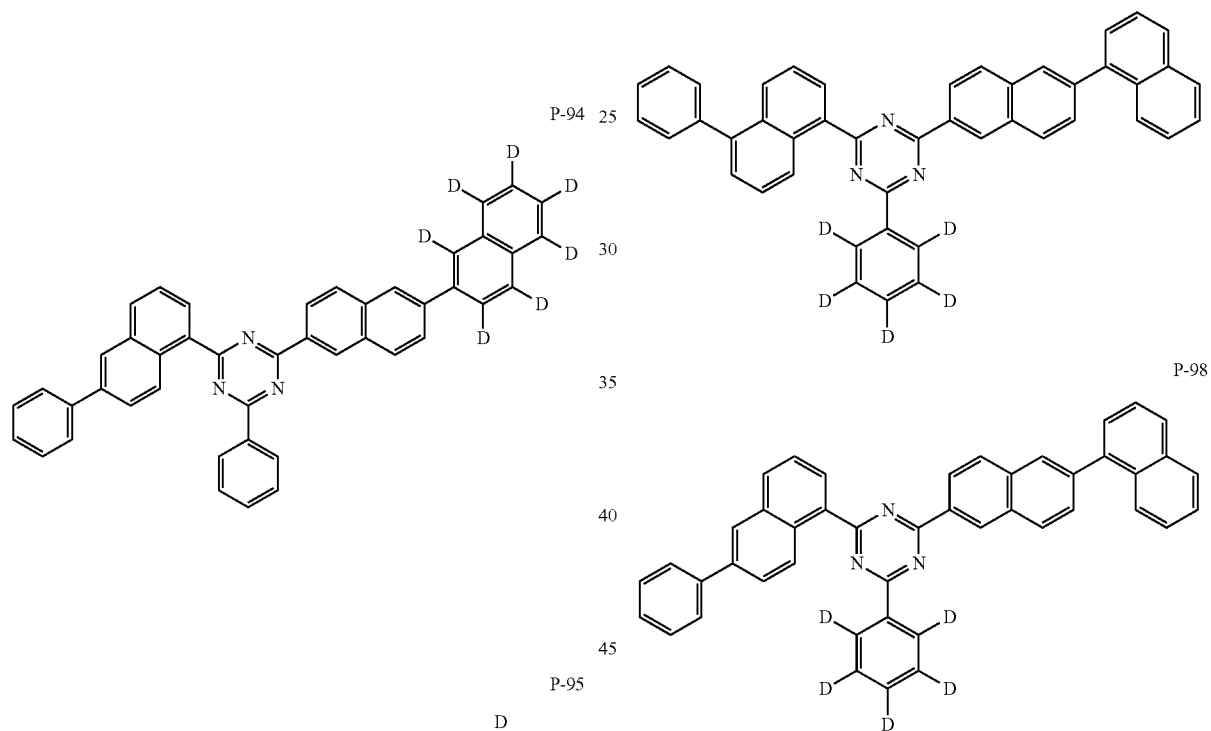
P-94
P-97
P-95
P-98
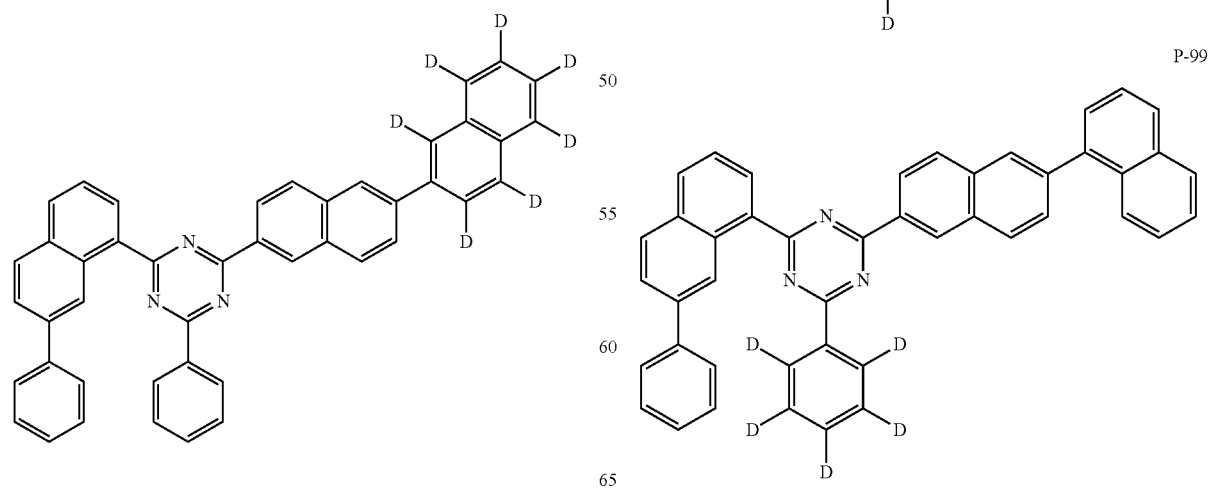
P-99

P-100
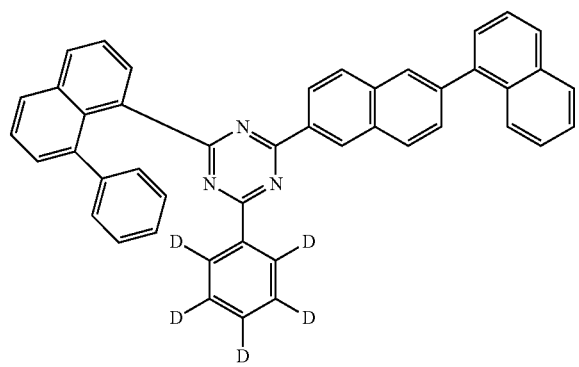
P-103
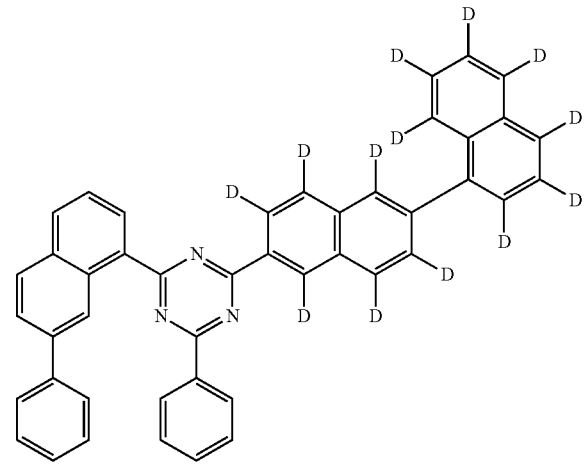
P-101
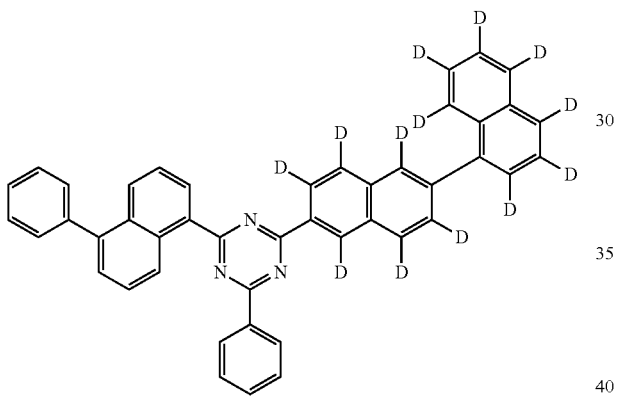
P-104
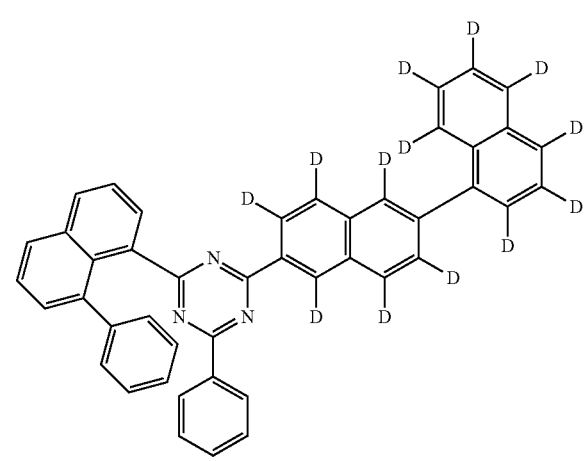
P-102
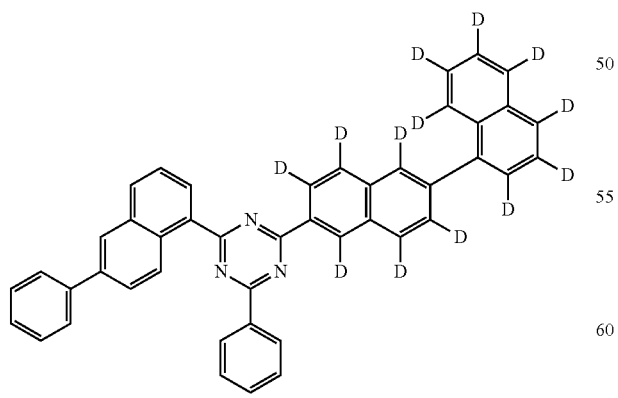
P-105
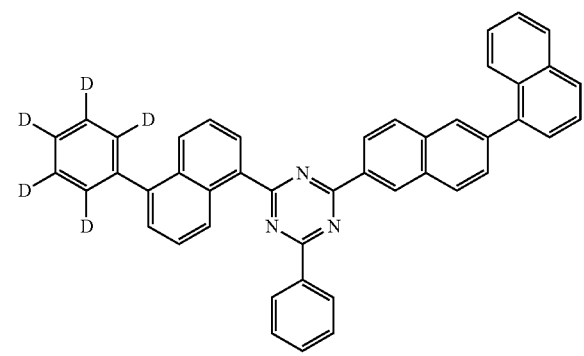

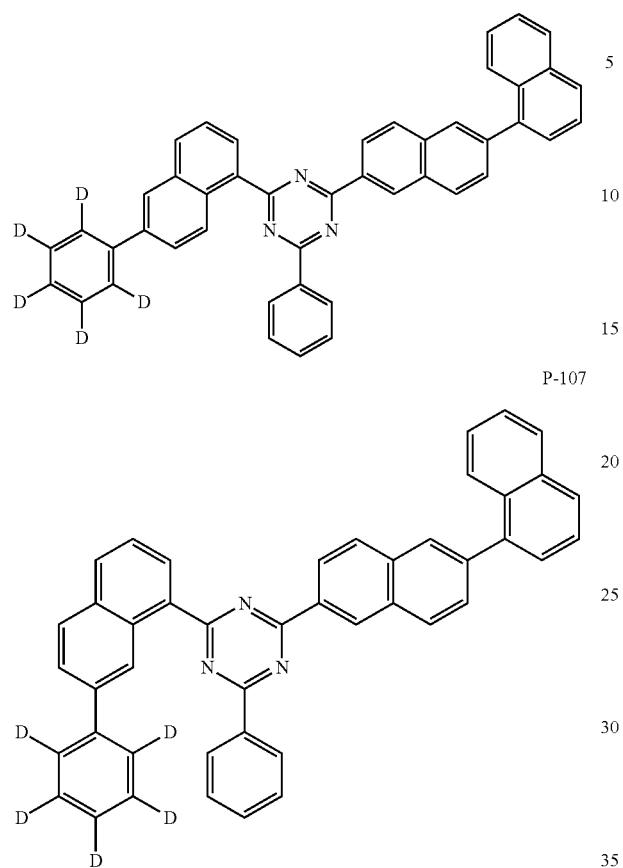
P-106
P-107
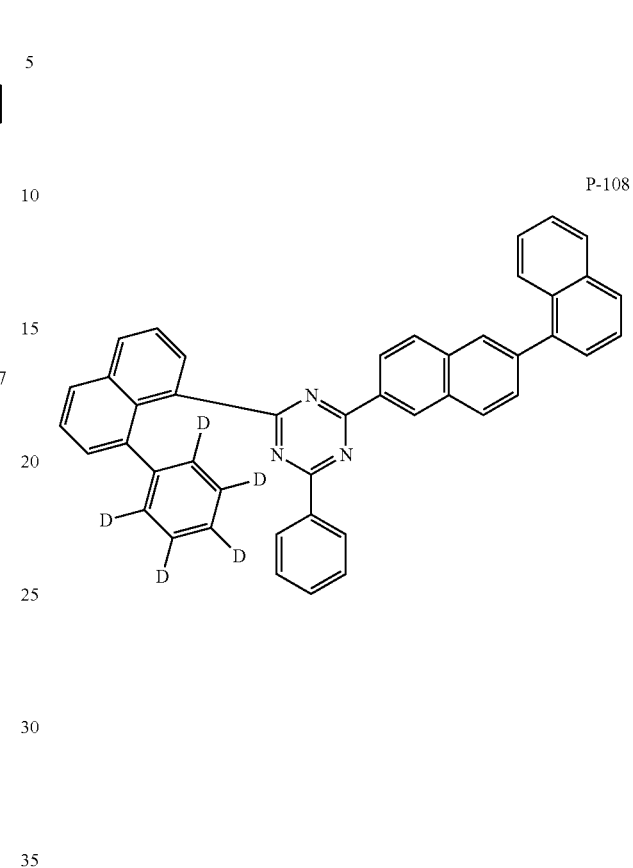
P-108
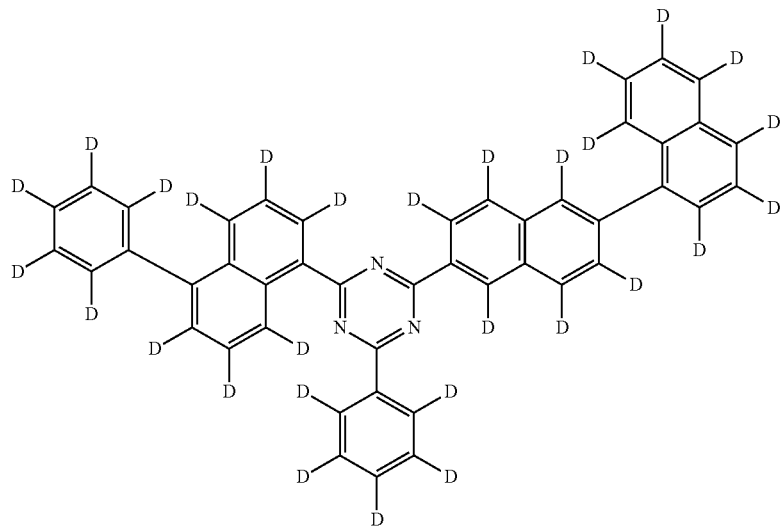
P-109

-continued
P-110
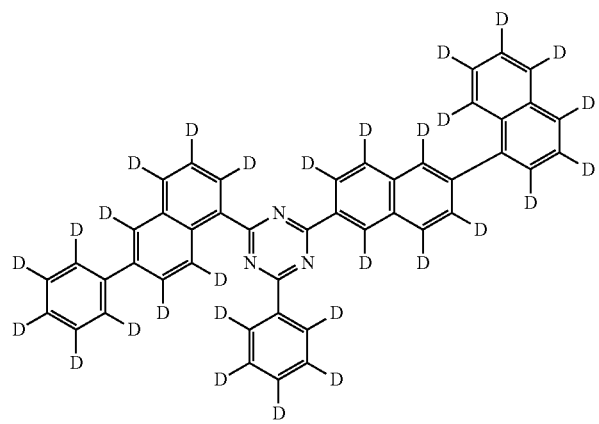
P-111
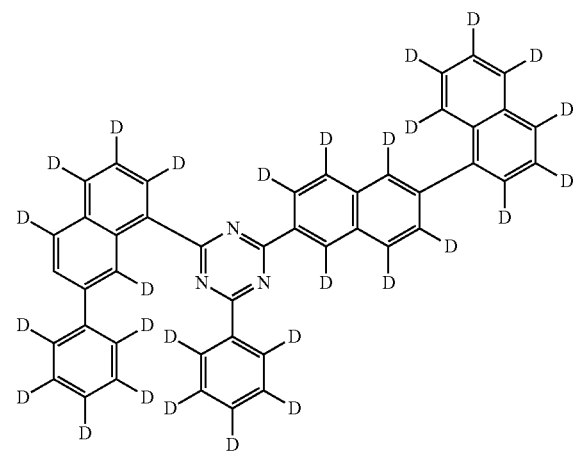
P-112
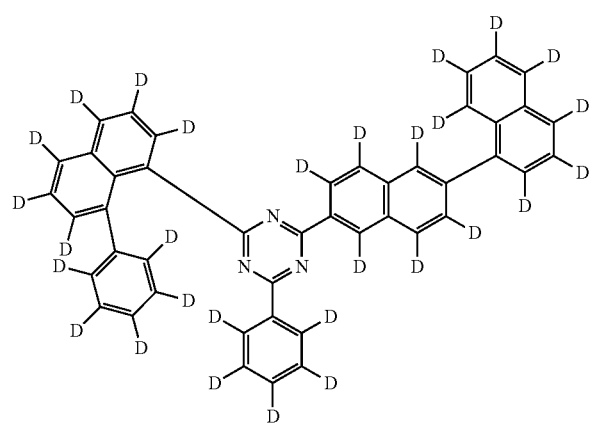
P-113
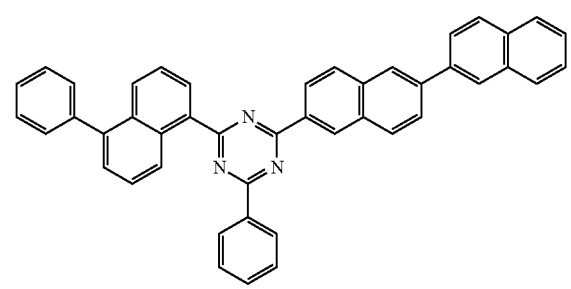
P-114
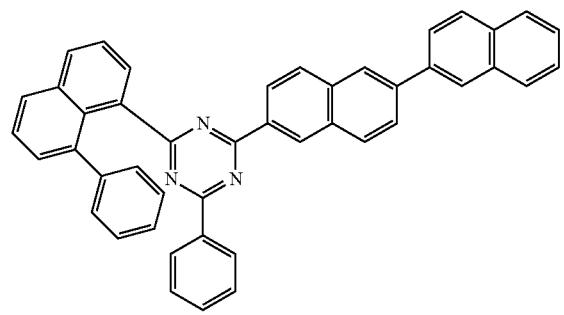
P-115
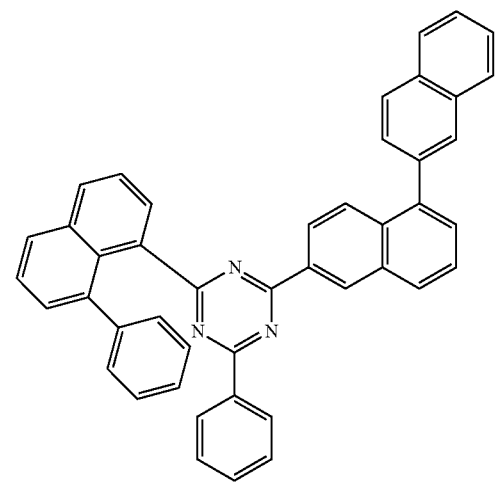

-continued
P-116
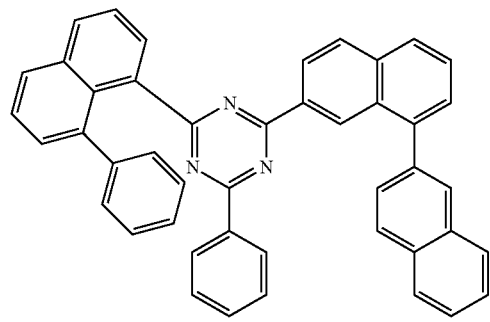
P-117
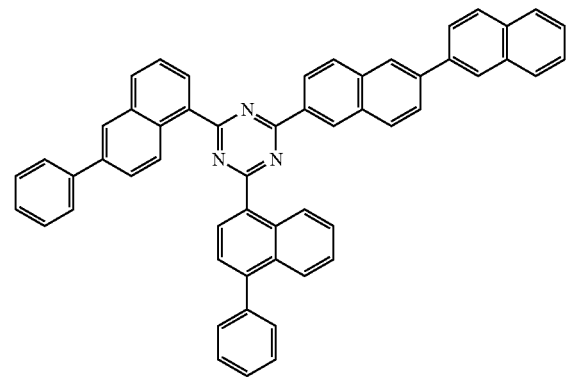
P-118
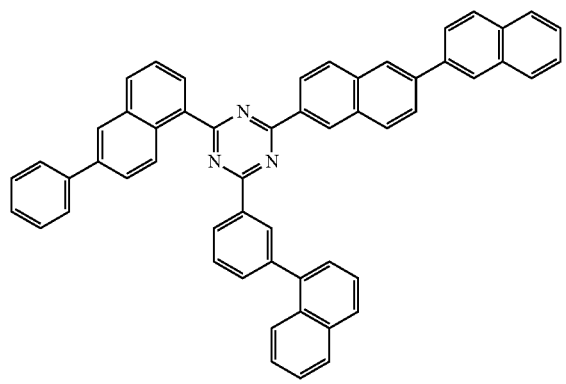
P-119
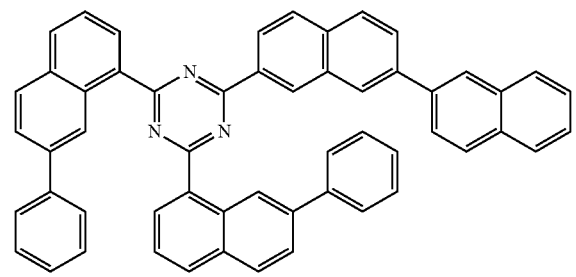
P-120
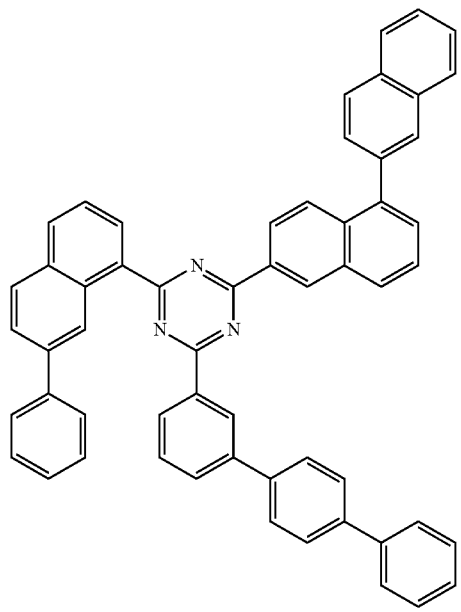
P-121
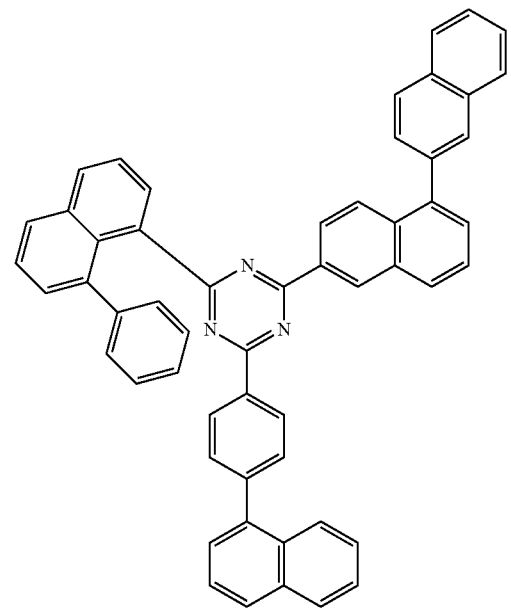

-continued
P-122
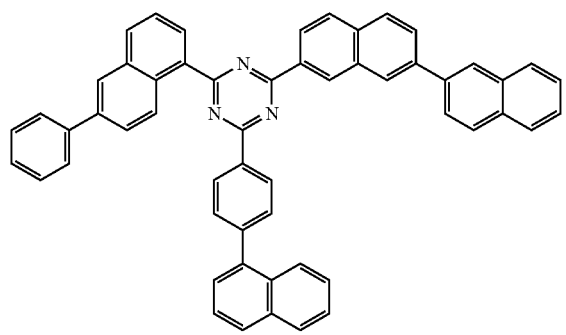
P-123
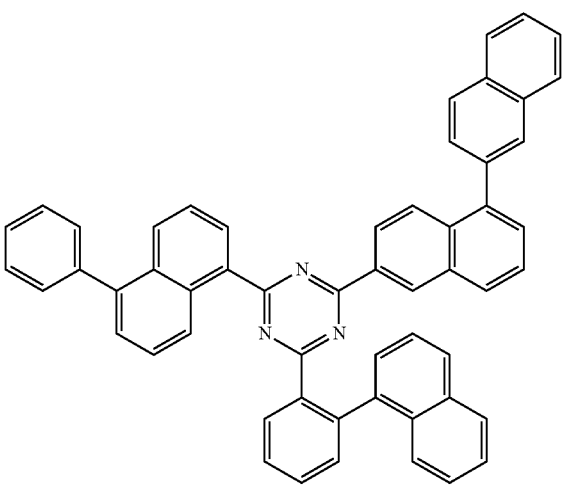
P-124
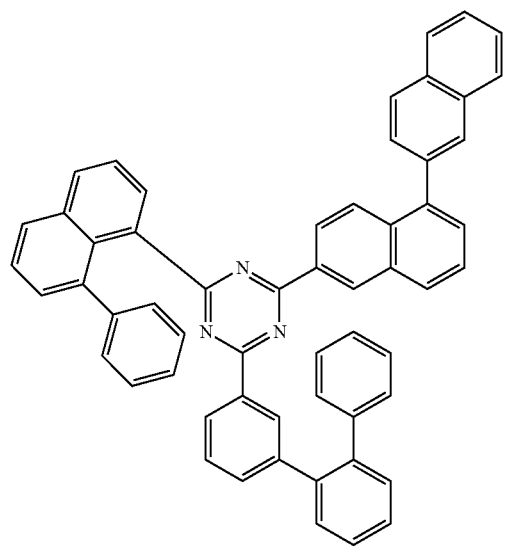
P-125
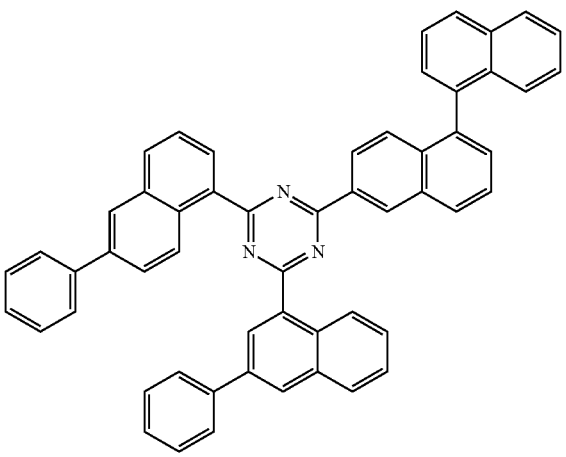
P-126
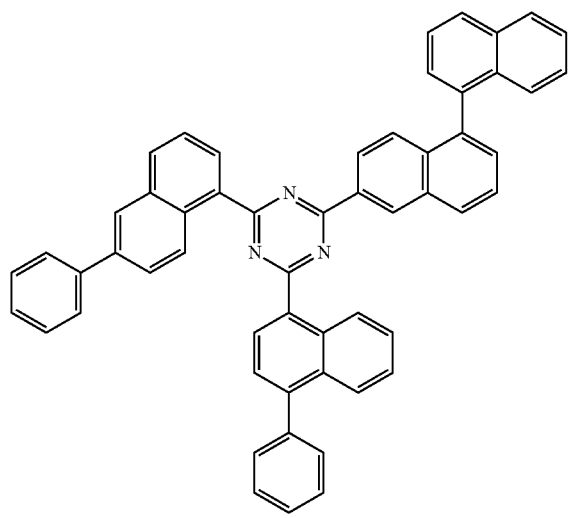
P-127
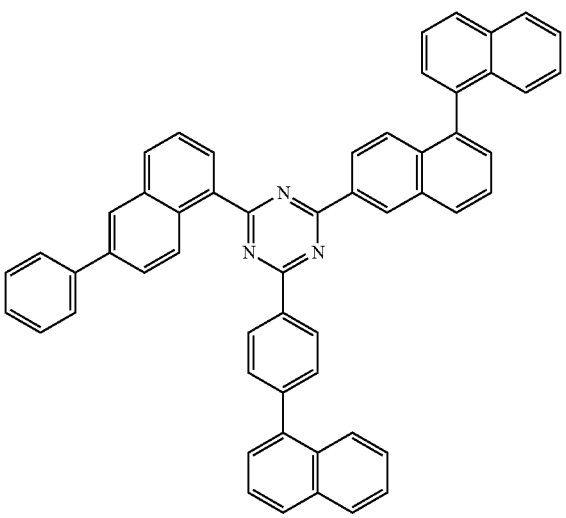

-continued
P-128
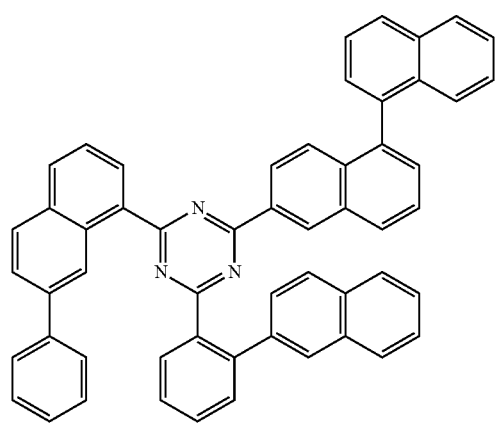
P-129
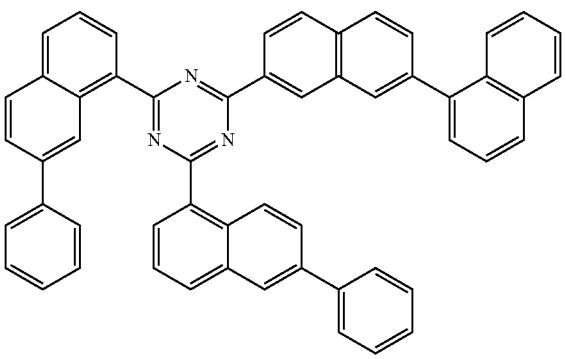
P-130
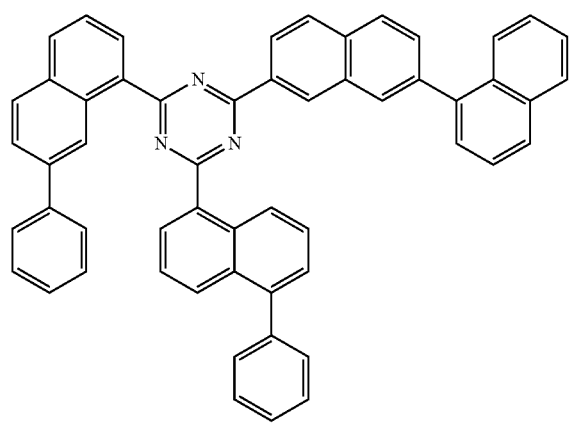
P-131
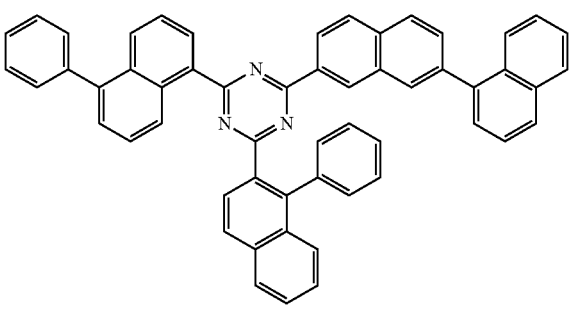
P-132
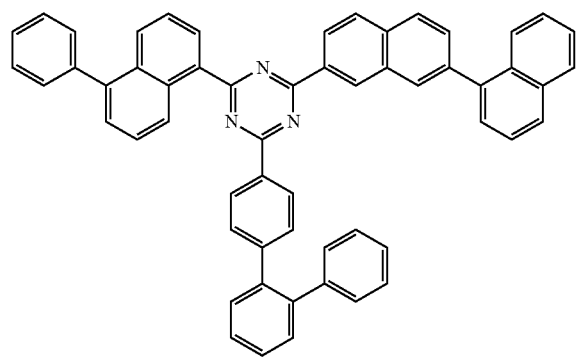
P-133
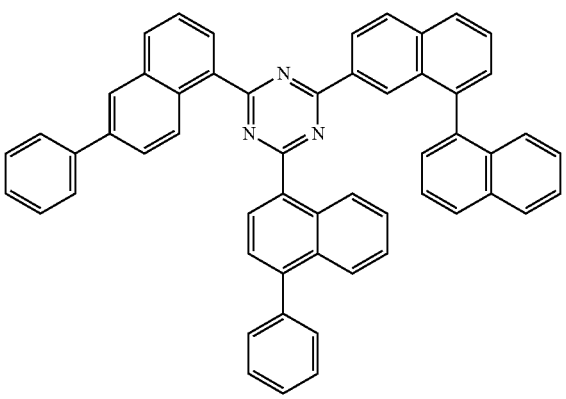

-continued

P-134

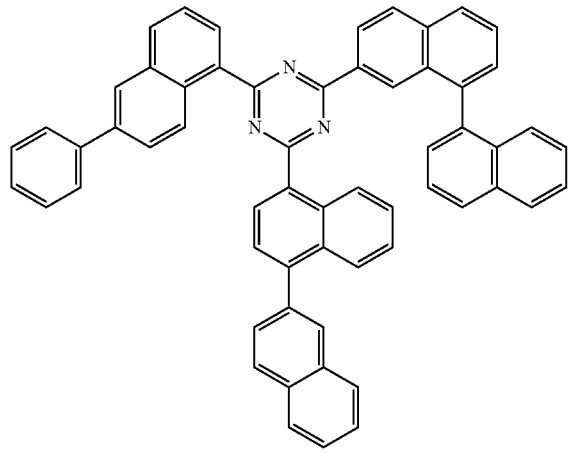

P-135

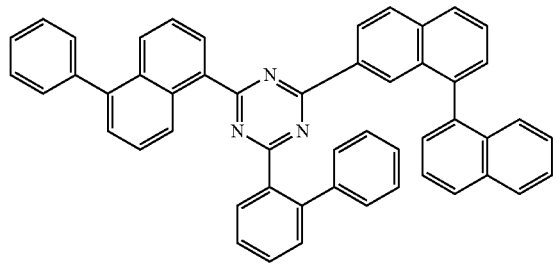

P-136

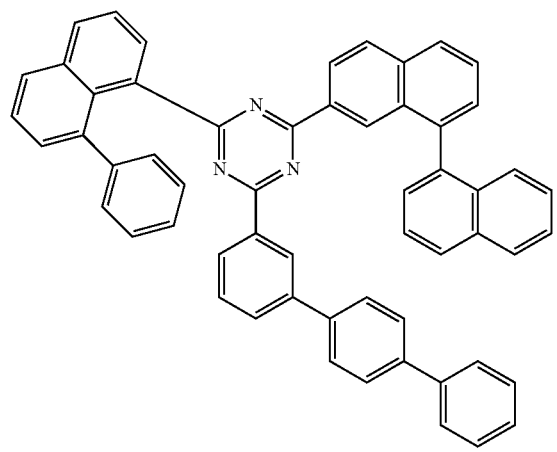

In another aspect, the present invention provides a composition for an organic electronic element comprising a mixture of a compound represented by Formula 1 and a compound represented by Formula 2 or 3.

<Formula 2>

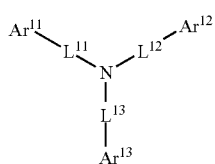

<Formula 3>

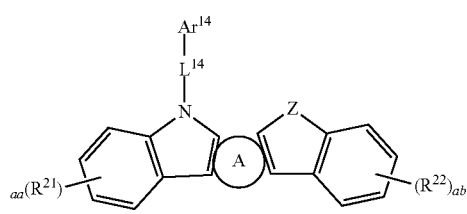

Wherein:

$L^{11}$, $L^{12}$, $L^{13}$ and $L^{14}$ are each independently selected from the group consisting of single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

Wherein when $L^{11}$, $L^{12}$, $L^{13}$ and $L^{14}$ are an arylene group, preferably an $C_6$-$C_{30}$ arylene group, more preferably an $C_6$-$C_{25}$ arylene group, an $C_6$-$C_{18}$ arylene group or an $C_6$-$C_{12}$ arylene group, such as phenylene, biphenylene, naphthylene, terphenylene, anthracenylene, phenanthrenylen, etc.

Wherein when $L^{11}$, $L^{12}$, $L^{13}$ and $L^{14}$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $L^{11}$, $L^{12}$, $L^{13}$ and $L^{14}$ are a fused ring group, preferably a fused ring group of an $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

$Ar^{11}$, $Ar^{12}$ and $Ar^{13}$ are each independently selected from the group consisting of an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

Wherein when $Ar^{11}$, $Ar^{12}$ and $Ar^{13}$ are an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, chryshen, etc.

Wherein when $Ar^{11}$, $Ar^{12}$ and $Ar^{13}$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $Ar^{11}$, $Ar^{12}$ and $Ar^{13}$ are a fused ring group, preferably a fused ring group of an $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

Wherein when $Ar^{11}$, $Ar^{12}$ and $Ar^{13}$ are an aliphatic ring group, preferably a $C_3$-$C_{30}$ aliphatic ring group, more preferably a $C_3$-$C_{25}$ aliphatic ring group, a $C_3$-$C_{18}$ aliphatic ring group, and a $C_3$-$C_{12}$ aliphatic ring group, and specifically, cyclobutane, cyclopentane, cyclohexane, bicycloheptane, adamantyl, etc.

Wherein when $Ar^{11}$, $Ar^{12}$ and $Ar^{13}$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $Ar^{11}$, $Ar^{12}$ and $Ar^{13}$ are an alkoxyl group, preferably a $C_1$-$C_{25}$ alkoxyl group, a $C_1$-$C_{18}$ alkoxyl group or a $C_1$-$C_{12}$ alkoxyl group.

Wherein when $Ar^{11}$, $Ar^{12}$ and $Ar^{13}$ are an aryloxy group, preferably a $C_6$-$C_{25}$ aryloxy group, a $C_6$-$C_{18}$ an aryloxy group or a $C_6$-$C_{12}$ aryloxyl group.

$Ar^{14}$ is each independently selected from the group consisting of an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^a$)($R^b$);

Wherein when $Ar^{14}$ is an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, chryshen, etc.

Wherein when $Ar^{14}$ is a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $Ar^{14}$ is a fused ring group, preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

Wherein L' is selected from the group consisting of a single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring;

Wherein when L' is an arylene group, preferably an $C_6$-$C_{30}$ arylene group, more preferably an $C_6$-$C_{25}$ arylene group, an $C_6$-$C_{18}$ arylene group or an $C_6$-$C_{12}$ arylene group, such as phenylene, biphenylene, naphthylene, terphenylene, anthracenylene, phenanthrenylene, etc.

Wherein when L' is a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when L' is an aliphatic ring, preferably a $C_3$-$C_{30}$ aliphatic ring; more preferably a $C_3$-$C_{25}$ aliphatic ring; a $C_3$-$C_{18}$ aliphatic ring; or a $C_3$-$C_{12}$ aliphatic ring; and specifically, cyclobutane, cyclopentane, cyclohexane, bicycloheptane, adamantyl, etc.

Z is O, S, C($R^{51}$)($R^{52}$) or $NR^{53}$,

Wherein $R^{51}$, $R^{52}$, $R^{53}$, $R^a$ and $R^b$ are the same as the definition of $Ar^{11}$, or $R^{51}$ and $R^{52}$ can be bonded to each other to form a spiro, Ring A is an $C_6$-$C_{20}$ aryl group, $R^{21}$ and $R^{22}$ are each the same or different, and each independently selected from the group consisting of a hydrogen; deuterium; halogen; cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^{21}$ or plurality of $R^{22}$ may be bonded to each other to form a ring, Wherein when $R^{21}$ and $R^{22}$ are an aryl group, preferably an $C_6$-$C_{30}$ aryl group, more preferably an $C_6$-$C_{25}$ aryl group, an $C_6$-$C_{18}$ aryl group or an $C_6$-$C_{12}$ aryl group, such as phenyl, biphenyl, terphenyl, naphthalene, phenanthrene, chryshen, etc.

Wherein when $R^{21}$ and $R^{22}$ are a heterocyclic group, preferably a $C_2$-$C_{30}$ heterocyclic group, more preferably a $C_2$-$C_{25}$ heterocyclic group, a $C_2$-$C_{18}$ heterocyclic group, or a $C_2$-$C_{12}$ heterocyclic group, such as pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

Wherein when $R^{21}$ and $R^{22}$ are a fused ring group, preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

Wherein when $R^{21}$ and $R^{22}$ are an alkyl group, preferably a $C_1$-$C_{30}$ alkyl group, more preferably a $C_1$-$C_{25}$ alkyl group, a $C_1$-$C_{18}$ alkyl group or a $C_1$-$C_{12}$ alkyl group, such as a methyl group, ethyl group, propyl group, isopropyl group, butyl group, t-butyl group, pentyl group, etc.

Wherein when $R^{21}$ and $R^{22}$ are an alkoxyl group, preferably a $C_1$-$C_{25}$ alkoxyl group, a $C_1$-$C_{18}$ alkoxyl group or a $C_1$-$C_{12}$ alkoxyl group.

Wherein when $R^{21}$ and $R^{22}$ are an aryloxy group, preferably a $C_6$-$C_{25}$ aryloxy group, a $C_6$-$C_{18}$ aryloxy group or a $C_6$-$C_{12}$ aryloxy group.

aa and ab are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; a $C_3$-$C_{20}$ aliphatic ring; a $C_7$-$C_{20}$ arylalkyl group; a $C_8$-$C_{20}$ arylalkenyl group; a $C_7$-$C_{20}$ alkylaryl group; and -L'-N(R')(R"); also the hydrogen of these substituents may be further substituted with one or more deuterium, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Preferably, the composition for an organic electronic element may be used as a host for an emitting layer.

Formula 2 may be represented by any one of the following Formulas 2-1 to 2-3.

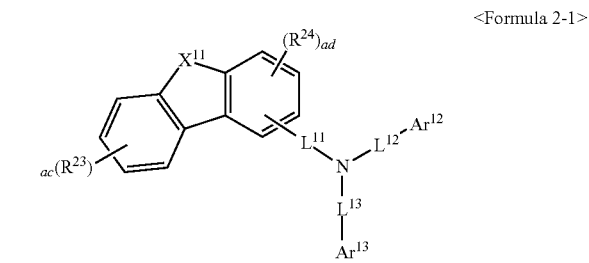

<Formula 2-1>

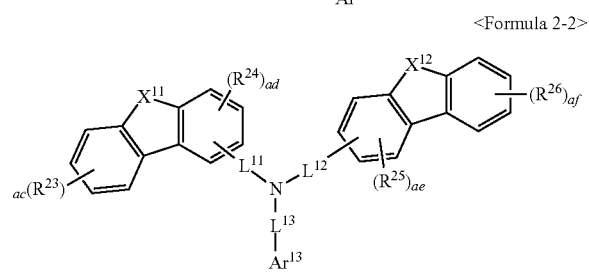

<Formula 2-2>

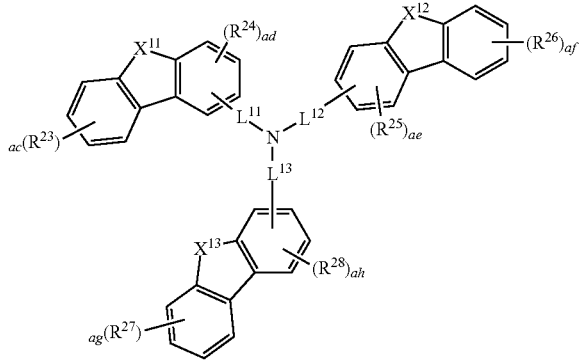

<Formula 2-3>

Wherein:
$Ar^{12}$, $Ar^{13}$, $L^{11}$, $L^{12}$ and $L^{13}$ are the same as defined in Formula 2, $X^{11}$, $X^{12}$ and $X^{13}$ are the same as the definition of Z in Formula 3, $R^{23}$, $R^{24}$, $R^{25}$, $R^{26}$, $R^{27}$ and $R^{28}$ are each the same or different, and each independently selected from the group consisting of a hydrogen; deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ aliphatic group; $C_7$-$C_{20}$ arylalkyl group; $C_8$-$C_{20}$ arylalkenyl group; and a $C_7$-$C_{20}$ alkylaryl group; or an adjacent plurality of $R^{23}$ or plurality of $R^{24}$ or plurality of $R^{25}$ or plurality of $R^{26}$ or plurality of $R^{27}$ or plurality of $R^{28}$ may be bonded to each other to form a ring, ac, af and ag are independently integers from 0 to 4, and ad, ae and ah are independently integers from 0 to 3.

Formula 3 may be represented by any one of the following Formulas 3-1 to 3-6.

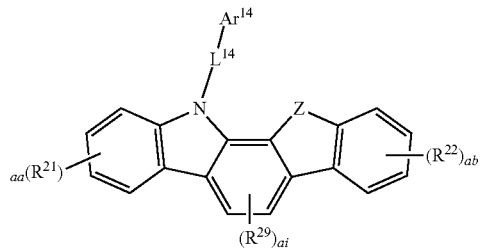

<Formula 3-1>

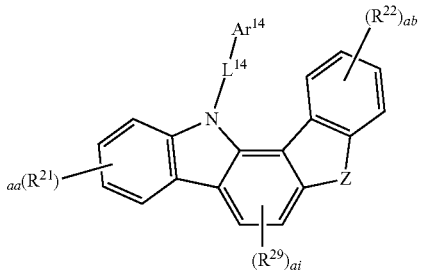

<Formula 3-2>

<Formula 3-3>

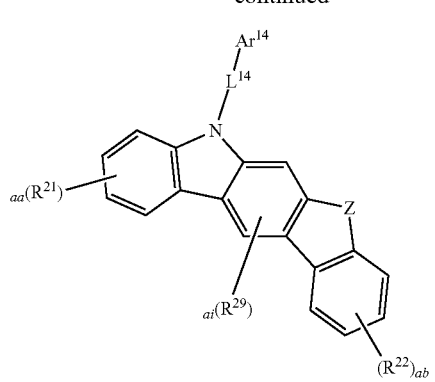

<Formula 3-4>

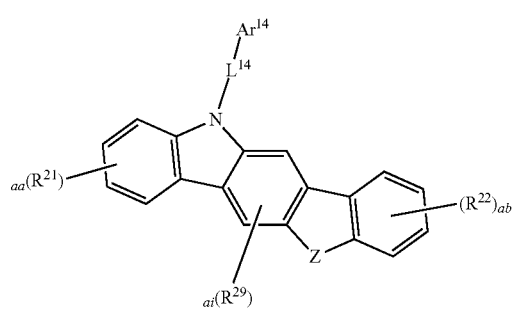

<Formula 3-5>

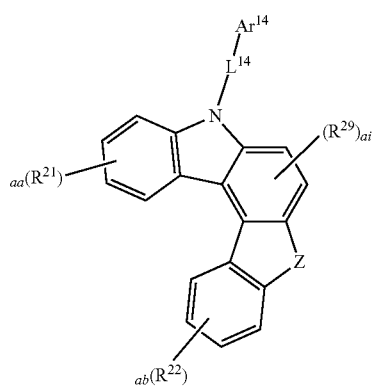

<Formula 3-6>

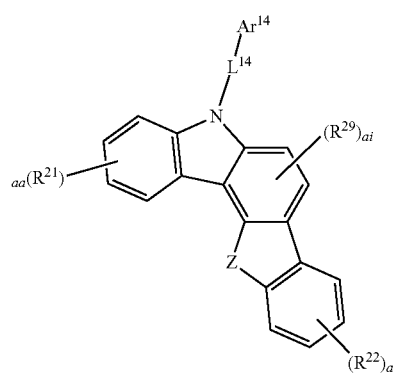

Wherein:
Z, $Ar^{14}$, $L^{14}$, $R^{21}$, $R^{22}$, aa and ab are the same as defined in Formula 3,
$R^{29}$ is the same as the definition of $R^{21}$, or an adjacent plurality of $R^{29}$ may be bonded to each other to form a ring,
ai is an integer of 0 to 2.

Formula 3 may be represented by any one of the following Formulas 3-7 to 3-9.

<Formula 3-7>

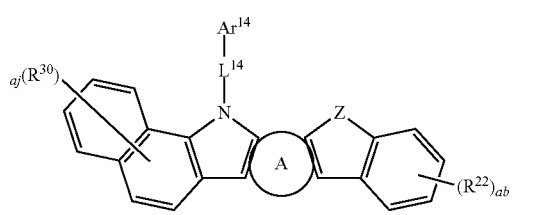

<Formula 3-8>

<Formula 3-9>

Wherein:
Z, Ring A, $Ar^{14}$, $L^{14}$, $R^{22}$ and ab are the same as defined in Formula 3,
$R^{30}$ is the same as the definition of $R^{21}$, or an adjacent plurality of $R^{30}$ may be bonded to each other to form a ring,
aj is an integer of 0 to 6.

Formula 3 may be represented by any one of the following Formulas 3-10 to 3-12.

<Formula 3-10>

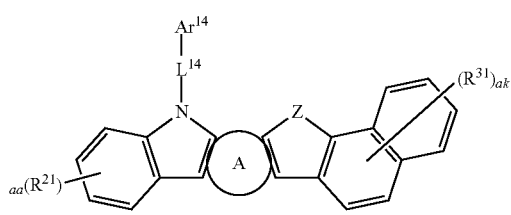

<Formula 3-11>

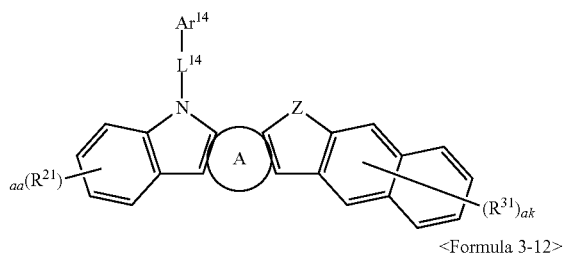

<Formula 3-12>

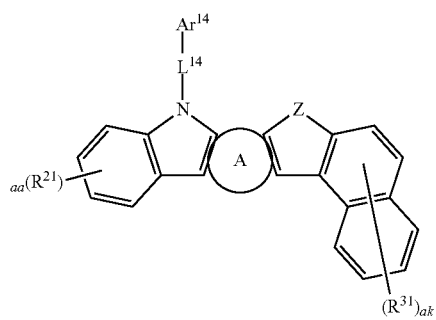

Wherein:

Z, Ring A, Ar$^{14}$, L$^{14}$, R$^{22}$ and ab are the same as defined in Formula 3, R$^{31}$ is the same as the definition of R$^{21}$, or an adjacent plurality of R$^{31}$ may be bonded to each other to form a ring, ak is an integer of 0 to 6.

Formula 3 may be represented by any one of the following Formulas 3-13 to 3-18.

<Formula 3-13>

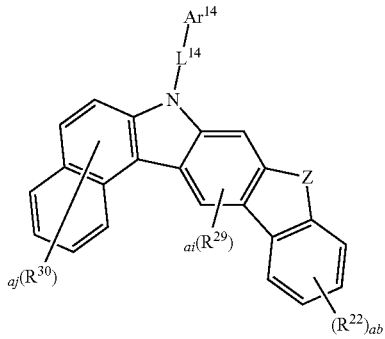

<Formula 3-14>

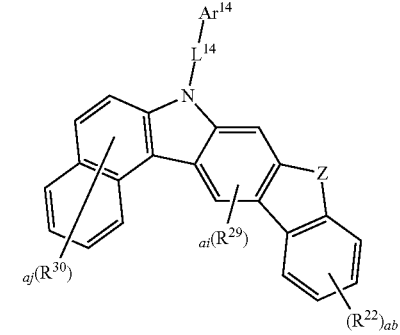

<Formula 3-15>

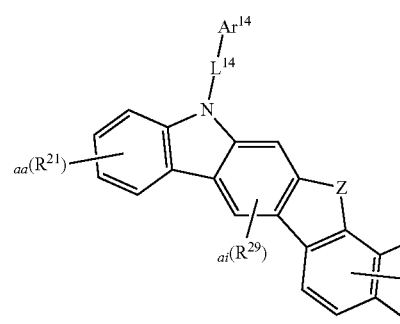

<Formula 3-16>


<Formula 3-17>

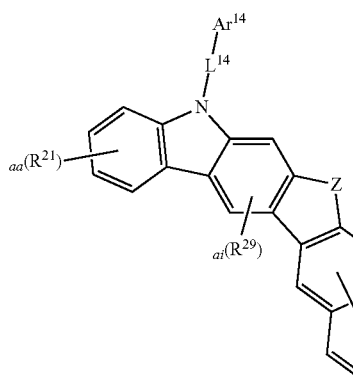

<Formula 3-18>

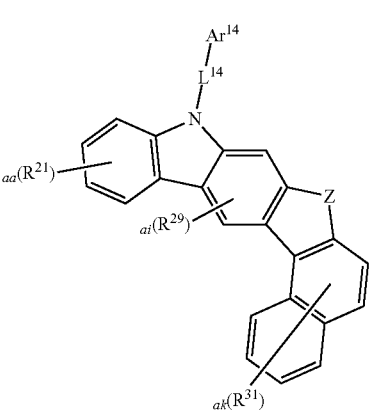

Wherein:

Z, Ar$^{14}$, L$^{14}$, R$^{21}$, R$^{22}$, aa and ab are the same as defined in Formula 3, $R^{29}$, $R^{30}$ and $R^{31}$ are the same as the definition of $R^{21}$, or an adjacent plurality of $R^{30}$ or an adjacent plurality of $R^{31}$ may be bonded to each other to form a ring, ai is an integer from 0 to 2, and aj and ak are integers from 0 to 6, independently of each other.

Formula 3 may be represented by Formula 3-19.

<Formula 5-19>

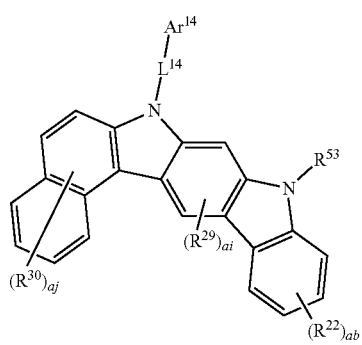

Wherein:

$Ar^{14}$, $L^{14}$, $R^{22}$, $R^{53}$ and ab are the same as defined in Formula 3, $R^{29}$ and $R^{30}$ are the same as the definition of $R^{21}$, or an adjacent plurality of $R^{30}$ may be bonded to each other to form a ring, ai is an integer of 0 to 2, and aj is an integer of 0 to 6.

Specifically, the compound represented by Formula 2 may be a compound represented by any one of the compounds N-1 to N-128, but is not limited thereto.

N-1

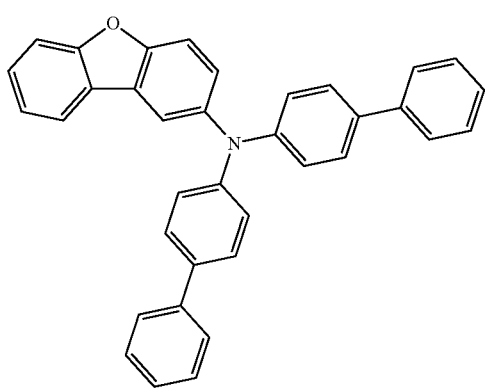

-continued

N-2

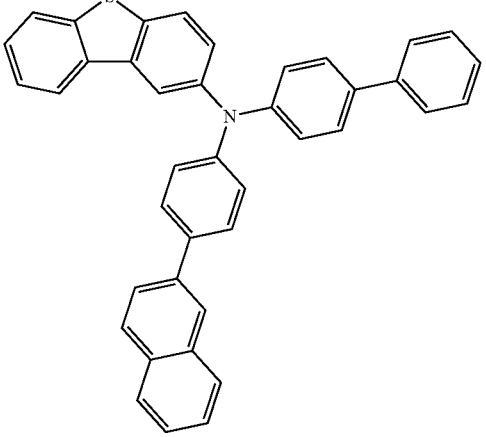

N-3

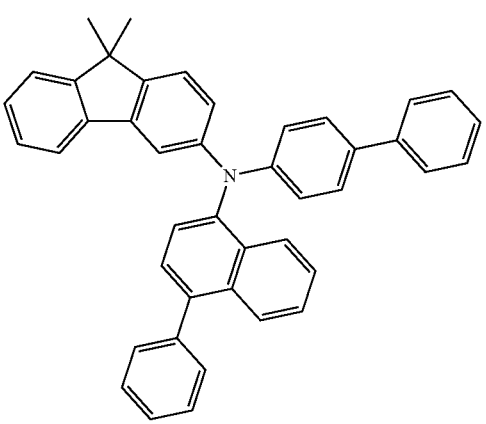

N-4

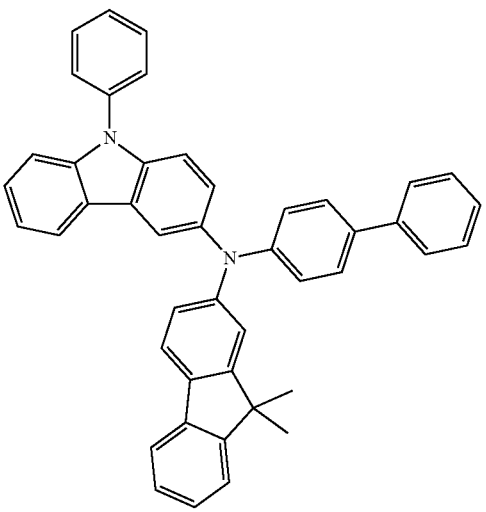

N-5
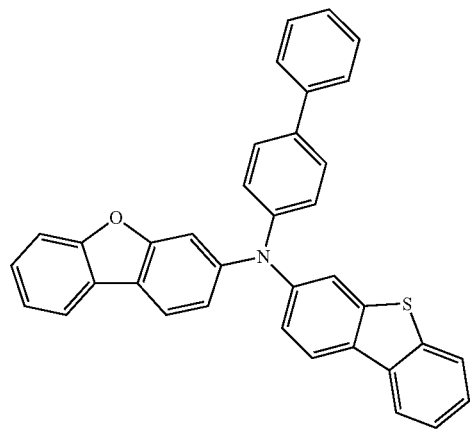
N-6
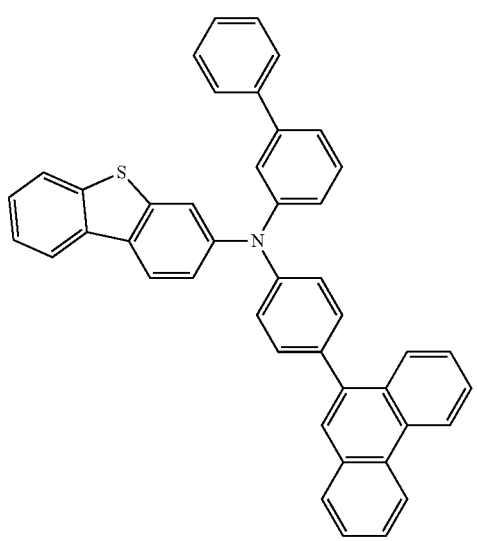
N-7
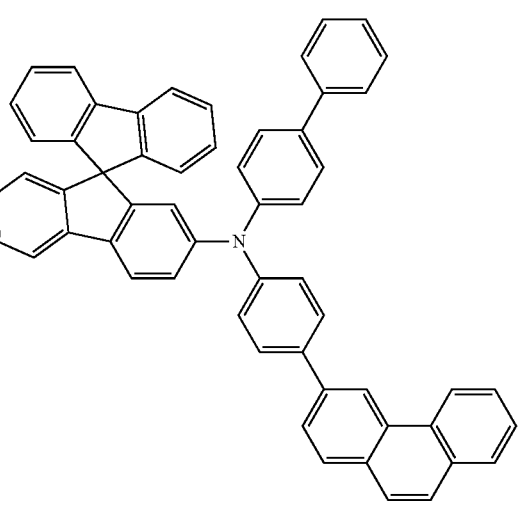
N-8
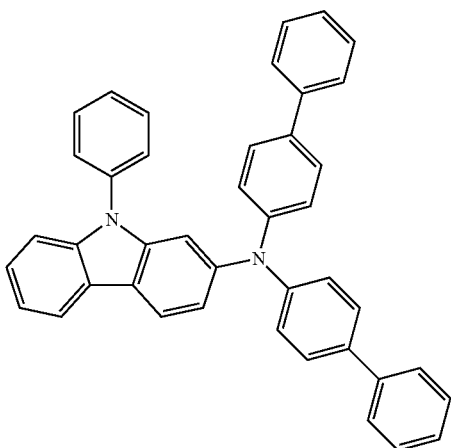
N-9
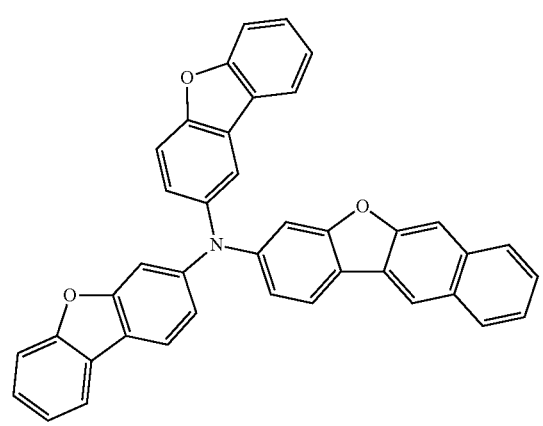
N-10
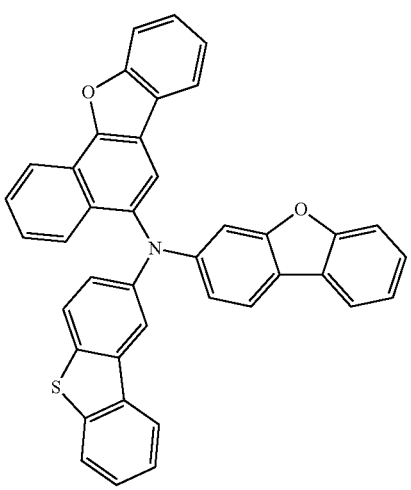

N-11
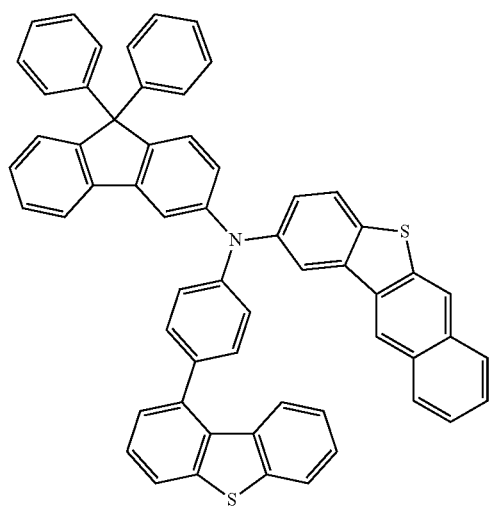
N-12
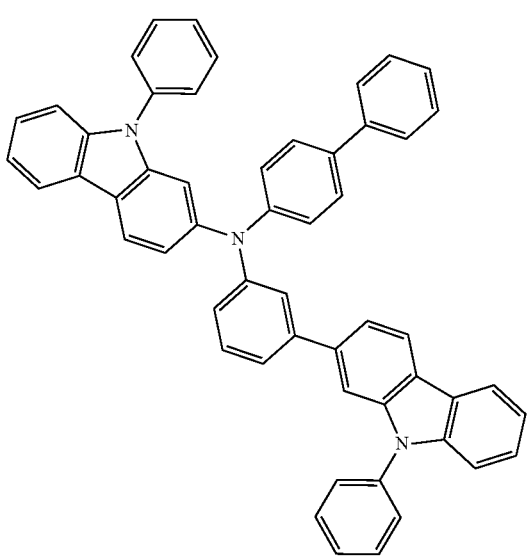
N-13
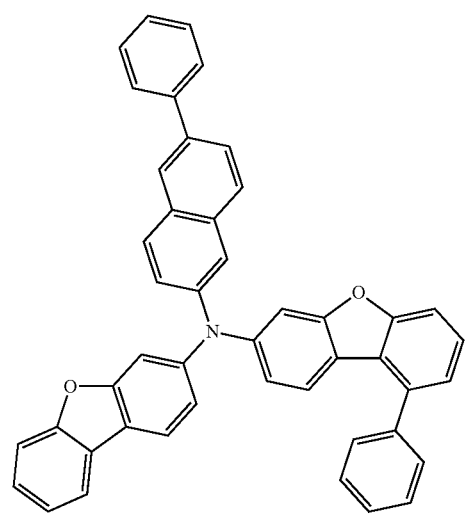
N-14
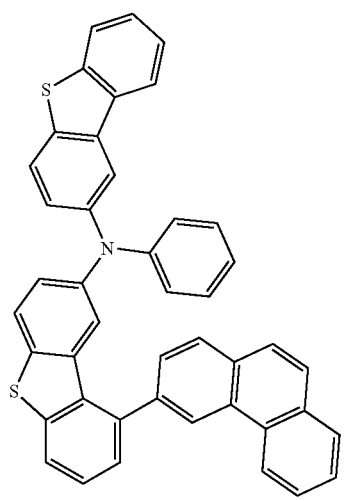
N-15
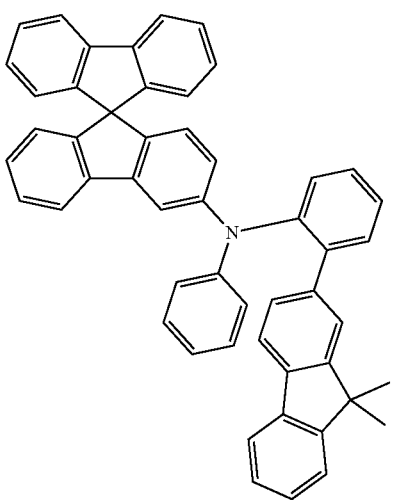
N-16
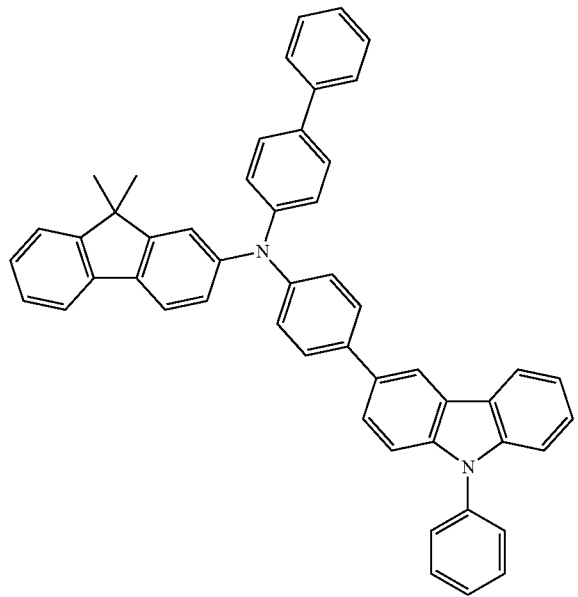

N-17
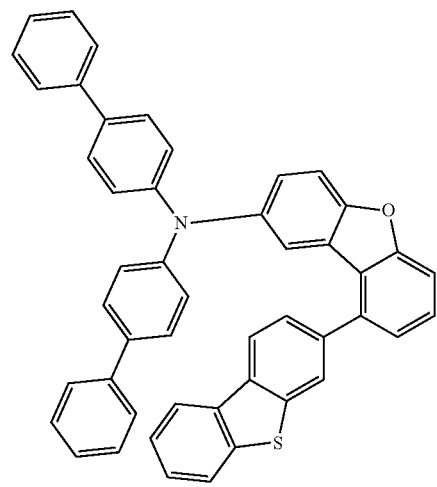
N-18
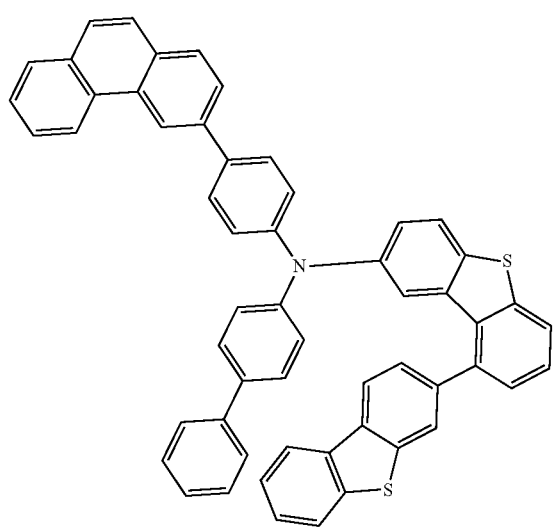
N-19
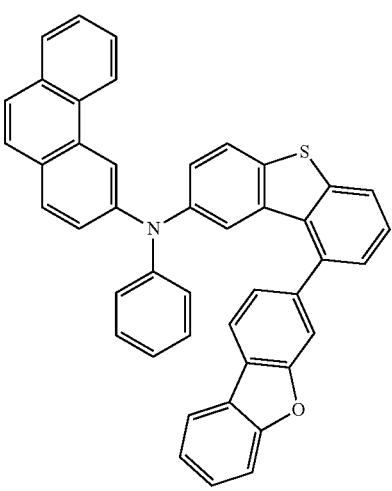
N-20
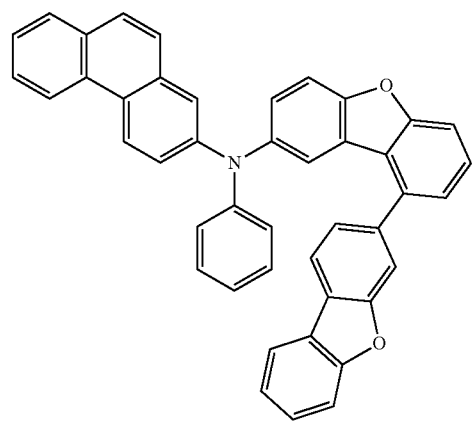
N-21
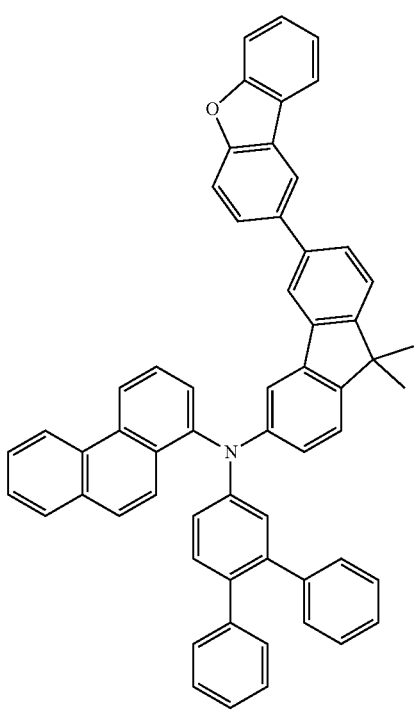
N-22
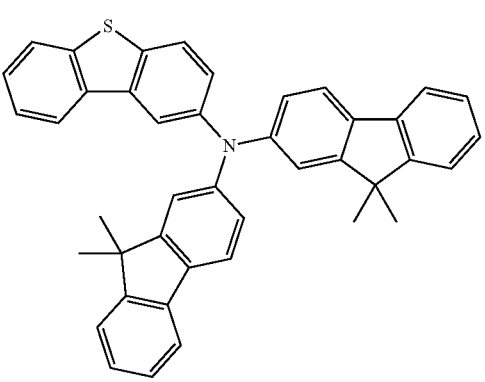

N-23
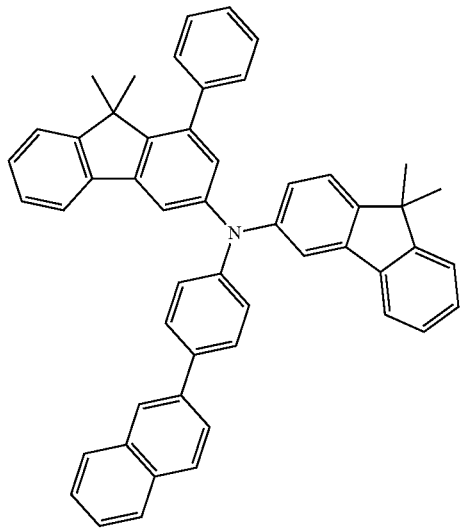
N-24
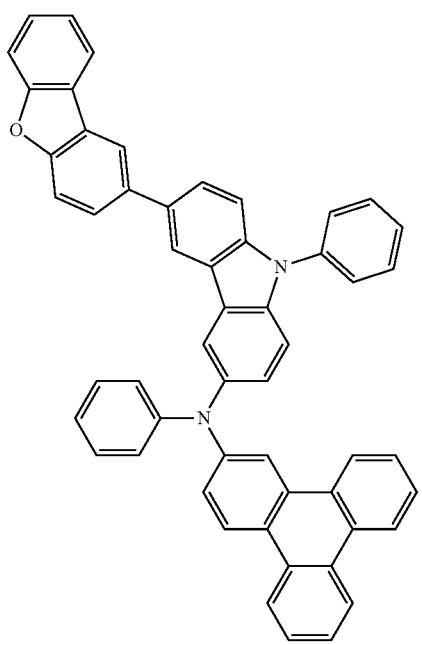
N-25
N-26
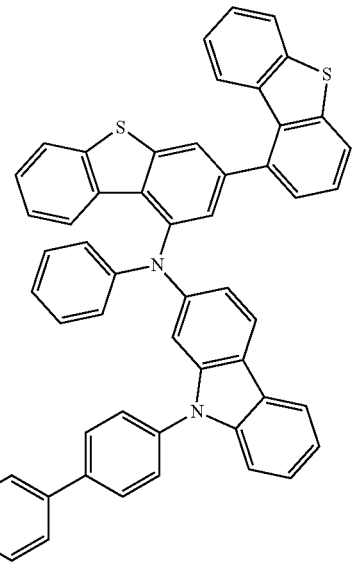
N-27
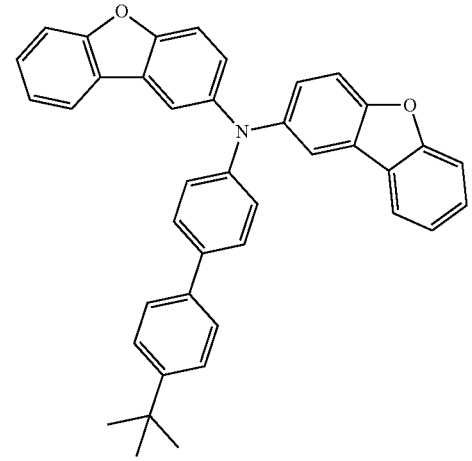
N-28
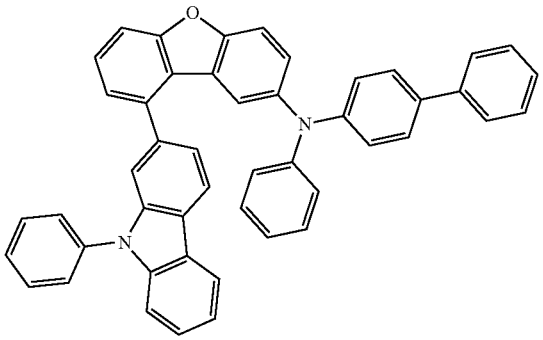

N-29
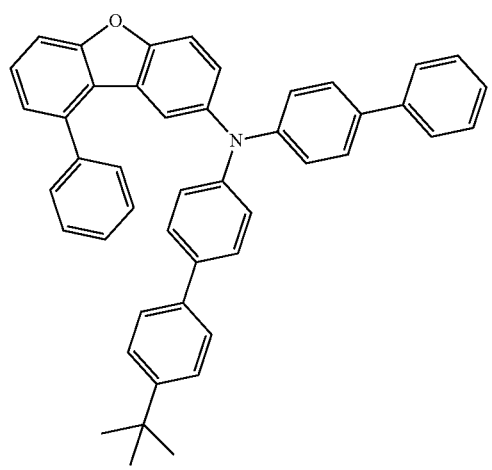
N-30
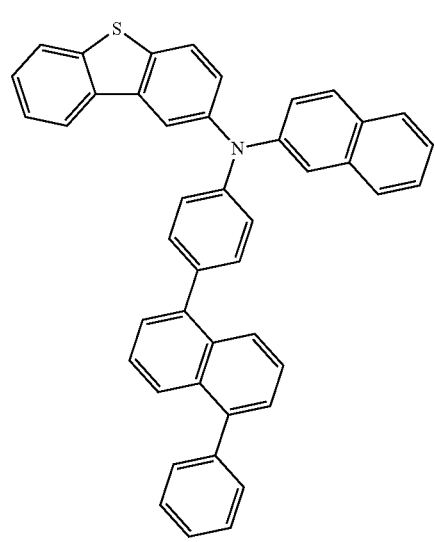
N-31
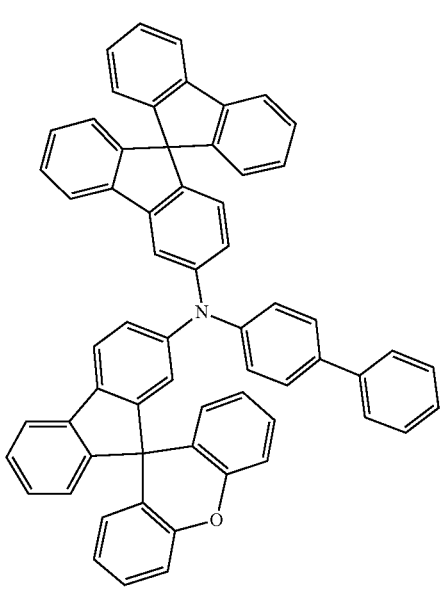
N-32
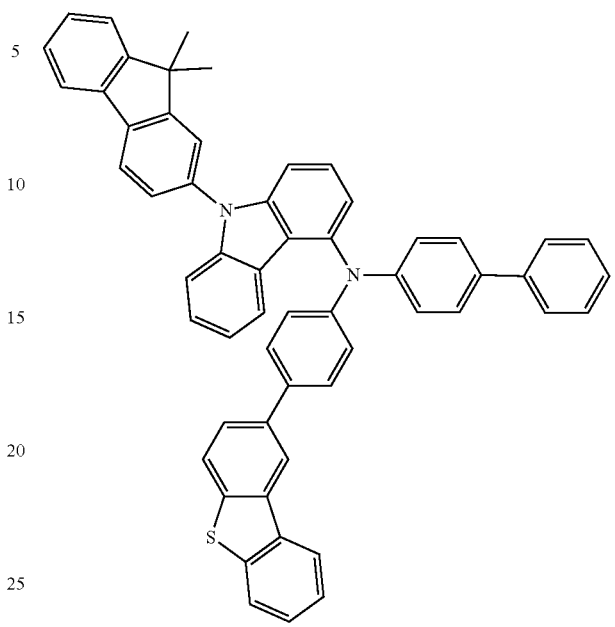
N-33
N-34

-continued
N-35
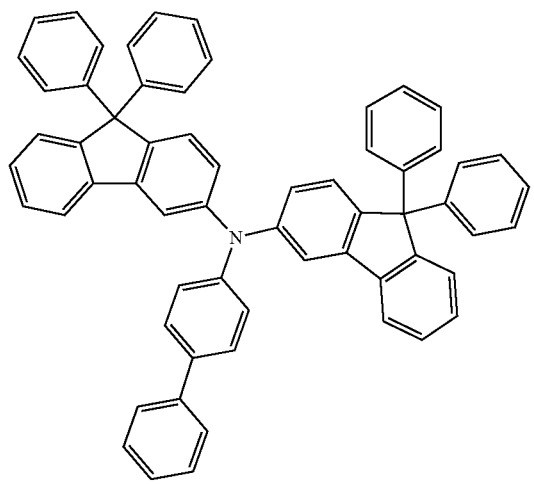
N-36
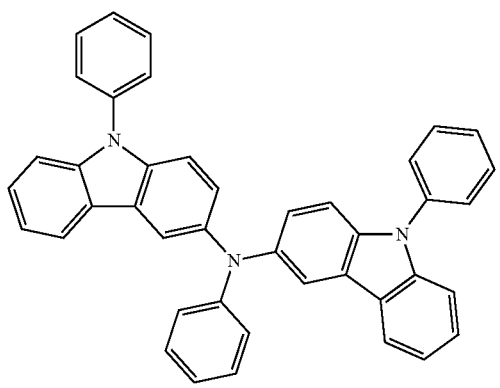
N-37
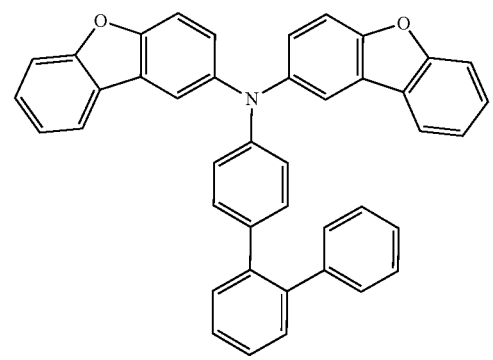
N-38
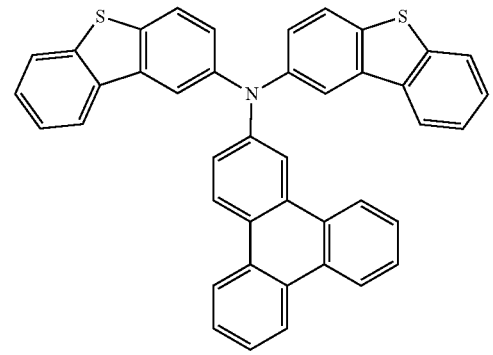
-continued
N-39
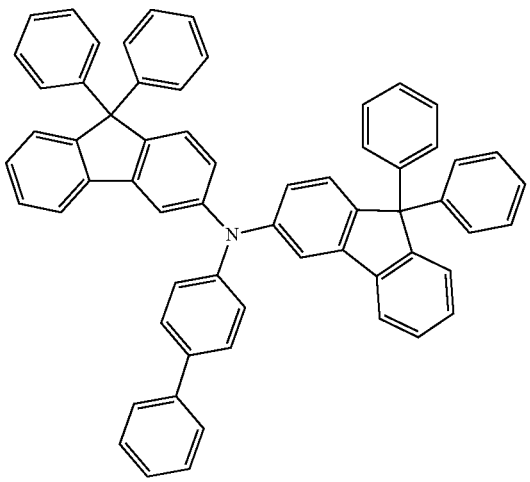
N-40
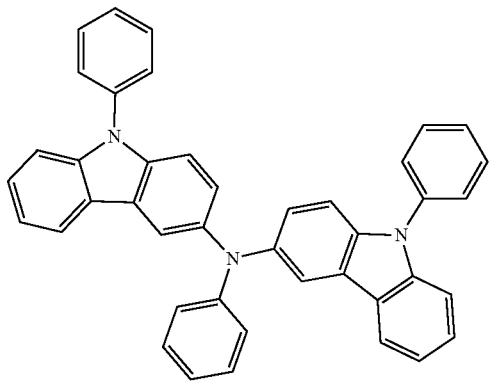
N-41
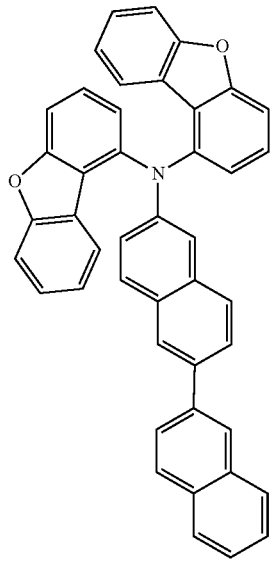

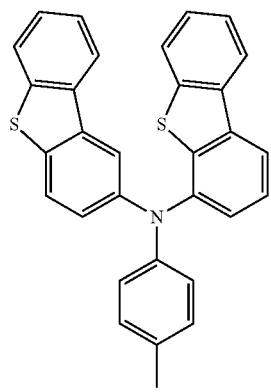
N-42
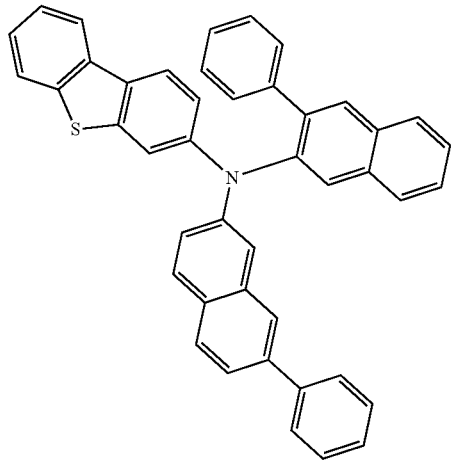
N-45
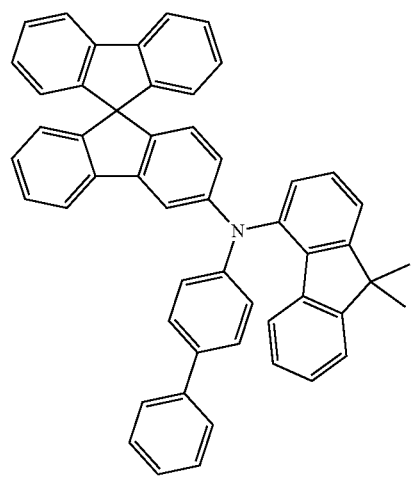
N-43
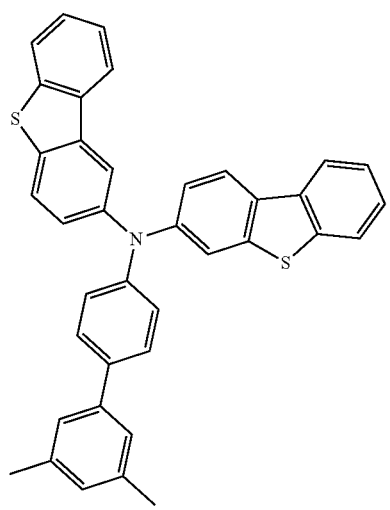
N-46
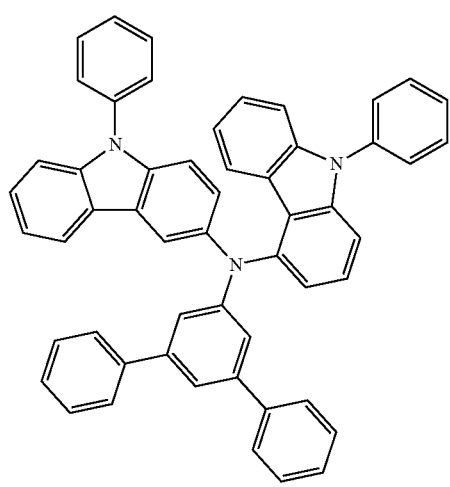
N-44
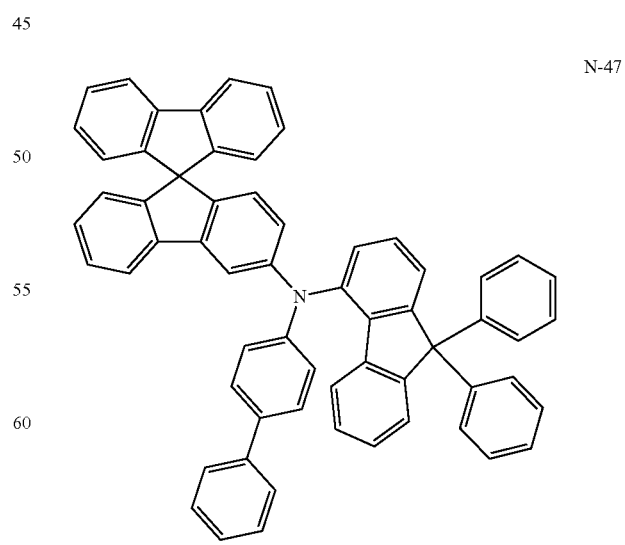
N-47

N-48
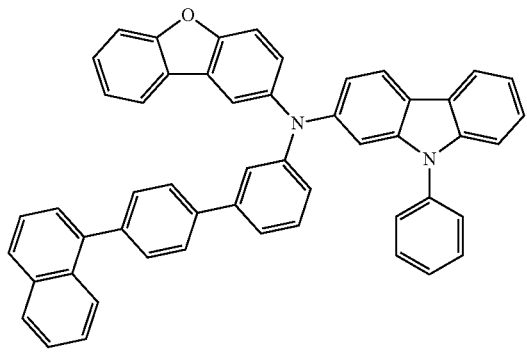
N-49
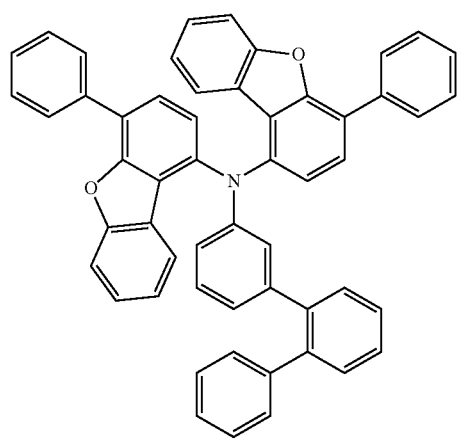
N-50
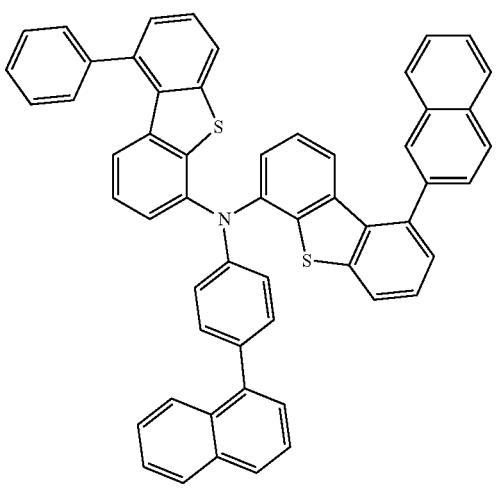
N-51
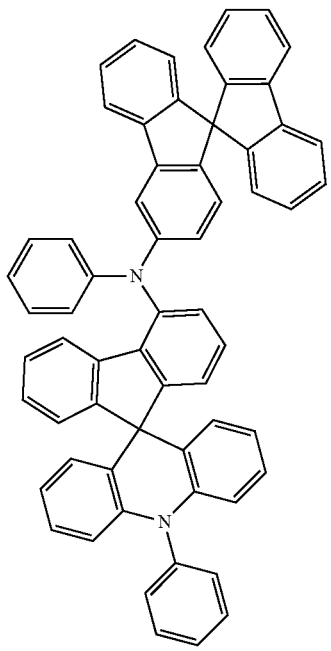
N-52
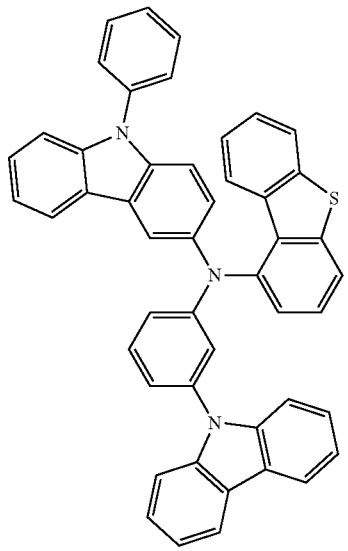
N-53
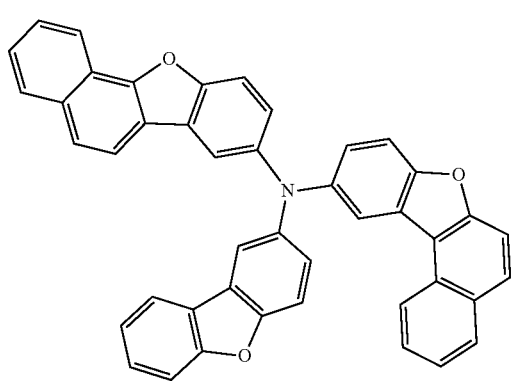

N-54
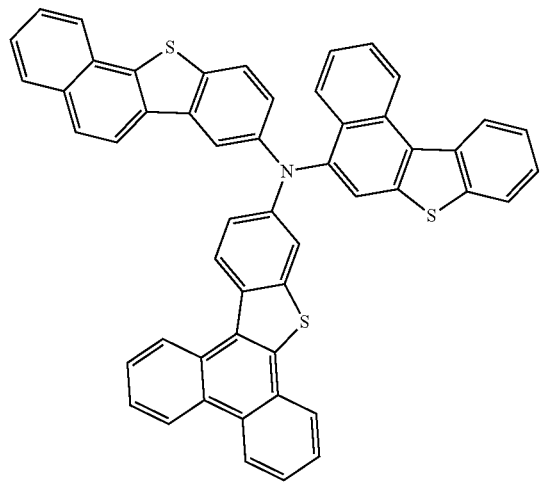
N-55
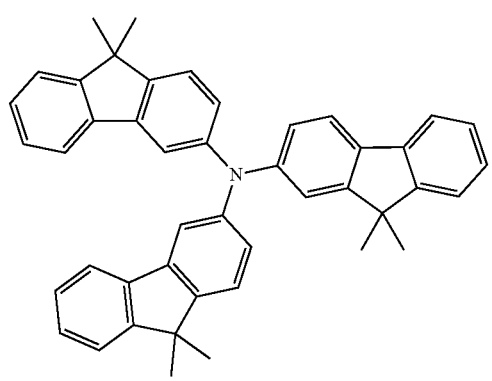
N-56
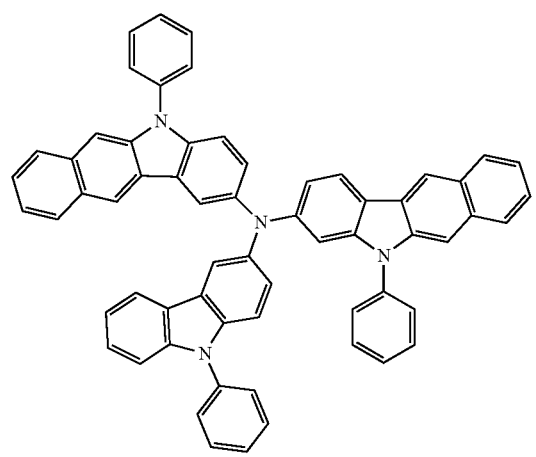
N-57
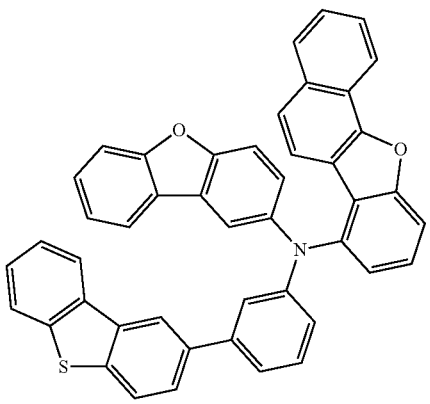
N-58
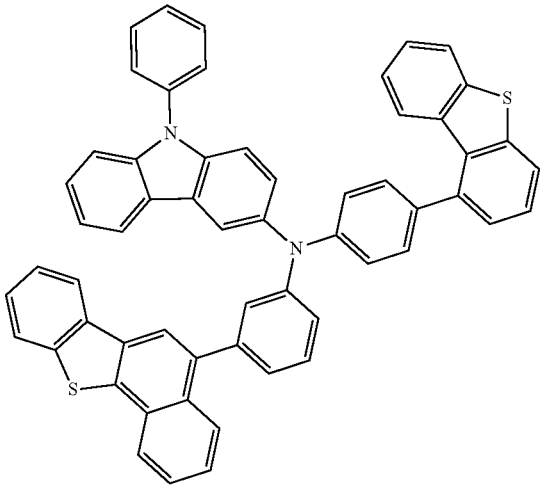
N-59
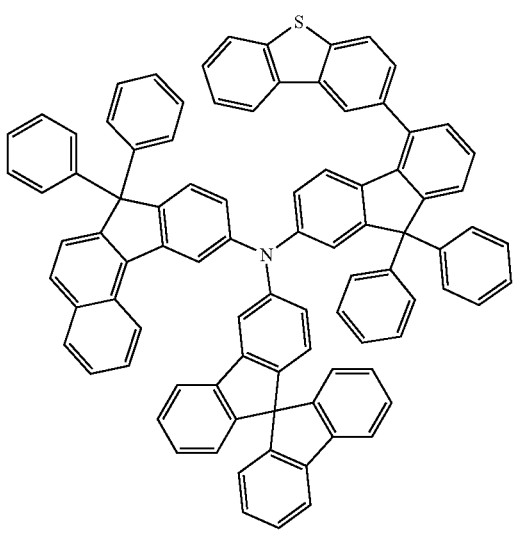

-continued
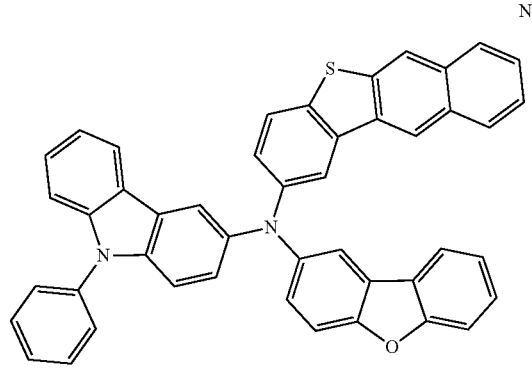
N-60
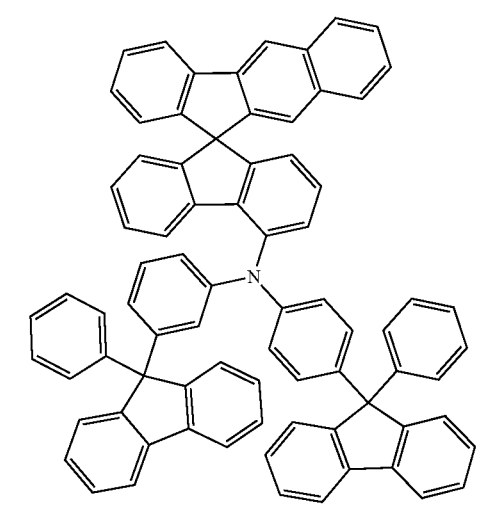
N-63
N-61
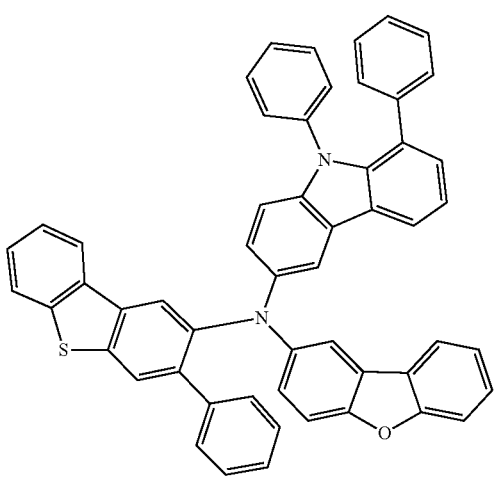
N-64
N-65
N-62
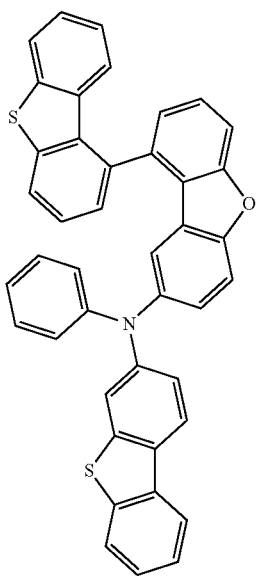

N-66
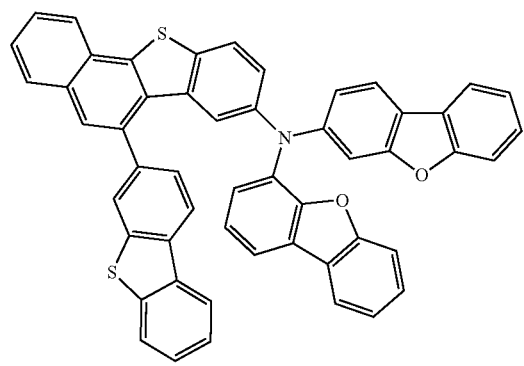
N-67
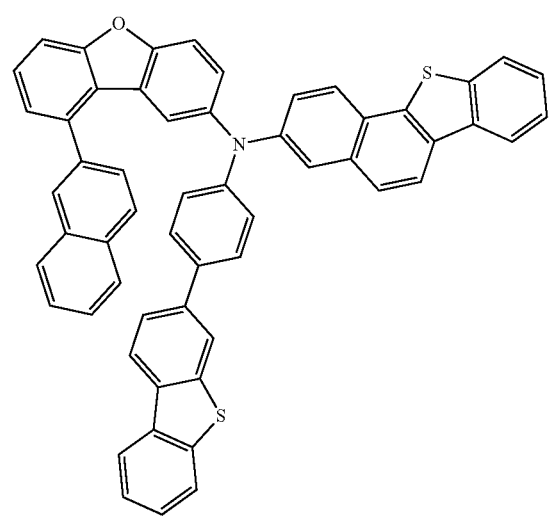
N-68
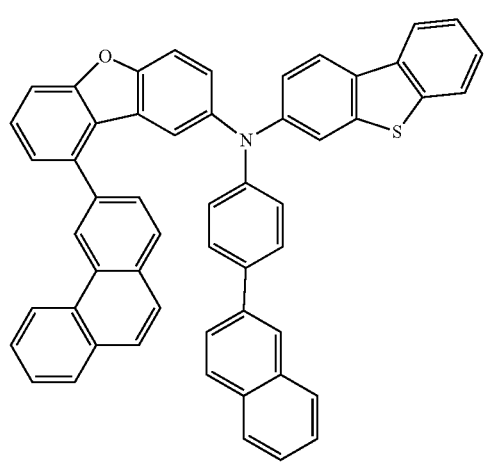
N-69
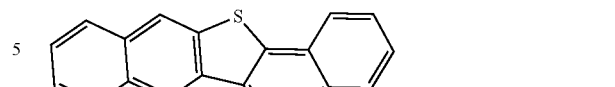
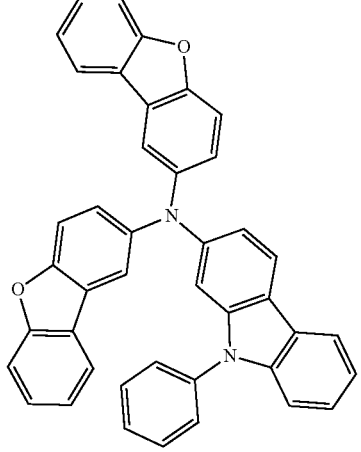
N-70
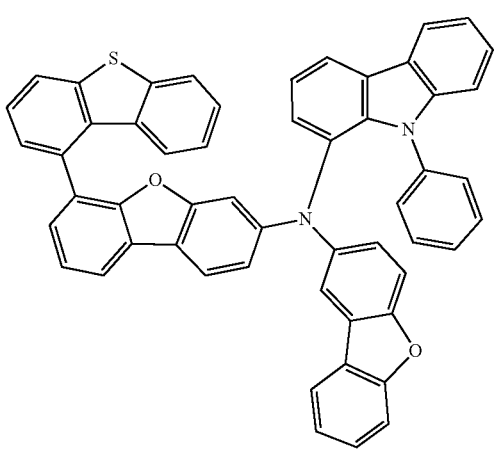
N-71
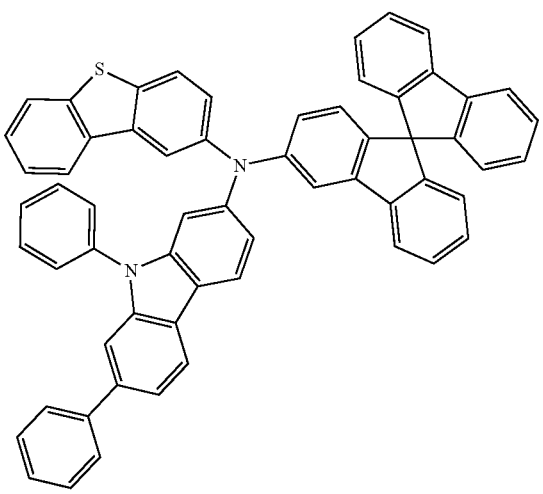

N-72
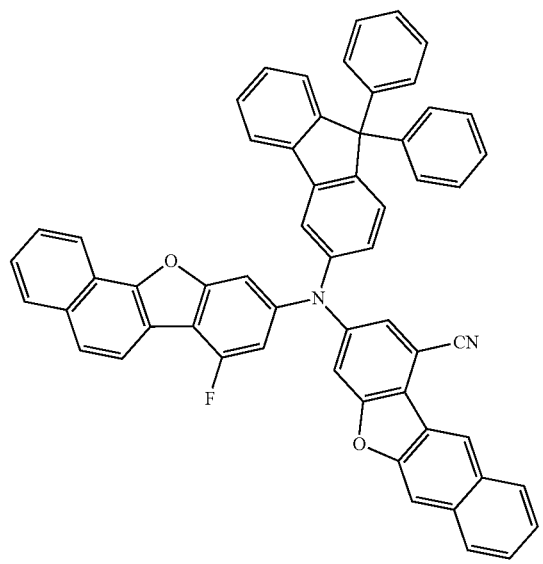
N-73
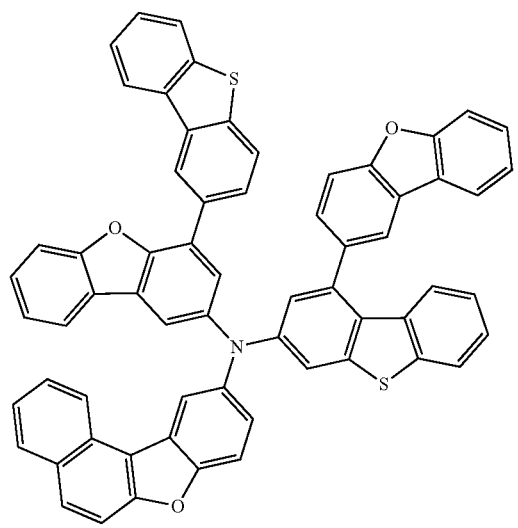
N-74
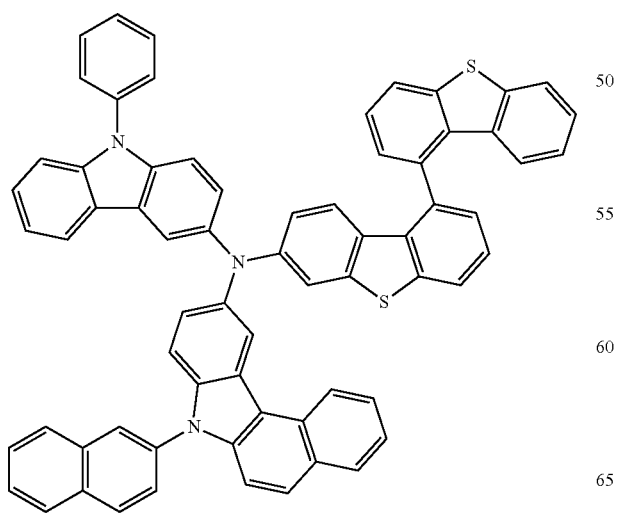
N-75
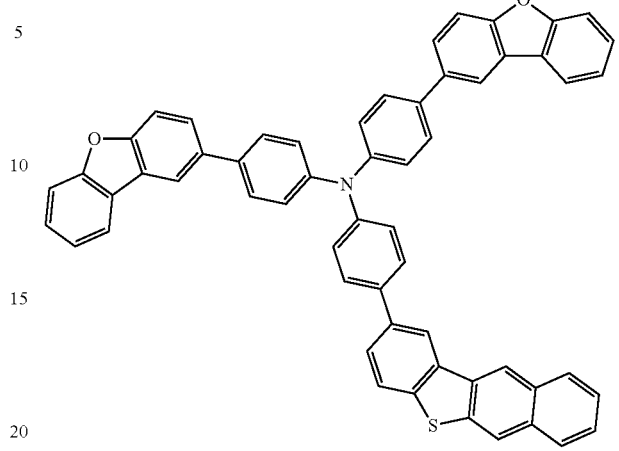
N-76
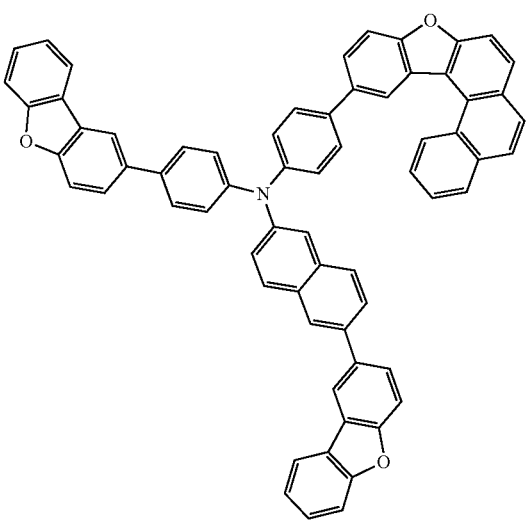
N-77
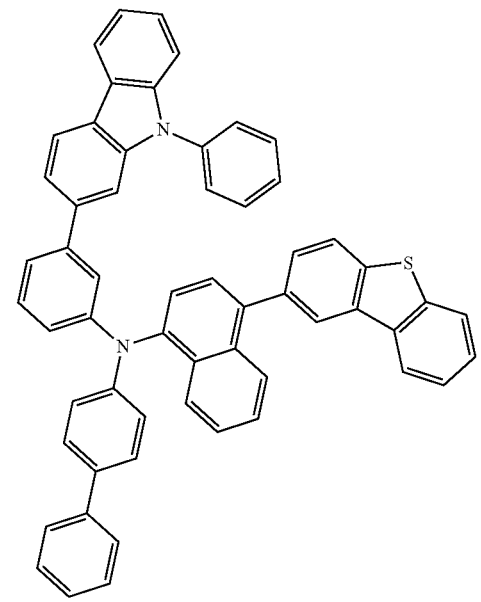

N-78
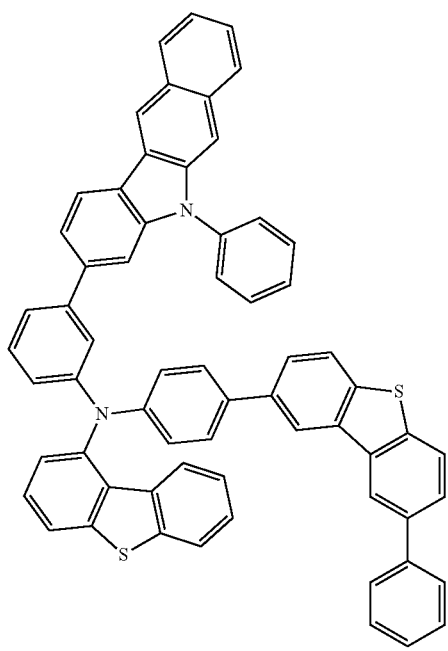
N-80
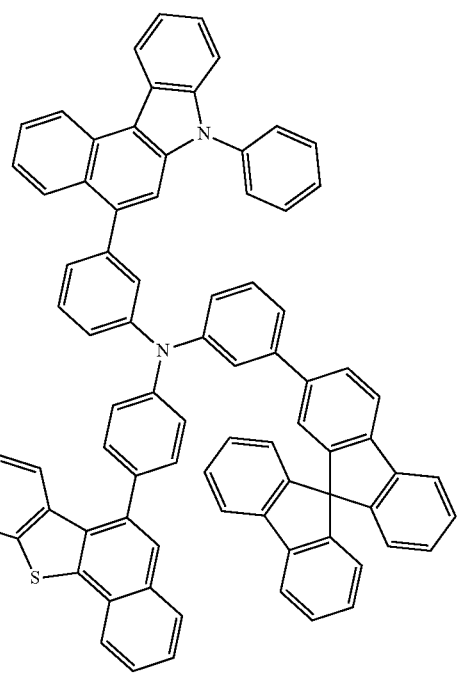
N-79
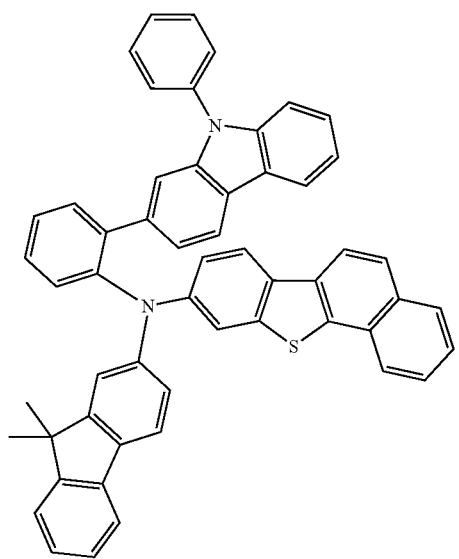
N-81
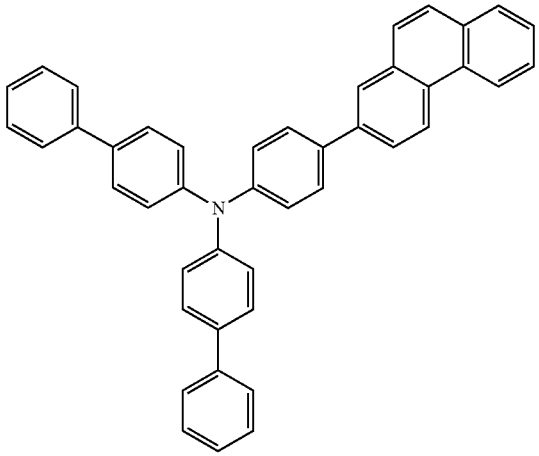

N-82
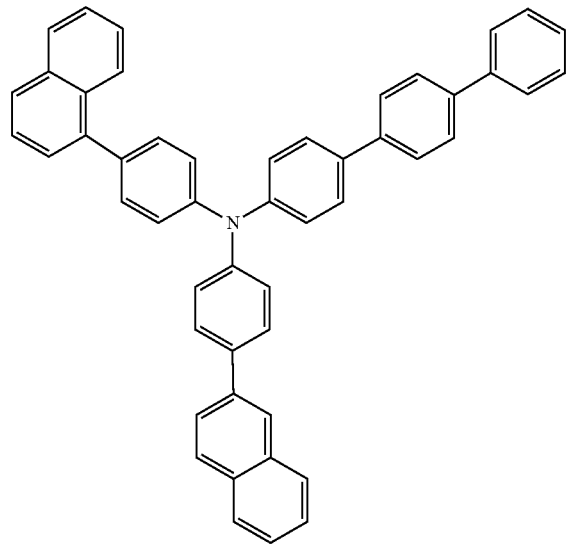
N-83
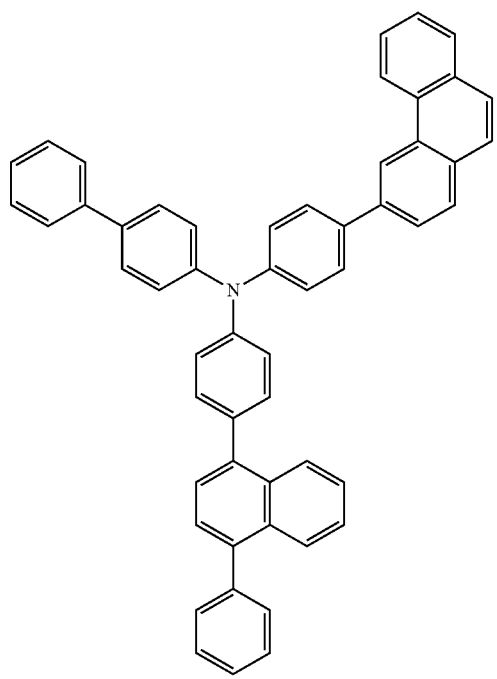
N-84
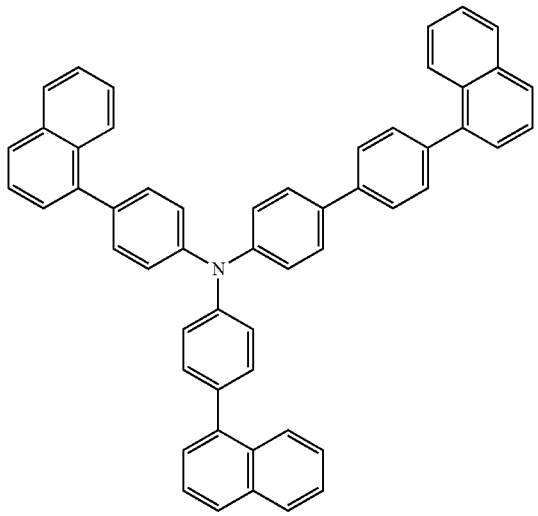
N-85
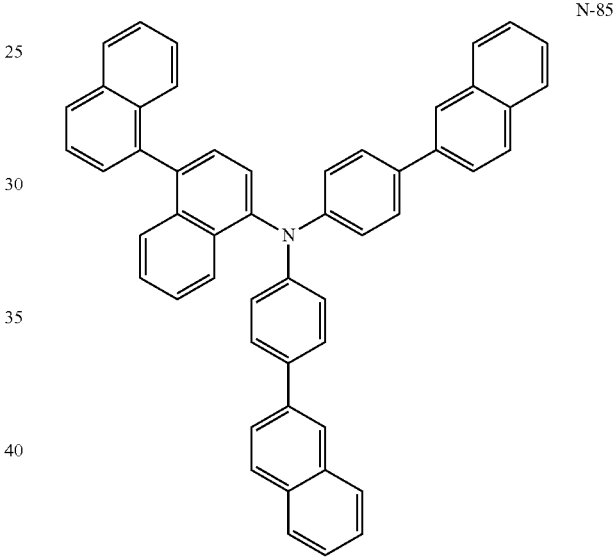
N-86
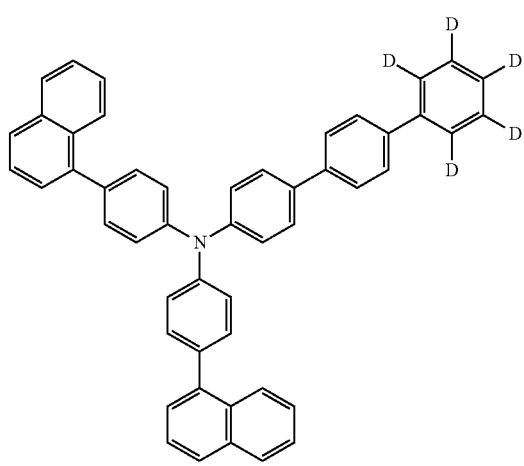

N-87
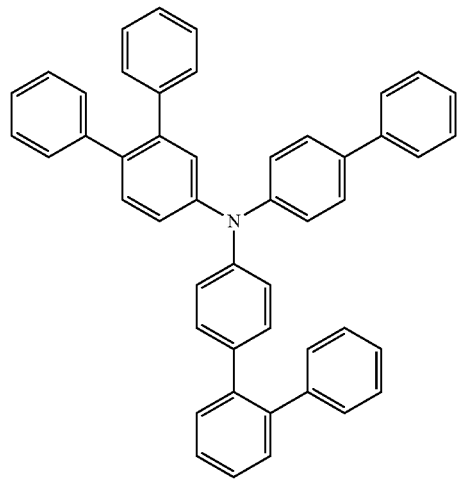
N-88
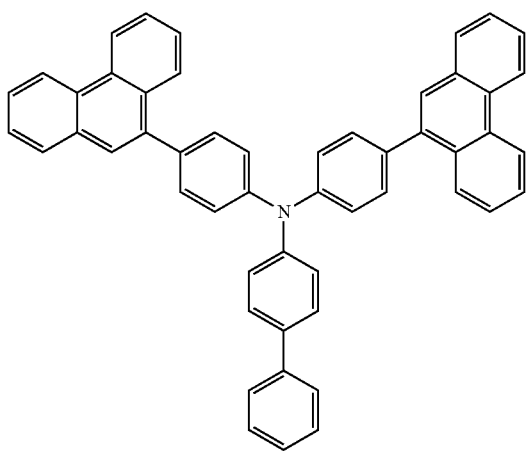
N-89
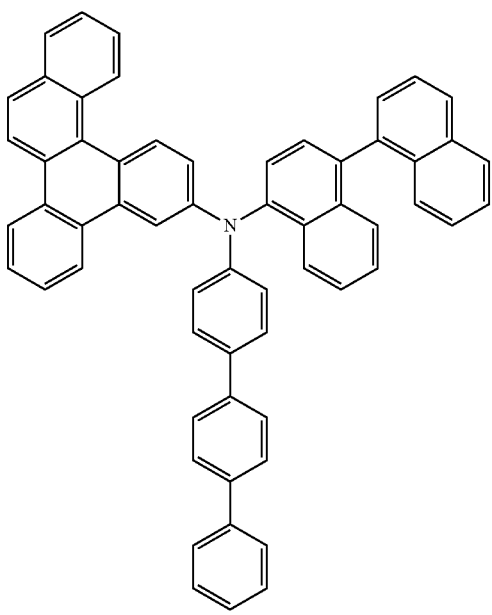
N-90
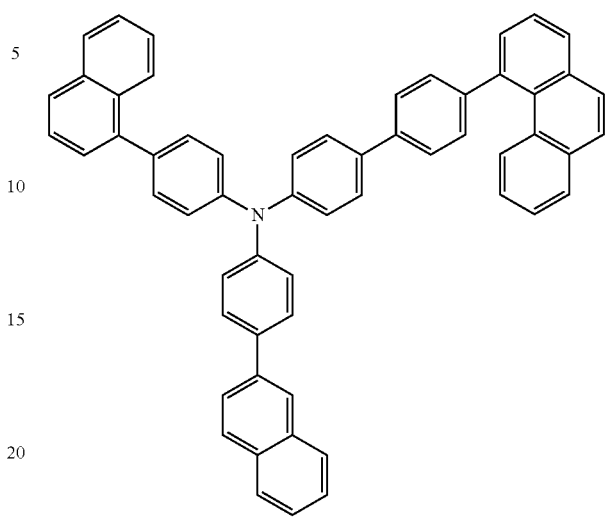
N-91
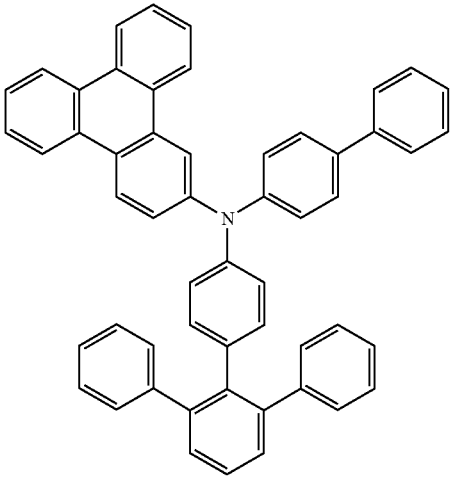
N-92
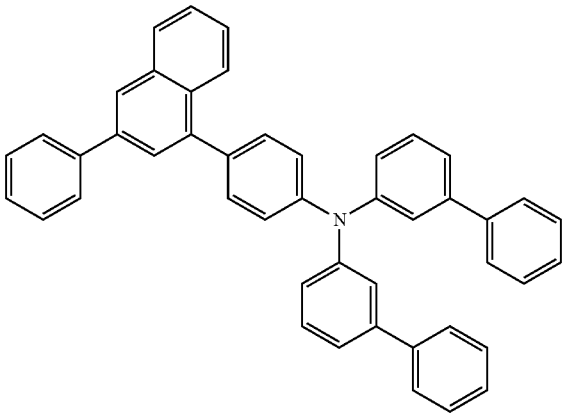

-continued
N-93
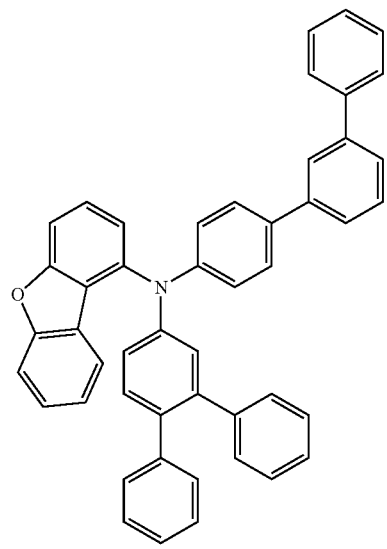
N-94
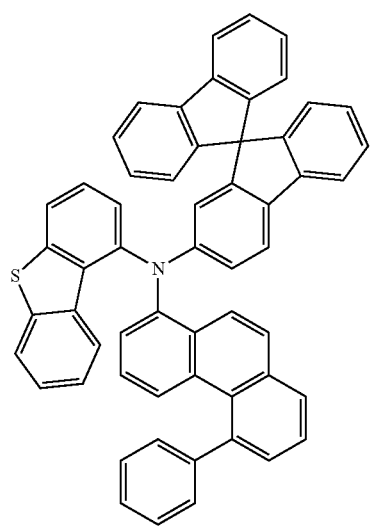
N-95
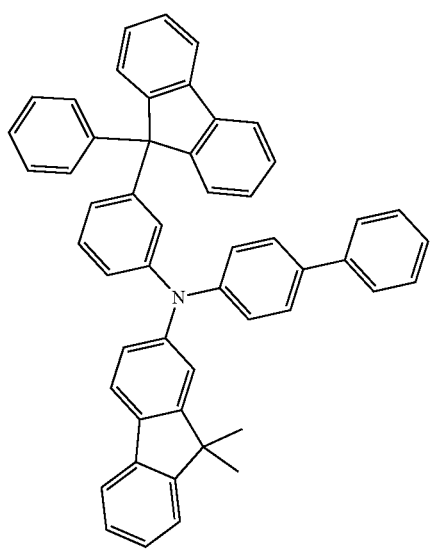
-continued
N-96
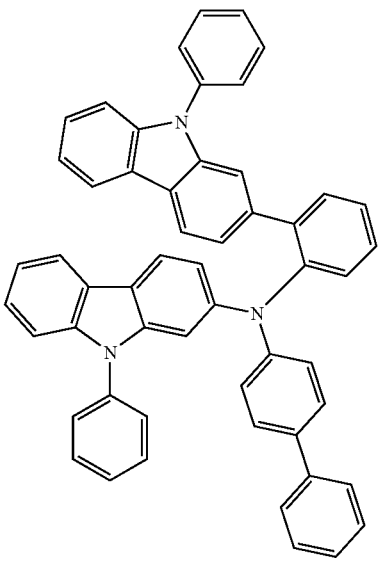
N-97
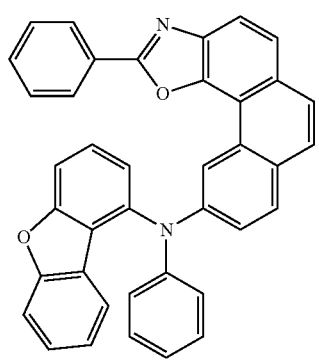
N-98
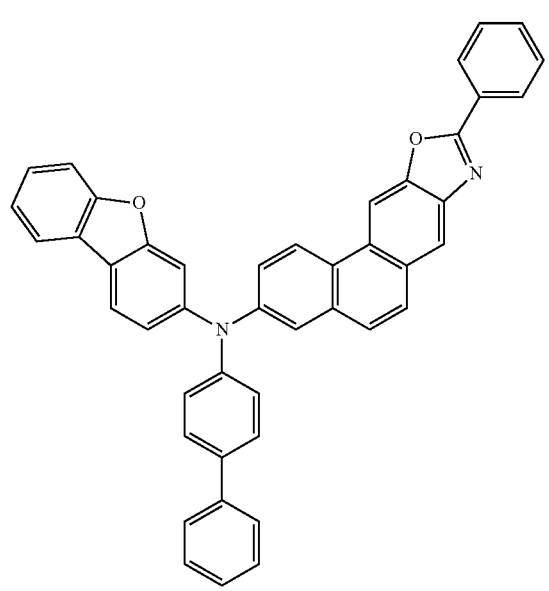

-continued
N-99
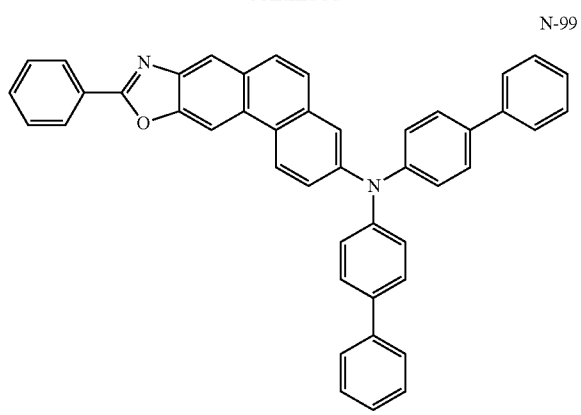
N-100
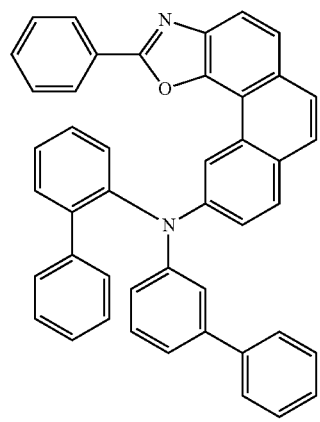
N-101
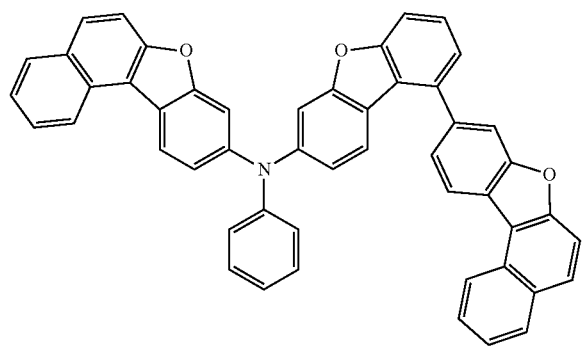
N-102
N-103
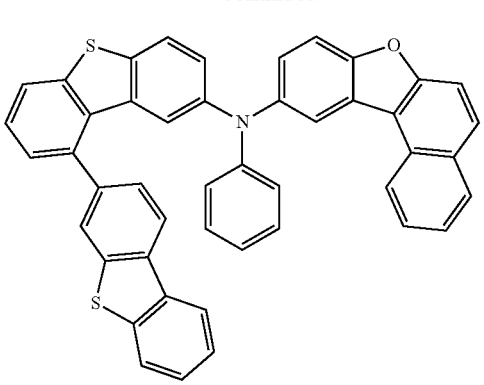
N-104
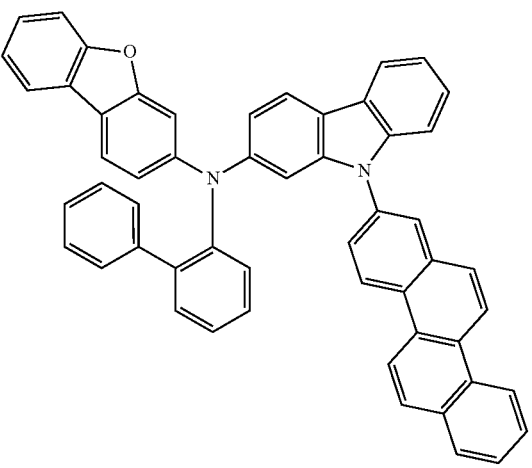
N-105
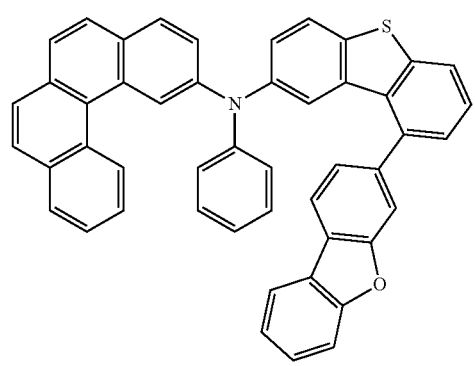

-continued
N-106
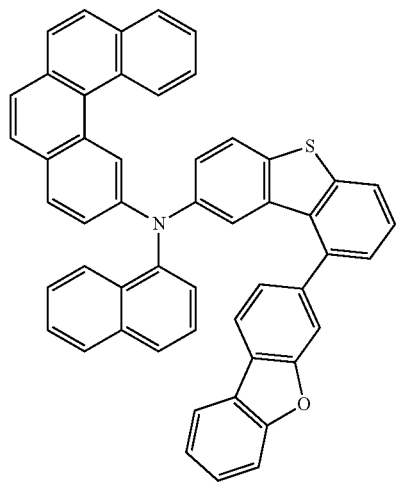
N-110
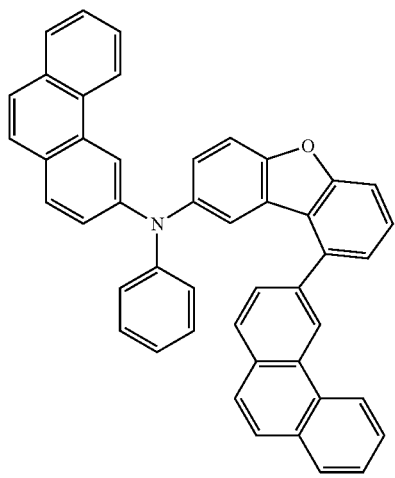
N-107
N-108
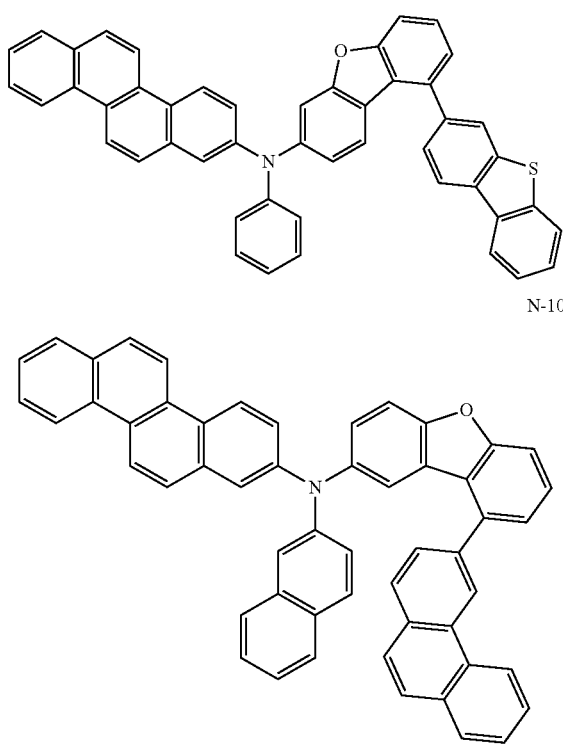
N-111
N-109
N-112
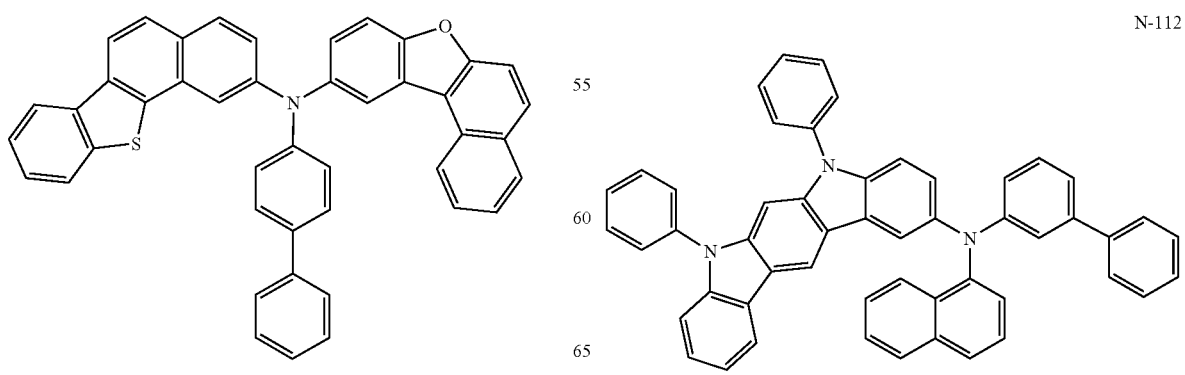

N-113
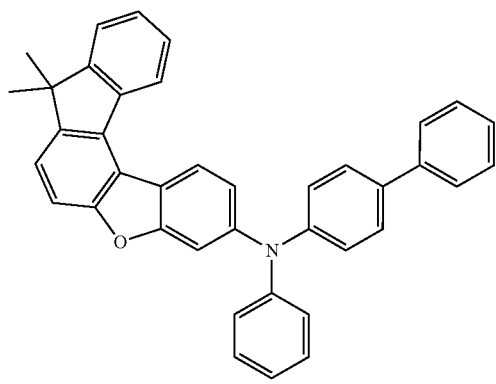
N-114
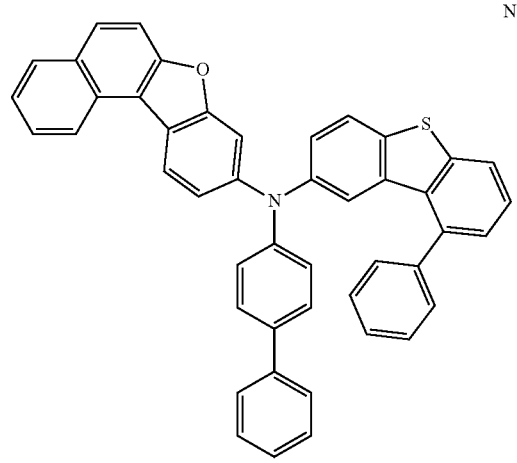
N-115
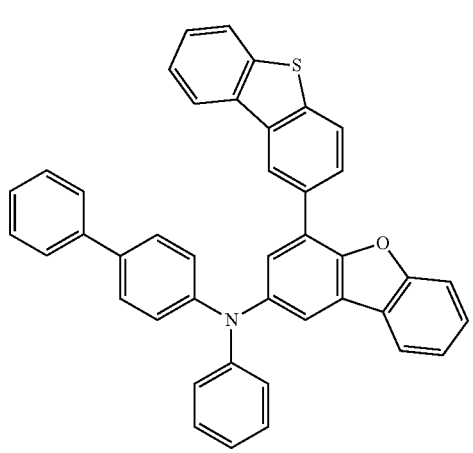
N-116
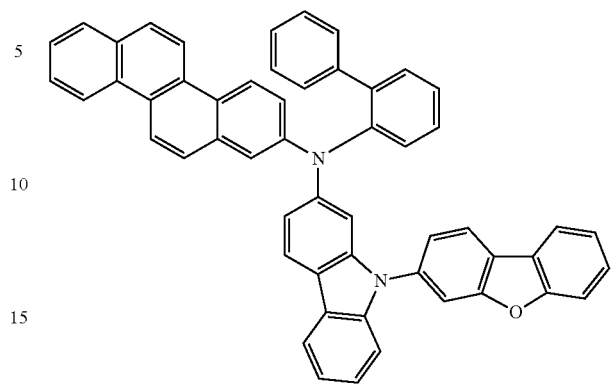
N-117
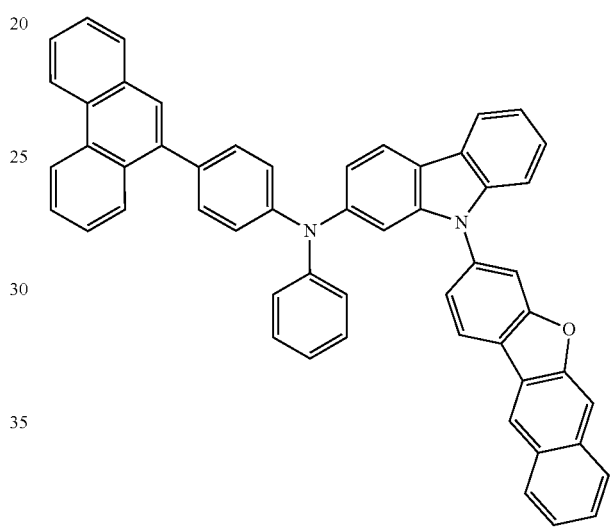
N-118
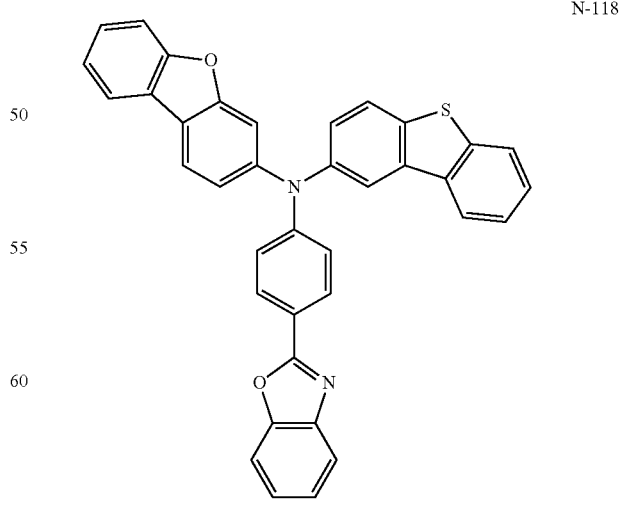

N-119
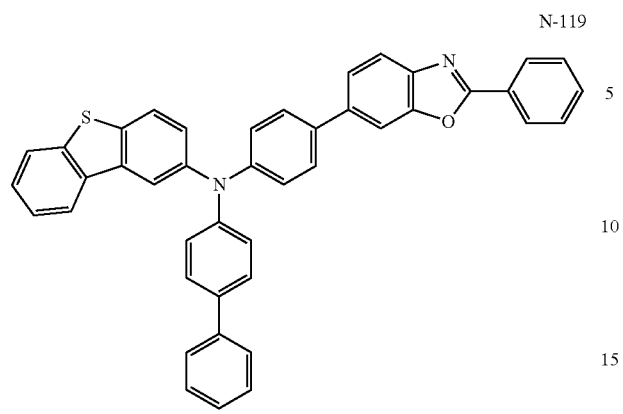
N-120
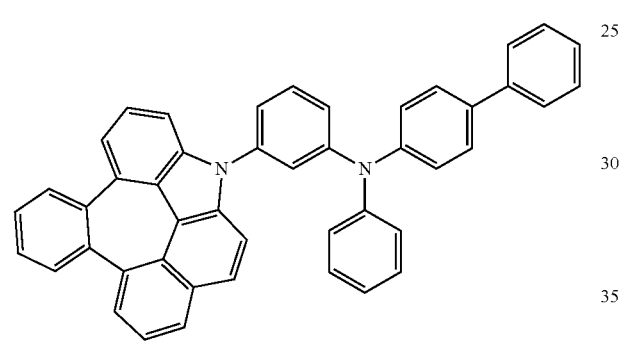
N-121
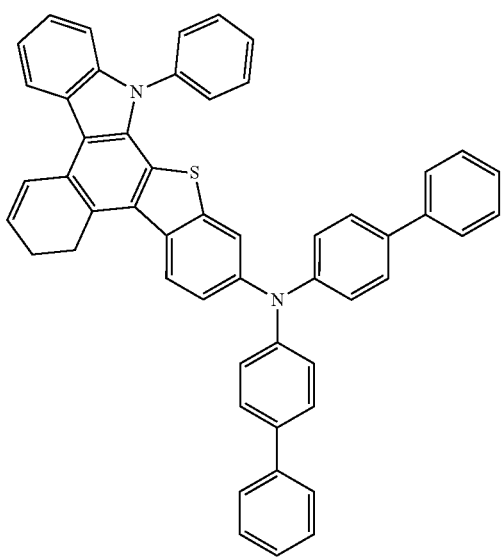
N-122
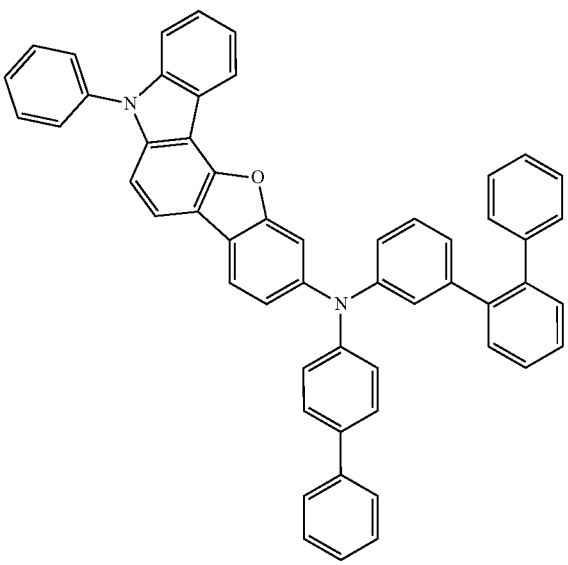
N-123
N-124
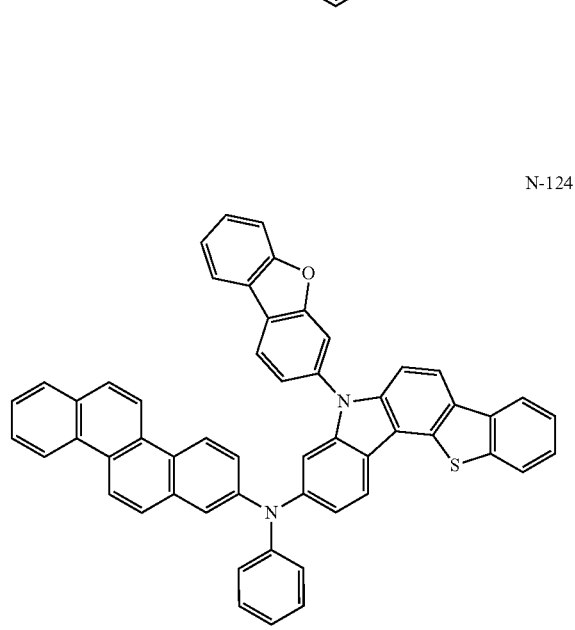

N-125
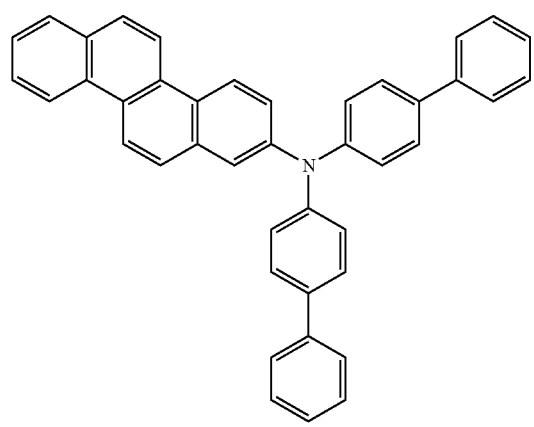
N-128
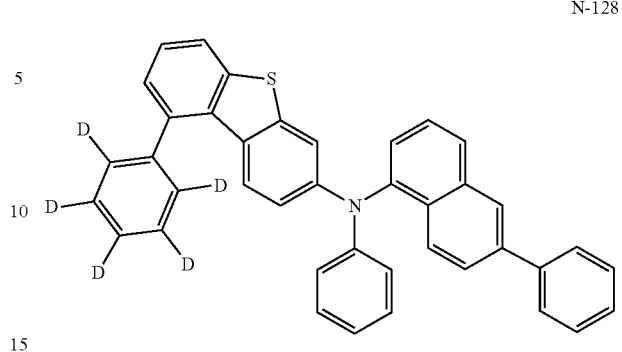
Specifically, the compound represented by Formula 3 may be a compound represented by any one of the compounds S-1 to S-120, but is not limited thereto.
N-126
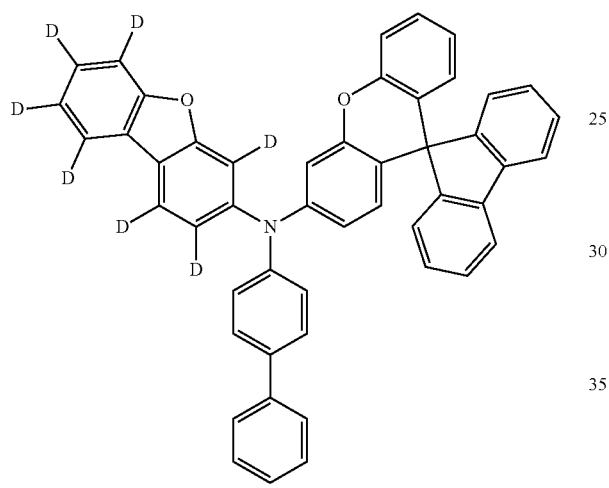
S-1
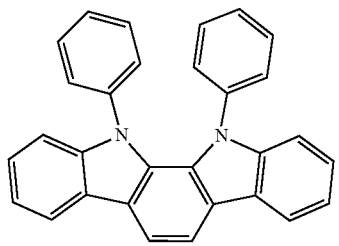
S-2
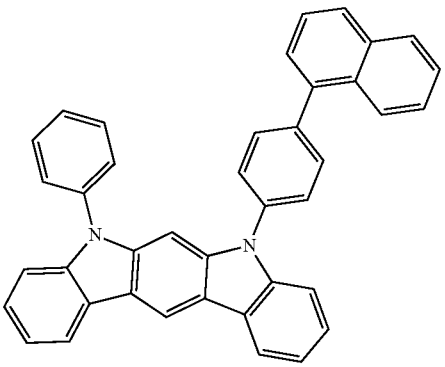
N-127
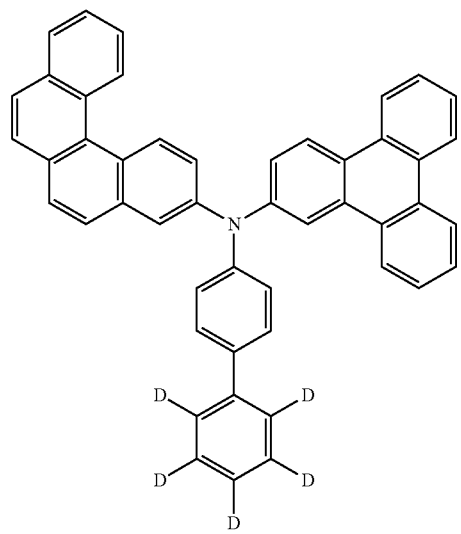
S-3
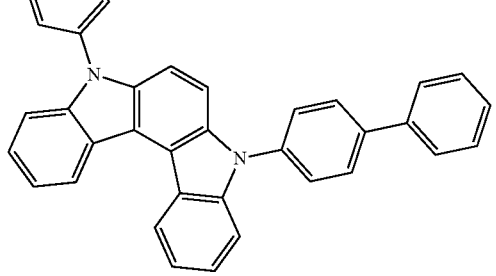

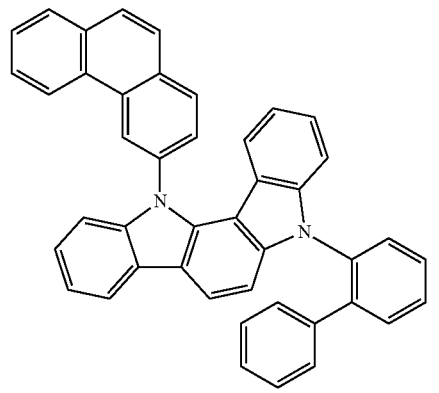
S-4
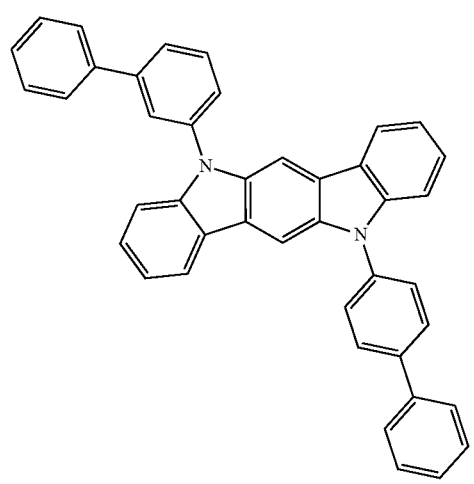
S-5
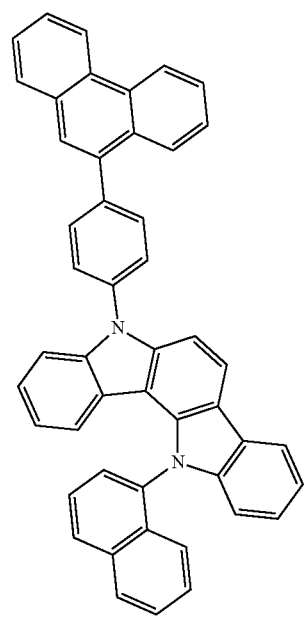
S-6
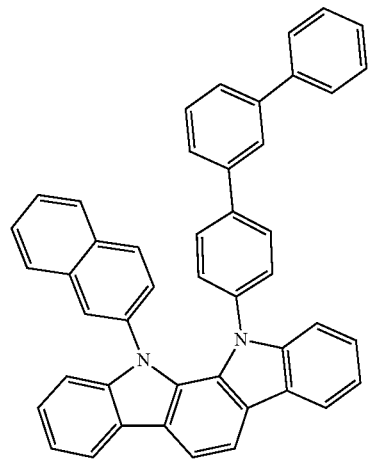
S-7
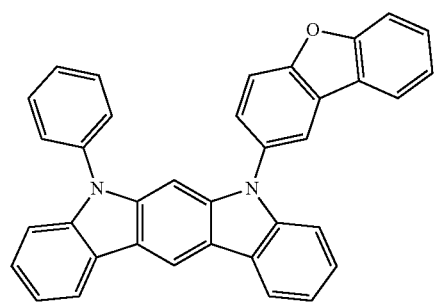
S-8
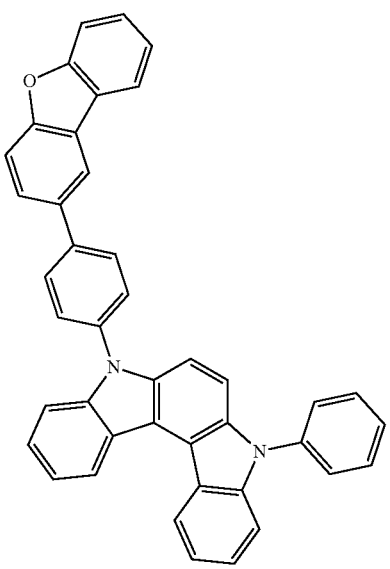
S-9

-continued
S-10
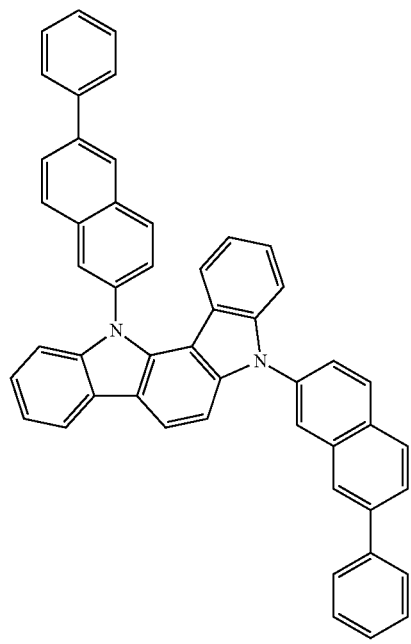
S-11
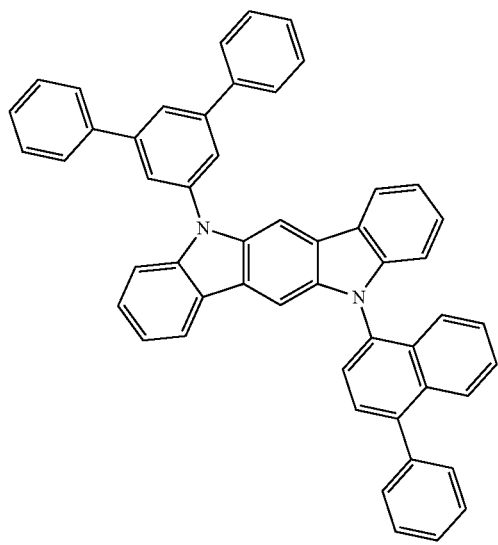
S-12
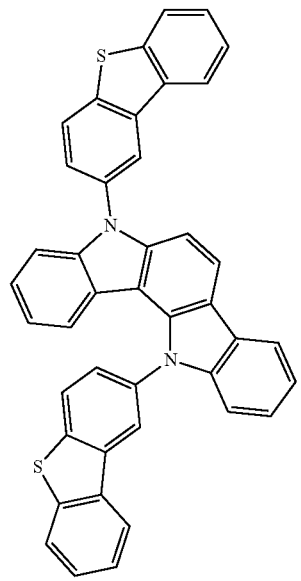
S-13
S-14
S-15
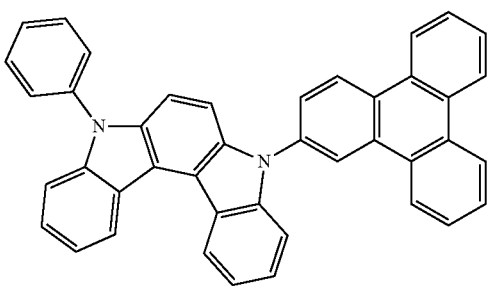

-continued
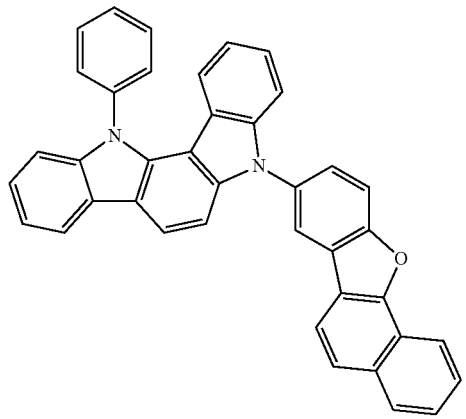
S-16
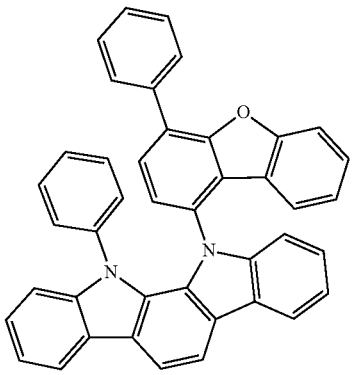
S-19
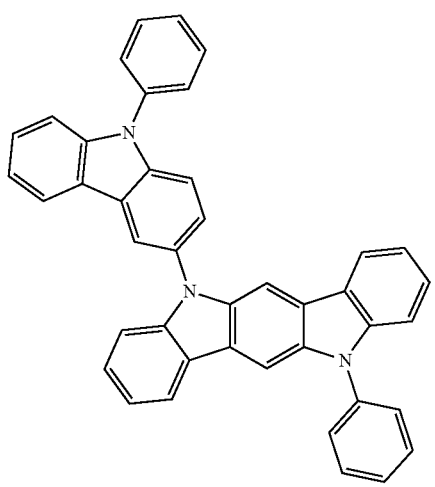
S-17
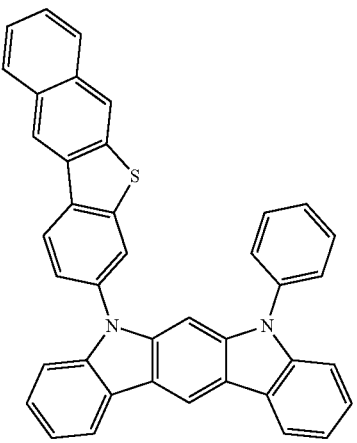
S-20
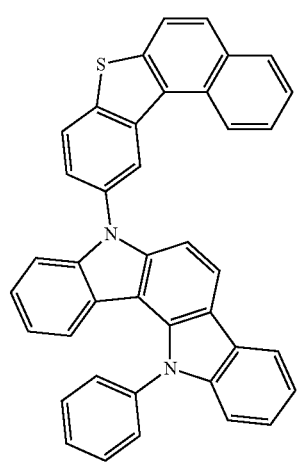
S-18
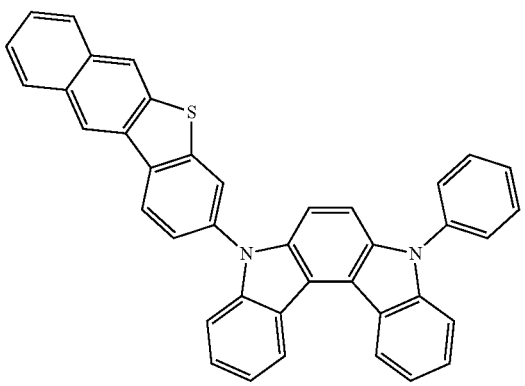
S-21

S-22
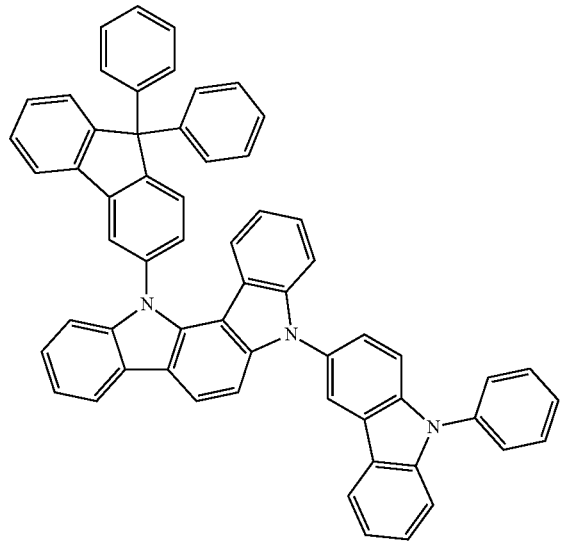
S-23
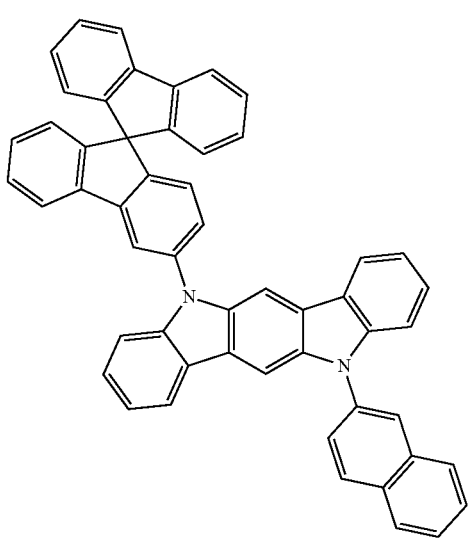
S-24
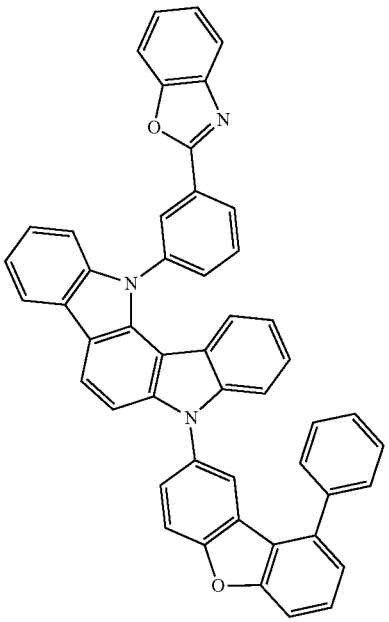
S-25
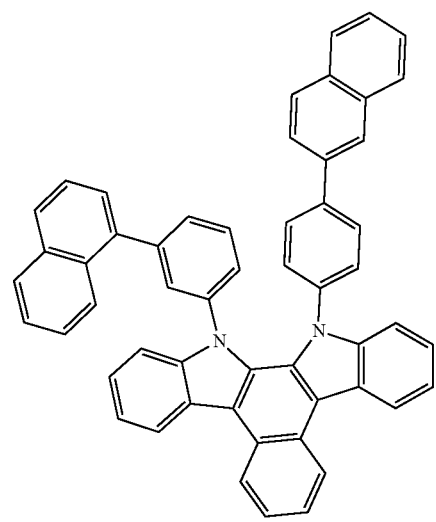
S-26
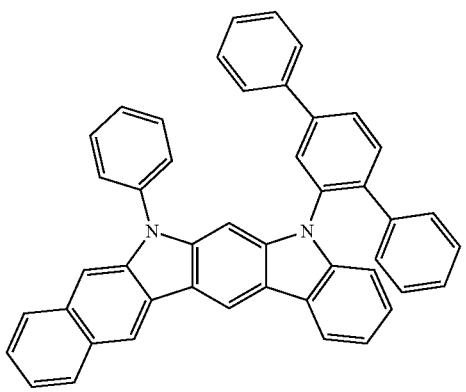

S-27
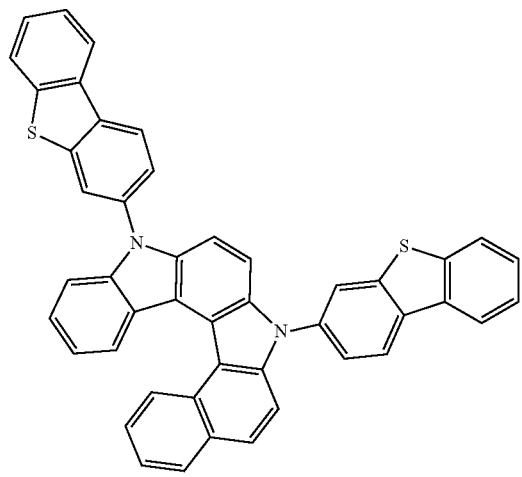
S-28
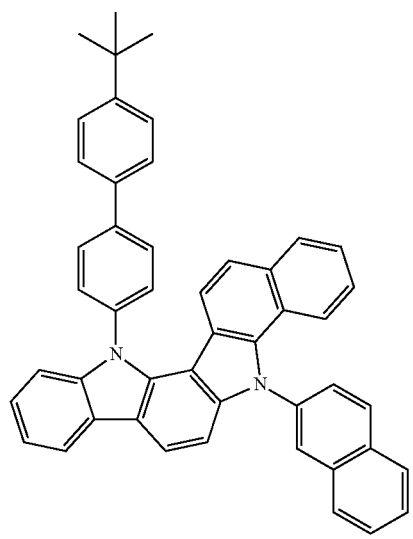
S-29
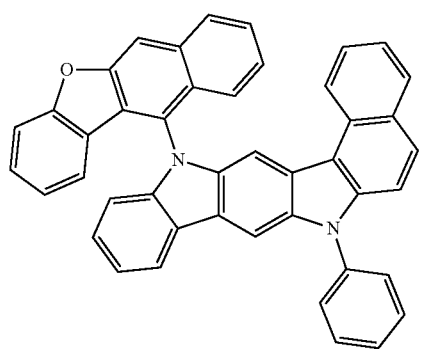
S-30
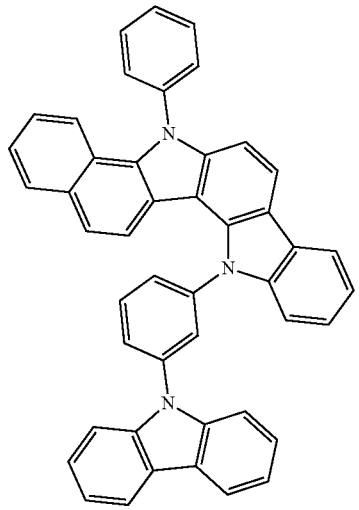
S-31
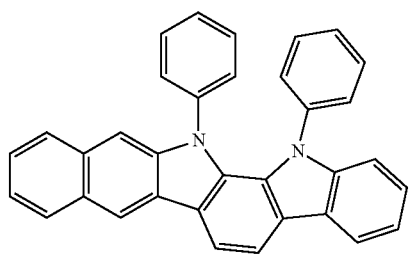
S-32
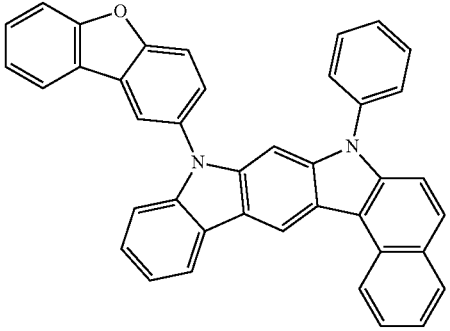
S-33
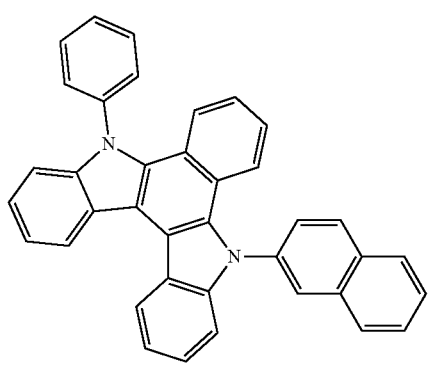

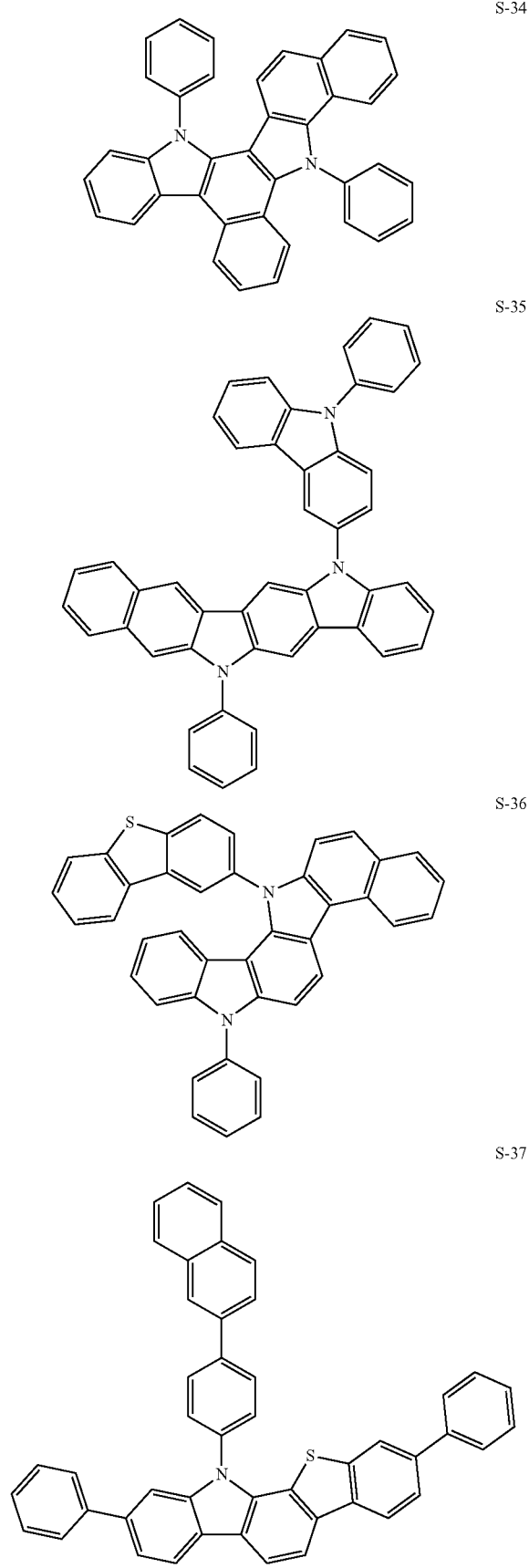
S-34
S-35
S-36
S-37
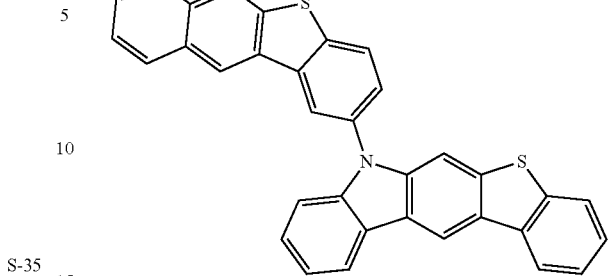
S-38
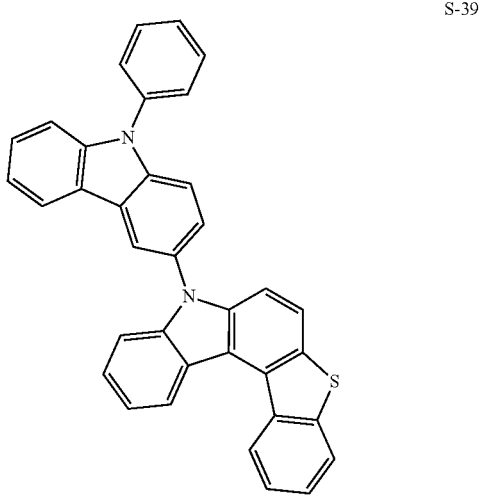
S-39
S-40

S-41
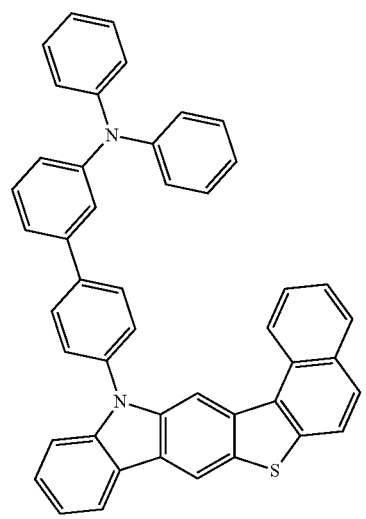
S-42
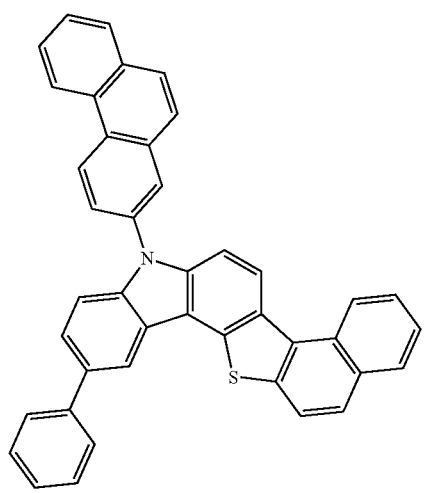
S-43
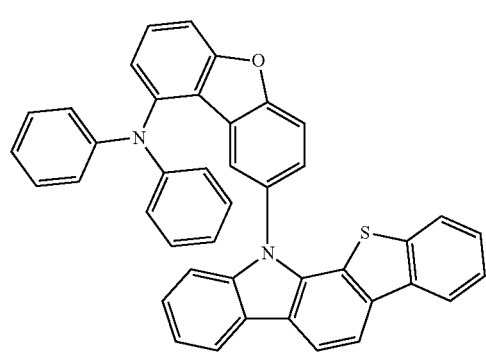
S-44
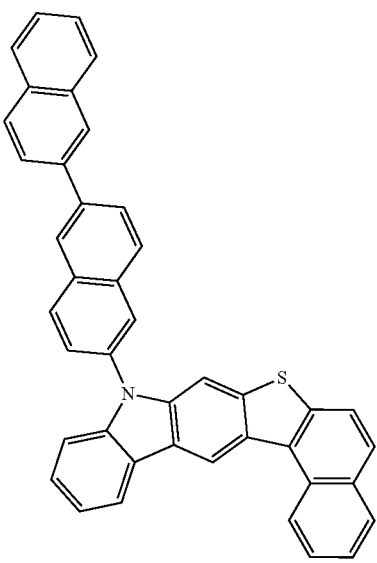
S-45
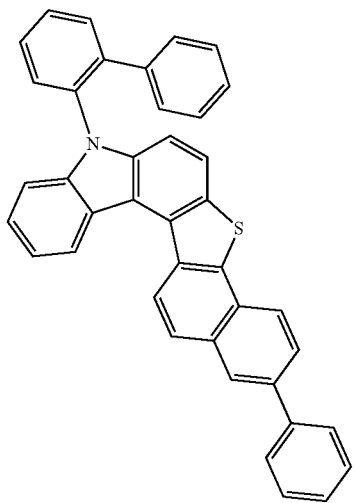
S-46
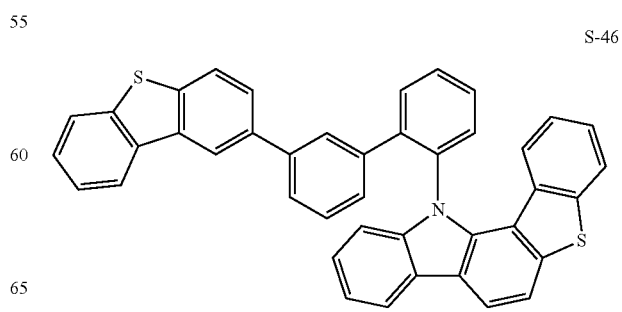

S-47
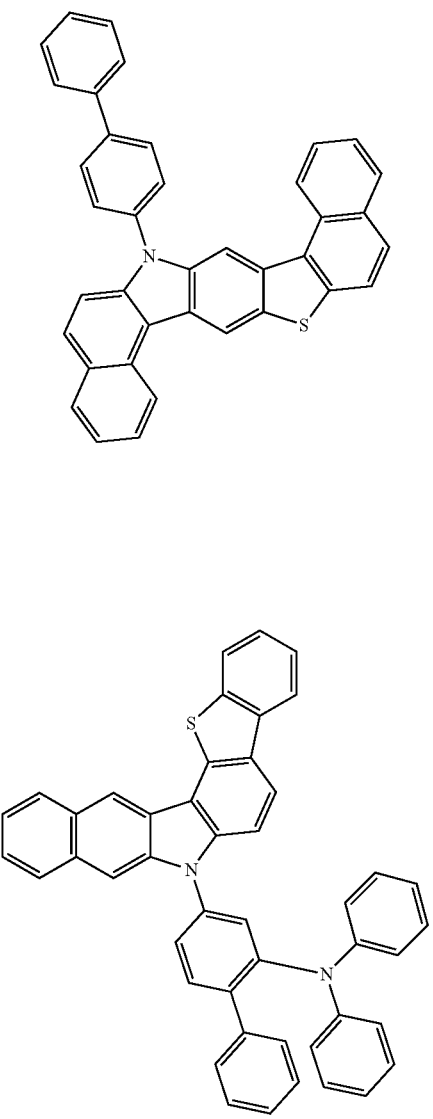
S-48
S-49
S-50
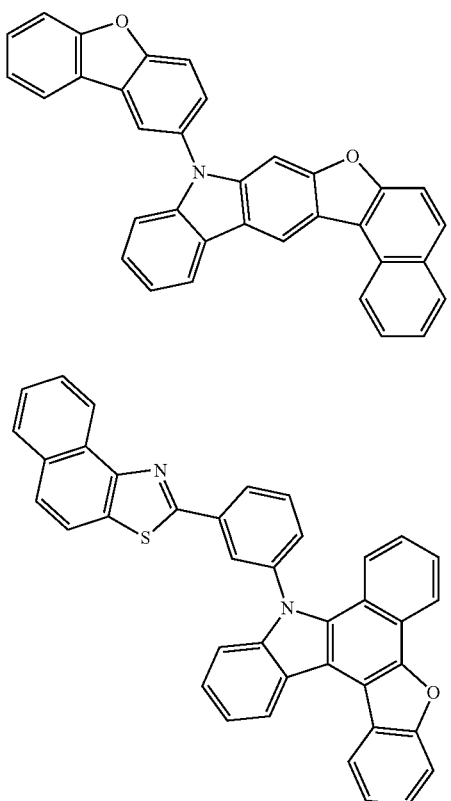
S-51
S-52
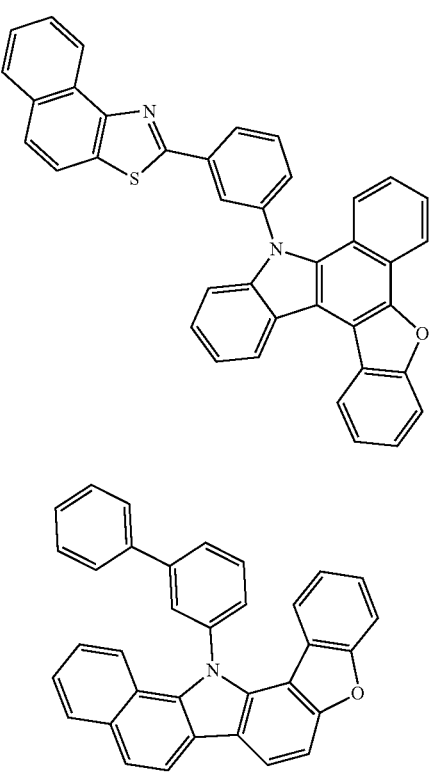
S-53
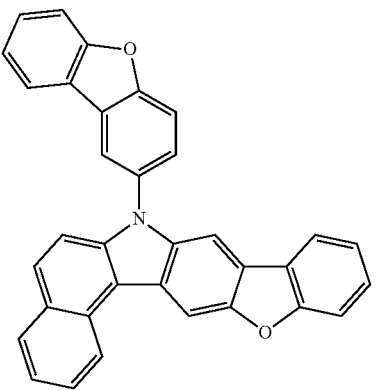

S-54
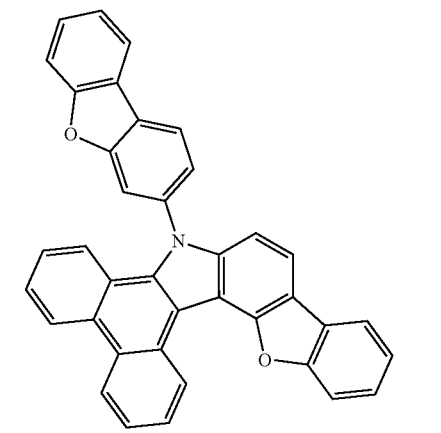
S-55
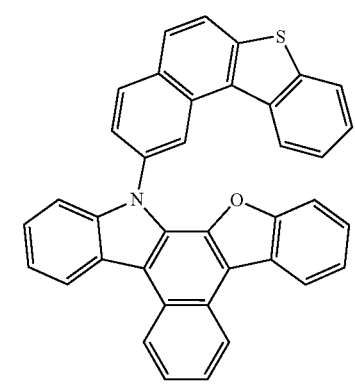
S-56
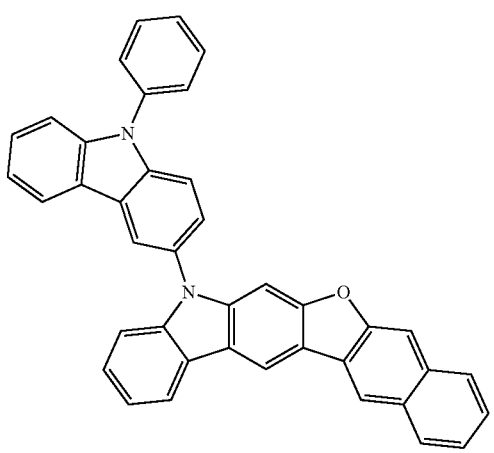
S-57
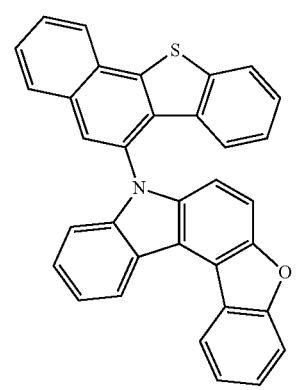
S-58
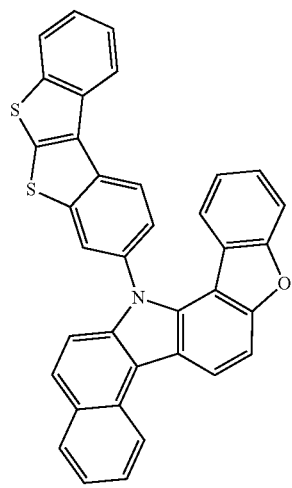
S-59
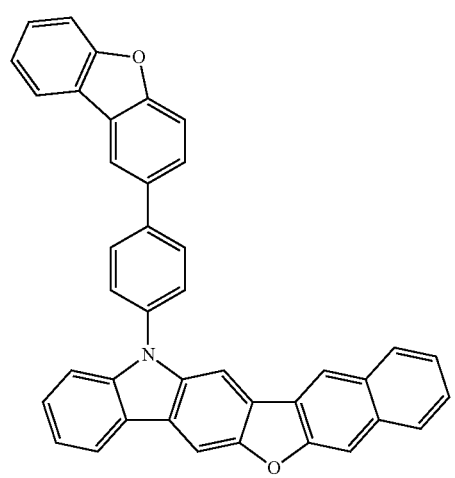
S-60
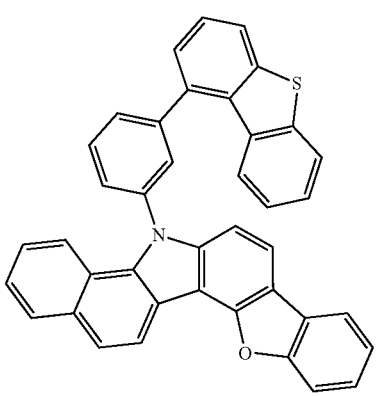

S-61
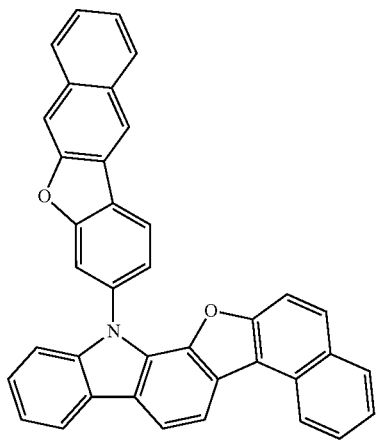
S-62
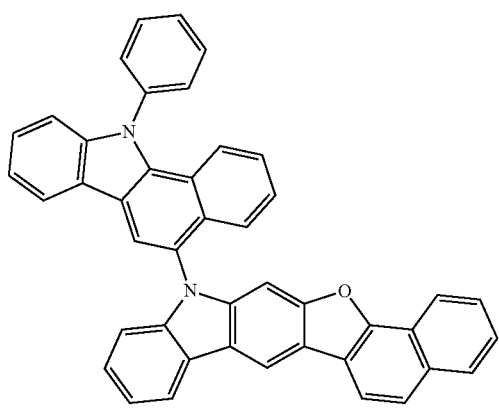
S-63
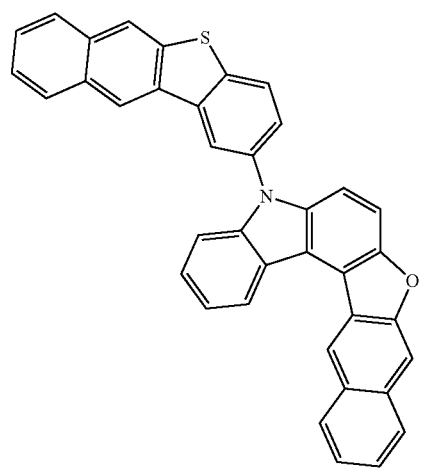
S-64
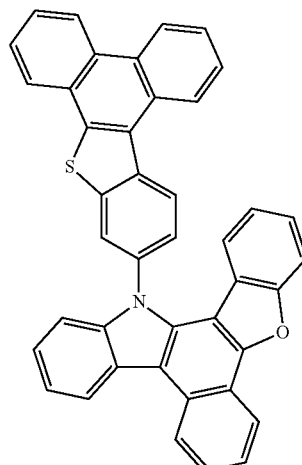
S-65
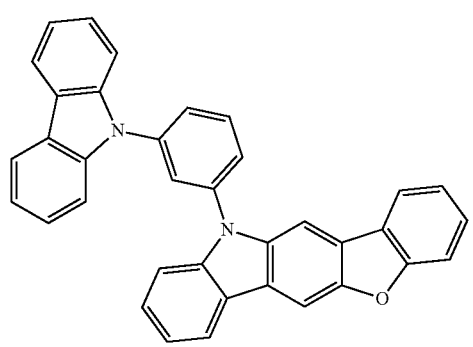
S-66
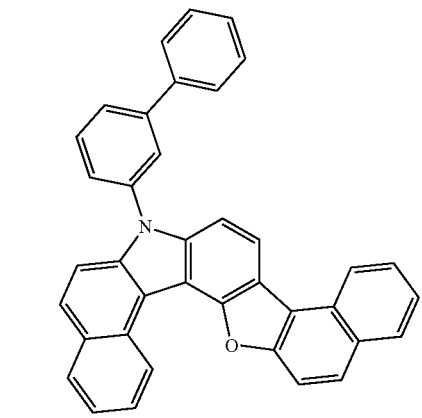
S-67
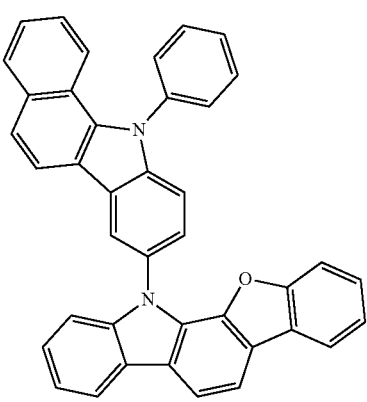

S-68
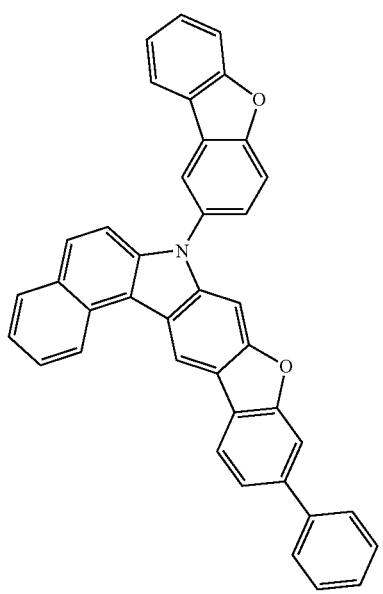
S-69
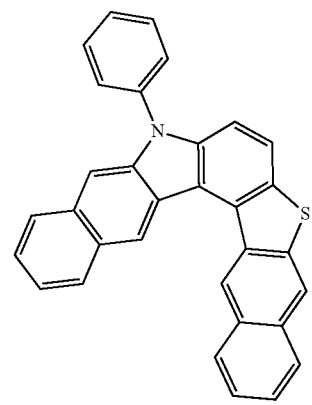
S-70
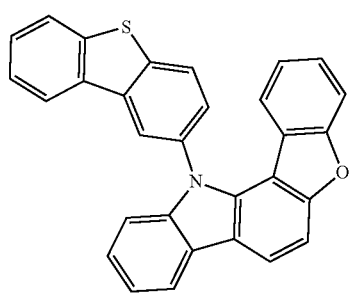
S-71
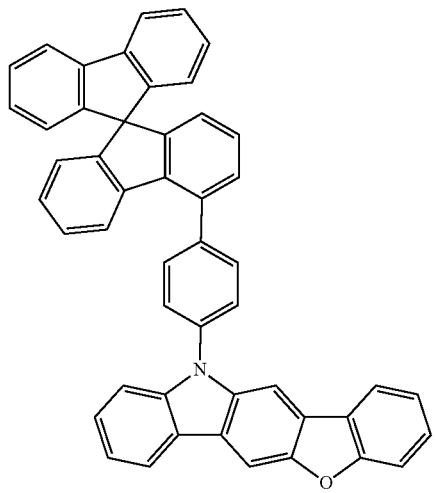
S-72
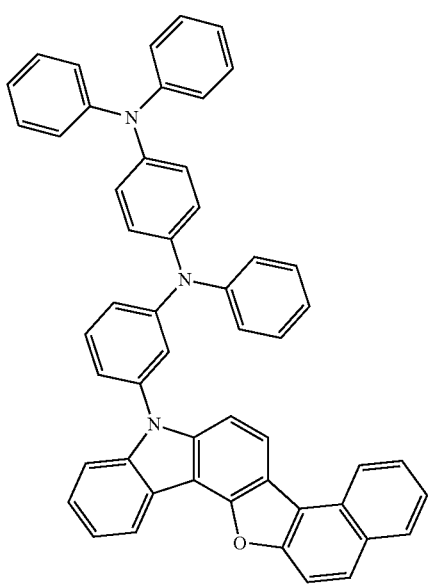
S-73
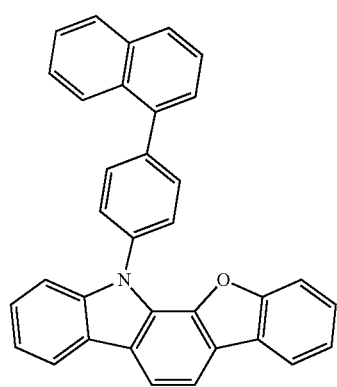

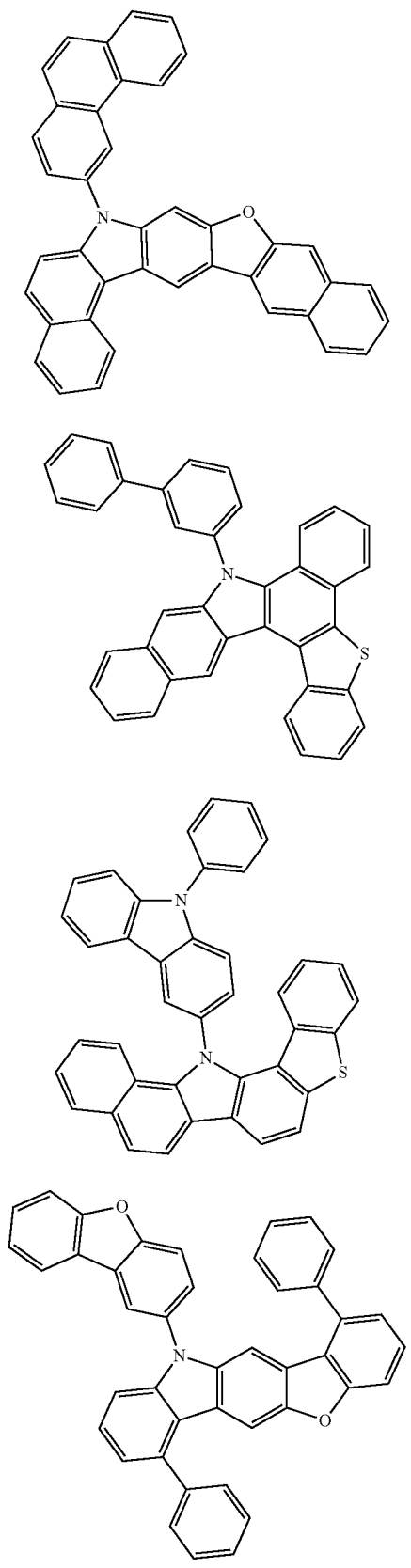
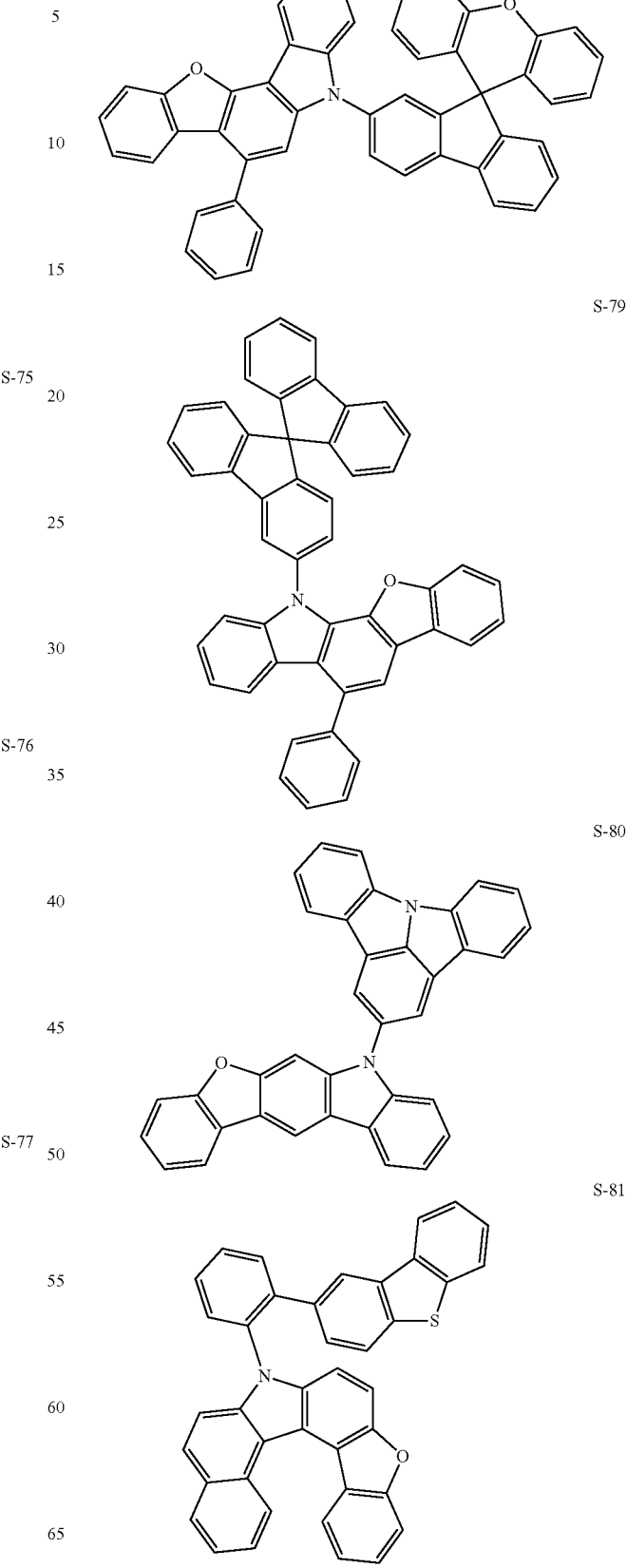

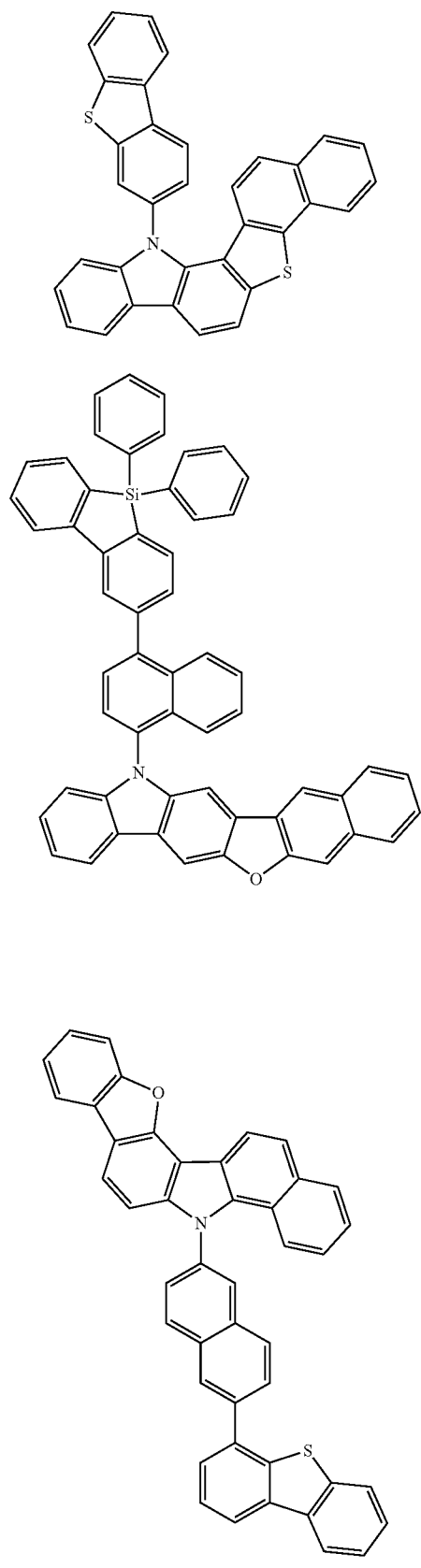
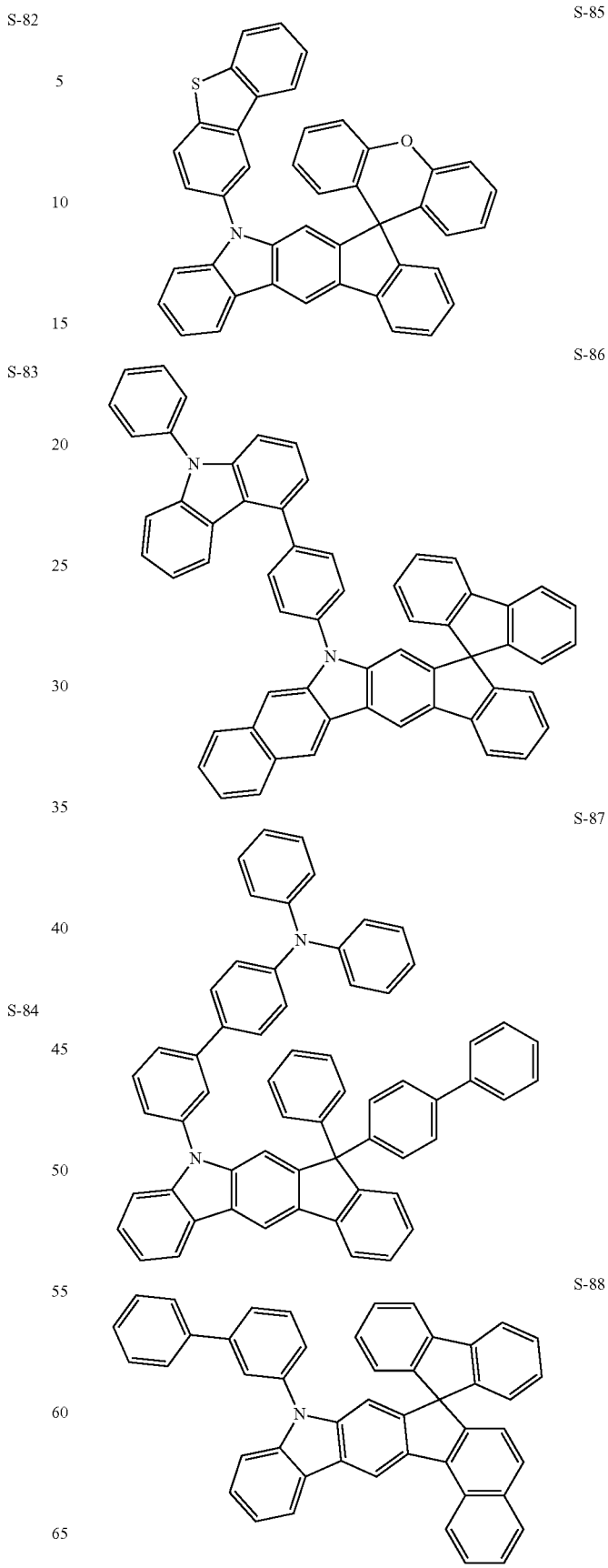

S-89
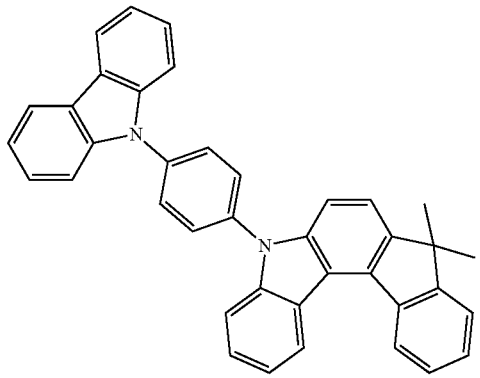
S-90
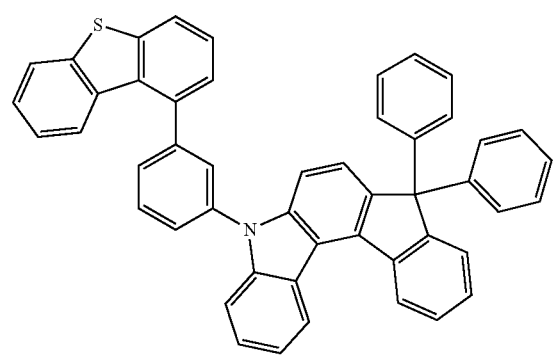
S-91
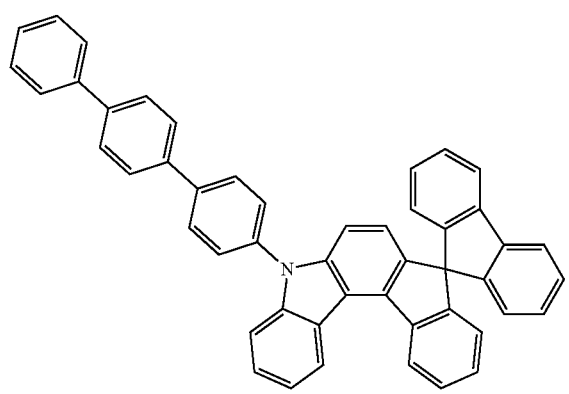
S-92
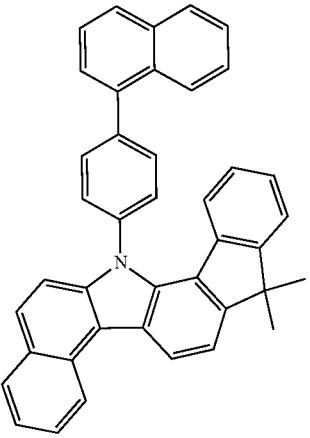
S-93
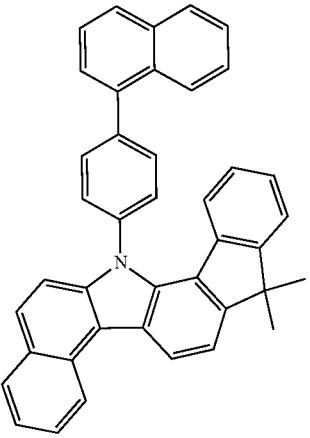
S-94
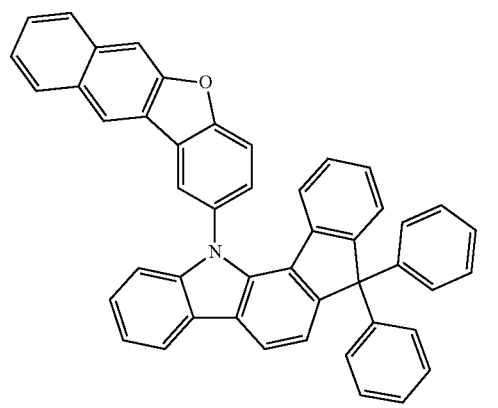
S-95
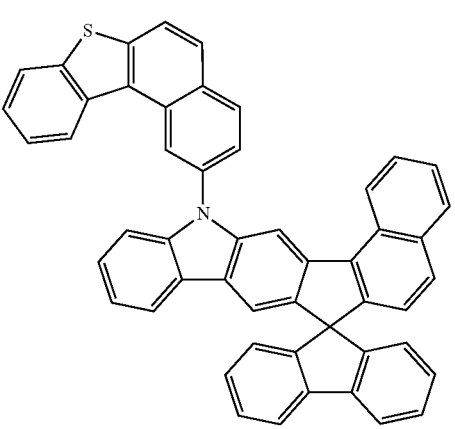

-continued
S-96
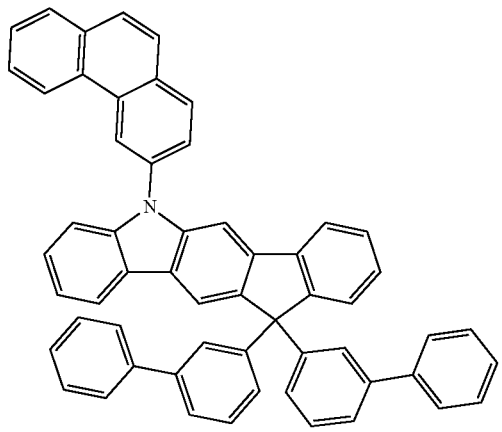
S-97
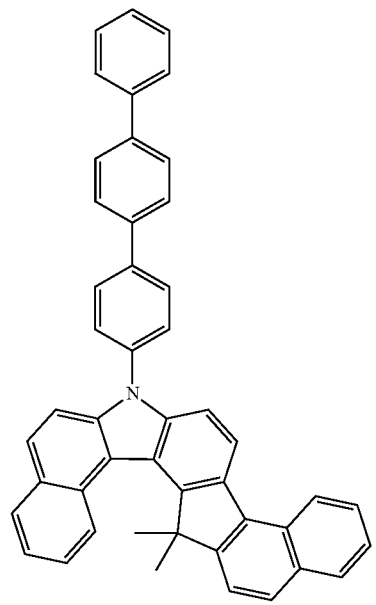
S-98
S-99
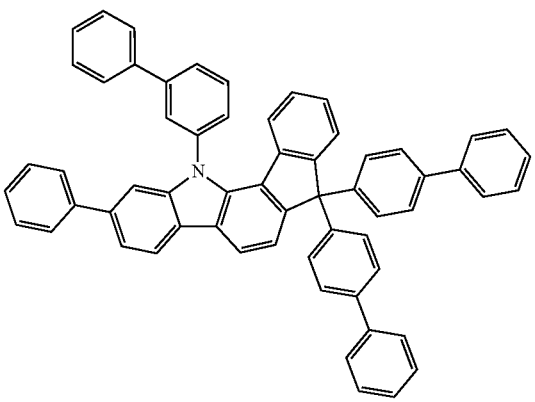
S-100
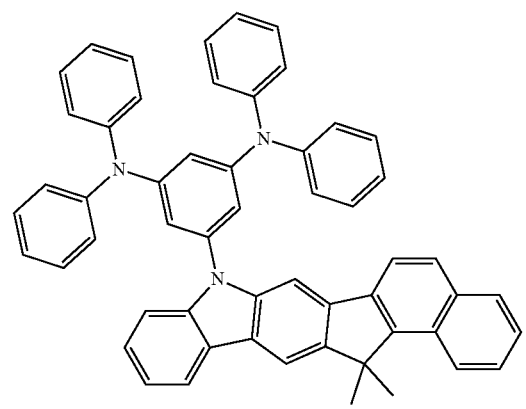
S-101
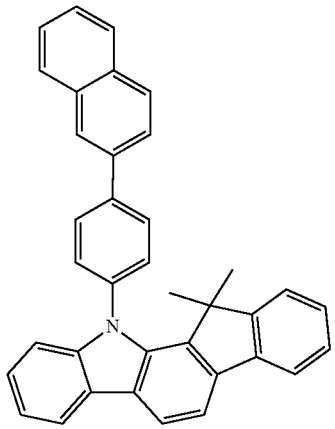
S-102
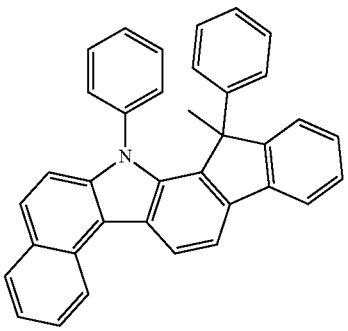

-continued
S-103
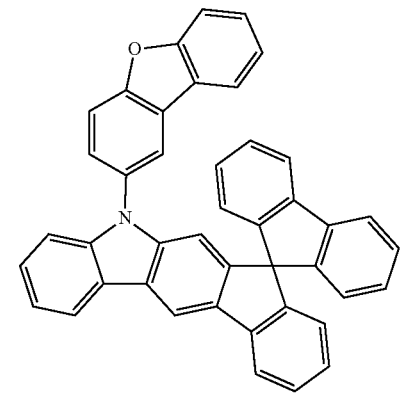
S-104
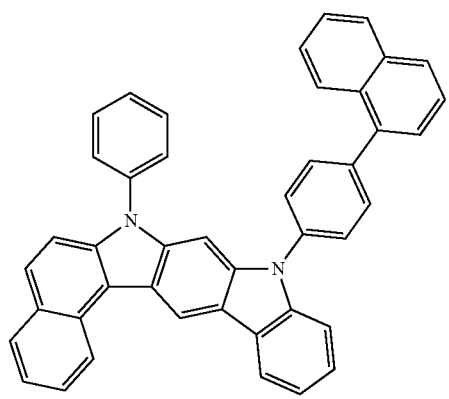
S-105
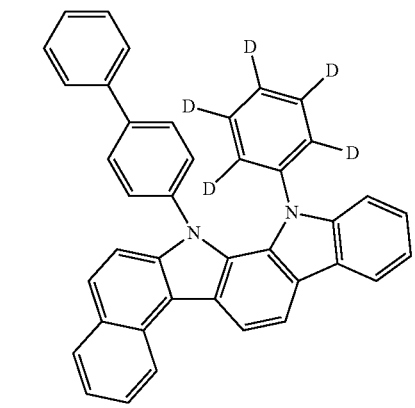
S-106
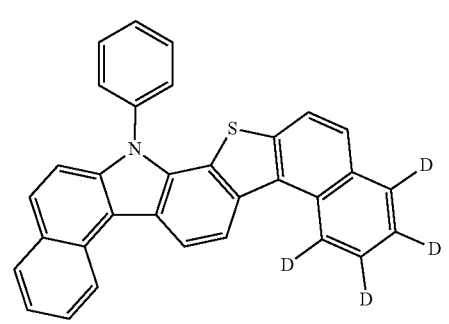
-continued
S-107
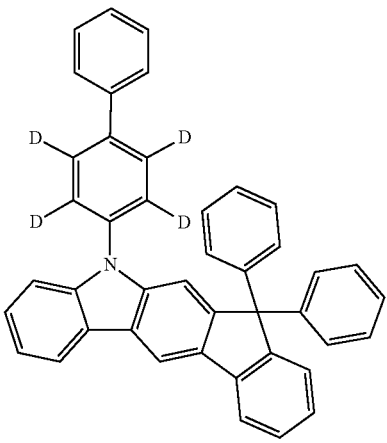
S-108
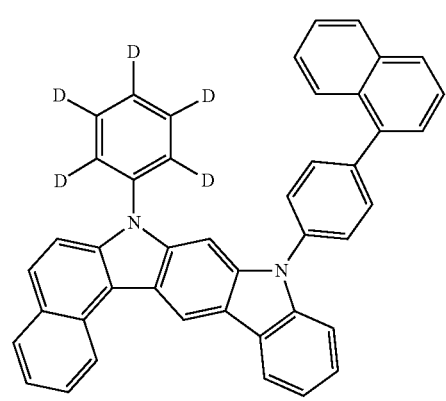
S-109
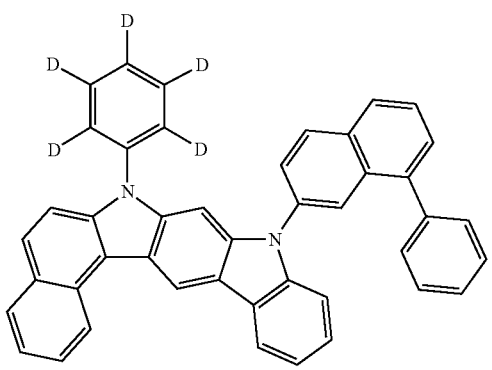
S-110
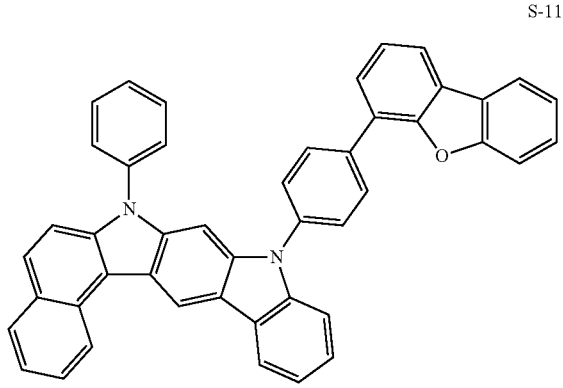

S-111
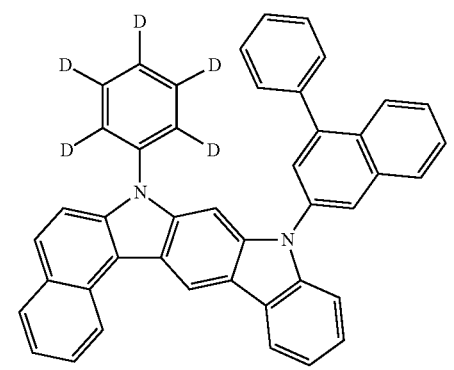
S-112
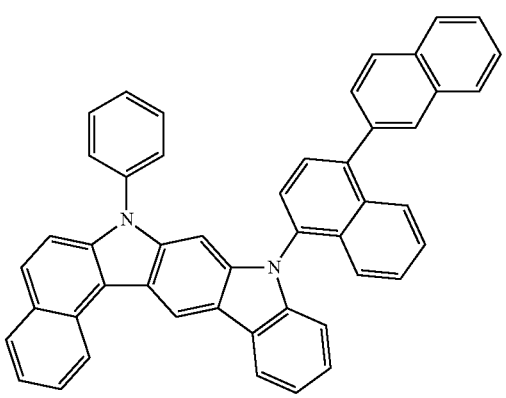
S-113
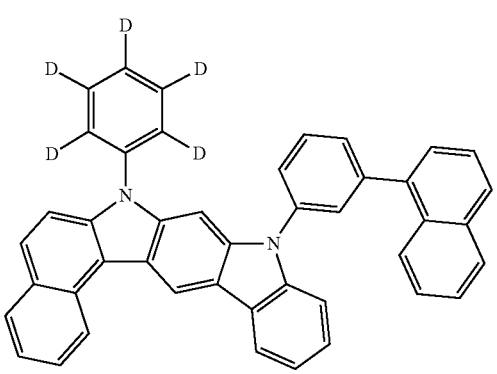
S-114
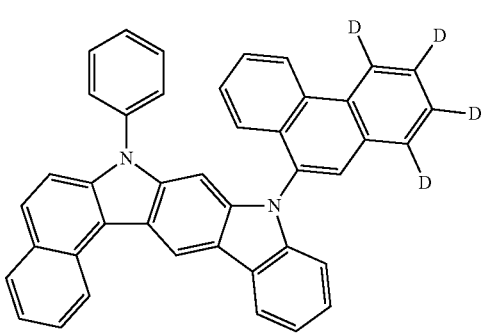
S-115
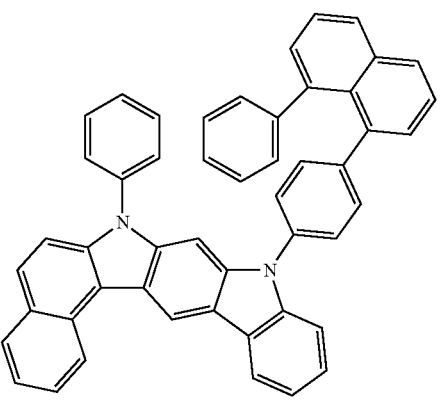
S-116
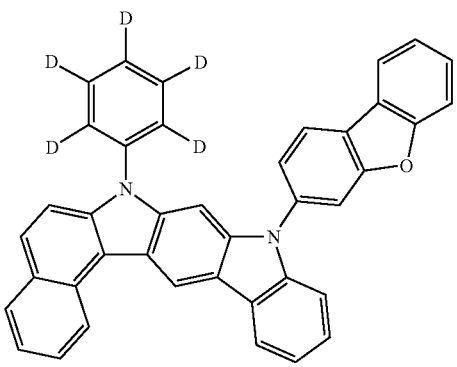
S-117
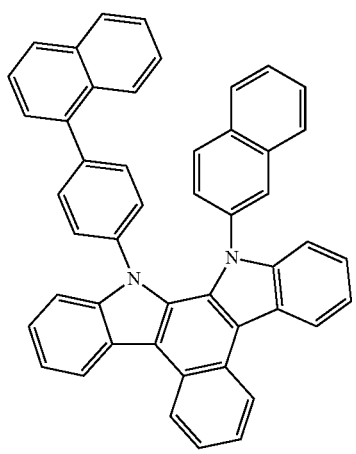

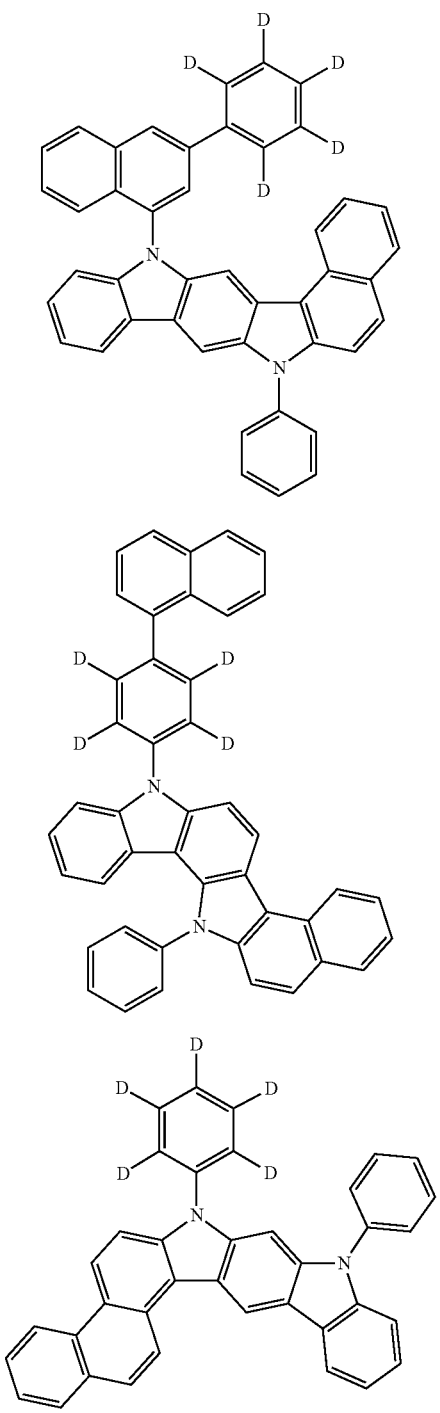

apparatus used in the process for depositing the organic emitting material to prepare an organic light emitting device;
removing impurities from the crude organic light emitting material;
recovering the organic light emitting material after the impurities are removed; and
purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent is preferably a single solvent of N-Methylpyrrolidone (NMP); or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a mixture of a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula 1 between the first electrode (110) and the second electrode (170). Wherein, the first electrode Also, in another aspect, the present invention provides an organic electronic element comprising a first electrode; a second electrode; and an organic material layer formed between the first electrode and the second electrode; wherein the organic material layer comprises a compound represented by Formula 1 or the composition for the organic electronic element.

In another aspect, the present invention provides a method for reusing a compound of Formula 1 comprising:
recovering a crude organic light emitting material comprising the compound of Formula 1 from a deposition (110) may be an anode or a positive electrode, and the second electrode (170) may be a cathode or a negative electrode. In the case of an inverted organic electronic element, the first electrode may be a cathode, and the second electrode may be an anode.

Figure 2:
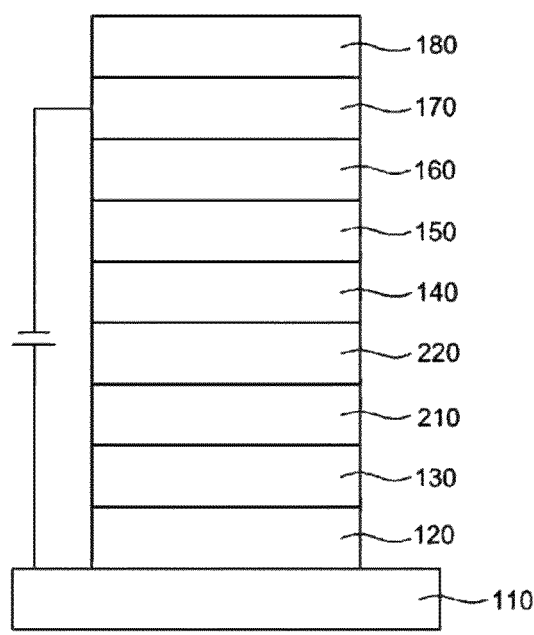

The organic material layer may sequentially comprise a hole injection layer (120), a hole transport layer (130), an emitting layer (140), an electron transport layer (150), and an electron injection layer (160) on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150), etc. may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, a composition for an organic electronic element comprising a compound according to Formula 1 of the present invention, or a mixture of a compound represented by Formula 1 and a compound represented by Formula 2 or 3, can be used as a host material of an emitting layer.

Figure 3:
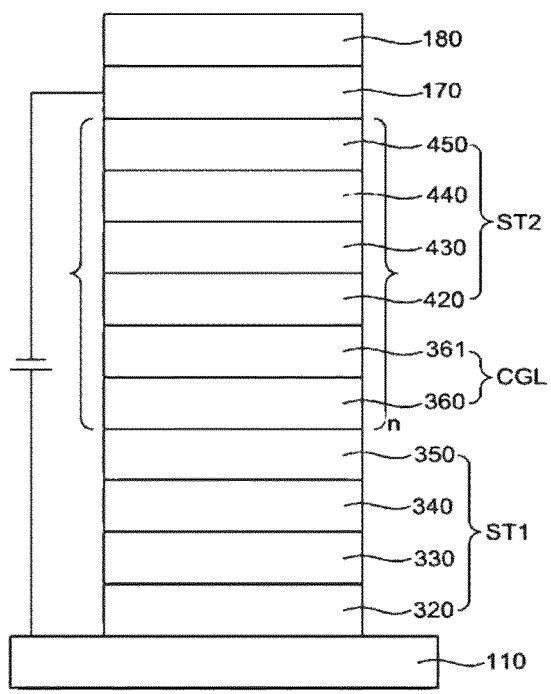

The organic material layer may comprise 2 or more stacks comprising a hole transport layer, an emitting layer and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, etc. may vary depending on which substituent is bonded at which position, therefore the choice of core and the combination of sub-substituents associated therewith is also very important, and in particular, when the optimal combination of energy levels and T1 values, and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound or a composition for an organic electronic element as an electron transport material.

As another specific example, the present invention provides an organic electronic element used by mixing the same or different compounds of the compound represented by Formula 1 to the organic material layer. Preferably, the organic material layer comprises an emitting layer, wherein the emitting layer comprises a composition for an organic electronic element comprising a compound represented by Formula 1 or a mixture of a compound represented by Formula 1 and a compound represented by Formula 2 or Formula 3.

Also, the present invention provides a composition for an organic electronic element comprising a compound represented by Formula 1, or a mixture of a compound represented by Formula 1 and a compound represented by Formula 2 or Formula 2, and provides an organic electronic element comprising the composition.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1, Formula 2 and Formula 3 according to the present invention and preparation examples of the organic electronic element of the present invention will be described in detail by way of example, but are not limited to the following examples.

SYNTHESIS EXAMPLE

The compound (final products) represented by Formula 1 according to the present invention can be synthesized by reacting Sub 1 and Sub 2 as shown in Scheme 1, but is not limited thereto.

<Reaction Scheme 1>

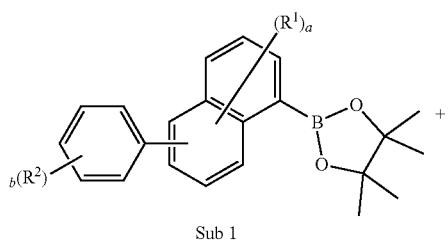

Sub 1

-continued

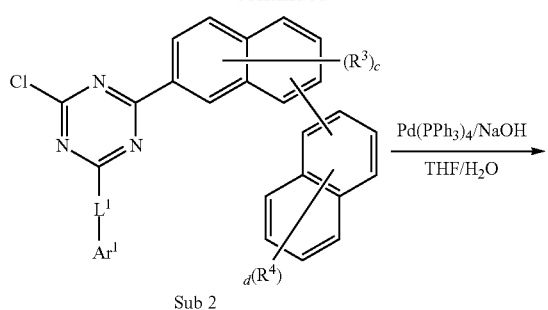
Sub 2

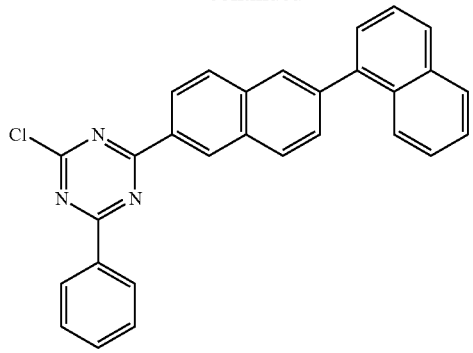
Sub 2-1

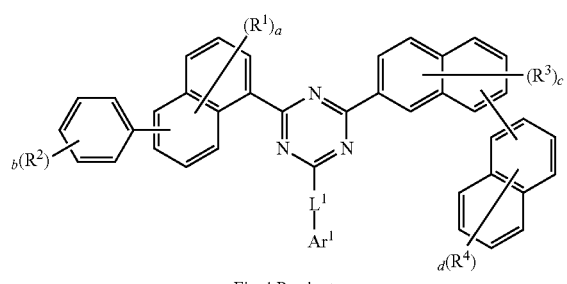
Final Products

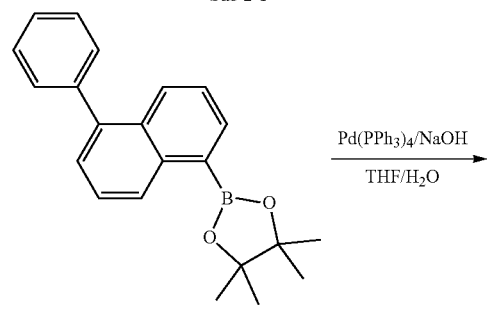
Sub 1-1

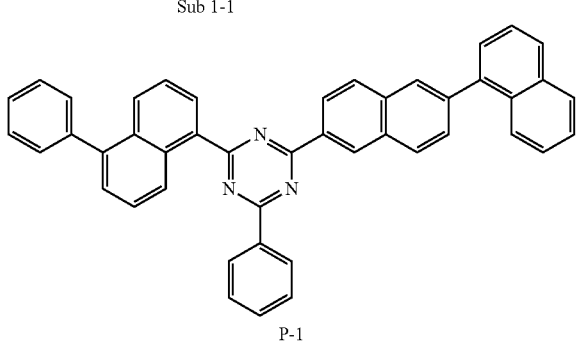
P-1

Wherein, the definitions of $Ar^1$, $L^1$, $R^1$, $R^2$, $R^3$, $R^4$, a, b, c, d are the same as defined in Formula 1.

I. Synthesis of Final Product

1. Synthesis Example of P-1

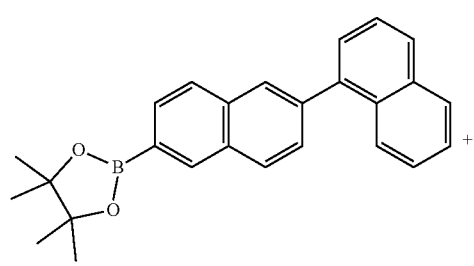
Sub 2-1a

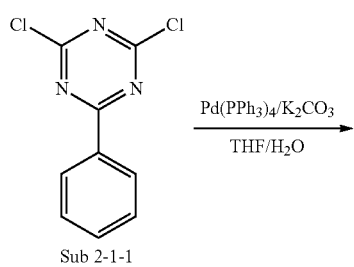
Sub 2-1-1

1) Synthesis of Sub 2-1

Sub 2-1a (100.00 g, 262.96 mmol), Sub 2-1-1 (118.89 g, 525.91 mmol), Pd(PPh$_3$)$_4$ (9.12 g, 7.89 mmol), K$_2$CO$_3$ (36.34 g, 262.96 mmol) were placed in a round-bottom flask, dissolved in THF (877 mL) and water (292 mL) and refluxed at 75° C. for 12 hours. When the reaction was complete, the reaction product was cooled to room temperature, extracted with CH$_2$Cl$_2$ and water, and then treated with MgSO$_4$. The product was produced by concentrating the organic solvent and recrystallizing using a silica gel column to obtain 59.53 g (51%) of Sub 2-1.

2) Synthesis of P-1

Sub 1-1 (35.00 g, 105.99 mmol), Sub 2-1 (47.05 g, 105.99 mmol), Pd(PPh$_3$)$_4$ (3.67 g, 3.18 mmol), NaOH (8.48 g, 211.97 mmol) and THF (353 mL) and water (118 mL) were added in a round-bottom flask, and the mixture was reacted at 75° C. for 8 hours. When the reaction is complete, the temperature of the reaction product is cooled to room temperature, and the reaction solvent is removed. After that, the concentrated reaction product is purified through a silica gel column and recrystallized to obtain 51.87 g (80%) of product P-1.

2. Synthesis Example of P-2

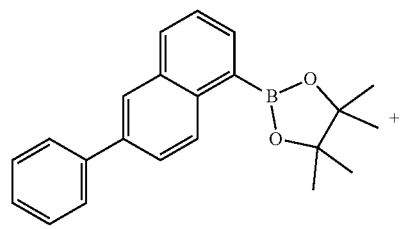

Sub 1-2

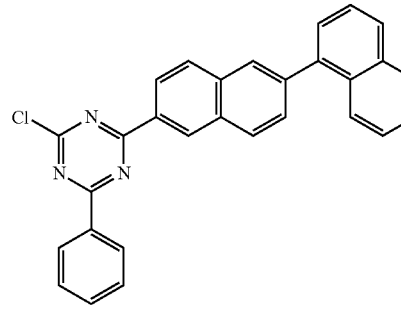

Sub 2-1

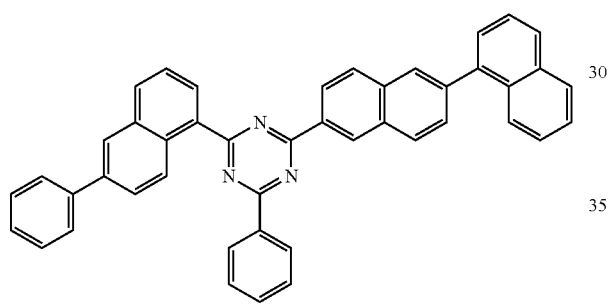

P-2

Sub 1-2 (35.00 g, 105.99 mmol), Sub 2-1 (47.05 g, 105.99 mmol), Pd(PPh₃)₄ (3.67 g, 3.18 mmol), NaOH (8.48 g, 211.97 mmol) and THF (353 mL) and water (118 mL) were added in a round-bottom flask, and 52.52 g (81%) of product P-2 was obtained using the synthetic method of P-1.

3. Synthesis Example of P-8

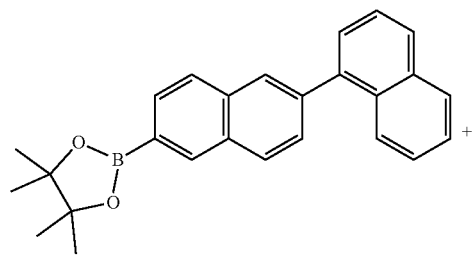

Sub 2-1a

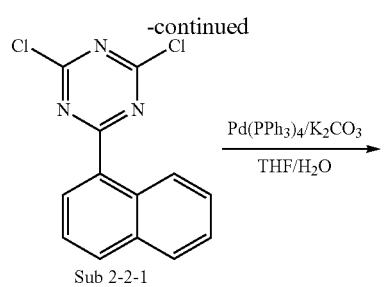

Sub 2-2-1

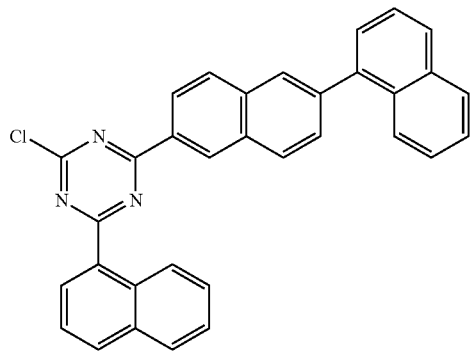

Sub 2-2

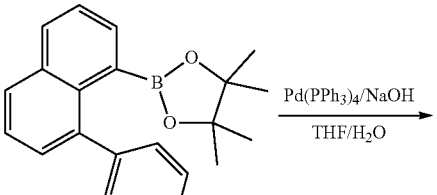

Sub 1-4

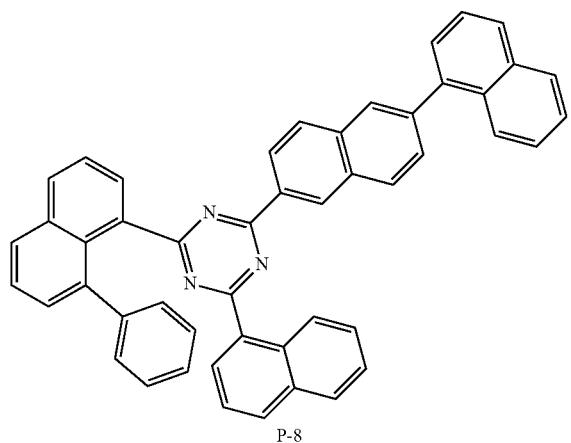

P-8

1) Synthesis of Sub 2-2

Sub 2-1a (100.00 g, 262.96 mmol), Sub 2-2-1 (145.22 g, 525.91 mmol), Pd(PPh₃)₄ (9.12 g, 7.89 mmol), K₂CO₃ (36.34 g, 262.96 mmol) were added in a round bottom flask and after dissolving in THF (877 mL) and water (292 mL), 63.65 g (49%) of Sub 2-2 was obtained using the synthetic method of Sub 2-1.

2) Synthesis of P-8

Sub 1-4 (35.00 g, 70.85 mmol), Sub 2-2 (31.45 g, 70.85 mmol), Pd(PPh₃)₄ (2.46 g, 2.13 mmol), NaOH (5.67 g, 141.70 mmol) and THF (236 mL) and water (79 mL) were added in a round-bottom flask, and 36.84 g (85%) of product P-8 was obtained using the synthetic method of P-1.

4. Synthesis Example of P-26

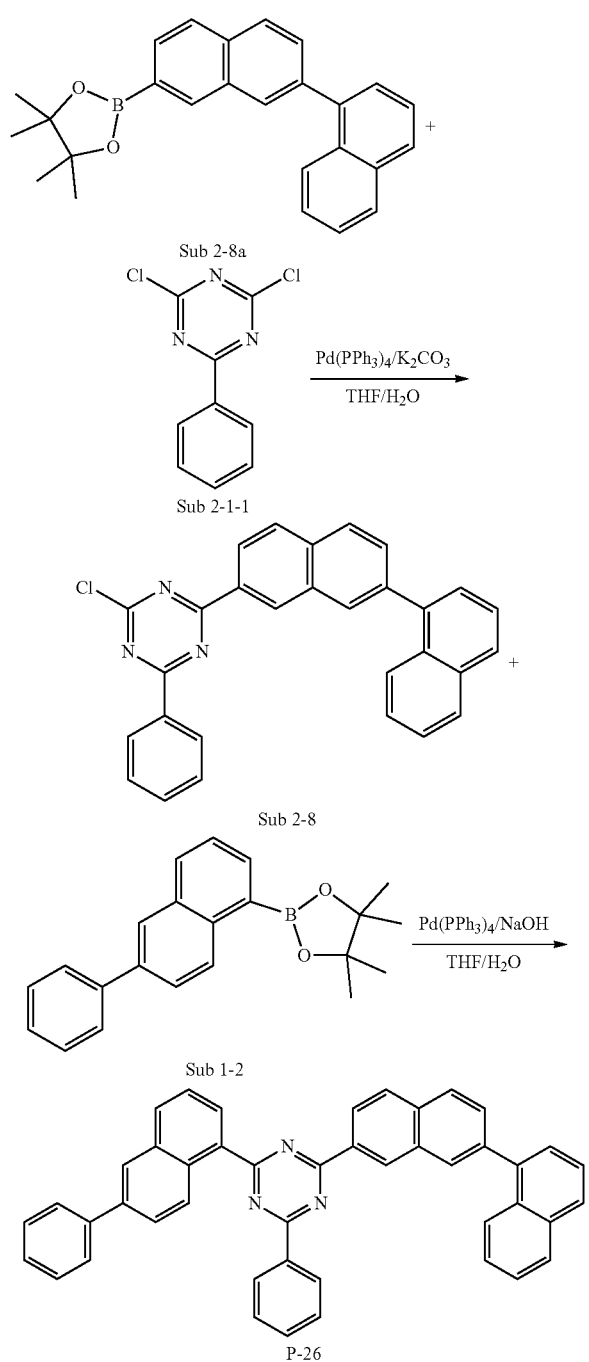

5. Synthesis Example of P-44

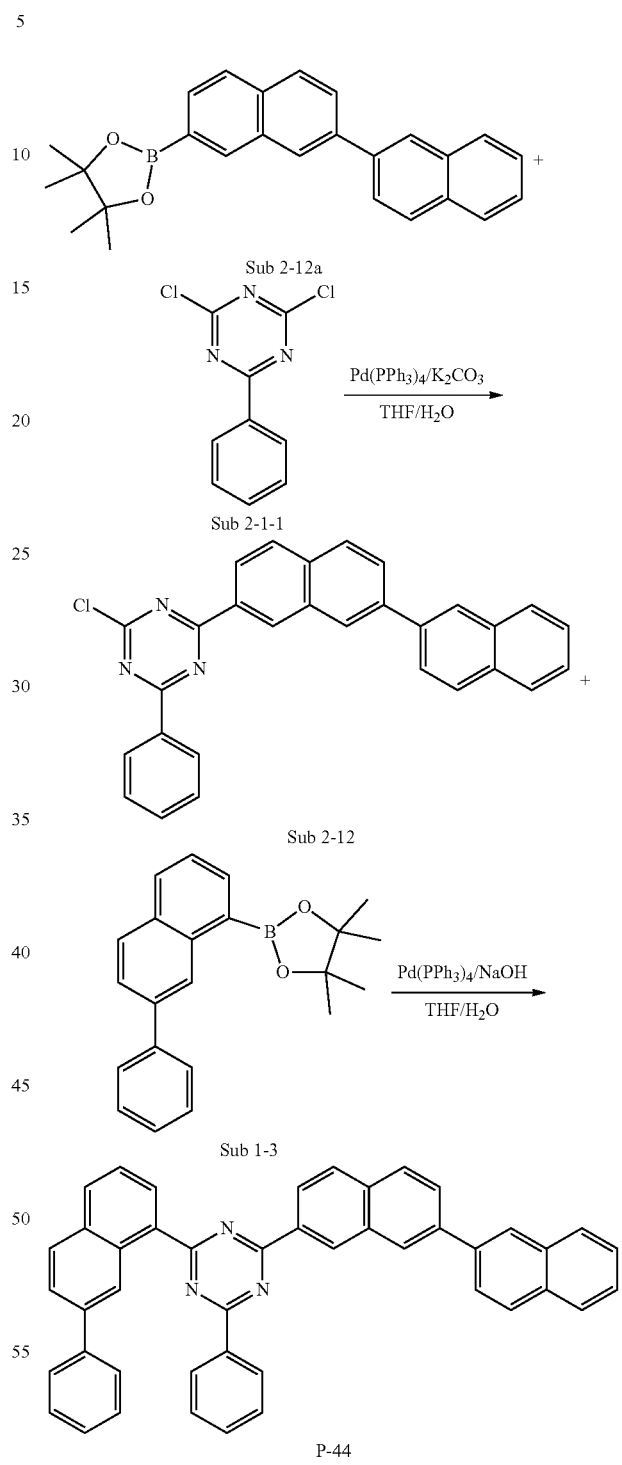

1) Synthesis of Sub 2-8
  Sub 2-8a (100.00 g, 262.96 mmol), Sub 2-1-1 (118.89 g, 525.91 mmol), Pd(PPh$_3$)$_4$ (9.12 g, 7.89 mmol), K$_2$CO$_3$ (36.34 g, 262.96 mmol) were added in a round bottom flask and after dissolving in THF (877 mL) and water (292 mL), 61.87 g (53%) of Sub 2-8 was obtained using the synthetic method of Sub 2-1.

2) Synthesis of P-26
  Sub 1-2 (40.00 g, 121.13 mmol), Sub 2-8 (53.77 g, 121.13 mmol), Pd(PPh$_3$)$_4$ (4.20 g, 3.63 mmol), NaOH (9.69 g, 242.26 mmol) and THF (404 mL) and water (135 mL) were added in a round-bottom flask, and 60.02 g (81%) of product P-26 was obtained using the synthetic method of P-1.

1) Synthesis of Sub 2-12
  Sub 2-12a (100.00 g, 262.96 mmol), Sub 2-1-1 (118.89 g, 525.91 mmol), Pd(PPh$_3$)$_4$ (9.12 g, 7.89 mmol), K$_2$CO$_3$ (36.34 g, 262.96 mmol) were added in a round bottom flask and after dissolving in THF (877 mL) and water (292 mL), 64.20 g (55%) of Sub 2-12 was obtained using the synthetic method of Sub 2-1.

2) Synthesis of P-44

Sub 1-3 (40.00 g, 121.13 mmol), Sub 2-12 (53.77 g, 121.13 mmol), Pd(PPh₃)₄ (4.20 g, 3.63 mmol), NaOH (9.69 g, 242.26 mmol) and THF (404 mL) and water (135 mL) were added in a round-bottom flask, and 55.57 g (75%) of product P-44 was obtained using the synthetic method of P-1.

6. Synthesis Example of P-51

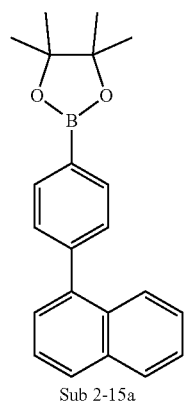

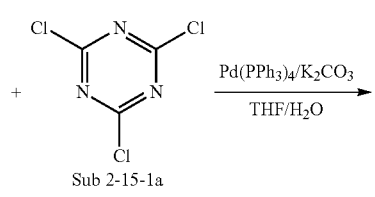

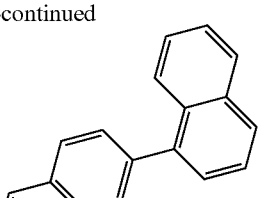

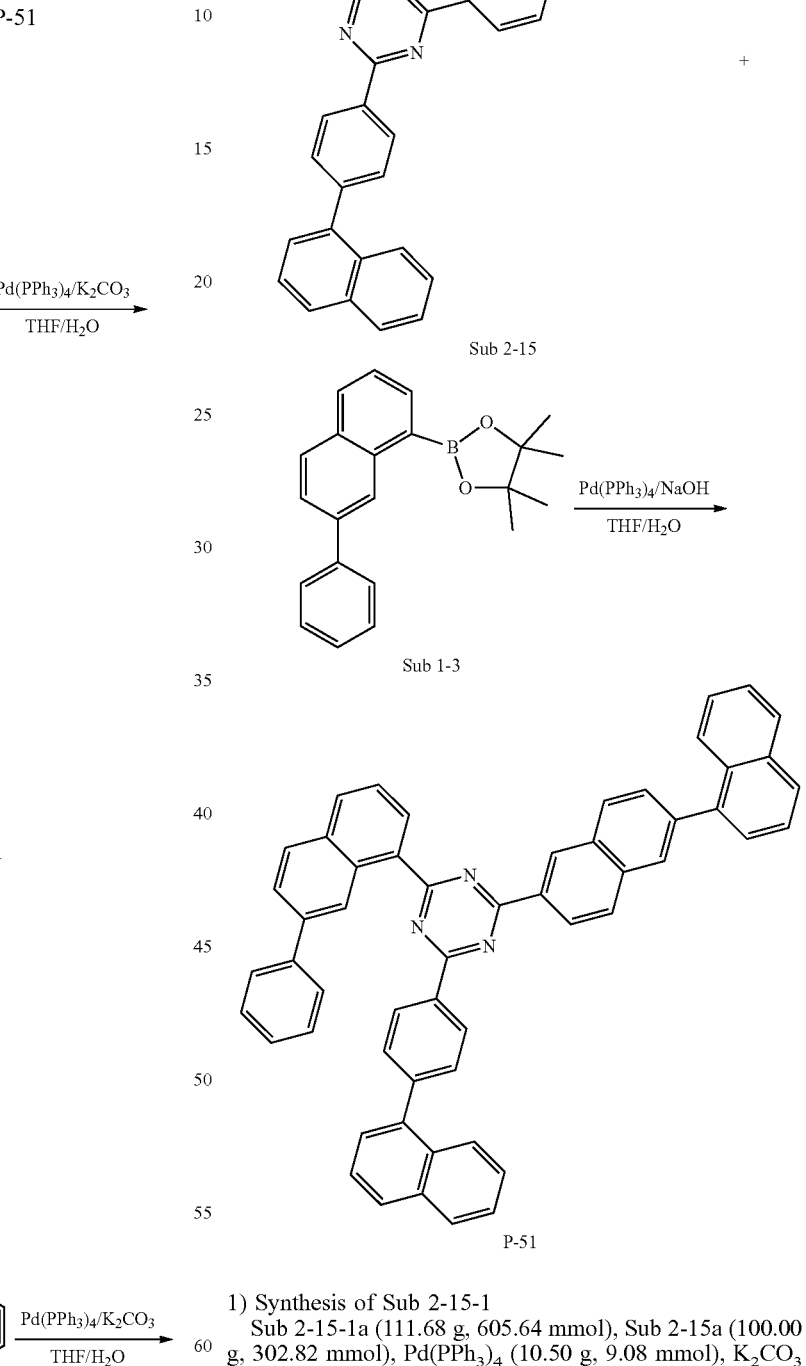

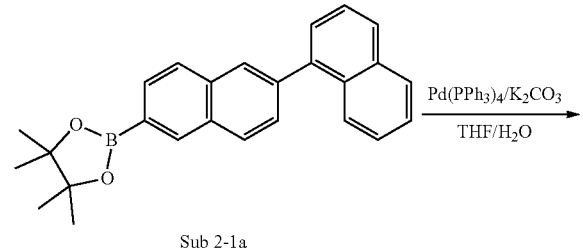

1) Synthesis of Sub 2-15-1

Sub 2-15-1a (111.68 g, 605.64 mmol), Sub 2-15a (100.00 g, 302.82 mmol), Pd(PPh₃)₄ (10.50 g, 9.08 mmol), K₂CO₃ (41.85 g, 302.82 mmol) were added in a round bottom flask and after dissolving in THF (1009 mL) and water (336 mL), 46.93 g (44%) of Sub 2-15-1 was obtained using the synthetic method of Sub 2-1.

2) Synthesis of Sub 2-15

Sub 2-1a (25.00 g, 65.74 mmol), Sub 2-15-1 (46.31 g, 131.48 mmol), Pd(PPh₃)₄ (2.28 g, 1.97 mmol), K₂CO₃ (9.09 g, 65.74 mmol) were added in a round bottom flask and after dissolving in THF (219 mL) and water (73 mL), 19.49 g (52%) of Sub 2-15 was obtained using the synthetic method of Sub 2-1.

3) Synthesis of P-51

Sub 1-3 (10.00 g, 30.28 mmol), Sub 2-15 (17.26 g, 30.28 mmol), Pd(PPh$_3$)$_4$ (1.05 g, 0.91 mmol), NaOH (2.42 g, 60.56 mmol) and THF (101 mL) and water (34 mL) were added in a round-bottom flask, and 15.87 g (71%) of product P-51 was obtained using the synthetic method of P-1.

7. Synthesis Example of P-69

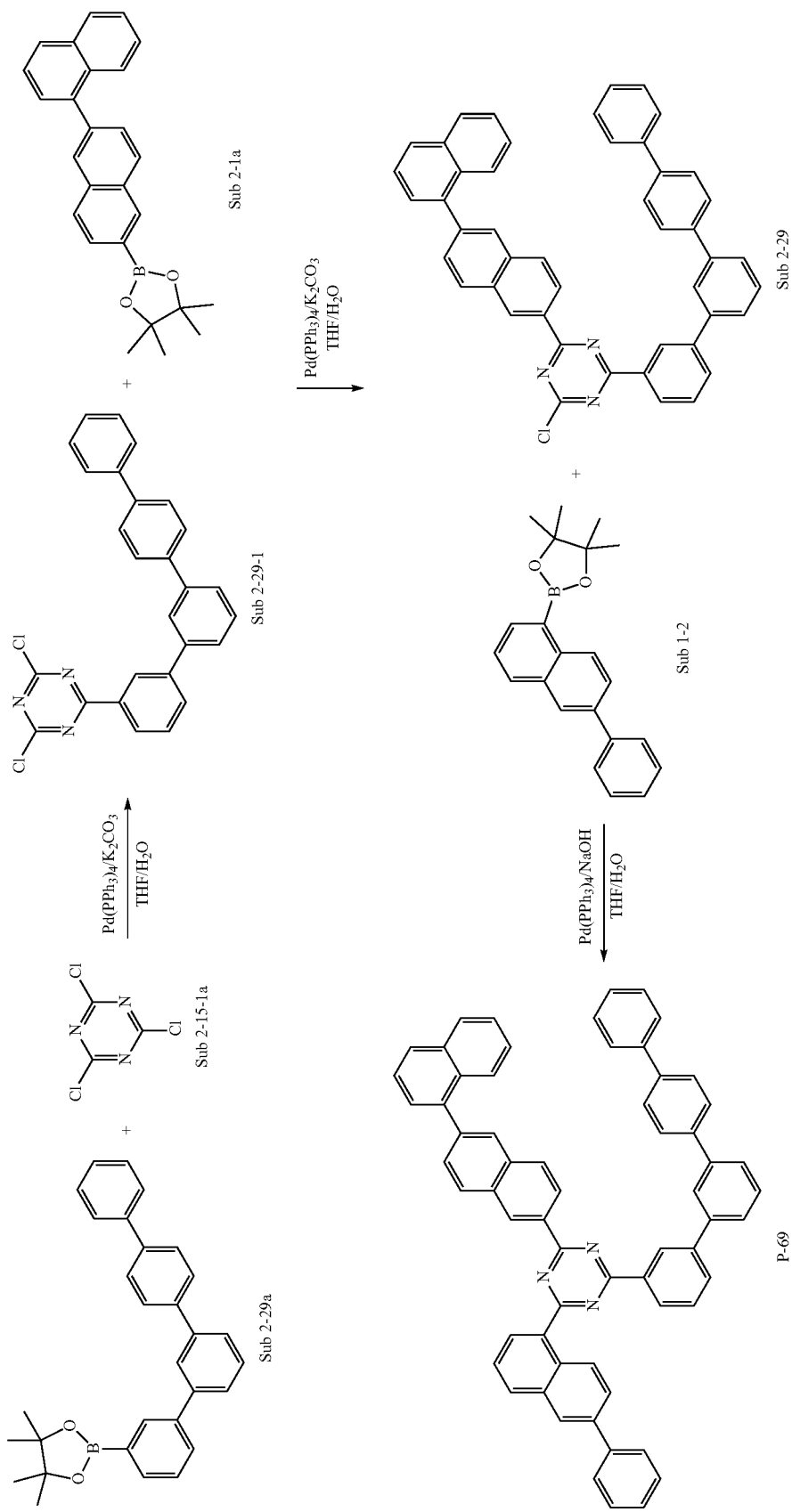

1) Synthesis of Sub 2-29-1

Sub 2-15-1a (127.95 g, 693.85 mmol), Sub 2-29a (150.00 g, 432.37 mmol), Pd(PPh$_3$)$_4$ (12.03 g, 10.41 mmol), K$_2$CO$_3$ (47.95 g, 346.93 mmol) were added in a round bottom flask and after dissolving in THF (1156 mL) and water (385 mL), 61.47 g (39%) of Sub 2-29-1 was obtained using the synthetic method of Sub 2-1.

2) Synthesis of Sub 2-29

Sub 2-1a (25.00 g, 65.74 mmol), Sub 2-29-1 (59.74 g, 131.48 mmol), Pd(PPh$_3$)$_4$ (2.28 g, 1.97 mmol), K$_2$CO$_3$ (9.09 g, 65.74 mmol) were added in a round bottom flask and after dissolving in THF (219 mL) and water (73 mL), 23.42 g (53%) of Sub 2-29 was obtained using the synthetic method of Sub 2-1.

3) Synthesis of P-69

Sub 1-2 (10.00 g, 30.28 mmol), Sub 2-29 (20.36 g, 30.28 mmol), Pd(PPh$_3$)$_4$ (1.05 g, 0.91 mmol), NaOH (2.42 g, 60.56 mmol) and THF (101 mL) and water (34 mL) were added in a round-bottom flask, and 19.08 g (75%) of product P-69 was obtained using the synthetic method of P-1.

8. Synthesis Example of P-80

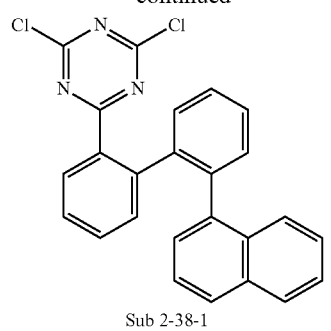
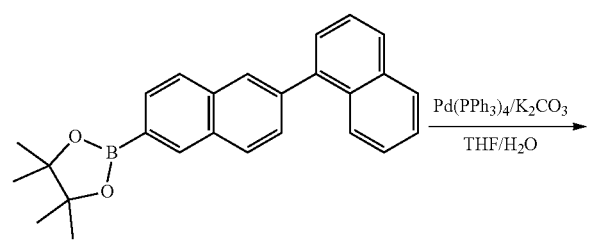
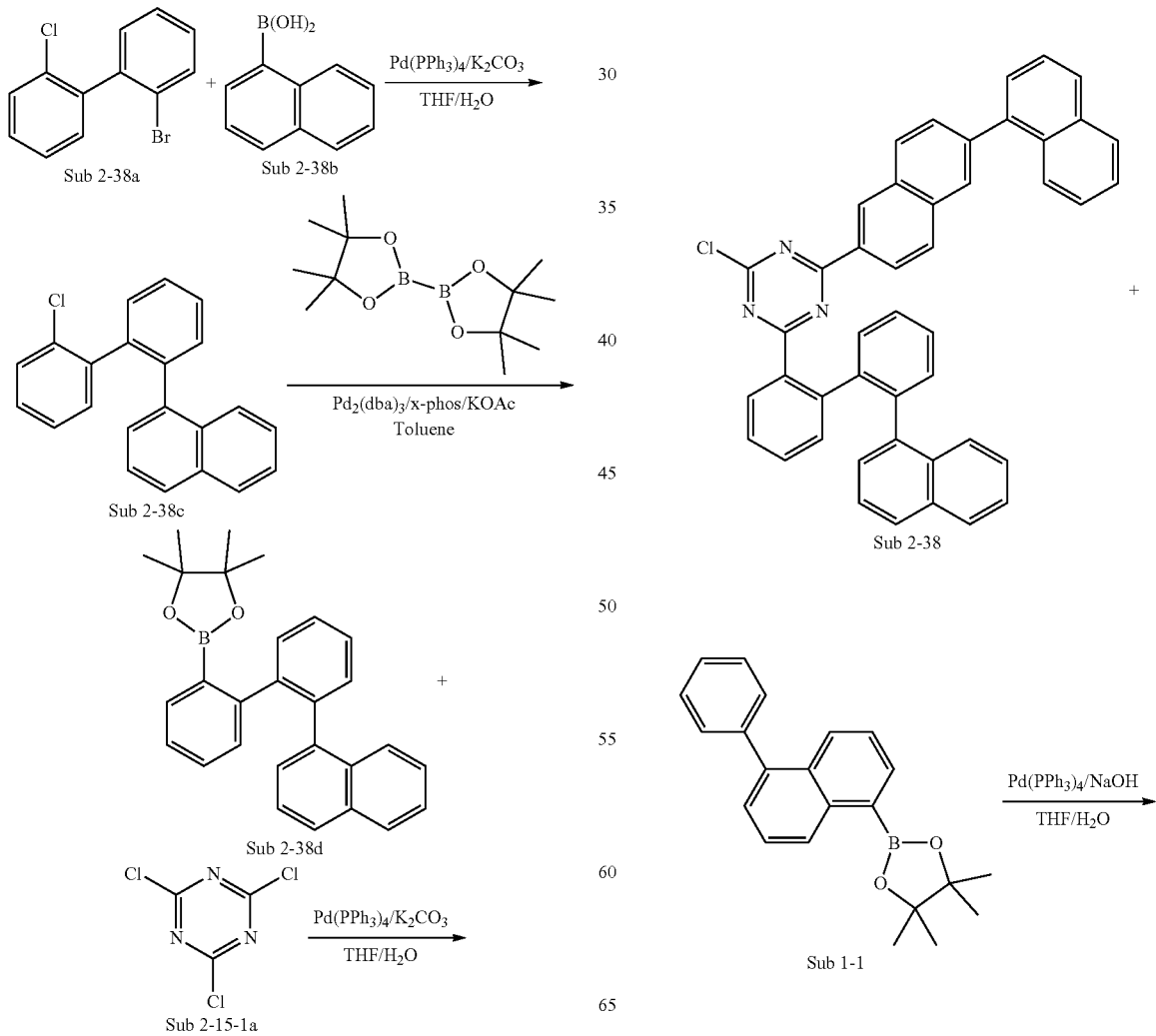

9. Synthesis Example of P-84

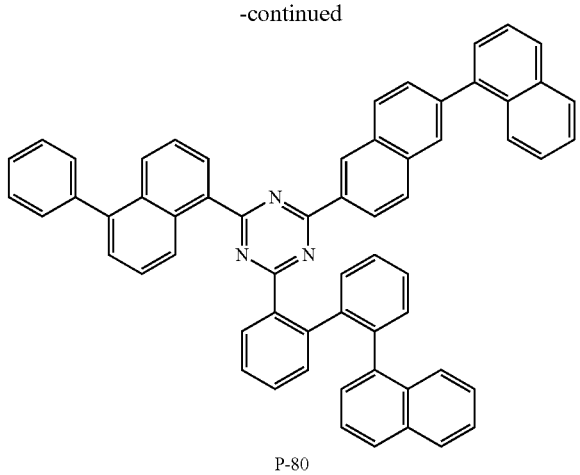

P-80

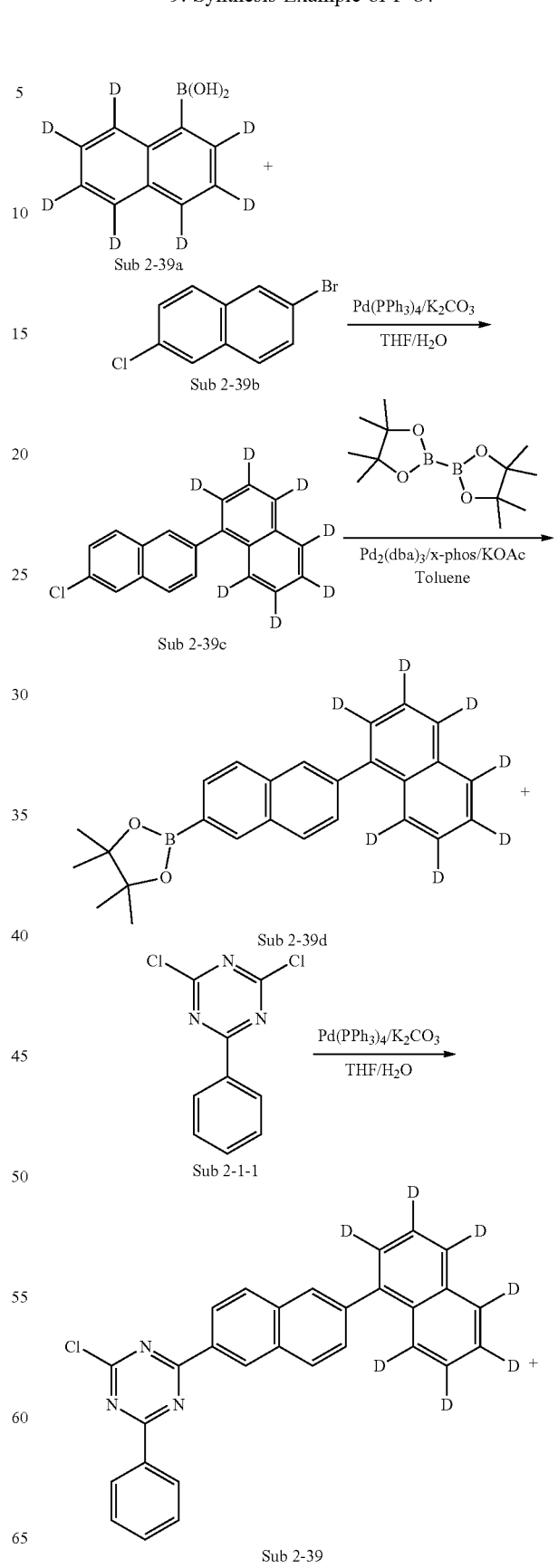

1) Synthesis of Sub 2-38c

Sub 2-38b (200.00 g, 1162.86 mmol), Sub 2-38a (311.12 g, 1162.86 mmol), Pd(PPh$_3$)$_4$ (40.31 g, 34.89 mmol), K$_2$CO$_3$ (321.44 g, 2325.72 mmol) were added in a round bottom flask and after dissolving in THF (3876 mL) and water (1292 mL), refluxed at 60° C. for 12 hours. After the reaction was completed, the reaction product was cooled to room temperature, extracted with CH$_2$C$_{12}$ and water, and treated with MgSO$_4$. The organic solvent was concentrated, and the resulting product was recrystallized using a silica gel column to obtain Sub 2-38c 314.83 g (86%).

2) Synthesis of Sub 2-38d

Sub 2-38c (300.00 g, 952.96 mmol) 0-|| 4,4,4',4',5,5,5',5'-octamethyl-2,2'-bi(1,3,2-dioxaborolane) (314.58 g, 1238.84 mmol), Pd$_2$(dba)$_3$ (26.18 g, 28.59 mmol), Xphos (27.26 g, 57.18 mmol), KOAc (187.07 g, 1905.91 mmol) were added to toluene (3177 mL) and stirred at 150° C. for 2 h. After the reaction was completed, the reaction solvent was removed and the concentrated organic matter was purified using a silica gel column or recrystallized to obtain 271.05 g (70%) of the product Sub 2-38d.

3) Synthesis of Sub 2-38-1

Sub 2-15-1a (226.91 g, 1230.53 mmol), Sub 2-38d (250.00 g, 615.26 mmol), Pd(PPh$_3$)$_4$ (21.33 g, 18.46 mmol), K$_2$CO$_3$ (85.04 g, 615.26 mmol) were added in a round bottom flask and after dissolving in THF (2051 mL) and water (684 mL), 84.33 g (32%) of Sub 2-38-1 was obtained using the synthetic method of Sub 2-1.

4) Synthesis of Sub 2-38

Sub 2-1a (35.00 g, 92.04 mmol), Sub 2-38-1 (78.84 g, 184.07 mmol), Pd(PPh$_3$)$_4$ (3.19 g, 2.76 mmol), K$_2$CO$_3$ (12.72 g, 92.04 mmol) were added in a round bottom flask and after dissolving in THF (307 mL) and water (102 mL), 32.11 g (54%) of Sub 2-38 was obtained using the synthetic method of Sub 2-1.

5) Synthesis of P-80

Sub 1-1 (15.00 g, 45.42 mmol), Sub 2-38 (29.35 g, 45.42 mmol), Pd(PPh$_3$)$_4$ (1.57 g, 1.36 mmol), NaOH (3.63 g, 90.85 mmol) and THF (151 mL) and water (50 mL) were added in a round-bottom flask, and 25.88 g (70%) of product P-80 was obtained using the synthetic method of P-1.

-continued

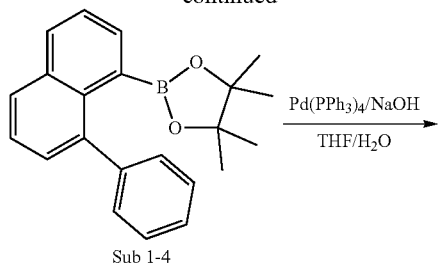

Sub 1-4

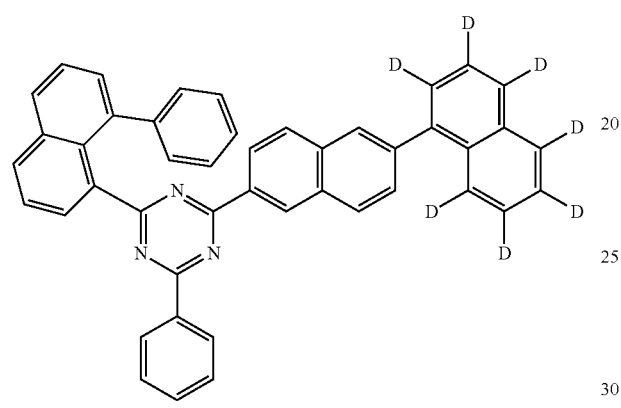

P-84

1) Synthesis of Sub 2-39c

Sub 2-39b (150.00 g, 837.85 mmol), Sub 2-39a (202.35 g, 837.85 mmol), Pd(PPh$_3$)$_4$ (29.05 g, 25.14 mmol), K$_2$CO$_3$ (231.60 g, 1675.70 mmol) were added in a round bottom flask. After dissolving in THF (2793 mL) and water (931 mL), 218.11 g (88%) of Sub 2-39c was obtained using the synthetic method of Sub 2-38c.

2) Synthesis of Sub 2-39d

Sub 2-39c (200.00 g, 676.09 mmol) 0-|| 4,4,4',4',5,5,5',5'-octamethyl-2,2'-bi(1,3,2-dioxaborolane) (223.18 g, 878.91 mmol), Pd$_2$(dba)$_3$ (18.57 g, 20.28 mmol), Xphos (19.34 g, 40.57 mmol), KOAc (132.72 g, 1352.17 mmol) were added to toluene (2254 mL) and 157.13 g (60%) of the product Sub 2-39d was obtained using the synthetic method of Sub 2-38d.

3) Synthesis of Sub 2-39

Sub 2-39d (150.00 g, 387.26 mmol), Sub 2-1-1 (175.09 g, 774.51 mmol), Pd(PPh$_3$)$_4$ (13.42 g, 11.62 mmol), K$_2$CO$_3$ (53.52 g, 387.26 mmol) were added in a round bottom flask and after dissolving in THF (1291 mL) and water (430 mL), 85.58 g (49%) of Sub 2-39 was obtained using the synthetic method of Sub 2-1.

4) Synthesis of P-84

Sub 1-4 (50.00 g, 151.41 mmol), Sub 2-39 (68.28 g, 151.41 mmol), Pd(PPh$_3$)$_4$ (5.25 g, 4.54 mmol), NaOH (12.11 g, 302.82 mmol) and THF (505 mL) and water (168 mL) were added in a round-bottom flask, and 75.89 g (81%) of product P-84 was obtained using the synthetic method of P-1.

10. Synthesis Example of P-85

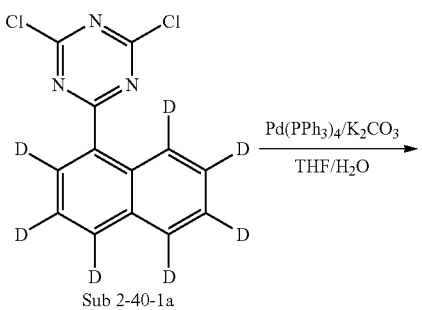

Sub 2-1a

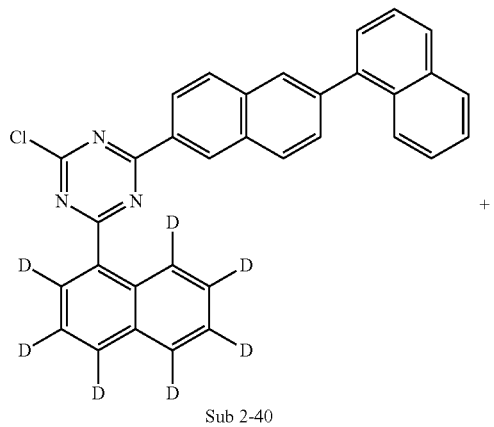

Sub 2-40-1a

Sub 2-40

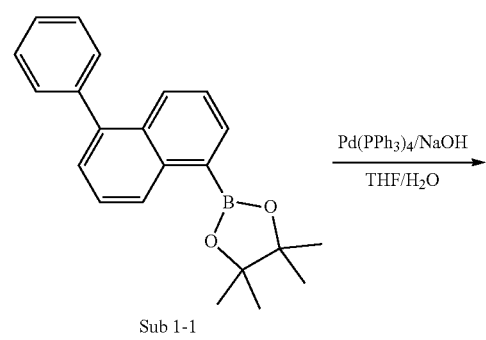

Sub 1-1

-continued

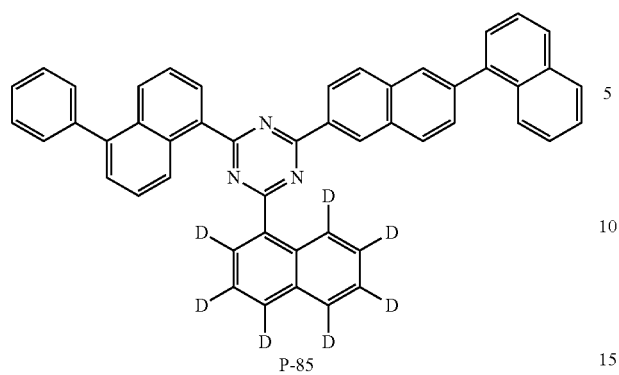

P-85

1) Synthesis of Sub 2-40

Sub 2-1a (100.00 g, 262.96 mmol), Sub 2-40-1a (148.92 g, 525.91 mmol), Pd(PPh$_3$)$_4$ (9.12 g, 7.89 mmol), K$_2$CO$_3$ (36.34 g, 262.96 mmol) were added in a round bottom flask and after dissolving in THF (877 mL) and water (292 mL), 72.46 g (55%) of Sub 2-40 was obtained using the synthetic method of Sub 2-1.

2) Synthesis of P-85

Sub 1-1 (40.00 g, 121.13 mmol), Sub 2-40 (60.69 g, 121.13 mmol), Pd(PPh$_3$)$_4$ (4.20 g, 3.63 mmol), NaOH (9.69 g, 242.26 mmol) and THF (404 mL) and water (135 mL) were added in a round-bottom flask, and 64.81 g (80%) of product P-85 was obtained using the synthetic method of P-1.

11. Synthesis Example of P-98

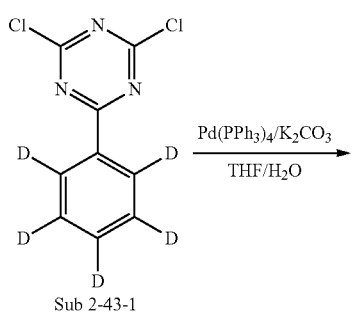

Sub 2-1a

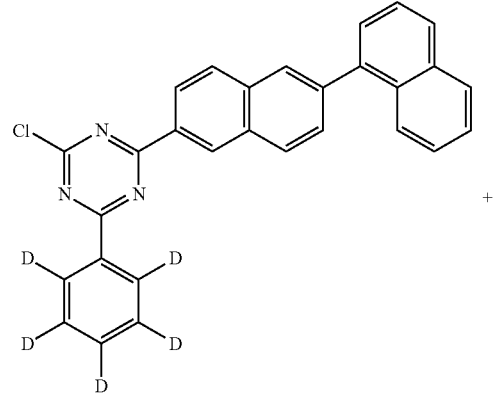

Sub 2-43

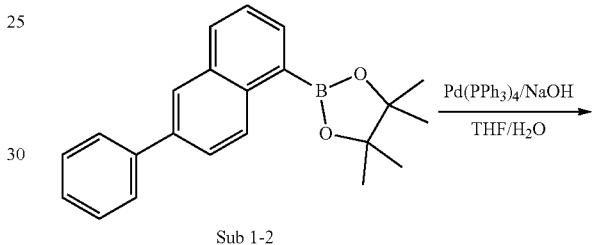

Sub 1-2

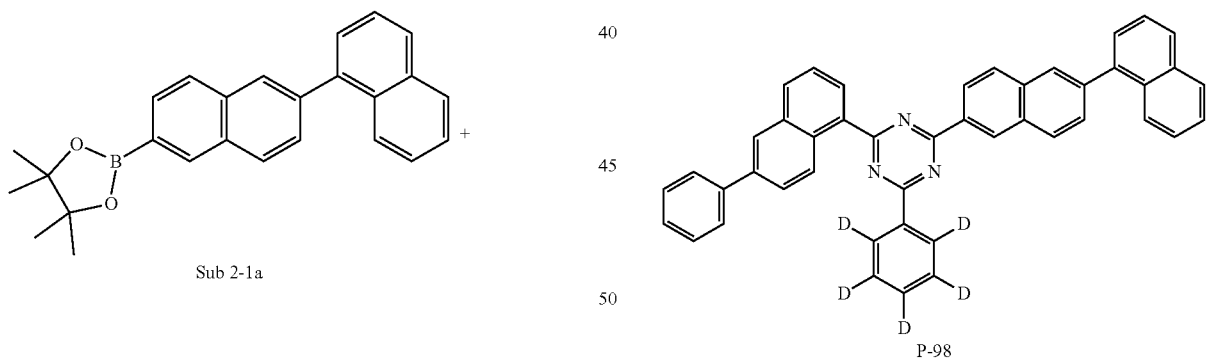

P-98

1) Synthesis of Sub 2-43

Sub 2-1a (100.00 g, 262.96 mmol), Sub 2-43-1 (121.53 g, 525.91 mmol), Pd(PPh$_3$)$_4$ (9.12 g, 7.89 mmol), K$_2$CO$_3$ (36.34 g, 262.96 mmol) were added in a round bottom flask and after dissolving in THF (877 mL) and water (292 mL), 56.67 g (48%) of Sub 2-43 was obtained using the synthetic method of Sub 2-1.

2) Synthesis of P-98

Sub 1-2 (40 g, 121.13 mmol), Sub 2-43 (54.38 g, 121.13 mmol), Pd(PPh$_3$)$_4$ (4.20 g, 3.63 mmol), NaOH (9.69 g, 242.26 mmol) and THF (404 mL) and water (135 mL) were added in a round-bottom flask, and 61.26 g (82%) of product P-98 was obtained using the synthetic method of P-1.

12. Synthesis Example of P-111
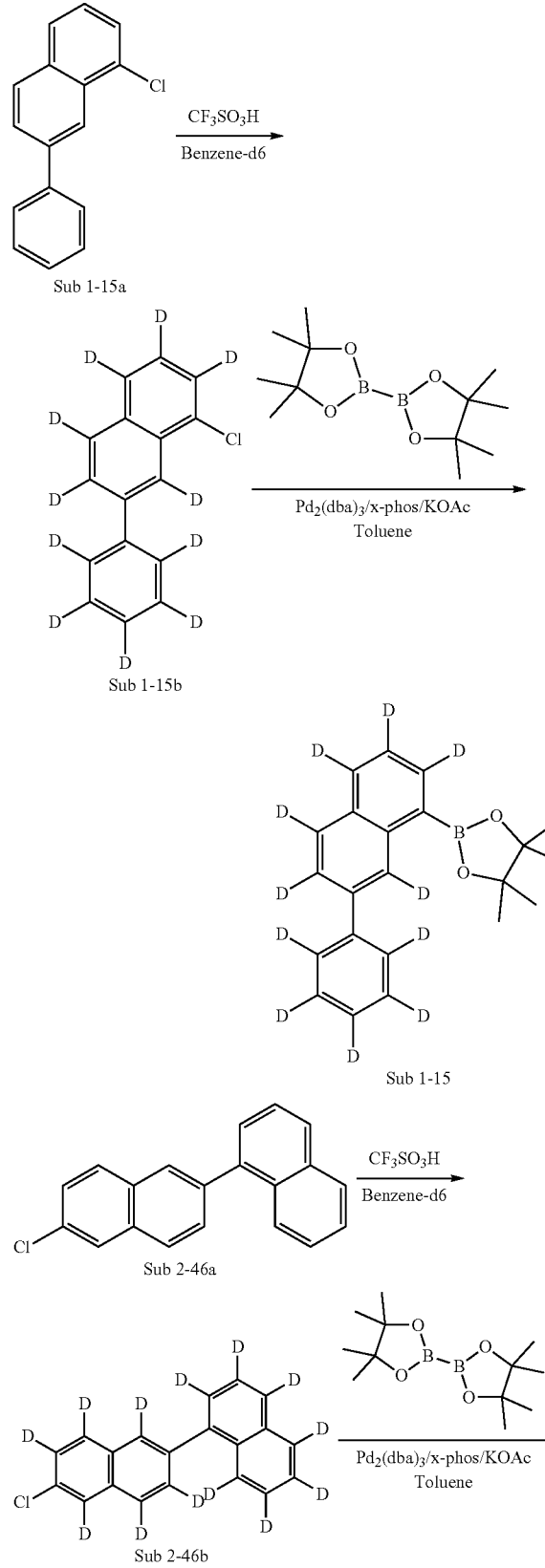
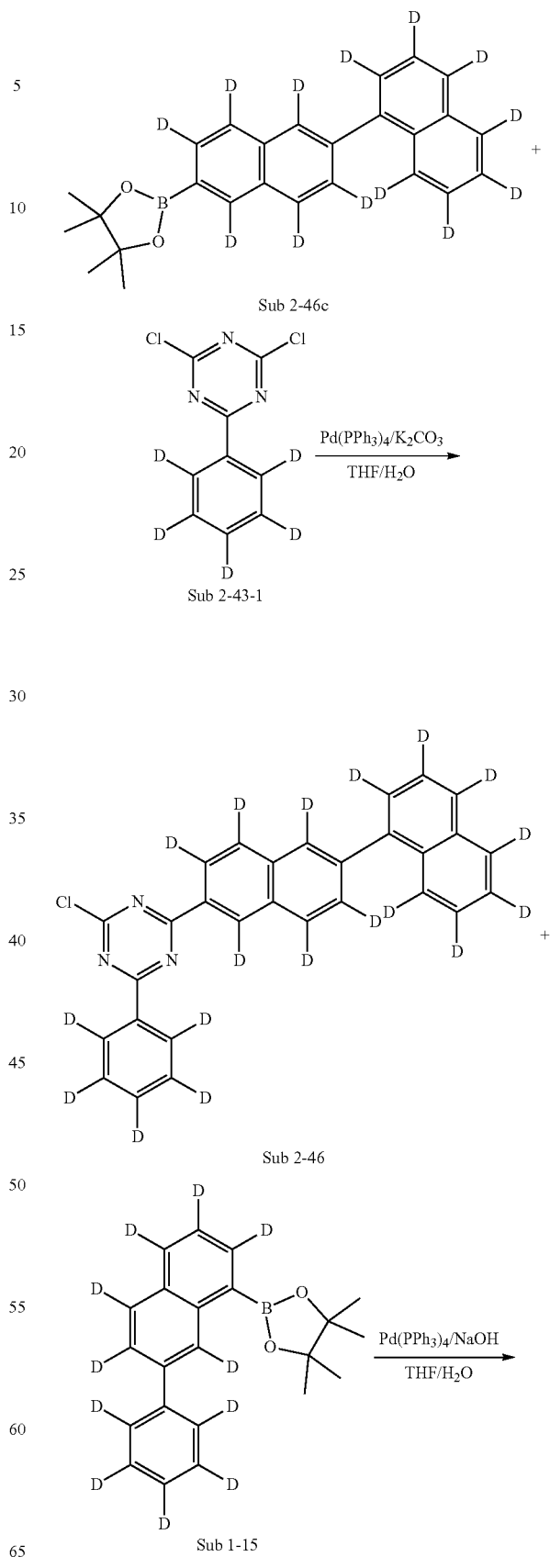

-continued

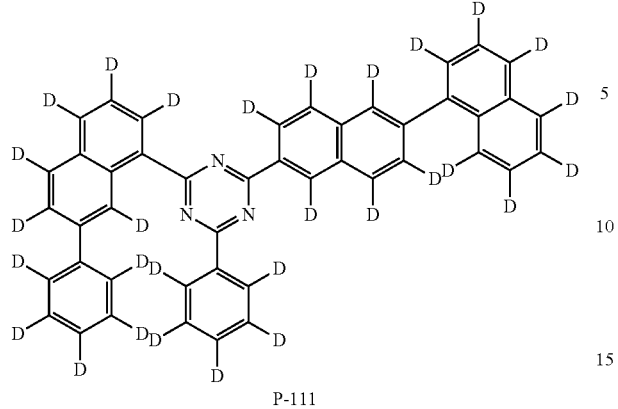

P-111

1) Synthesis of Sub 1-15b

Sub 1-15a (50.00 g, 209.46 mmol), Benzene-d6 (705.04 g, 8378.37 mmol) were added to a round-bottomed flask, an Ice-bath was installed, CF₃SO₃H (63.29 g, 418.92 mmol) was slowly added dropwise, and the mixture was reacted at room temperature for 8 hours. When the reaction is complete, a saturated Na₂CO₃ solution is added, the organic layer is extracted, and the reaction solvent is removed. The concentrated reactant is then passed through a silica gel column and recrystallized to obtain 49.70 g (95%) of the product Sub 1-15b. 2) Synthesis of Sub 1-15

Sub 2-15b (45.00 g, 180.16 mmol) 0-‖ 4,4,4',4',5,5,5',5'-octamethyl-2,2'-bi(1,3,2-dioxaborolane) (59.47 g, 234.21 mmol), Pd₂(dba)₃ (4.95 g, 5.40 mmol), Xphos (5.15 g, 10.81 mmol), KOAc (35.37 g, 360.32 mmol) were added to toluene (601 mL), and 43.04 g (70%) of the product Sub 1-15 was obtained using the synthetic method of Sub 2-38d.

3) Synthesis of Sub 2-46d

Sub 2-46a (100.00 g, 346.30 mmol), Benzene-d6 (1165.63 g, 13851.85 mmol) were added to a round-bottomed flask, an Ice-bath was installed, CF₃SO₃H (104.64 g, 692.59 mmol) was slowly added dropwise, and the mixture was reacted at room temperature for 8 hours. When the reaction is complete, a saturated Na₂CO₃ solution is added, the organic layer is extracted, and the reaction solvent is removed. The concentrated reactant is then passed through a silica gel column and recrystallized to obtain 94.08 g (90%) of the product Sub 2-46b.

4) Synthesis of Sub 2-46c

Sub 2-46b (90.00 g, 298.16 mmol), 4,4,4',4',5,5,5',5'-octamethyl-2,2'-bi(1,3,2-dioxaborolane) (98.43 g, 387.61 mmol), Pd₂(dba)₃ (8.19 g, 8.94 mmol), Xphos (8.53 g, 17.89 mmol), KOAc (58.53 g, 596.32 mmol) were added in Toluene (994 mL), 82.10 g (70%) of Sub 2-46c was obtained using the synthetic method of Sub 2-38d.

5) Synthesis of Sub 2-46

Sub 2-46c (80.00 g, 203.37 mmol), Sub 2-43-1 (93.99 g, 406.74 mmol), Pd(PPh₃)₄ (7.05 g, 6.10 mmol), K₂CO₃ (28.11 g, 203.37 mmol) and THF (678 mL) and water (226 mL) were added in a round-bottom flask, and 50.74 g (54%) of product Sub 2-46 was obtained using the synthetic method of Sub 2-1.

6) Synthesis of P-111

Sub 1-15 (35.00 g, 102.55 mmol), Sub 2-46 (47.38 g, 102.55 mmol), Pd(PPh₃)₄ (3.56 g, 3.08 mmol), NaOH (8.20 g, 205.10 mmol) and THF (342 mL) and water (114 mL) were added in a round-bottom flask, and 49.95 g (76%) of product P-111 was obtained using the synthetic method of P-1.

Sub 1 of the reaction scheme 1 may be, but is not limited to, the compounds below, and the FD-MS (Field Desorption-Mass Spectrometry) values of compounds belonging to Sub 1 are as shown in Table 1.

Sub 1-1

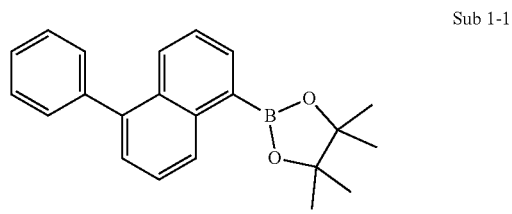

Sub 1-2

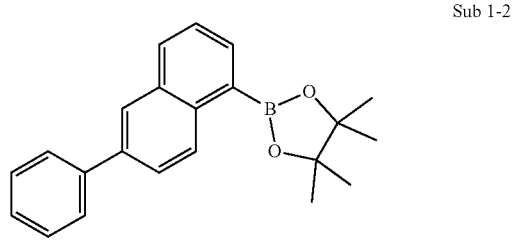

Sub 1-3

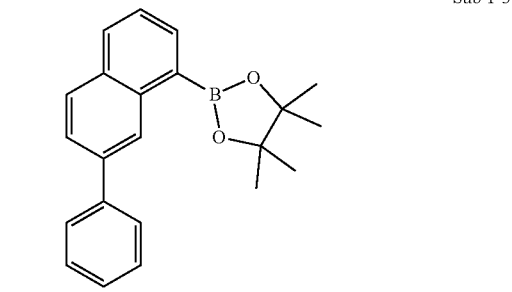

Sub 1-4

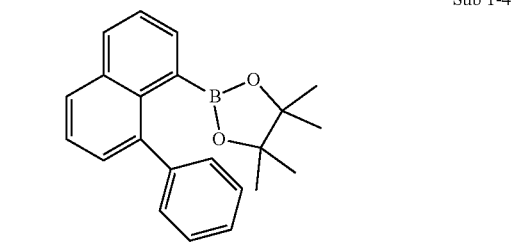

Sub 1-5

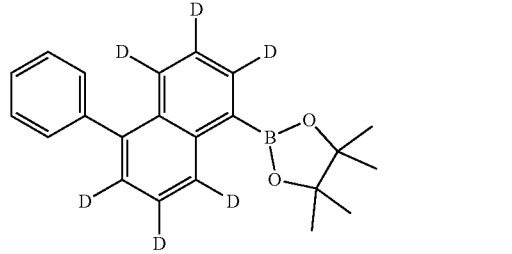

Sub 1-6

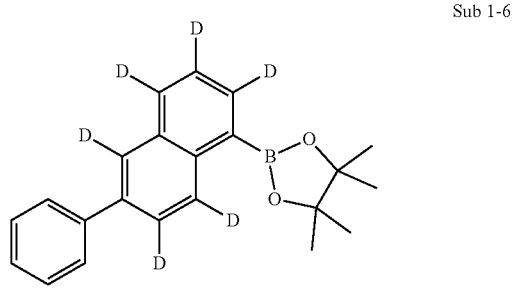

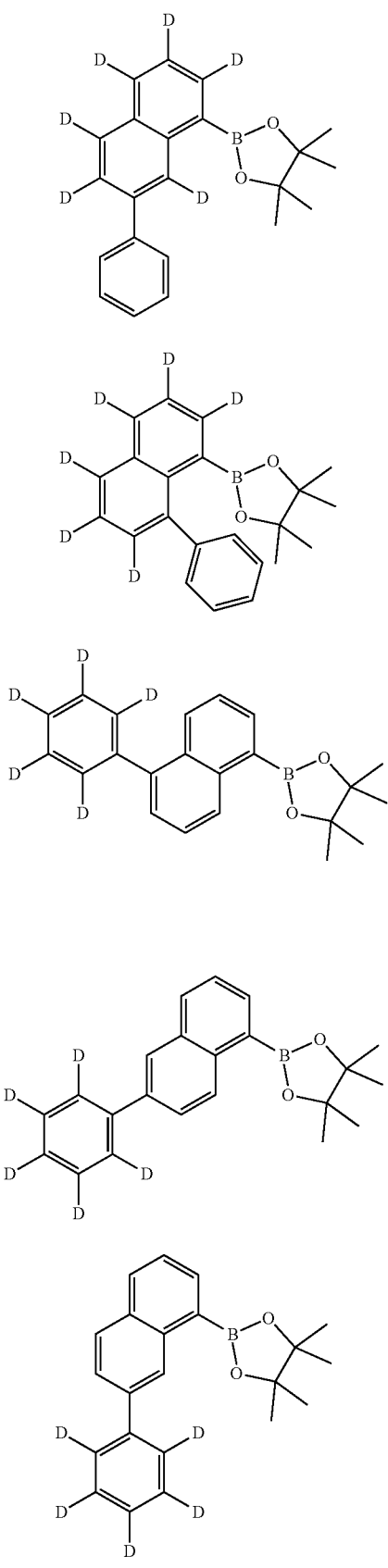
Sub 1-7
Sub 1-8
Sub 1-9
Sub 1-10
Sub 1-11
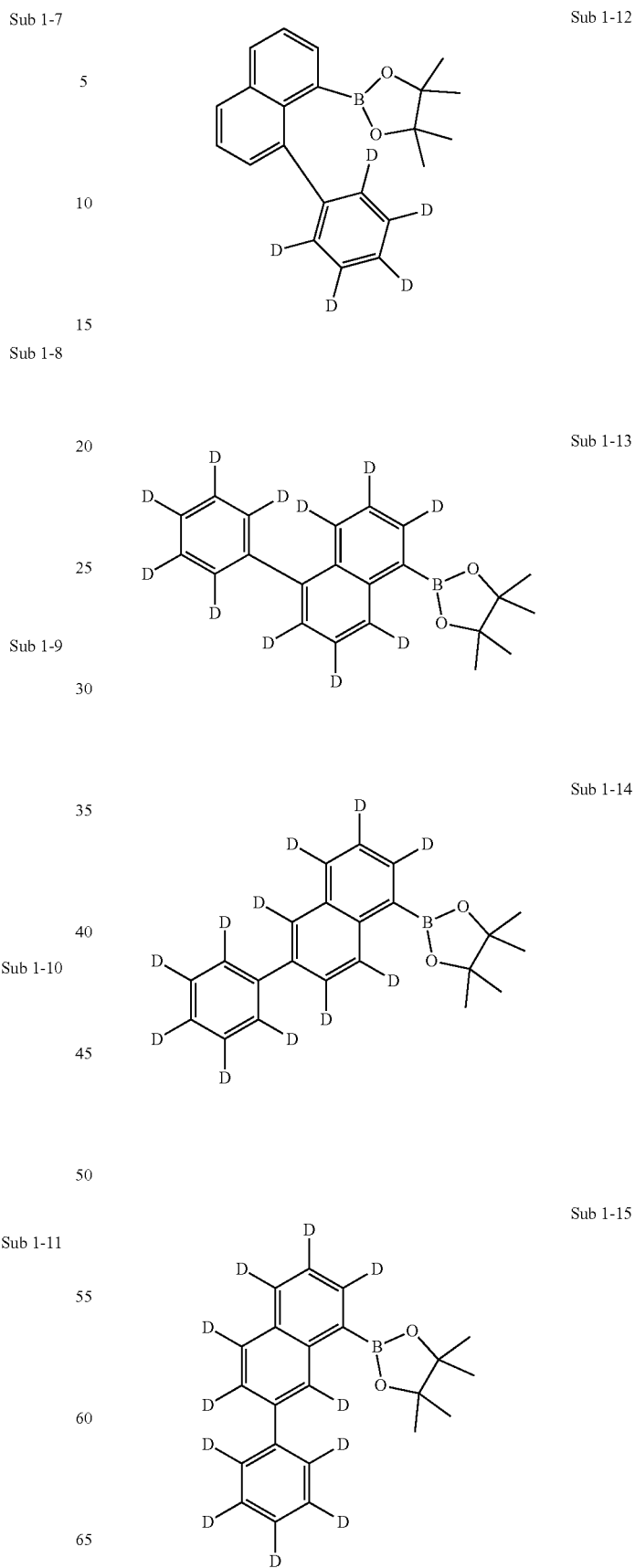
Sub 1-12
Sub 1-13
Sub 1-14
Sub 1-15

Sub 1-16

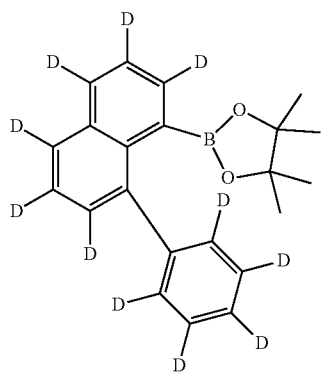

Sub 2-3

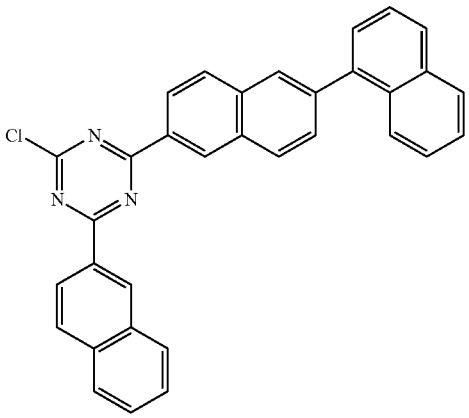

TABLE 1

| compound | FD-MS | compound | FD-MS |
|---|---|---|---|
| Sub1-1 | m/z = 330.18($C_{22}H_{23}BO_2$ = 330.23) | Sub1-2 | m/z = 330.18($C_{22}H_{23}BO_2$ = 330.23) |
| Sub1-3 | m/z = 330.18($C_{22}H_{23}BO_2$ = 330.23) | Sub1-4 | m/z = 330.18($C_{22}H_{23}BO_2$ = 330.23) |
| Sub1-5 | m/z = 336.22($C_{22}H_{17}D_6BO_2$ = 336.27) | Sub1-6 | m/z = 336.22($C_{22}H_{17}D_6BO_2$ = 336.27) |
| Sub1-7 | m/z = 336.22($C_{22}H_{17}D_6BO_2$ = 336.27) | Sub1-8 | m/z = 336.22($C_{22}H_{17}D_6BO_2$ = 336.27) |
| Sub1-9 | m/z = 335.21($C_{22}H_{18}D_5BO_2$ = 335.26) | Sub1-10 | m/z = 335.21($C_{22}H_{18}D_5BO_2$ = 335.26) |
| Sub1-11 | m/z = 335.21($C_{22}H_{18}D_5BO_2$ = 335.26) | Sub1-12 | m/z = 335.21($C_{22}H_{18}D_5BO_2$ = 335.26) |
| Sub1-13 | m/z = 341.25($C_{22}H_{12}D_{11}BO_2$ = 341.30) | Sub1-14 | m/z = 341.25($C_{22}H_{12}D_{11}BO_2$ = 341.30) |
| Sub1-15 | m/z = 341.25($C_{22}H_{12}D_{11}BO_2$ = 341.30) | Sub1-16 | m/z = 341.25($C_{22}H_{12}D_{11}BO_2$ = 341.30) |

Compounds belonging to the Sub 2 may be, but are not limited to, the compounds below, and Table 2 shows the FD-MS (Field Desorption-Mass Spectrometry) values of compounds belonging to Sub 2.

Sub 2-1

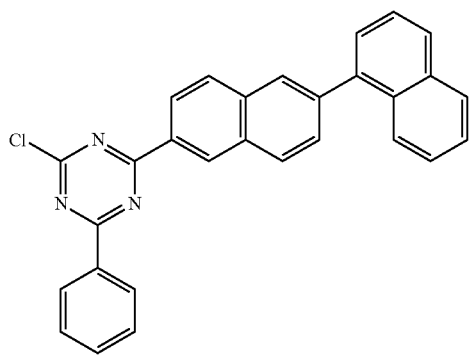

Sub 2-2

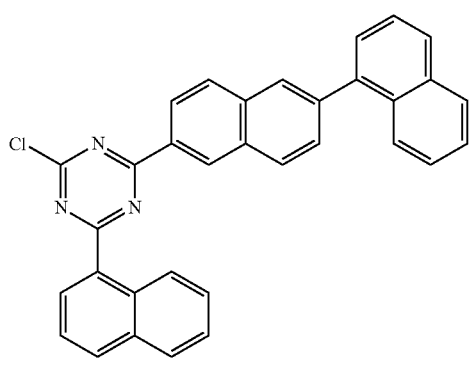

Sub 2-4

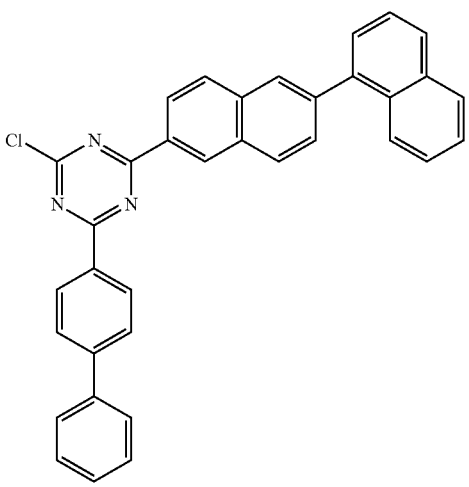

Sub 2-5
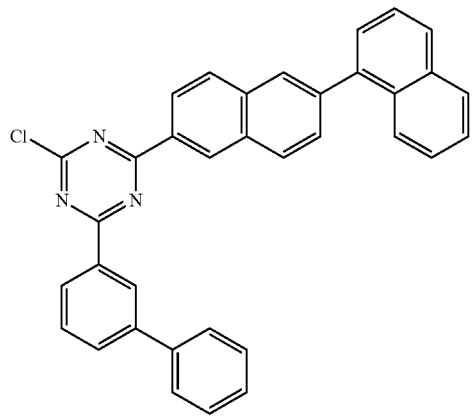
Sub 2-6
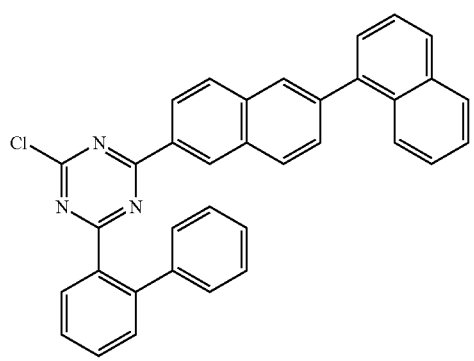
Sub 2-7
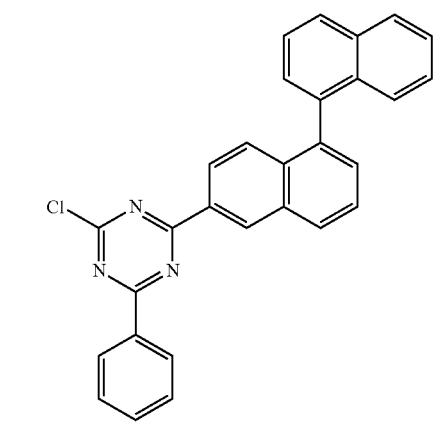
Sub 2-8
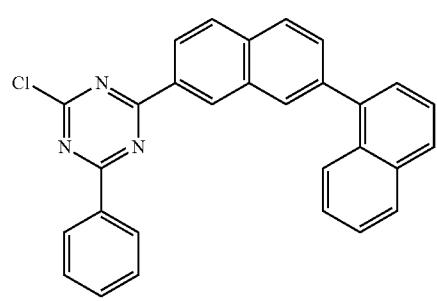
Sub 2-9
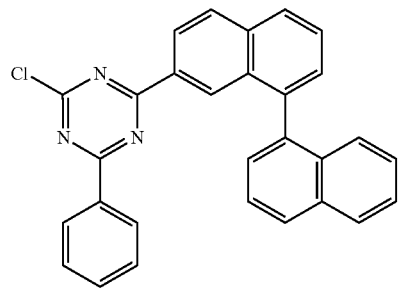
Sub 2-10
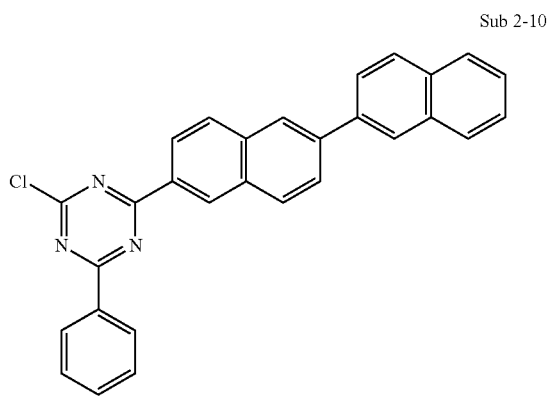
Sub 2-11
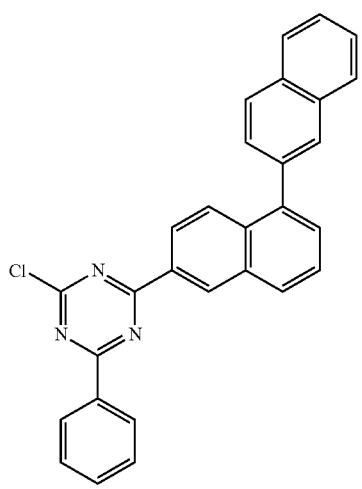
Sub 2-12
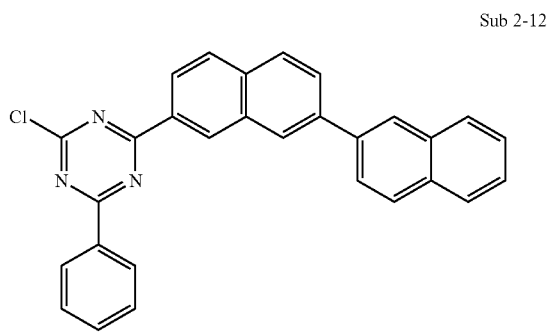

Sub 2-13
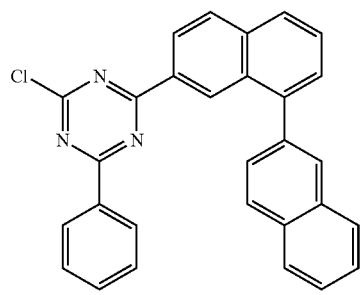
Sub 2-16
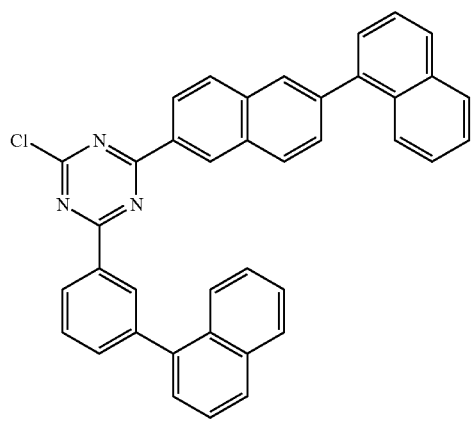
Sub 2-14
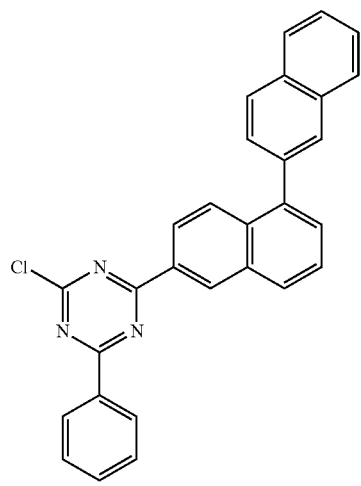
Sub 2-17
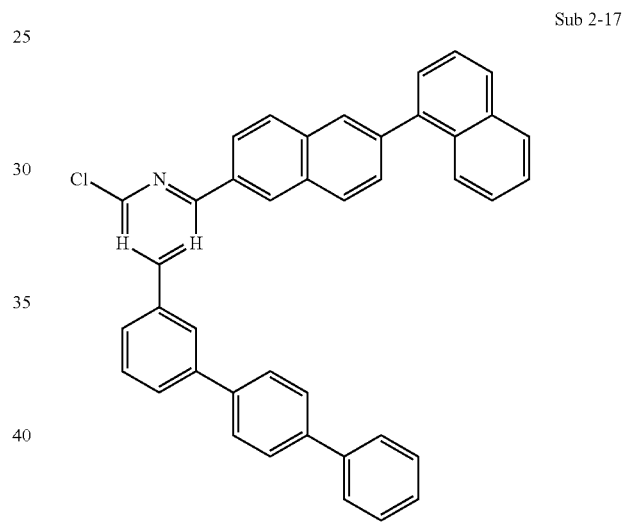
Sub 2-15
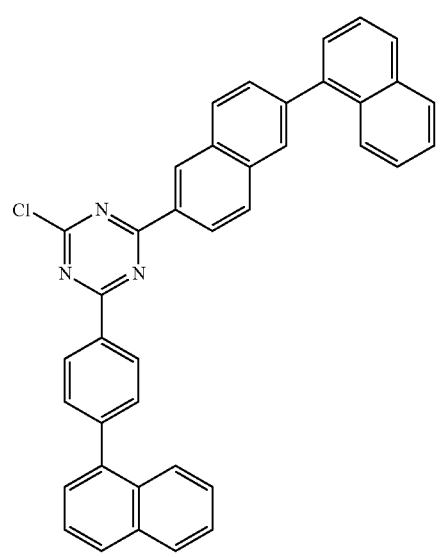
Sub 2-18
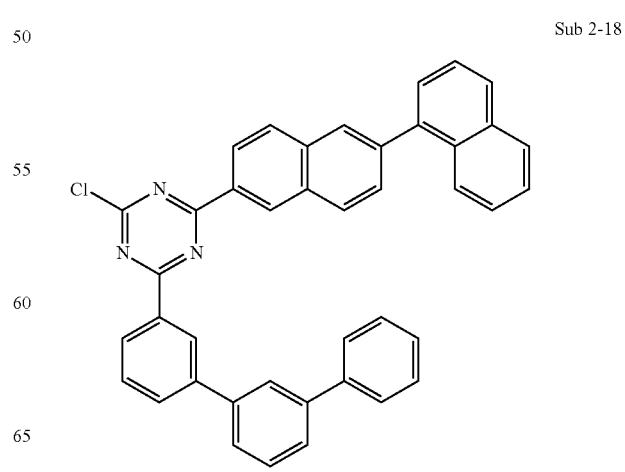

Sub 2-19
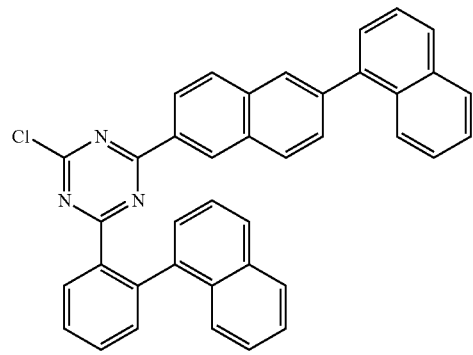
Sub 2-22
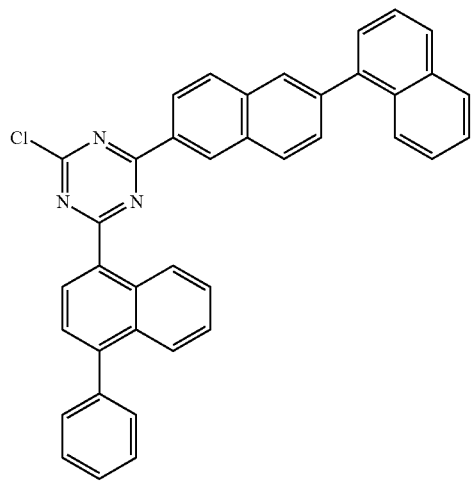
Sub 2-20
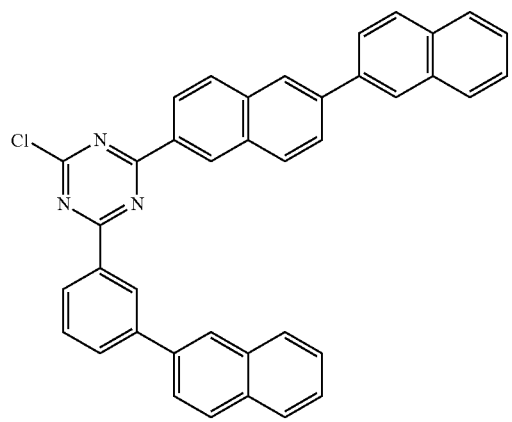
Sub 2-23
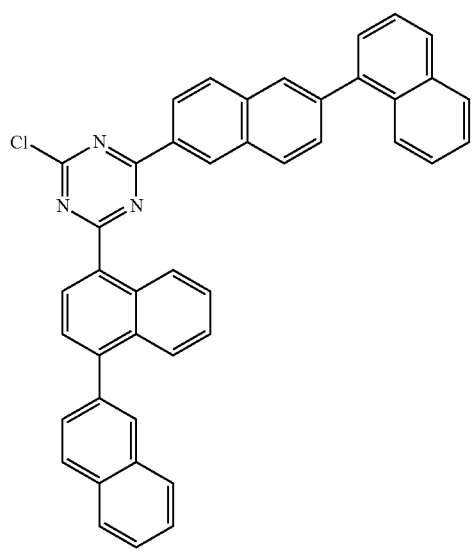
Sub 2-21
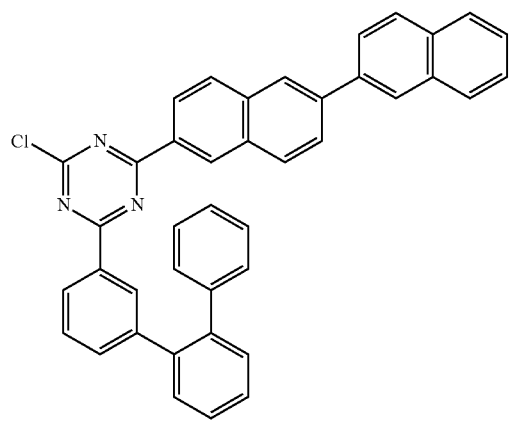
Sub 2-24
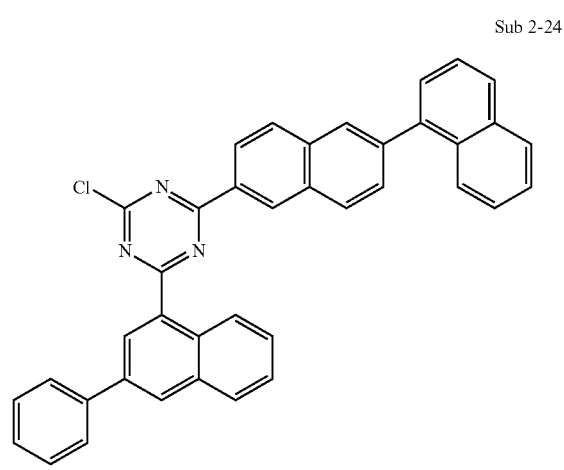

Sub 2-25
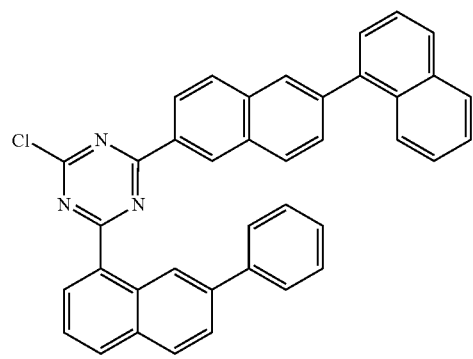
Sub 2-26
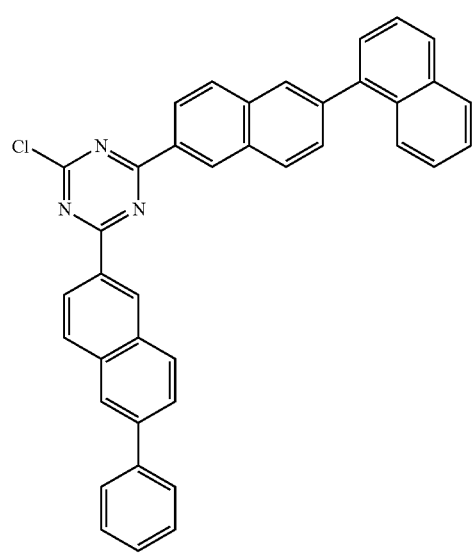
Sub 2-27
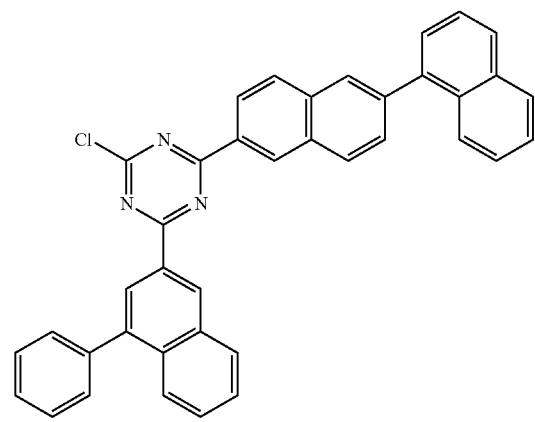
Sub 2-28
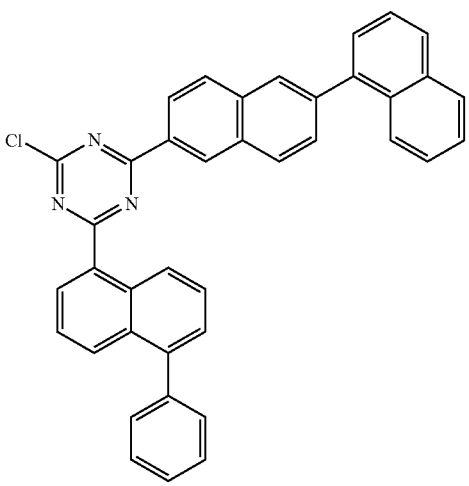
Sub 2-29
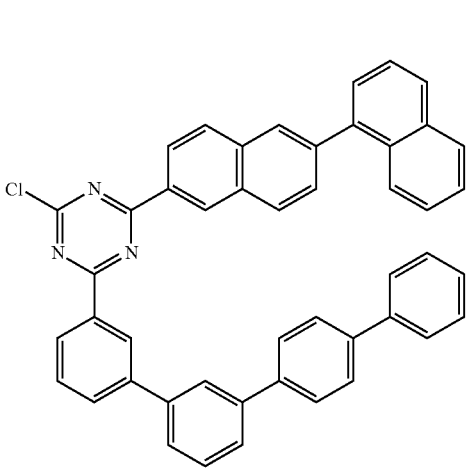
Sub 2-30
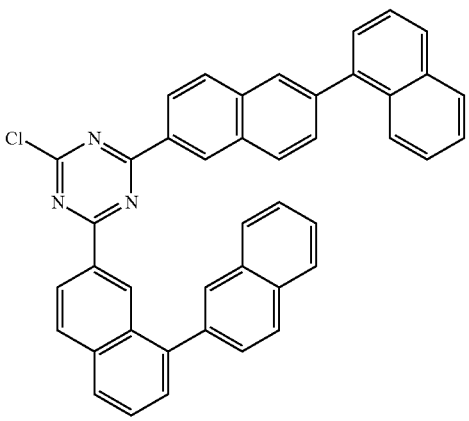

Sub 2-31
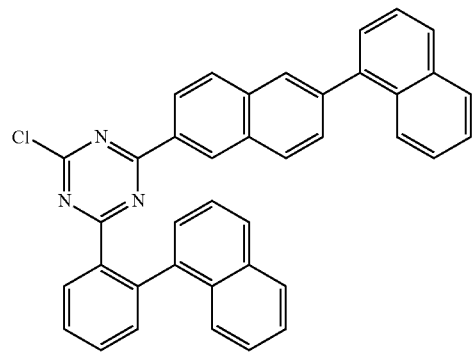
Sub 2-32
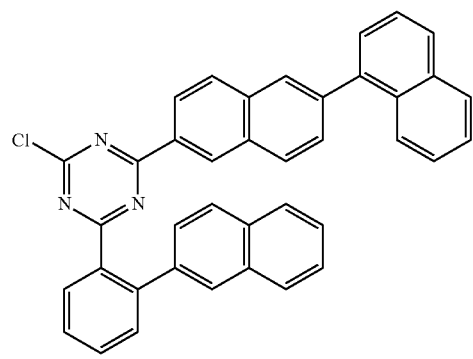
Sub 2-33
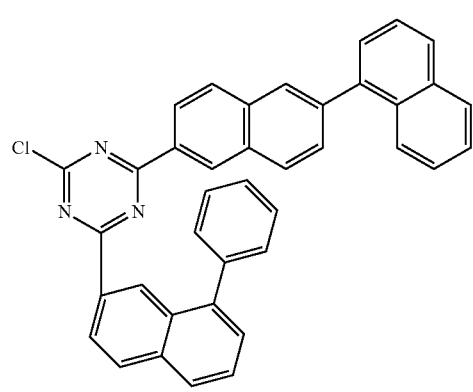
Sub 2-34
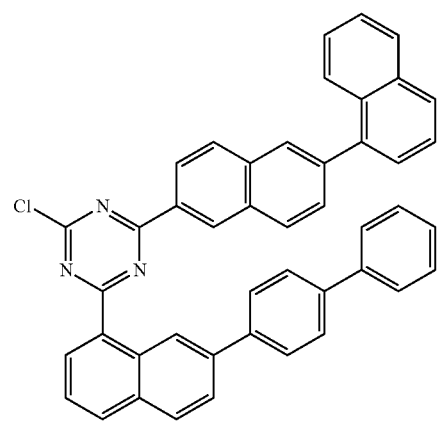
Sub 2-35
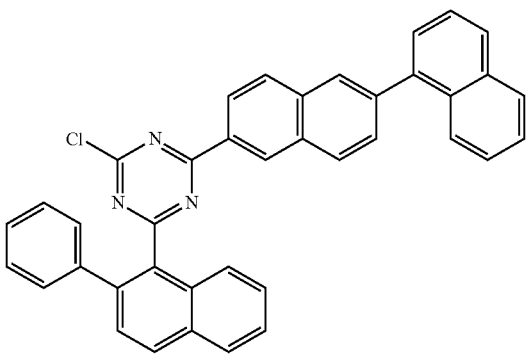
Sub 2-36
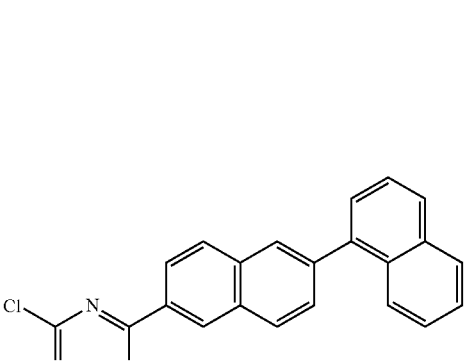
Sub 2-37
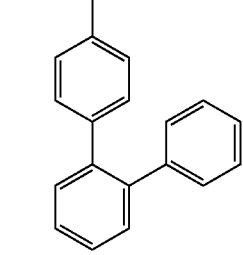

Sub 2-38
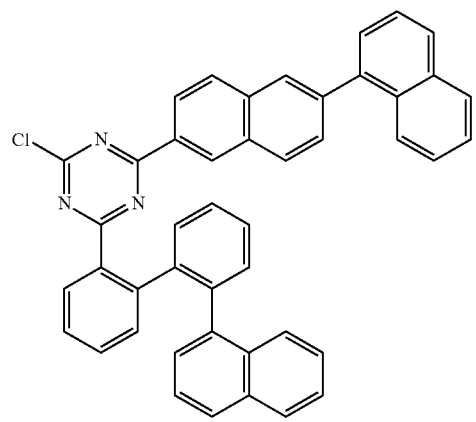
Sub 2-41
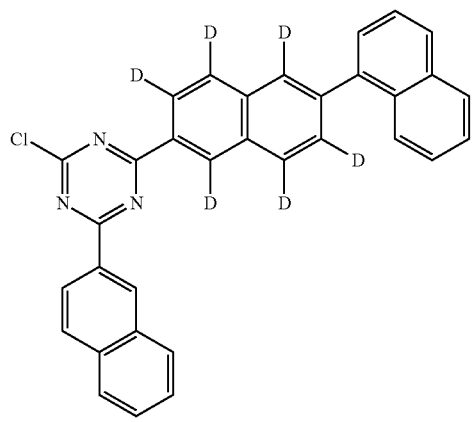
Sub 2-39
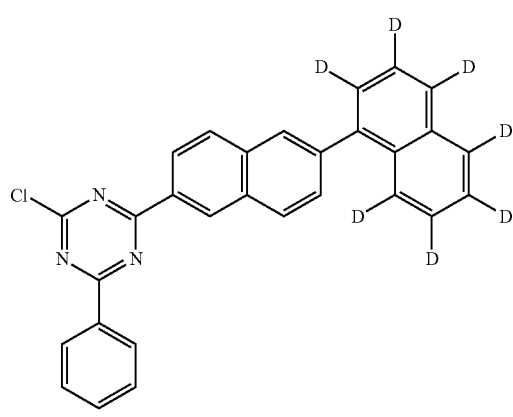
Sub 2-42
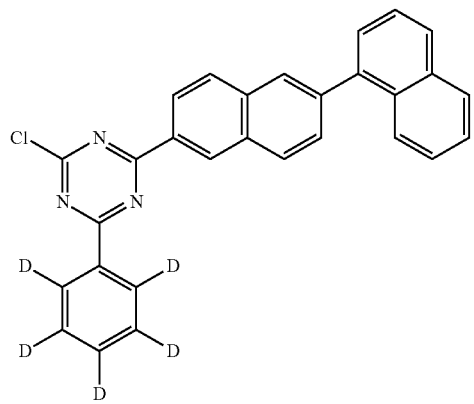
Sub 2-40
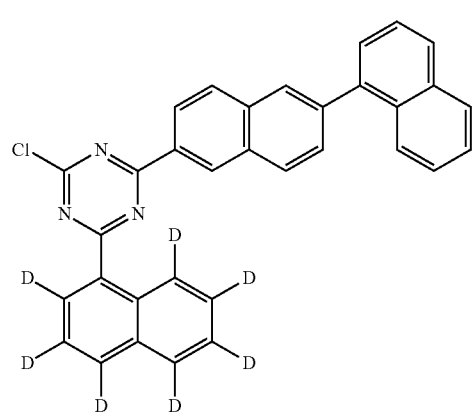
Sub 2-43

Sub 2-44
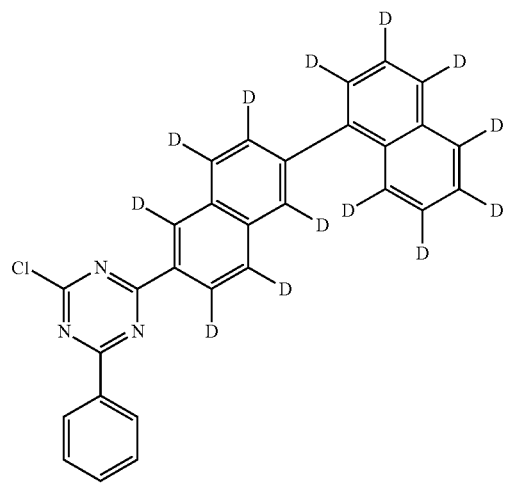
Sub 2-45
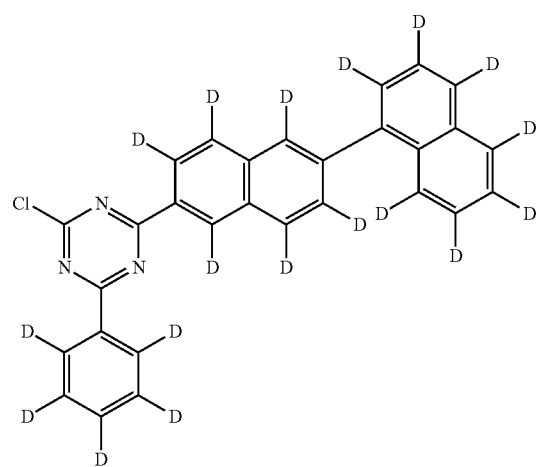
Sub 2-46
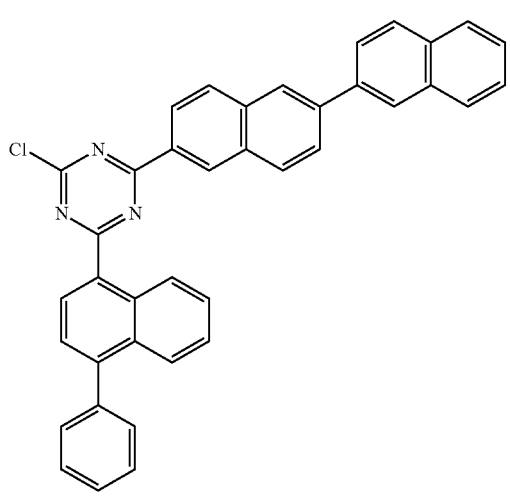
Sub 2-47
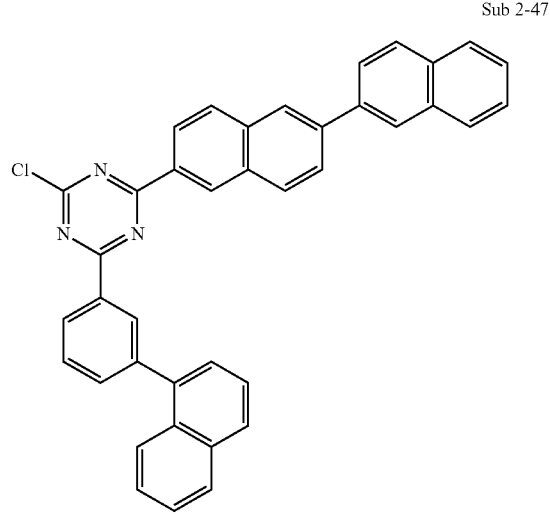
Sub 2-48
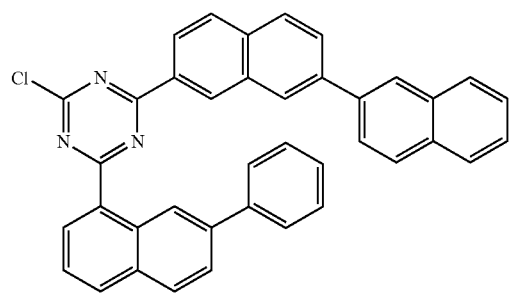
Sub 2-49
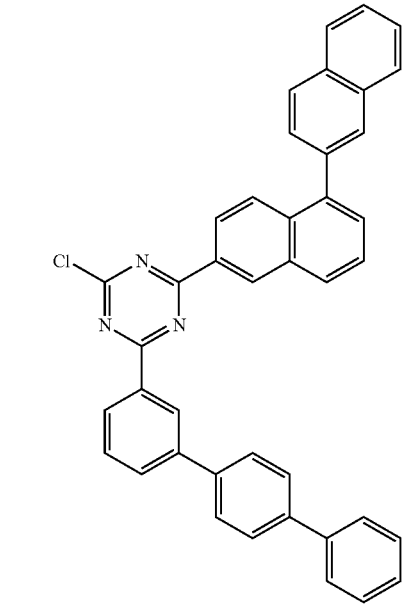

Sub 2-50
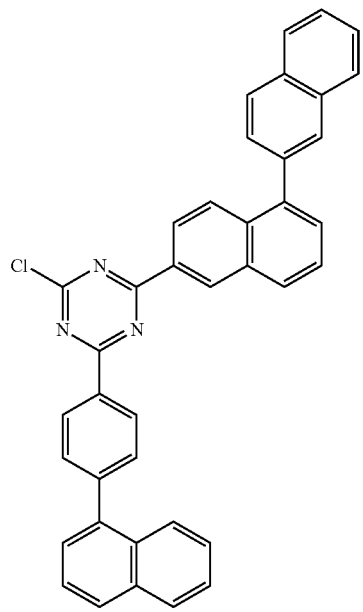
Sub 2-51
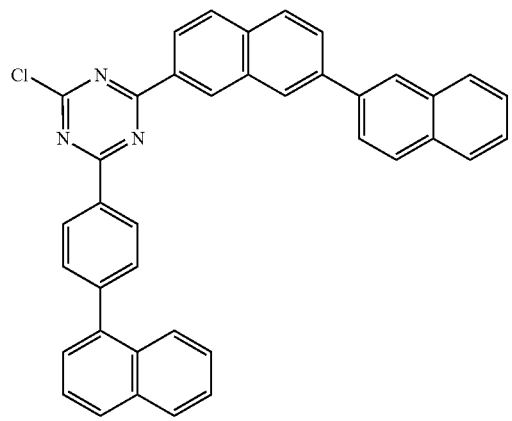
Sub 2-52
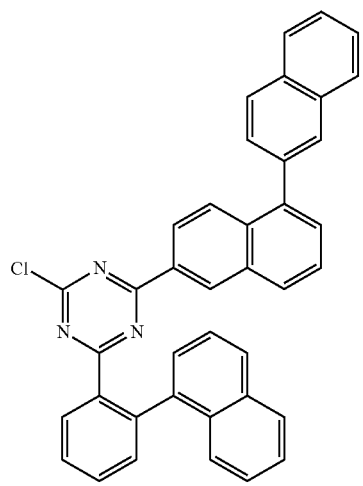
Sub 2-53
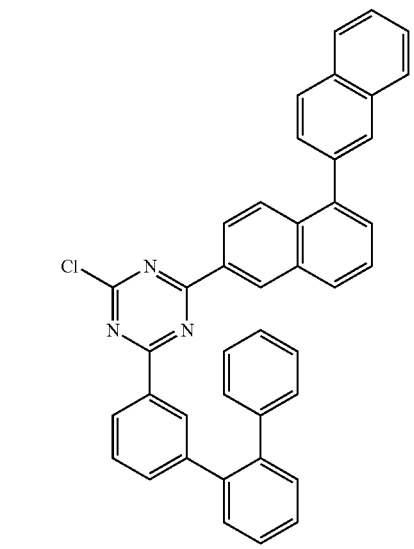
Sub 2-54
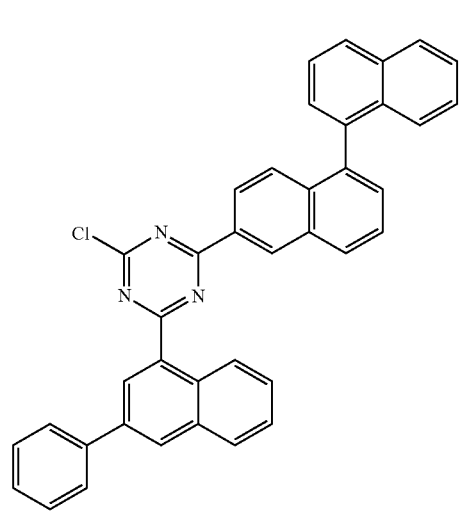
Sub 2-55
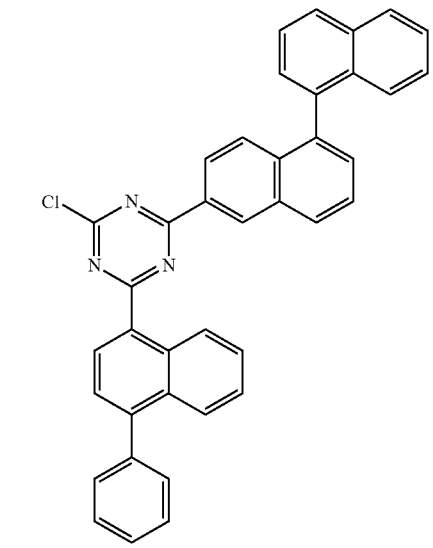

-continued
Sub 2-56
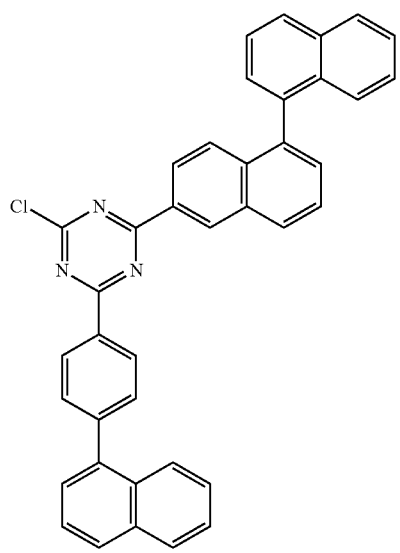
Sub 2-57
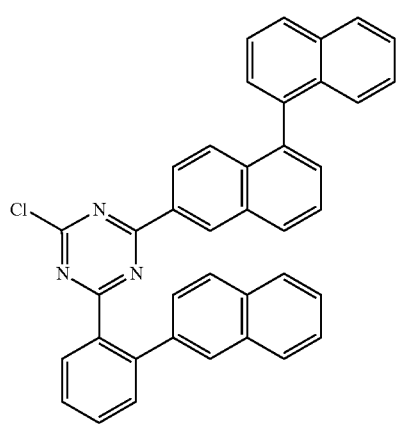
Sub 2-58
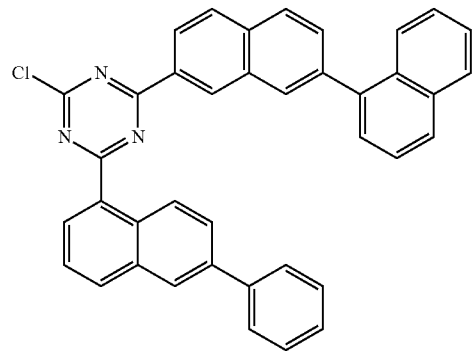
-continued
Sub 2-59
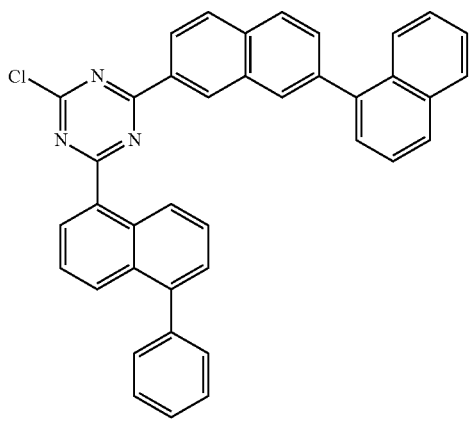
Sub 2-60
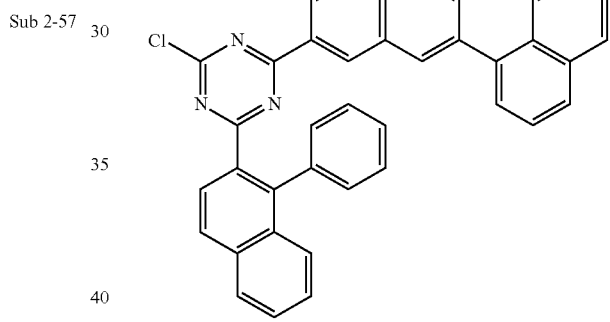
Sub 2-61
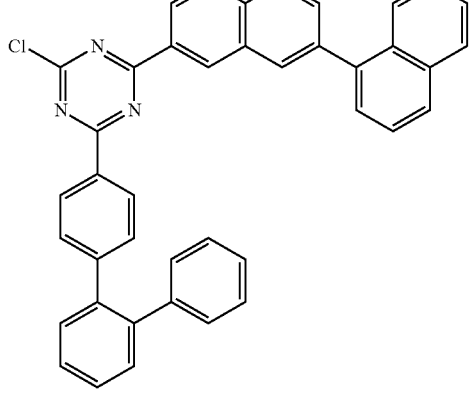

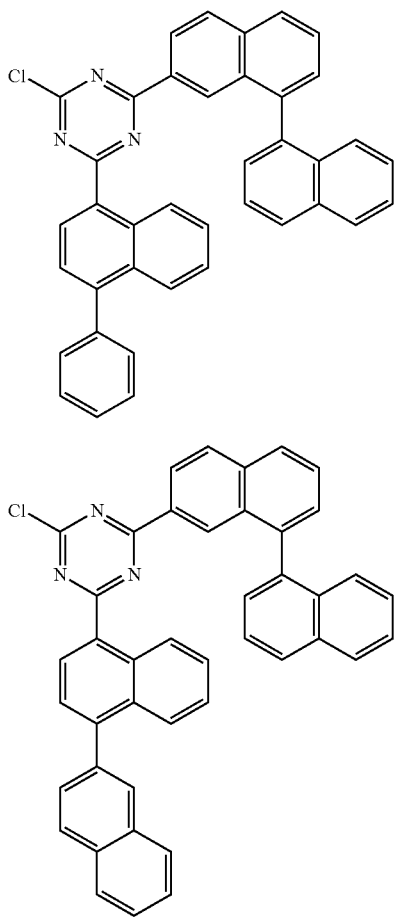

Sub 2-62

Sub 2-63

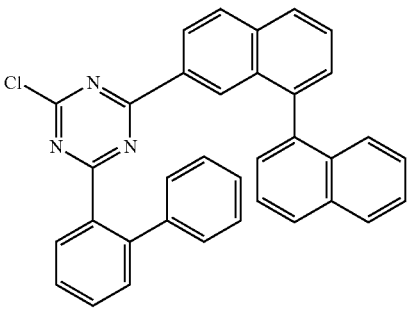

Sub 2-64

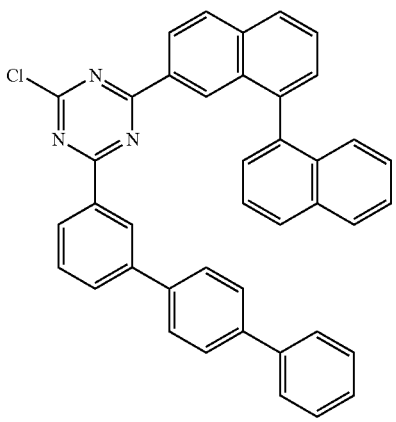

Sub 2-65

TABLE 2

| Compound | FD-MS | Compound | FD-MS |
|---|---|---|---|
| Sub2-1 | m/z = 443.12($C_{29}H_{18}ClN_3$ = 443.93) | Sub2-2 | m/z = 493.13($C_{33}H_{20}ClN_3$ = 493.99) |
| Sub2-3 | m/z = 493.13($C_{33}H_{20}ClN_3$ = 493.99) | Sub2-4 | m/z = 519.15($C_{35}H_{22}ClN_3$ = 520.03) |
| Sub2-5 | m/z = 519.15($C_{35}H_{22}ClN_3$ = 520.03) | Sub2-6 | m/z = 519.15($C_{35}H_{22}ClN_3$ = 520.03) |
| Sub2-7 | m/z = 443.12($C_{29}H_{18}ClN_3$ = 443.93) | Sub2-8 | m/z = 443.12($C_{29}H_{18}ClN_3$ = 443.93) |
| Sub2-9 | m/z = 443.12($C_{29}H_{18}ClN_3$ = 443.93) | Sub2-10 | m/z = 443.12($C_{29}H_{18}ClN_3$ = 443.93) |
| Sub2-11 | m/z = 443.12($C_{29}H_{18}ClN_3$ = 443.93) | Sub2-12 | m/z = 443.12($C_{29}H_{18}ClN_3$ = 443.93) |
| Sub2-13 | m/z = 443.12($C_{29}H_{18}ClN_3$ = 443.93) | Sub2-14 | m/z = 443.12($C_{29}H_{18}ClN_3$ = 443.93) |
| Sub2-15 | m/z = 569.17($C_{39}H_{24}ClN_3$ = 570.09) | Sub2-16 | m/z = 569.17($C_{39}H_{24}ClN_3$ = 570.09) |
| Sub2-17 | m/z = 595.18($C_{41}H_{26}ClN_3$ = 596.13) | Sub2-18 | m/z = 595.18($C_{41}H_{26}ClN_3$ = 596.13) |
| Sub2-19 | m/z = 569.17($C_{39}H_{24}ClN_3$ = 570.09) | Sub2-20 | m/z = 569.17($C_{39}H_{24}ClN_3$ = 570.09) |
| Sub2-21 | m/z = 595.18($C_{41}H_{26}ClN_3$ = 596.13) | Sub2-22 | m/z = 569.17($C_{39}H_{24}ClN_3$ = 570.09) |
| Sub2-23 | m/z = 619.18($C_{43}H_{26}ClN_3$ = 620.15) | Sub2-24 | m/z = 569.17($C_{39}H_{24}ClN_3$ = 570.09) |
| Sub2-25 | m/z = 569.17($C_{39}H_{24}ClN_3$ = 570.09) | Sub2-26 | m/z = 569.17($C_{39}H_{24}ClN_3$ = 570.09) |
| Sub2-27 | m/z = 569.17($C_{39}H_{24}ClN_3$ = 570.09) | Sub2-28 | m/z = 569.17($C_{39}H_{24}ClN_3$ = 570.09) |
| Sub2-29 | m/z = 671.21($C_{47}H_{30}ClN_3$ = 672.23) | Sub3-30 | m/z = 619.18($C_{43}H_{26}ClN_3$ = 620.15) |
| Sub2-31 | m/z = 569.17($C_{39}H_{24}ClN_3$ = 570.09) | Sub2-32 | m/z = 569.17($C_{39}H_{24}ClN_3$ = 570.09) |
| Sub2-33 | m/z = 569.17($C_{39}H_{24}ClN_3$ = 570.09) | Sub2-34 | m/z = 645.20($C_{45}H_{28}ClN_3$ = 646.19) |
| Sub2-35 | m/z = 569.17($C_{39}H_{24}ClN_3$ = 570.09) | Sub2-36 | m/z = 595.18($C_{41}H_{26}ClN_3$ = 596.13) |
| Sub2-37 | m/z = 645.20($C_{45}H_{28}ClN_3$ = 646.19) | Sub2-38 | m/z = 645.20($C_{45}H_{28}ClN_3$ = 646.19) |
| Sub2-39 | m/z = 450.16($C_{29}H_{11}D_7ClN_3$ = 450.98) | Sub2-40 | m/z = 500.18($C_{33}H_{13}D_7ClN_3$ = 501.04) |
| Sub2-41 | m/z = 499.17($C_{33}H_{14}D_6ClN_3$ = 500.03) | Sub2-42 | m/z = 450.16($C_{29}H_{11}D_7ClN_3$ = 450.98) |
| Sub2-43 | m/z = 448.15($C_{29}H_{13}D_5ClN_3$ = 448.96) | Sub2-44 | m/z = 456.20($C_{29}H_5D_{13}ClN_3$ = 457.01) |
| Sub2-45 | m/z = 461.23($C_{29}D_{18}ClN_3$ = 462.04) | Sub2-46 | m/z = 569.17($C_{39}H_{24}ClN_3$ = 570.09) |
| Sub2-47 | m/z = 569.17($C_{39}H_{24}ClN_3$ = 570.09) | Sub2-48 | m/z = 569.17($C_{39}H_{24}ClN_3$ = 570.09) |
| Sub2-49 | m/z = 595.18($C_{41}H_{26}ClN_3$ = 596.13) | Sub2-50 | m/z = 569.17($C_{39}H_{24}ClN_3$ = 570.09) |
| Sub2-51 | m/z = 569.17($C_{39}H_{24}ClN_3$ = 570.09) | Sub2-52 | m/z = 569.17($C_{39}H_{24}ClN_3$ = 570.09) |

TABLE 2-continued

| Compound | FD-MS | Compound | FD-MS |
| --- | --- | --- | --- |
| Sub2-53 | m/z = 595.18($C_{41}H_{26}ClN_3$ = 596.13) | Sub2-54 | m/z = 569.17($C_{39}H_{24}ClN_3$ = 570.09) |
| Sub2-55 | m/z = 569.17($C_{39}H_{24}ClN_3$ = 570.09) | Sub2-56 | m/z = 569.17($C_{39}H_{24}ClN_3$ = 570.09) |
| Sub2-57 | m/z = 569.17($C_{39}H_{24}ClN_3$ = 570.09) | Sub2-58 | m/z = 569.17($C_{39}H_{24}ClN_3$ = 570.09) |
| Sub2-59 | m/z = 569.17($C_{39}H_{24}ClN_3$ = 570.09) | Sub2-60 | m/z = 569.17($C_{39}H_{24}ClN_3$ = 570.09) |
| Sub2-61 | m/z = 595.18($C_{41}H_{26}ClN_3$ = 596.13) | Sub2-62 | m/z = 569.17($C_{39}H_{24}ClN_3$ = 570.09) |
| Sub2-63 | m/z = 619.18($C_{43}H_{26}ClN_3$ = 620.15) | Sub2-64 | m/z = 519.15($C_{35}H_{22}ClN_3$ = 520.03) |
| Sub2-65 | m/z = 595.18($C_{41}H_{26}ClN_3$ = 596.13) | | |

The FD-MS (Field Desorption-Mass Spectrometry) values of compounds P-1 to P-136 of the present invention manufactured according to the synthetic examples are as shown in Table 3.

TABLE 3

| Compound | FD-MS | Compound | FD-MS |
| --- | --- | --- | --- |
| P-1 | m/z = 611.24($C_{45}H_{29}N_3$ = 611.75) | P-2 | m/z = 611.24($C_{45}H_{29}N_3$ = 611.75) |
| P-3 | m/z = 611.24($C_{45}H_{29}N_3$ = 611.75) | P-4 | m/z = 611.24($C_{45}H_{29}N_3$ = 611.75) |
| P-5 | m/z = 661.25($C_{49}H_{31}N_3$ = 661.81) | P-6 | m/z = 661.25($C_{49}H_{31}N_3$ = 661.81) |
| P-7 | m/z = 661.25($C_{49}H_{31}N_3$ = 661.81) | P-8 | m/z = 661.25($C_{49}H_{31}N_3$ = 661.81) |
| P-9 | m/z = 661.25($C_{49}H_{31}N_3$ = 661.81) | P-10 | m/z = 661.25($C_{49}H_{31}N_3$ = 661.81) |
| P-11 | m/z = 661.25($C_{49}H_{31}N_3$ = 661.81) | P-12 | m/z = 661.25($C_{49}H_{31}N_3$ = 661.81) |
| P-13 | m/z = 687.27($C_{51}H_{33}N_3$ = 687.85) | P-14 | m/z = 687.27($C_{51}H_{33}N_3$ = 687.85) |
| P-15 | m/z = 687.27($C_{51}H_{33}N_3$ = 687.85) | P-16 | m/z = 687.27($C_{51}H_{33}N_3$ = 687.85) |
| P-17 | m/z = 687.27($C_{51}H_{33}N_3$ = 687.85) | P-18 | m/z = 687.27($C_{51}H_{33}N_3$ = 687.85) |
| P-19 | m/z = 687.27($C_{51}H_{33}N_3$ = 687.85) | P-20 | m/z = 687.27($C_{51}H_{33}N_3$ = 687.85) |
| P-21 | m/z = 687.27($C_{51}H_{33}N_3$ = 687.85) | P-22 | m/z = 687.27($C_{51}H_{33}N_3$ = 687.85) |
| P-23 | m/z = 687.27($C_{51}H_{33}N_3$ = 687.85) | P-24 | m/z = 687.27($C_{51}H_{33}N_3$ = 687.85) |
| P-25 | m/z = 611.24($C_{45}H_{29}N_3$ = 611.75) | P-26 | m/z = 611.24($C_{45}H_{29}N_3$ = 611.75) |
| P-27 | m/z = 611.24($C_{45}H_{29}N_3$ = 611.75) | P-28 | m/z = 611.24($C_{45}H_{29}N_3$ = 611.75) |
| P-29 | m/z = 611.24($C_{45}H_{29}N_3$ = 611.75) | P-30 | m/z = 611.24($C_{45}H_{29}N_3$ = 611.75) |
| P-31 | m/z = 611.24($C_{45}H_{29}N_3$ = 611.75) | P-32 | m/z = 611.24($C_{45}H_{29}N_3$ = 611.75) |
| P-33 | m/z = 611.24($C_{45}H_{29}N_3$ = 611.75) | P-34 | m/z = 611.24($C_{45}H_{29}N_3$ = 611.75) |
| P-35 | m/z = 611.24($C_{45}H_{29}N_3$ = 611.75) | P-36 | m/z = 611.24($C_{45}H_{29}N_3$ = 611.75) |
| P-37 | m/z = 611.24($C_{45}H_{29}N_3$ = 611.75) | P-38 | m/z = 611.24($C_{45}H_{29}N_3$ = 611.75) |
| P-39 | m/z = 611.24($C_{45}H_{29}N_3$ = 611.75) | P-40 | m/z = 611.24($C_{45}H_{29}N_3$ = 611.75) |
| P-41 | m/z = 611.24($C_{45}H_{29}N_3$ = 611.75) | P-42 | m/z = 611.24($C_{45}H_{29}N_3$ = 611.75) |
| P-43 | m/z = 611.24($C_{45}H_{29}N_3$ = 611.75) | P-44 | m/z = 611.24($C_{45}H_{29}N_3$ = 611.75) |
| P-45 | m/z = 611.24($C_{45}H_{29}N_3$ = 611.75) | P-46 | m/z = 611.24($C_{45}H_{29}N_3$ = 611.75) |
| P-47 | m/z = 611.24($C_{45}H_{29}N_3$ = 611.75) | P-48 | m/z = 611.24($C_{45}H_{29}N_3$ = 611.75) |
| P-49 | m/z = 737.28($C_{55}H_{35}N_3$ = 737.91) | P-50 | m/z = 737.28($C_{55}H_{35}N_3$ = 737.91) |
| P-51 | m/z = 737.28($C_{55}H_{35}N_3$ = 737.91) | P-52 | m/z = 737.28($C_{55}H_{35}N_3$ = 737.91) |
| P-53 | m/z = 763.30($C_{57}H_{37}N_3$ = 763.94) | P-54 | m/z = 763.30($C_{57}H_{37}N_3$ = 763.94) |
| P-55 | m/z = 737.28($C_{55}H_{35}N_3$ = 737.91) | P-56 | m/z = 737.28($C_{55}H_{35}N_3$ = 737.91) |
| P-57 | m/z = 763.30($C_{57}H_{37}N_3$ = 763.94) | P-58 | m/z = 737.28($C_{55}H_{35}N_3$ = 737.91) |
| P-59 | m/z = 737.28($C_{55}H_{35}N_3$ = 737.91) | P-60 | m/z = 737.28($C_{55}H_{35}N_3$ = 737.91) |
| P-61 | m/z = 787.30($C_{59}H_{37}N_3$ = 787.97) | P-62 | m/z = 737.28($C_{55}H_{35}N_3$ = 737.91) |
| P-63 | m/z = 737.28($C_{55}H_{35}N_3$ = 737.91) | P-64 | m/z = 737.28($C_{55}H_{35}N_3$ = 737.91) |
| P-65 | m/z = 737.28($C_{55}H_{35}N_3$ = 737.91) | P-66 | m/z = 737.28($C_{55}H_{35}N_3$ = 737.91) |
| P-67 | m/z = 737.28($C_{55}H_{35}N_3$ = 737.91) | P-68 | m/z = 737.28($C_{55}H_{35}N_3$ = 737.91) |
| P-69 | m/z = 839.33($C_{63}H_{41}N_3$ = 840.04) | P-70 | m/z = 787.30($C_{59}H_{37}N_3$ = 787.97) |
| P-71 | m/z = 737.28($C_{55}H_{35}N_3$ = 737.91) | P-72 | m/z = 737.28($C_{55}H_{35}N_3$ = 737.91) |
| P-73 | m/z = 687.27($C_{51}H_{33}N_3$ = 687.85) | P-74 | m/z = 687.27($C_{51}H_{33}N_3$ = 687.85) |
| P-75 | m/z = 737.28($C_{55}H_{35}N_3$ = 737.91) | P-76 | m/z = 813.31($C_{61}H_{39}N_3$ = 814.00) |
| P-77 | m/z = 737.28($C_{55}H_{35}N_3$ = 737.91) | P-78 | m/z = 763.30($C_{57}H_{37}N_3$ = 763.94) |
| P-79 | m/z = 813.31($C_{61}H_{39}N_3$ = 814.00) | P-80 | m/z = 813.31($C_{61}H_{39}N_3$ = 814.00) |
| P-81 | m/z = 618.28($C_{45}H_{22}D_7N_3$ = 618.79) | P-82 | m/z = 618.28($C_{45}H_{22}D_7N_3$ = 618.79) |
| P-83 | m/z = 618.28($C_{45}H_{22}D_7N_3$ = 618.79) | P-84 | m/z = 618.28($C_{45}H_{22}D_7N_3$ = 618.79) |
| P-85 | m/z = 668.30($C_{49}H_{24}D_7N_3$ = 668.85) | P-86 | m/z = 668.30($C_{49}H_{24}D_7N_3$ = 668.85) |
| P-87 | m/z = 668.30($C_{49}H_{24}D_7N_3$ = 668.85) | P-88 | m/z = 668.30($C_{49}H_{24}D_7N_3$ = 668.85) |
| P-89 | m/z = 673.33($C_{49}H_{19}D_{12}N_3$ = 673.88) | P-90 | m/z = 673.33($C_{49}H_{19}D_{12}N_3$ = 673.88) |
| P-91 | m/z = 673.33($C_{49}H_{19}D_{12}N_3$ = 673.88) | P-92 | m/z = 673.33($C_{49}H_{19}D_{12}N_3$ = 673.88) |
| P-93 | m/z = 618.28($C_{45}H_{22}D_7N_3$ = 618.79) | P-94 | m/z = 618.28($C_{45}H_{22}D_7N_3$ = 618.79) |
| P-95 | m/z = 618.28($C_{45}H_{22}D_7N_3$ = 618.79) | P-96 | m/z = 618.28($C_{45}H_{22}D_7N_3$ = 618.79) |
| P-97 | m/z = 616.27($C_{45}H_{24}D_5N_3$ = 616.78) | P-98 | m/z = 616.27($C_{45}H_{24}D_5N_3$ = 616.78) |
| P-99 | m/z = 616.27($C_{45}H_{24}D_5N_3$ = 616.78) | P-100 | m/z = 616.27($C_{45}H_{24}D_5N_3$ = 616.78) |
| P-101 | m/z = 624.32($C_{45}H_{16}D_{13}N_3$ = 624.83) | P-102 | m/z = 624.32($C_{45}H_{16}D_{13}N_3$ = 624.83) |
| P-103 | m/z = 624.32($C_{45}H_{16}D_{13}N_3$ = 624.83) | P-104 | m/z = 624.32($C_{45}H_{16}D_{13}N_3$ = 624.83) |
| P-105 | m/z = 616.27($C_{45}H_{24}D_5N_3$ = 616.78) | P-106 | m/z = 616.27($C_{45}H_{24}D_5N_3$ = 616.78) |
| P-107 | m/z = 616.27($C_{45}H_{24}D_5N_3$ = 616.78) | P-108 | m/z = 616.27($C_{45}H_{24}D_5N_3$ = 616.78) |
| P-109 | m/z = 640.42($C_{45}D_{29}N_3$ = 640.92) | P-110 | m/z = 640.42($C_{45}D_{29}N_3$ = 640.92) |
| P-111 | m/z = 640.42($C_{45}D_{29}N_3$ = 640.92) | P-112 | m/z = 640.42($C_{45}D_{29}N_3$ = 640.92) |
| P-113 | m/z = 611.24($C_{45}H_{29}N_3$ = 611.75) | P-114 | m/z = 611.24($C_{45}H_{29}N_3$ = 611.75) |
| P-115 | m/z = 611.24($C_{45}H_{29}N_3$ = 611.75) | P-116 | m/z = 611.24($C_{45}H_{29}N_3$ = 611.75) |

TABLE 3-continued

| Compound | FD-MS | Compound | FD-MS |
|---|---|---|---|
| P-117 | m/z = 737.28($C_{55}H_{35}N_3$ = 737.91) | P-118 | m/z = 737.28($C_{55}H_{35}N_3$ = 737.91) |
| P-119 | m/z = 737.28($C_{55}H_{35}N_3$ = 737.91) | P-120 | m/z = 763.30($C_{57}H_{37}N_3$ = 763.94) |
| P-121 | m/z = 737.28($C_{55}H_{35}N_3$ = 737.91) | P-122 | m/z = 737.28($C_{55}H_{35}N_3$ = 737.91) |
| P-123 | m/z = 737.28($C_{55}H_{35}N_3$ = 737.91) | P-124 | m/z = 763.30($C_{57}H_{37}N_3$ = 763.94) |
| P-125 | m/z = 737.28($C_{55}H_{35}N_3$ = 737.91) | P-126 | m/z = 737.28($C_{55}H_{35}N_3$ = 737.91) |
| P-127 | m/z = 737.28($C_{55}H_{35}N_3$ = 737.91) | P-128 | m/z = 737.28($C_{55}H_{35}N_3$ = 737.91) |
| P-129 | m/z = 737.28($C_{55}H_{35}N_3$ = 737.91) | P-130 | m/z = 737.28($C_{55}H_{35}N_3$ = 737.91) |
| P-131 | m/z = 737.28($C_{55}H_{35}N_3$ = 737.91) | P-132 | m/z = 763.30($C_{57}H_{37}N_3$ = 763.94) |
| P-133 | m/z = 737.28($C_{55}H_{35}N_3$ = 737.91) | P-134 | m/z = 737.30($C_{59}H_{37}N_3$ = 787.97) |
| P-135 | m/z = 687.27($C_{51}H_{33}N_3$ = 687.85) | P-136 | m/z = 763.30($C_{57}H_{37}N_3$ = 763.94) |

Synthesis Example 2

The compound represented by Formula 2 or Formula 3 can be prepared by a known synthetic method (named reaction) or by referring to published patent publications, such as Korean Patent Registration No. 10-2395819 and U.S. Patent Publication No. 2023-0129535, but is not limited thereto.

In the above, exemplary synthesis examples of the present invention represented by Formula 1 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh$_3$-mediated reductive cyclization reaction (*J. Org. Chem.* 2005, 70, 5014.), and it will be easily understood by those skilled in the art that the reaction proceeds even when other substituents defined in Formula 1 are bonded in addition to the substituents specified in the specific synthesis examples.

The FD-MS values of compounds N-1 to N-128 and S-1 to S-120 of the present invention manufactured according to Synthetic Example 2 as described above are as shown in Tables 4 and 5.

TABLE 4

| Compound | FD-MS | Compound | FD-MS |
|---|---|---|---|
| N-1 | m/z = 487.19($C_{36}H_{25}NO$ = 487.60) | N-2 | m/z = 553.19($C_{40}H_{27}NS$ = 553.72) |
| N-3 | m/z = 563.26($C_{43}H_{33}N$ = 563.74) | N-4 | m/z = 602.27($C_{45}H_{34}N_2$ = 602.78) |
| N-5 | m/z = 517.15($C_{36}H_{23}NOS$ = 517.65) | N-6 | m/z = 603.20($C_{44}H_{29}NS$ = 603.78) |
| N-7 | m/z = 735.29($C_{57}H_{37}N$ = 735.93) | N-8 | m/z = 562.24($C_{42}H_{30}N_2$ = 562.72) |
| N-9 | m/z = 565.17($C_{40}H_{23}NO_3$ = 565.63) | N-10 | m/z = 581.14($C_{40}H_{23}NO_2S$ = 581.69) |
| N-11 | m/z = 823.24($C_{59}H_{37}NS_2$ = 824.07) | N-12 | m/z = 727.30($C_{54}H_{37}N_3$ = 727.91) |
| N-13 | m/z = 627.22($C_{46}H_{29}NO_2$ = 627.74) | N-14 | m/z = 633.16($C_{44}H_{27}NS_2$ = 633.83) |
| N-15 | m/z = 675.29($C_{52}H_{37}N$ = 675.88) | N-16 | m/z = 678.30($C_{51}H_{38}N_2$ = 678.88) |
| N-17 | m/z = 669.21($C_{48}H_{31}NOS$ = 669.84) | N-18 | m/z = 785.22($C_{56}H_{35}NS_2$ = 786.02) |
| N-19 | m/z = 617.18($C_{44}H_{27}NOS$ = 617.77) | N-20 | m/z = 601.20($C_{44}H_{27}NO_2$ = 601.71) |
| N-21 | m/z = 779.32($C_{59}H_{41}NO$ = 779.98) | N-22 | m/z = 583.23($C_{42}H_{33}NS$ = 583.79) |
| N-23 | m/z = 679.32($C_{52}H_{41}N$ = 679.91) | N-24 | m/z = 726.27($C_{54}H_{34}N_2O$ = 726.88) |
| N-25 | m/z = 593.18($C_{42}H_{27}NOS$ = 593.74) | N-26 | m/z = 774.22($C_{54}H_{34}N_2S_2$ = 775.00) |
| N-27 | m/z = 557.24($C_{40}H_{31}NO_2$ = 557.69) | N-28 | m/z = 652.25($C_{48}H_{32}N_2O$ = 652.80) |
| N-29 | m/z = 619.29($C_{46}H_{37}NO$ = 619.81) | N-30 | m/z = 603.20($C_{44}H_{29}NS$ = 603.78) |
| N-31 | m/z = 813.30($C_{62}H_{39}NO$ = 814.00) | N-32 | m/z = 784.29($C_{57}H_{40}N_2S$ = 785.02) |
| N-33 | m/z = 577.20($C_{42}H_{27}NO_2$ = 577.68) | N-34 | m/z = 607.14($C_{42}H_{25}NS_2$ = 607.79) |
| N-35 | m/z = 801.34($C_{62}H_{43}N$ = 802.03) | N-36 | m/z = 575.24($C_{42}H_{29}N_3$ = 575.72) |
| N-37 | m/z = 577.20($C_{42}H_{27}NO_2$ = 577.68) | N-38 | m/z = 607.14($C_{42}H_{25}NS_2$ = 607.79) |
| N-39 | m/z = 801.34($C_{62}H_{43}N$ = 802.03) | N-40 | m/z = 575.24($C_{42}H_{29}N_3$ = 575.72) |
| N-41 | m/z = 601.20($C_{44}H_{27}NO_2$ = 601.71) | N-42 | m/z = 471.11($C_{31}H_{21}NS_2$ = 471.64) |
| N-43 | m/z = 675.29($C_{52}H_{37}N$ = 675.88) | N-44 | m/z = 727.30($C_{54}H_{37}N_3$ = 727.91) |
| N-45 | m/z = 603.20($C_{44}H_{29}NS$ = 603.78) | N-46 | m/z = 561.16($C_{38}H_{27}NS_2$ = 561.76) |
| N-47 | m/z = 799.32($C_{62}H_{41}N$ = 800.02) | N-48 | m/z = 702.27($C_{52}H_{34}N_2O$ = 702.86) |
| N-49 | m/z = 729.27($C_{54}H_{35}NO_2$ = 729.88) | N-50 | m/z = 785.22($C_{56}H_{35}NS_2$ = 786.02) |
| N-51 | m/z = 812.32($C_{62}H_{40}N_2$ = 813.02) | N-52 | m/z = 681.22($C_{48}H_{31}N_3S$ = 681.86) |
| N-53 | m/z = 615.18($C_{44}H_{25}NO_3$ = 615.69) | N-54 | m/z = 763.15($C_{52}H_{29}NS_3$ = 763.99) |
| N-55 | m/z = 593.31($C_{45}H_{39}N$ = 593.81) | N-56 | m/z = 840.33($C_{62}H_{40}N_4$ = 841.03) |
| N-57 | m/z = 657.18($C_{46}H_{27}NO_2S$ = 657.79) | N-58 | m/z = 824.23($C_{58}H_{36}N_2S_2$ = 825.06) |
| N-59 | m/z = 1195.42($C_{91}H_{57}NS$ = 1196.52) | N-60 | m/z = 656.19($C_{46}H_{28}N_2OS$ = 656.80) |
| N-61 | m/z = 607.16($C_{42}H_{25}NO_2S$ = 607.73) | N-62 | m/z = 773.20($C_{54}H_{31}NO_3S$ = 773.91) |
| N-63 | m/z = 1013.40($C_{79}H_{51}N$ = 1014.28) | N-64 | m/z = 758.24($C_{54}H_{34}N_2OS$ = 758.94) |
| N-65 | m/z = 623.14($C_{42}H_{25}NOS_2$= 623.79) | N-66 | m/z = 763.16($C_{52}H_{29}NO_2S_2$ = 763.93) |
| N-67 | m/z = 799.20($C_{56}H_{33}NOS_2$= 800.01) | N-68 | m/z = 743.23($C_{54}H_{33}NOS$ = 743.92) |
| N-69 | m/z = 872.25($C_{62}H_{36}N_2O_2S$ = 873.04) | N-70 | m/z = 772.22($C_{54}H_{32}N_2O_2S$ = 772.92) |
| N-71 | m/z = 830.28($C_{61}H_{38}N_2S$ = 831.05) | N-72 | m/z = 808.25($C_{58}H_{33}FN_2O_2$ = 808.91) |
| N-73 | m/z = 929.21($C_{64}H_{35}NO_3S_2$ = 930.11) | N-74 | m/z = 963.27($C_{68}H_{41}N_3S_2$ = 964.22) |
| N-75 | m/z = 809.24($C_{58}H_{35}NO_2S$ = 809.98) | N-76 | m/z = 893.29($C_{66}H_{39}NO_3$ = 894.04) |
| N-77 | m/z = 794.28($C_{58}H_{38}N_2S$ = 795.02) | N-78 | m/z = 900.26($C_{64}H_{40}N_2S_2$ = 901.16) |
| N-79 | m/z = 758.28($C_{55}H_{38}N_2S$ = 758.98) | N-80 | m/z = 1082.37($C_{81}H_{50}N_2S$ = 1083.37) |
| N-81 | m/z = 573.25($C_{44}H_{31}N$ = 573.74) | N-82 | m/z = 649.28($C_{50}H_{35}N$ = 649.84) |
| N-83 | m/z = 699.29($C_{54}H_{37}N$ = 699.90) | N-84 | m/z = 699.29($C_{54}H_{37}N$ = 699.90) |
| N-85 | m/z = 673.28($C_{52}H_{35}N$ = 673.86) | N-86 | m/z = 649.28($C_{50}H_{35}N$ = 649.84) |
| N-87 | m/z = 625.28($C_{48}H_{35}N$ = 625.82) | N-88 | m/z = 673.28($C_{52}H_{35}N$ = 673.86) |

TABLE 4-continued

| Compound | FD-MS | Compound | FD-MS |
|---|---|---|---|
| N-89 | m/z = 773.31($C_{60}H_{39}N$ = 773.98) | N-90 | m/z = 749.31($C_{58}H_{39}N$ = 749.96) |
| N-91 | m/z = 699.29($C_{54}H_{37}N$ = 699.90) | N-92 | m/z = 599.26($C_{46}H_{33}N$ = 599.78) |
| N-93 | m/z = 639.26($C_{48}H_{33}NO$ = 639.80) | N-94 | m/z = 765.25($C_{57}H_{35}NS$ = 765.97) |
| N-95 | m/z = 677.31($C_{52}H_{39}N$ = 677.89) | N-96 | m/z = 727.30($C_{54}H_{37}N_3$ = 727.91) |
| N-97 | m/z = 552.18($C_{39}H_{24}N_2O_2$ = 552.63) | N-98 | m/z = 628.22($C_{45}H_{28}N_2O_2$ = 628.73) |
| N-99 | m/z = 614.24($C_{45}H_{30}N_2O$ = 614.75) | N-100 | m/z = 614.24($C_{45}H_{30}N_2O$ = 614.75) |
| N-101 | m/z = 691.21 ($C_{50}H_{29}NO_3$ = 691.79) | N-102 | m/z = 739.29($C_{56}H_{37}NO$ = 739.92) |
| N-103 | m/z = 673.15($C_{46}H_{27}NOS_2$ = 673.85) | N-104 | m/z = 726.27($C_{54}H_{34}N_2O$ = 726.88) |
| N-105 | m/z = 667.2($C_{48}H_{29}NOS$ = 667.83) | N-106 | m/z = 717.21($C_{52}H_{31}NOS$ = 717.89) |
| N-107 | m/z = 667.2($C_{48}H_{29}NOS$ = 667.83) | N-108 | m/z = 711.26($C_{54}H_{33}NO$ = 711.86) |
| N-109 | m/z = 617.18($C_{44}H_{27}NOS$ = 617.77) | N-110 | m/z = 611.22($C_{46}H_{29}NO$ = 611.74) |
| N-111 | m/z = 769.24($C_{56}H_{35}NOS$ = 769.96) | N-112 | m/z = 701.28($C_{52}H_{35}N_3$ = 701.87) |
| N-113 | m/z = 527.22($C_{39}H_{29}NO$ = 527.67) | N-114 | m/z = 643.2($C_{46}H_{29}NOS$ = 643.8) |
| N-115 | m/z = 593.18($C_{42}H_{27}NOS$ = 593.74) | N-116 | m/z = 726.27($C_{54}H_{34}N_2O$ = 726.88) |
| N-117 | m/z = 726.27($C_{54}H_{34}N_2O$ = 726.88) | N-118 | m/z = 558.14($C_{37}H_{22}N_2O_2S$ = 558.66) |
| N-119 | m/z = 620.19($C_{43}H_{28}N_2OS$ = 620.77) | N-120 | m/z = 610.24($C_{46}H_{30}N_2$ = 610.76) |
| N-121 | m/z = 718.24($C_{52}H_{34}N_2S$ = 718.92) | N-122 | m/z = 728.28($C_{54}H_{36}N_2O$ = 728.9) |
| N-123 | m/z = 592.2($C_{42}H_{28}N_2S$ = 592.76) | N-124 | m/z = 756.22($C_{54}H_{32}N_2OS$ = 756.92) |
| N-125 | m/z = 547.23($C_{42}H_{29}N$ = 547.7) | N-126 | m/z = 672.28($C_{49}H_{24}D_7NO_2$ = 672.83) |
| N-127 | m/z = 626.28($C_{48}H_{26}D_5N$ = 626.81) | N-128 | m/z = 558.22($C_{40}H_{22}D_5NS$ = 558.75) |

TABLE 5

| Compound | FD-MS | Compound | FD-MS |
|---|---|---|---|
| S-1 | m/z = 408.16($C_{30}H_{20}N_2$ = 408.50) | S-2 | m/z = 534.21($C_{40}H_{26}N_2$ = 534.66) |
| S-3 | m/z = 560.23($C_{42}H_{28}N_2$ = 560.70) | S-4 | m/z = 584.23($C_{44}H_{28}N_2$ = 584.72) |
| S-5 | m/z = 560.23($C_{42}H_{28}N_2$ = 560.70) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2$ = 498.59) |
| S-9 | m/z = 574.20($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.20($C_{46}H_{28}N_2S$ = 640.80) | S-14 | m/z = 560.23($C_{42}H_{28}N_2$ = 560.70) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.70) | S-18 | m/z = 564.17($C_{40}H_{24}N_2S$ = 564.71) |
| S-19 | m/z = 574.20($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814.00) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.20($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.20($C_{46}H_{29}NS$ = 627.81) | S-38 | m/z = 505.10($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{26}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.20($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.10($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.10($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.20($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |

TABLE 5-continued

| Compound | FD-MS | Compound | FD-MS |
|---|---|---|---|
| S-101 | m/z = 485.21($C_{37}H_{27}N$ = 485.63) | S-102 | m/z = 471.20($C_{36}H_{25}N$ = 471.60) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.60) |
| S-107 | m/z = 563.26($C_{43}H_{26}D_4NO$ = 563.74) | S-108 | m/z = 589.26($C_{44}H_{23}D_5N_2$ = 584.72) |
| S-109 | m/z = 589.26($C_{44}H_{23}D_5N_2$ = 589.75) | S-110 | m/z = 624.22($C_{46}H_{28}N_2O$ = 624.74) |
| S-111 | m/z = 589.26($C_{44}H_{23}D_5N_2$ = 589.75) | S-112 | m/z = 634.24($C_{48}H_{30}N_2$ = 634.78) |
| S-113 | m/z = 589.26($C_{44}H_{23}D_5N_2$ = 589.75) | S-114 | m/z = 562.23($C_{42}H_{22}D_4N_2$ = 562.71) |
| S-115 | m/z = 660.26($C_{50}H_{32}N_2$ = 660.82) | S-116 | m/z = 553.22($C_{40}H_{19}D_5N_2O$ = 553.68) |
| S-117 | m/z = 634.24($C_{48}H_{30}N_2$ = 634.78) | S-118 | m/z = 589.26($C_{44}H_{23}D_5N_2$ = 589.75) |
| S-119 | m/z = 588.25($C_{44}H_{24}D_4N_2$ = 588.75) | S-120 | m/z = 513.23($C_{38}H_{19}D_5N_2$ = 513.65) |

In the above, exemplary synthesis examples of the present invention represented by Formula 1, Formula 2, and Formula 3 have been described, but these are all based on the Buchwald-Hartwig cross coupling reaction, Miyaura boration reaction, Suzuki cross-coupling reaction, Intramolecular acid-induced cyclization reaction (J. mater. Chem. 1999, 9, 2095.), Pd(II)-catalyzed oxidative cyclization reaction (Org. Lett. 2011, 13, 5504), and PPh$_3$-mediated reductive cyclization reaction (J. Org. Chem. 2005, 70, 5014.), and it will be easily understood by those skilled in the art that the reaction proceeds even when other substituents defined in Formula 1, Formula 2 and Formula 3 are bonded in addition to the substituents specified in the specific synthesis examples.

[Example 1] Red Organic Light Emitting Device (Phosphorescent Host)

Compound A and Compound B were used on the ITO layer (anode) formed on a glass substrate, and Compound B was doped at a weight ratio of 98:2 to form a hole injection layer with a thickness of 10 nm. Then, Compound A was vacuum-deposited on the hole injection layer with a thickness of 110 nm to form a hole transport layer.

Next, compound C—R was vacuum-deposited on the hole transport layer to a thickness of 10 nm to form an emitting auxiliary layer. Thereafter, the host material of the emitting layer uses compound P-2, a compound of the present invention, as a first host, and compound N-19, a compound of the present invention, as a second host, and uses a mixture in which the first host and the second host are mixed at a weight ratio of 5:5, and bis-(1-phenylisoquinolyl)iridium(III)acetylacetonate (hereinafter abbreviated as '(piq)$_2$Ir(acac)') was used as the dopant material, and the dopant was doped so that the weight ratio of the host and the dopant was 95:5 to form an emitting layer with a thickness of 30 nm.

Next, compound E was vacuum-deposited on the emitting layer to form a hole-blocking layer with a thickness of 10 nm, and a mixture of compound F and compound G at a weight ratio of 5:5 was used to form an electron-transporting layer with a thickness of 30 nm on the hole-blocking layer. Afterwards, compound G was deposited on the electron transport layer to form an electron injection layer with a thickness of 0.2 nm, and then Al was deposited to form a cathode with a thickness of 150 nm.

compound A: N-([1,1'-biphenyl]-4-yl)-9,9-dimethyl-N-(4-(9-phenyl-9H-carbazol-3-yl)phenyl)-9H-fluoren-2-amine compound B: 4,4',4''-((1E,1'E,1''E)-cyclopropane-1,2,3-triylidenetris(cyanomethaneylylidene))tris(2,3,5,6-tetrafluorobenzonitrile)

compound C—R: $N^7$-(dibenzo[b,d]thiophen-2-yl)-$N^2$,$N^2$, $N^7$-triphenyldibenzo[b,d]thiophene-2,7-diamine compound E: 2-(4'-(9,9-dimethyl-9H-fluoren-2-yl)-[1,1'-biphenyl]-3-yl)-4,6-diphenyl-1,3,5-triazine compound F: 2,7-bis(4-(4,6-diphenyl-1,3,5-triazin-2-yl)phenyl)naphthalene compound G: (8-quinolinolato)lithium

[Example 2] to [Example 30]

An organic light emitting device was manufactured in the same manner as in Example 1, except that the compounds described in Table 6 were used as the first host and second host of the emitting layer.

[Comparative Example 1] to [Comparative Example 3]

An organic light emitting device was manufactured in the same manner as in Example 1, except that Comparative Compounds A to C were used as the first host material of the emitting layer.

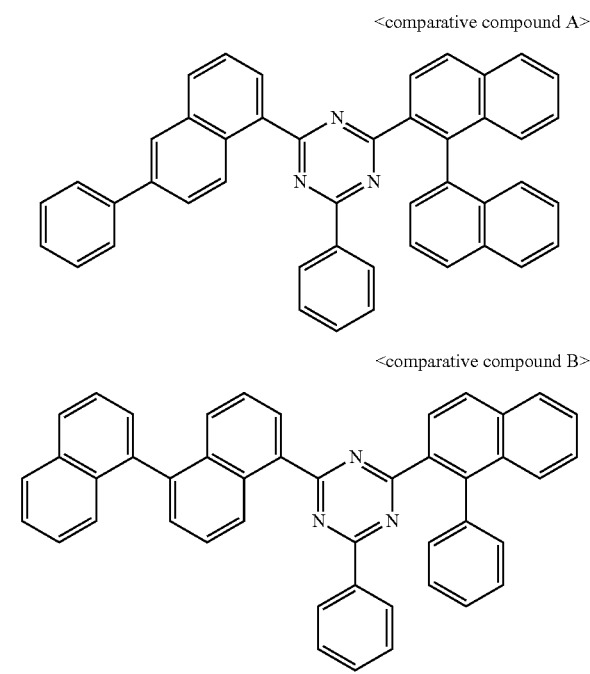

<comparative compound A>

<comparative compound B>

<comparative compound C>

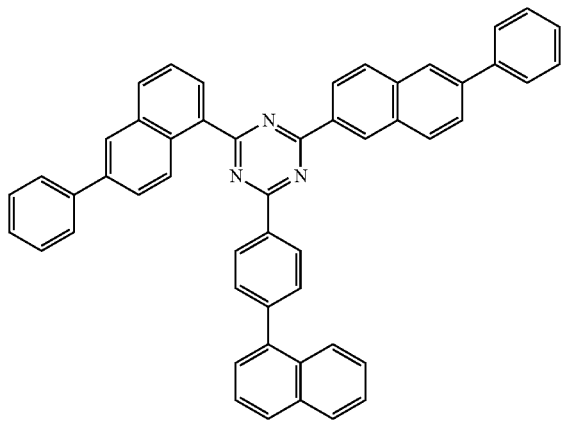

The electroluminescence (EL) characteristics were measured using PR-650 from Photoresearch by applying a forward bias DC voltage to the organic electroluminescence devices manufactured by the examples and comparative examples manufactured in this way. As a result of the measurement, the T95 lifespan was measured using a lifespan measuring device manufactured by Max Science at a standard brightness of 2500 cd/in$^2$. Table 6 shows the results of the device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 6

| | First compound | Second compound | Voltage (V) | Current Density (mA/cm$^2$) | Efficiency (cd/A) | T(95) |
|---|---|---|---|---|---|---|
| comparative example1 | comparative compound A | N-19 | 5.5 | 10.8 | 23.2 | 96.4 |
| comparative example2 | comparative compound B | N-19 | 5.6 | 11.7 | 21.3 | 93.5 |
| comparative example3 | comparative compound C | N-19 | 5.4 | 10.1 | 24.8 | 101.1 |
| example1 | P-2 | N-19 | 4.2 | 5.7 | 43.5 | 138.7 |
| example2 | P-3 | N-19 | 4.3 | 6.0 | 41.6 | 144.0 |
| example3 | P-9 | N-19 | 4.4 | 6.3 | 39.6 | 134.9 |
| example4 | P-12 | N-19 | 4.5 | 6.7 | 37.4 | 129.2 |
| example5 | P-14 | N-19 | 4.2 | 5.9 | 42.5 | 137.1 |
| example6 | P-23 | N-19 | 4.3 | 6.1 | 40.8 | 142.2 |
| example7 | P-25 | N-19 | 4.5 | 6.6 | 38.1 | 130.5 |
| example8 | P-32 | N-19 | 4.4 | 6.4 | 39.3 | 133.7 |
| example9 | P-37 | N-19 | 4.2 | 5.8 | 42.8 | 137.3 |
| example10 | P-41 | N-19 | 4.4 | 6.3 | 39.9 | 139.2 |
| example11 | P-52 | N-19 | 4.5 | 6.8 | 36.7 | 128.3 |
| example12 | P-82 | N-19 | 4.2 | 5.8 | 43.2 | 139.2 |
| example13 | P-111 | N-19 | 4.3 | 6.0 | 41.4 | 144.9 |
| example14 | P-116 | N-19 | 4.6 | 7.1 | 35.2 | 125.4 |
| example15 | P-120 | N-19 | 4.4 | 6.2 | 40.1 | 139.6 |
| example16 | P-121 | N-19 | 4.6 | 7.0 | 35.6 | 126.2 |
| example17 | P-122 | N-19 | 4.2 | 6.0 | 42.0 | 136.4 |
| example18 | P-129 | N-19 | 4.3 | 6.2 | 40.6 | 141.8 |
| example19 | P-132 | N-19 | 4.4 | 6.5 | 38.4 | 132.3 |
| example20 | P-134 | N-19 | 4.3 | 6.0 | 41.7 | 135.2 |

TABLE 6-continued

| | First compound | Second compound | Voltage (V) | Current Density (mA/cm$^2$) | Efficiency (cd/A) | T(95) |
|---|---|---|---|---|---|---|
| example21 | P-2 | S-9 | 4.1 | 5.8 | 43.1 | 137.6 |
| example22 | P-3 | S-9 | 4.2 | 6.1 | 41.2 | 143.0 |
| example23 | P-9 | S-9 | 4.3 | 6.4 | 39.1 | 133.7 |
| example24 | P-12 | S-9 | 4.4 | 6.8 | 36.9 | 127.9 |
| example25 | P-37 | S-9 | 4.1 | 5.9 | 42.4 | 136.2 |
| example26 | P-52 | S-9 | 4.4 | 6.9 | 36.1 | 127.0 |
| example27 | P-120 | S-9 | 4.3 | 6.3 | 39.6 | 138.5 |
| example28 | P-122 | S-9 | 4.1 | 6.0 | 41.6 | 135.2 |
| example29 | P-129 | S-9 | 4.2 | 6.2 | 40.2 | 140.9 |
| example30 | P-132 | S-9 | 4.3 | 6.6 | 37.9 | 130.9 |

As can be seen from the results in Table 6, when a red organic emitting device was manufactured using the compound of the present invention as a phosphorescent host material, not only was the driving voltage of the organic light emitting device lowered compared to when Comparative Compounds A to C were used, but the efficiency and lifespan were also significantly improved.

As can be seen from the above, when a plurality of compounds are mixed to form a host for the emitting layer, the characteristics differ depending on the type of the first compound and the second compound, and when the same compound is applied to the second compound, it can be confirmed that there is a significant difference in the characteristics depending on the type of the first compound. Similarly, the second compound shows differences in operating voltage, efficiency, and lifespan depending on the type.

Comparative compounds A to C have a similar skeleton to the compound of the present invention, but differ in the substitution position and type of substituent.

The compound of the present invention must have 1-naphthyl group bonded to a triazine and the 2-naphthyl group as a second naphthyl group, and specific aryl substituents must be bonded to different rings of each of the two naphthyl groups. That is, the compound of the present invention is characterized in that, in the case of the compound of the present invention, phenyl is substituted at positions 5 to 8 of the 1-naphthyl group substituted with triazine, and a naphthyl group is bonded at positions 5 to 8 of the 2-naphthyl group substituted with triazine. On the contrary, there is a difference between Compound A and Compound B in that a substituent is substituted at position 1 of the 2-naphthyl group of triazine. In particular, the types of substituents substituted on the 1- and 2-naphthyl groups of triazine in comparative compound B are different from those in the compound of the present invention. Also, comparative compound C differs from the compound of the present invention in that the substituent substituted on 2-naphthyl group is phenyl, not naphthyl.

In order to determine the difference in energy levels of compounds according to the structural differences of these compounds, the energy levels of Comparative Compounds A to C and the similar Compound P-2 of the present invention were measured using the DFT method (B3LYP/6-31g(D)) of the Gaussian program. The measurement results are shown in Tables 7 and 8.

TABLE 7

|  | P-2 | comparative compound A | comparative compound B | comparative compound C |
|---|---|---|---|---|
| LUMO(eV) | −2.000 | −1.841 | −1.815 | −1.979 |

Referring to Table 7, it can be seen that the compounds of the present invention have lower LUMO energy levels than the comparative compounds.

In the case of the compound of the present invention, it participates in electron transport within the emitting layer as a first host compound, and plays a role in accepting and moving electrons entering from the electron transport layer to the emitting layer. The compound of the present invention, which has a lower LUMO energy level compared to the comparative compounds, exhibits relatively easier electron transfer and thus faster EOD. That is, as the electron mobility of the electron-transport host improves, the charge balance between electrons and holes is well achieved within the emitting layer rather than at the interface, so the efficiency and lifespan appear to be improved.

TABLE 8

|  | P-2 | comparative compound A |
|---|---|---|
| HOMO(eV) | −5.676 | −5.539 |

In particular, in the case of the comparative compound A, which differs only in the substitution position of the substituent from the compound of the present invention, it can be seen that the HOMO energy level increases as shown in Table 8 when the position of the naphthyl substituent substituted on 2-naphthyl group of the triazine is changed from the 5th to 8th positions to the 1st position. That is, as the substitution position of the substituent changes, the hole characteristics of the electron-transport host are strengthened, so that the electron transfer characteristics are relatively lowered compared to the compound of the present invention.

Therefore, when the compound of the present invention is used as an emitting layer material, the transfer of electrons within the molecule is smooth, so that charge balance within the emitting layer is well achieved, and thus the operation, efficiency, and lifespan of the element are improved.

When an emitting layer is composed of multiple host compounds, the characteristics are different depending on the types of the first and second compounds, and it is judged that the driving, efficiency, and lifespan are determined depending on the ease of injection and movement of holes and electrons. Therefore, when the compound of the present invention is used in the emitting layer, it can be expected that the electron mobility of the electron-transport host will improve, the light-emitting region will move toward the interface between the hole transport layer and the emitting layer, and the extent to which holes flowing from the hole transport layer into the emitting layer accumulate will decrease. That is, it appears that the efficiency and lifespan have been improved because the charge balance between electrons and holes within the emitting layer has been well achieved.

From Tables 6 to 8, it can be confirmed that the compound of the present invention, which satisfies all complex elements such as the type of substituent and the substitution position of the substituent, even though it is a compound having a similar configuration, exhibits a remarkable effect in an organic electronic element compared to other comparative compounds, and through this, it can be seen that the compound of the present invention, which satisfies all specific configurations, exhibits a remarkable effect in an organic electronic element compared to other comparative compounds not described in this specification.

These results show that even in compounds with similar molecular components, depending on the type and substitution position of the substituent, the properties of compounds such as the hole characteristics, light efficiency characteristics, energy level, hole injection and mobility characteristics, charge balance of holes and electrons, volume density, and intermolecular distance of the molecule may vary significantly enough to be difficult to predict, additionally, it suggests that rather than one configuration affecting the overall results of the element, the performance of the element may vary due to complex factors.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:
1. A compound represented by Formula 1:

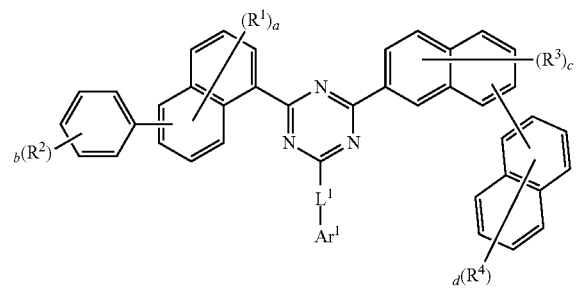

Formula 1 wherein:
$R^1$, $R^2$, $R^3$ and $R^4$ are the same or different from each other and each are independently hydrogen or deuterium;
a and c are each an integer of 0 to 6, b is an integer of 0 to 5, and d is an integer of 0 to 7,
$L^1$ is a single bond, or a $C_6$-$C_{12}$ arylene group;
$Ar^1$ is an $C_6$-$C_{12}$ aryl group;
wherein the aryl group and arylene group may be substituted with one or more substituents selected from the group consisting of deuterium, a $C_6$-$C_{20}$ aryl group, and a $C_6$-$C_{20}$ aryl group substituted with deuterium, and hydrogen of these substituents may be further substituted with one or more deuterium.
2. The compound according to claim 1, wherein $Ar^1$ is represented by any one of Formulas (A-1) to (A-6):

Formula (A-1)

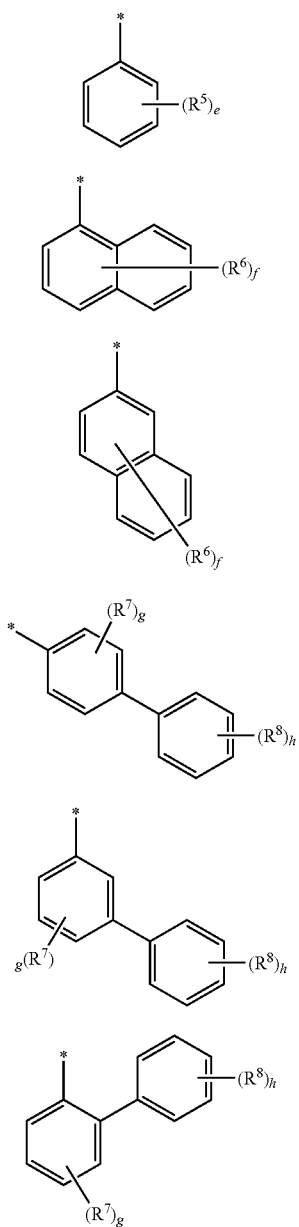

Formula (A-2)

Formula (A-3)

Formula (A-4)

Formula (A-5)

Formula (A-6)

wherein:
1) $R^5$, $R^6$, $R^7$ and $R^8$ are each the same or different and independently hydrogen or deuterium,
2) e is an integer of 0 to 5, f is an integer of 0 to 7, g is an integer of 0 to 4, h is an integer of 0 to 5, and
3) * indicates a position to be bonded.

3. The compound according to claim 1, wherein $L^1$ is represented by a single bond or any one of Formulas <L-1> to <L-19>:

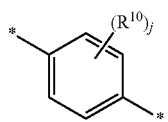 (L-1)

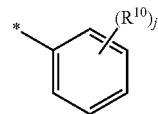 (L-2)

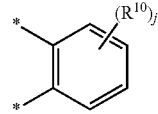 (L-3)

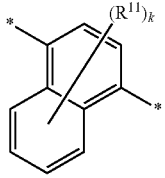 (L-4)

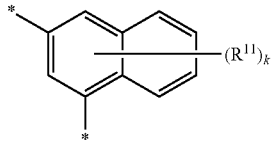 (L-5)

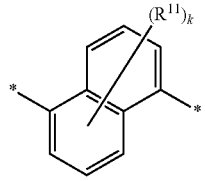 (L-6)

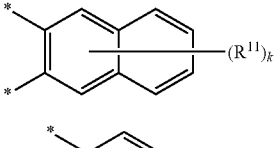 (L-7)

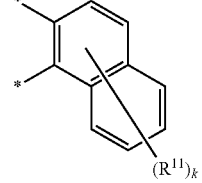 (L-8)

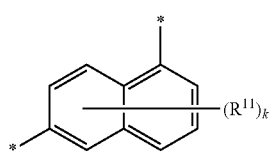 (L-9)

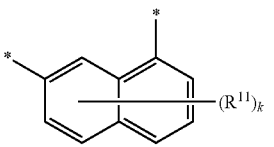 (L-10)

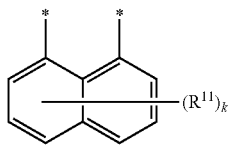 (L-11)

-continued

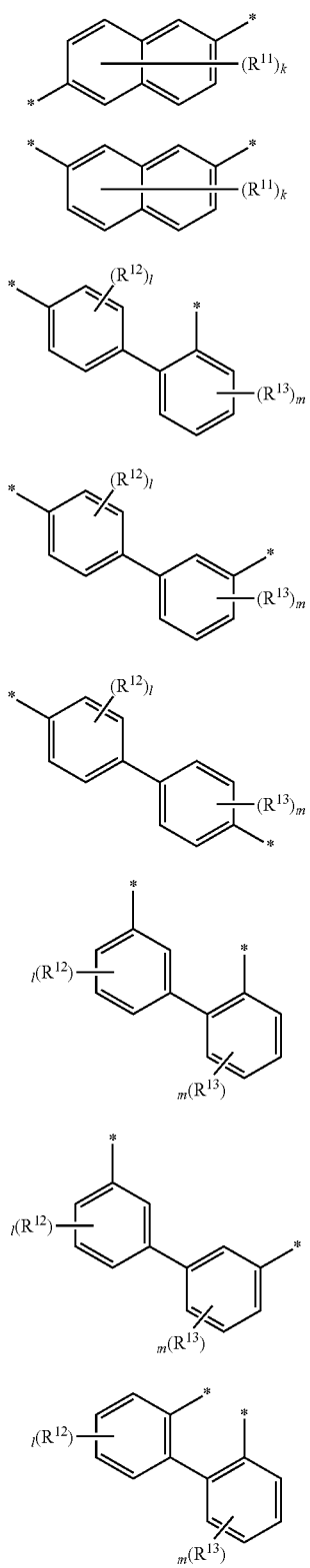

wherein:

R$^{10}$, R$^{11}$, R$^{12}$ and R$^{13}$ are each the same or different from each other and are independently hydrogen or deuterium;

j, l and m are each independently an integer of 0 to 4, k is an integer of 0 to 6, and

* indicates a position to be bonded.

4. The compound according to claim 1, wherein the compound represented by Formula 1 comprises at least one deuterium.

5. The compound according to claim 1, wherein the compound of Formula 1 is selected from the group consisting of compounds P-1 to P-136:

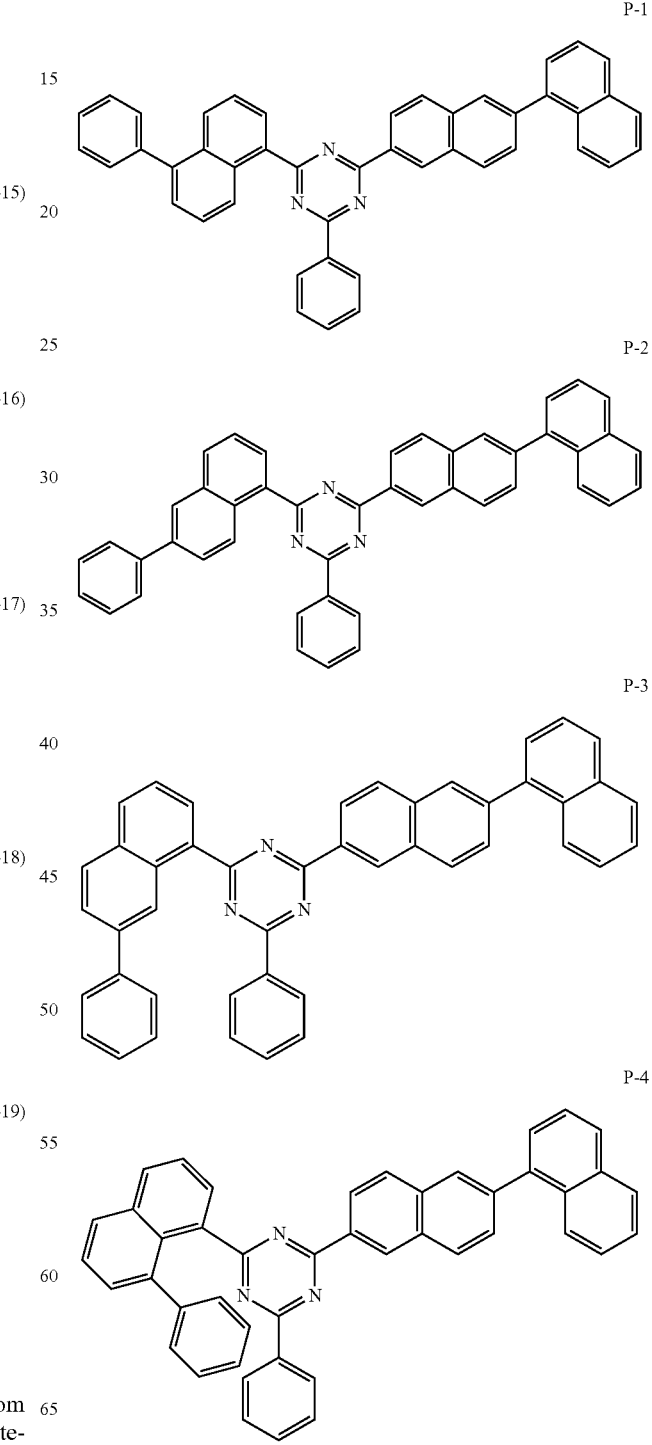

P-5
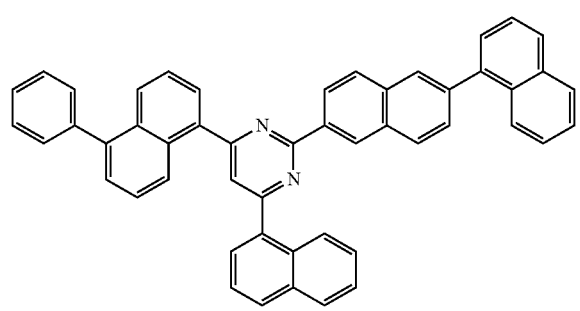
P-6
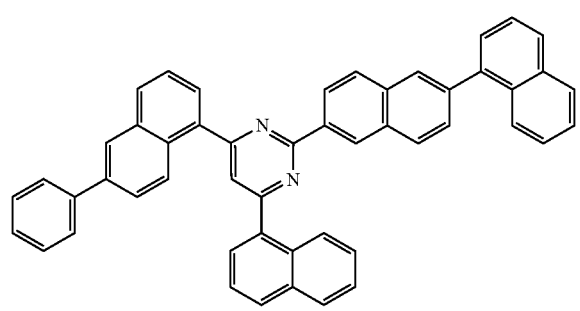
P-7
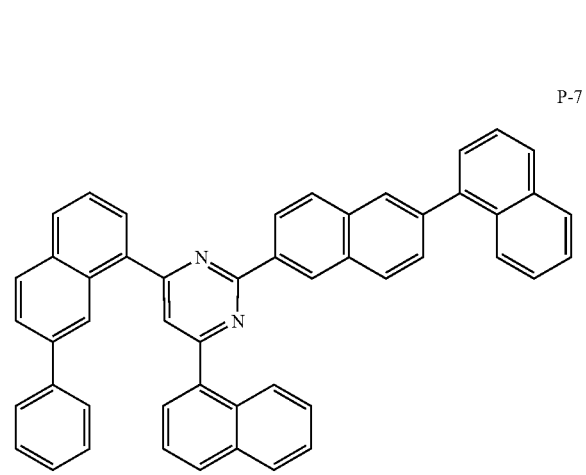
P-8
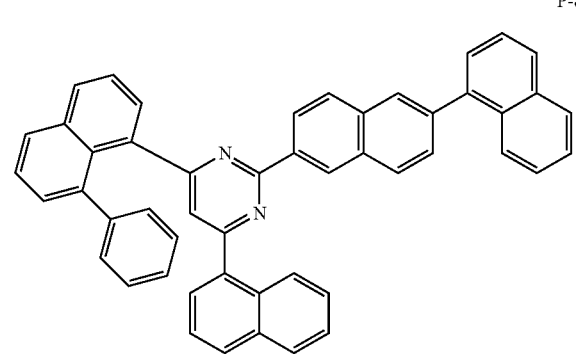
P-9
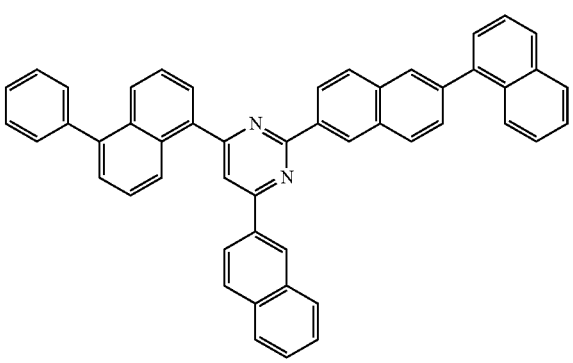
P-10
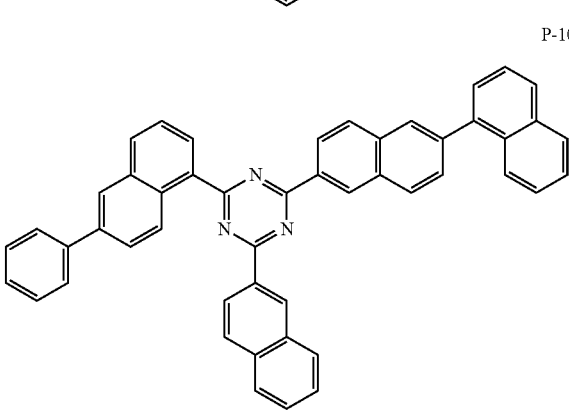
P-11
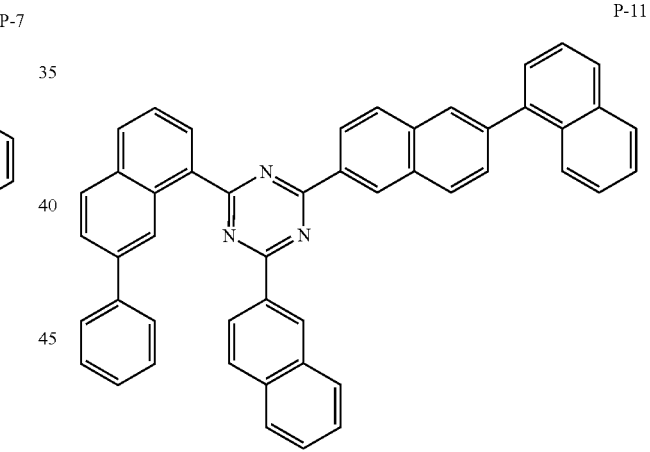
P-12
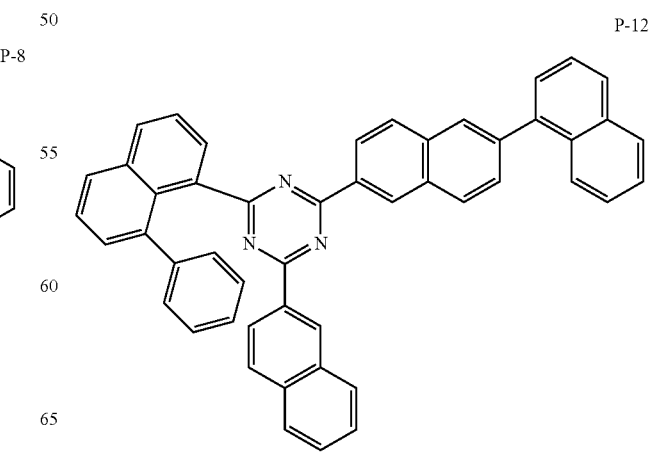

P-13
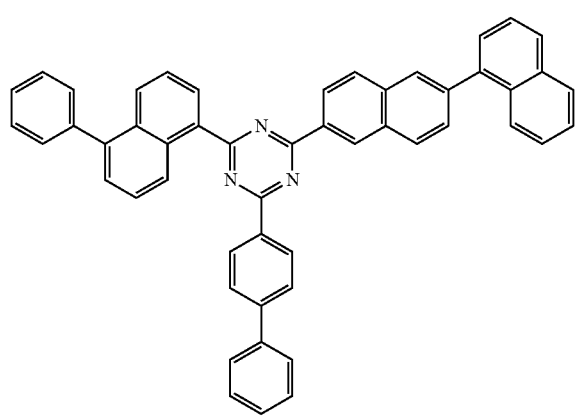
P-16
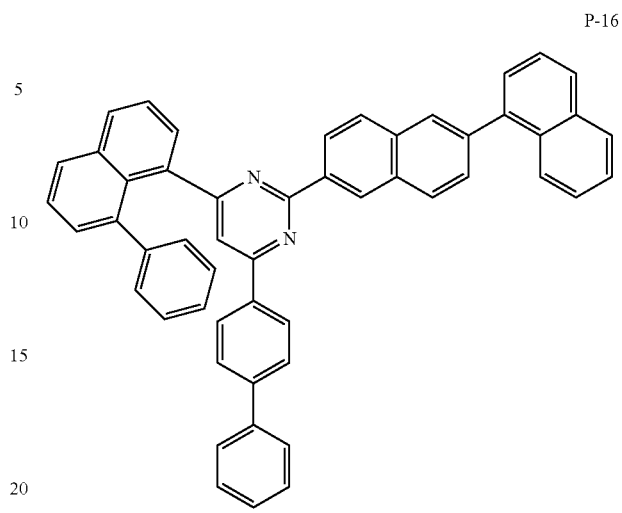
P-14
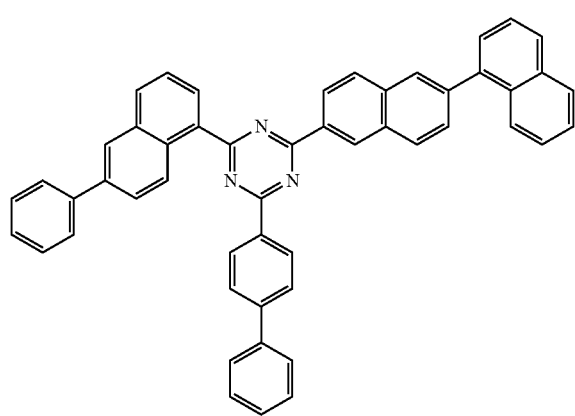
P-17
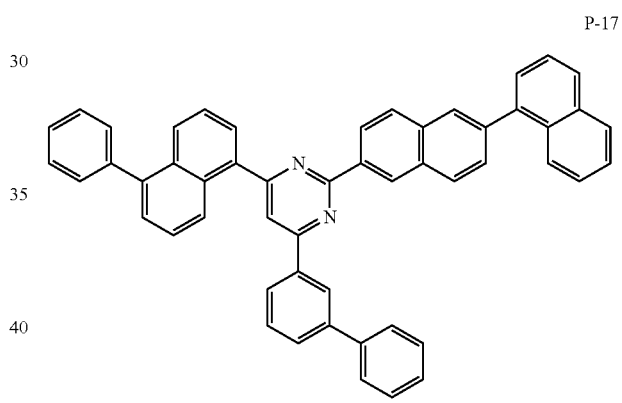
P-15
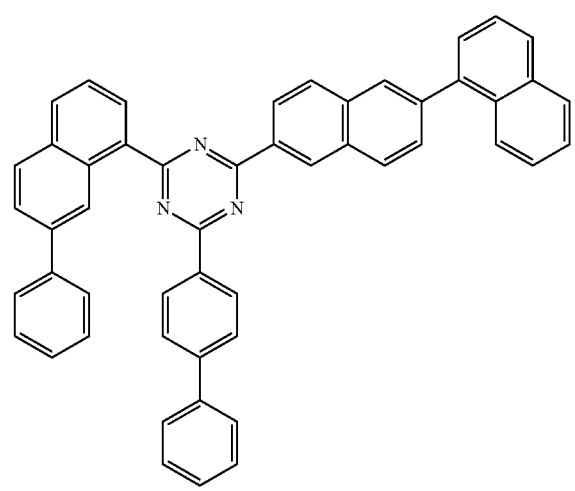
P-18
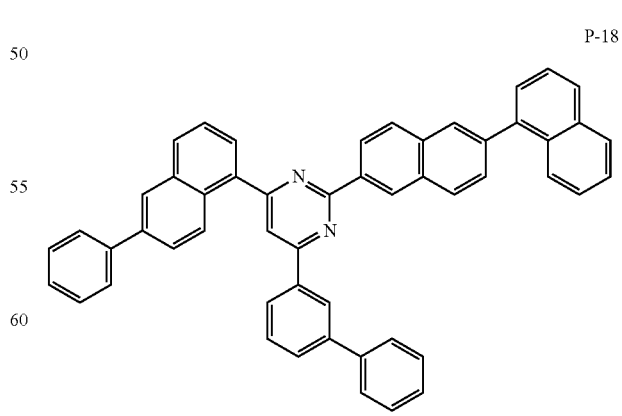

-continued
P-19
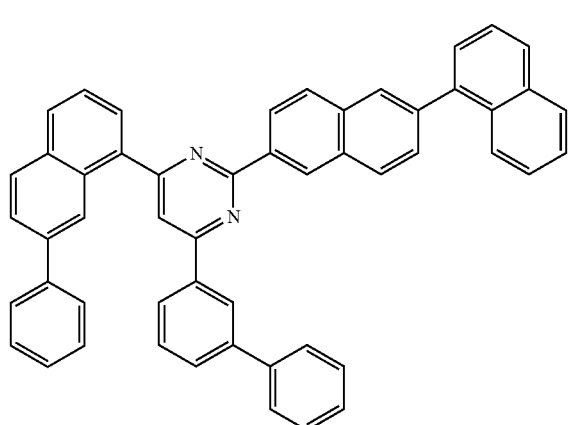
P-20
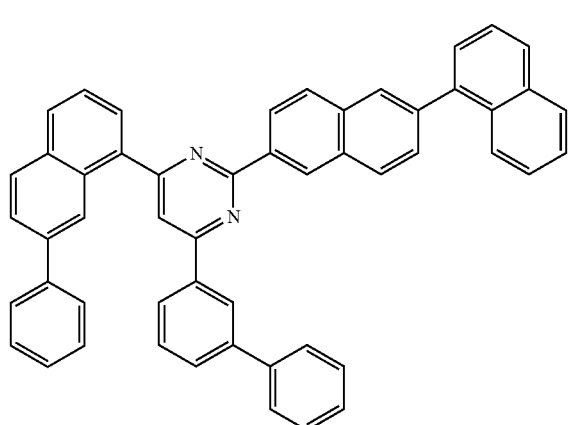
P-21
P-22
-continued
P-23
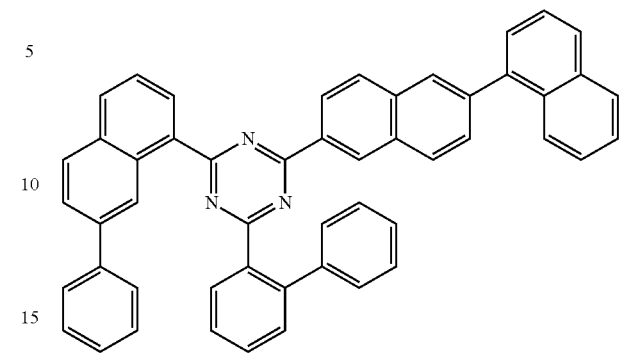
P-24
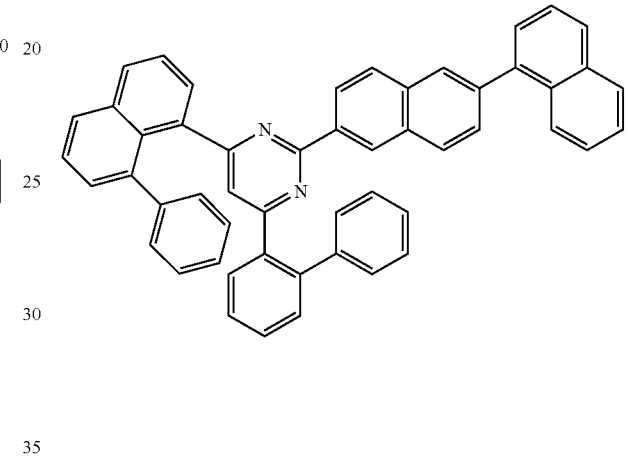
P-25
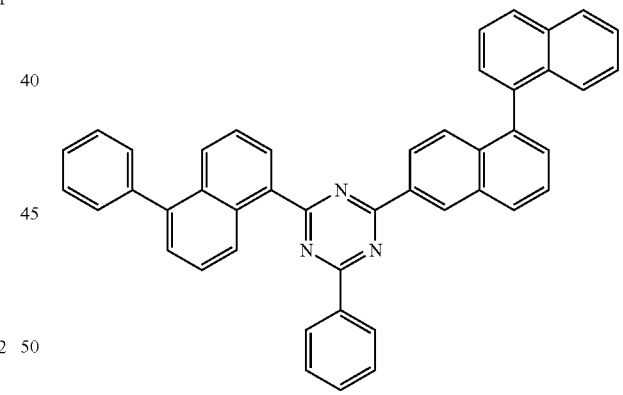
P-26
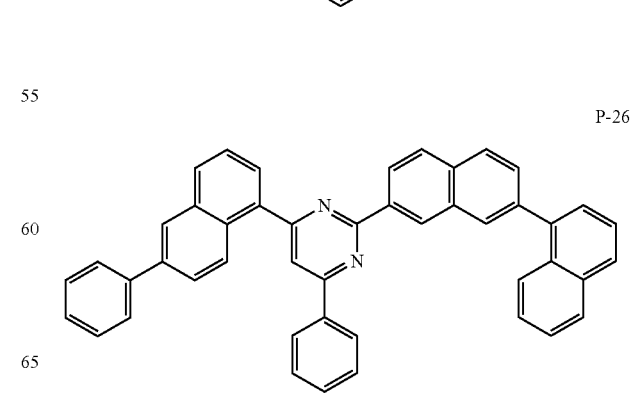

P-27
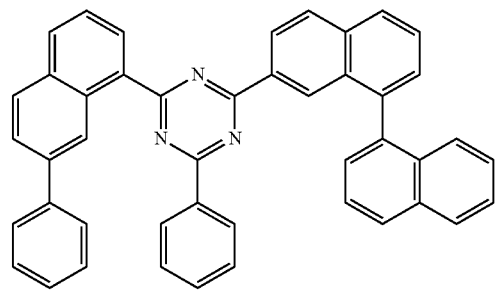
P-28
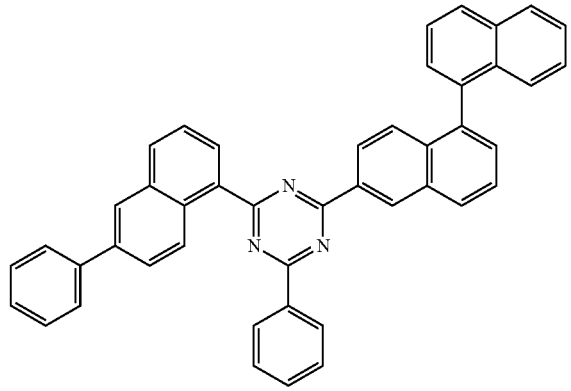
P-29
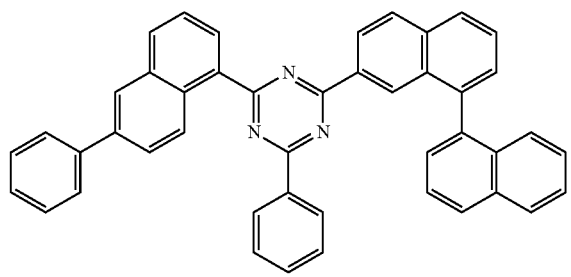
P-30
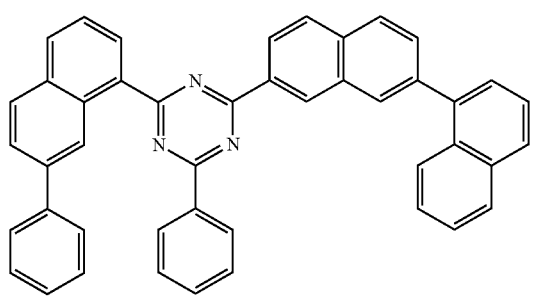
P-31
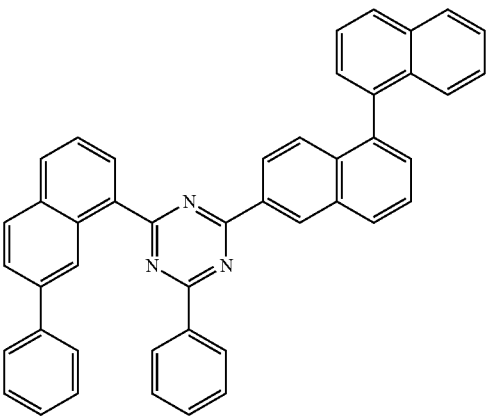
P-32
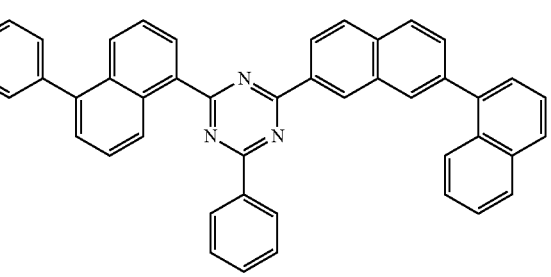
P-33
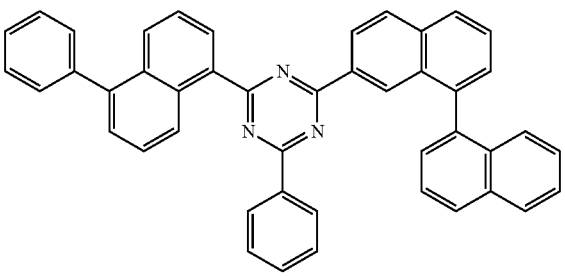
P-34
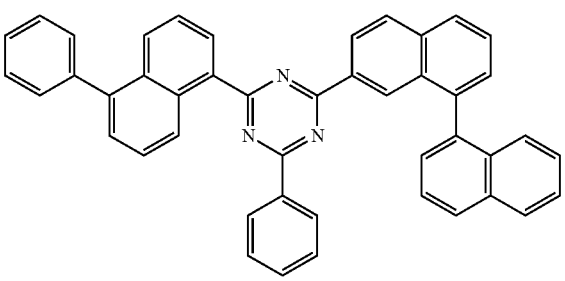
P-35
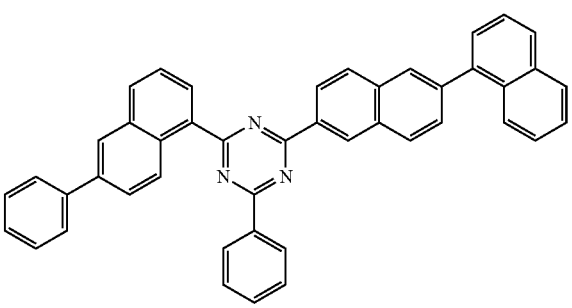

P-36
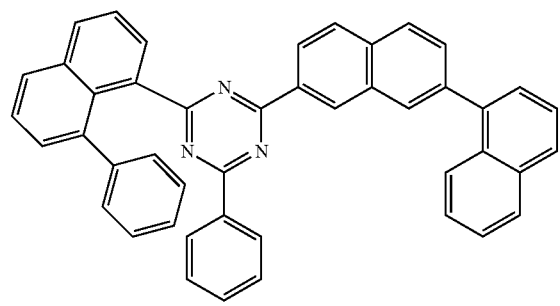
P-37
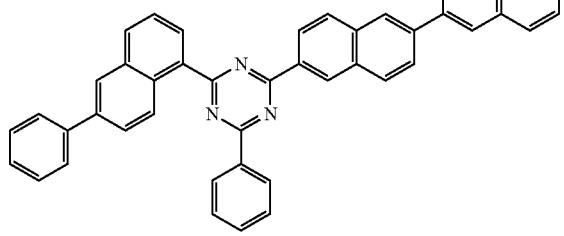
P-38
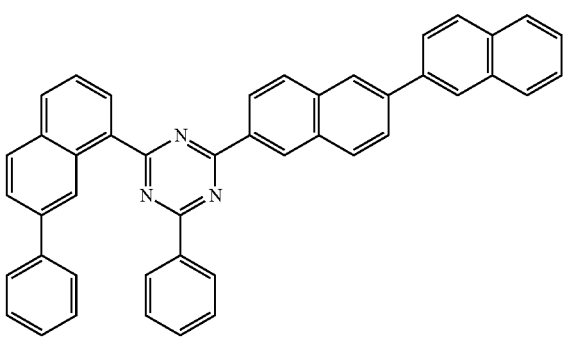
P-39
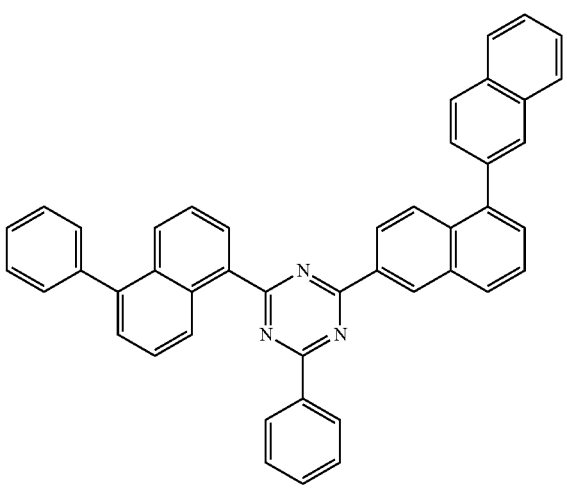
P-40
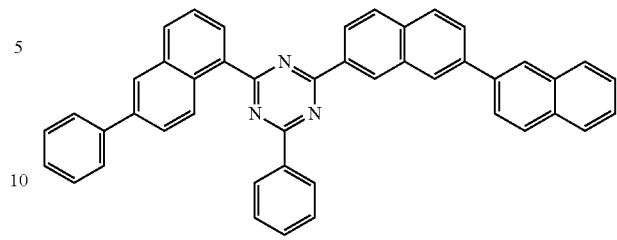
P-41
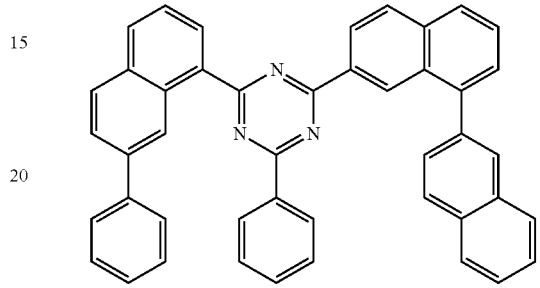
P-42
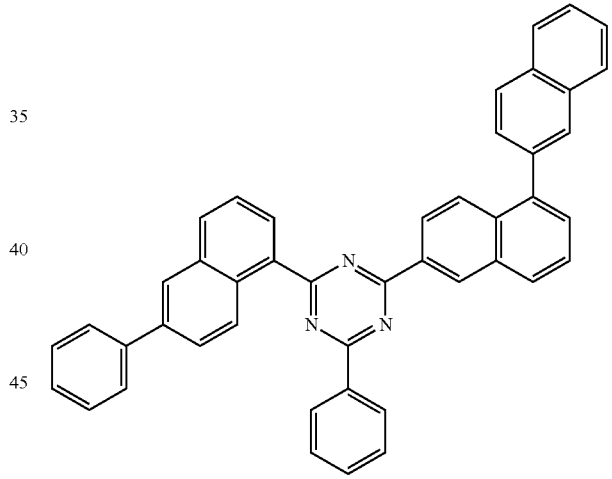
P-43
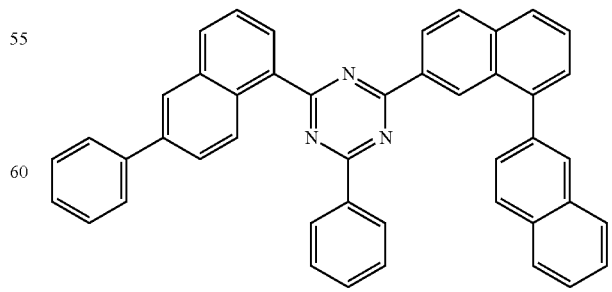

-continued

P-44

P-45

P-46

P-47

P-48

-continued

P-49

P-50

P-51

P-52
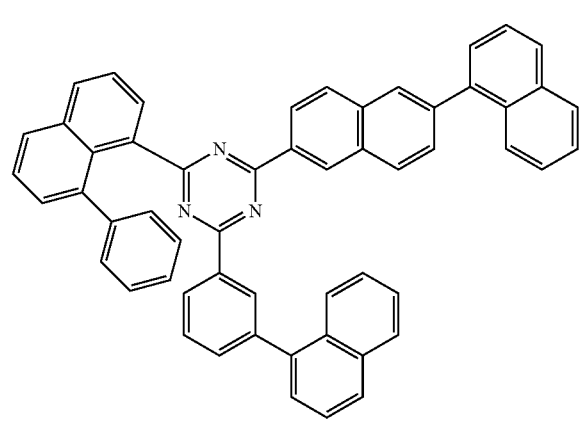
P-53
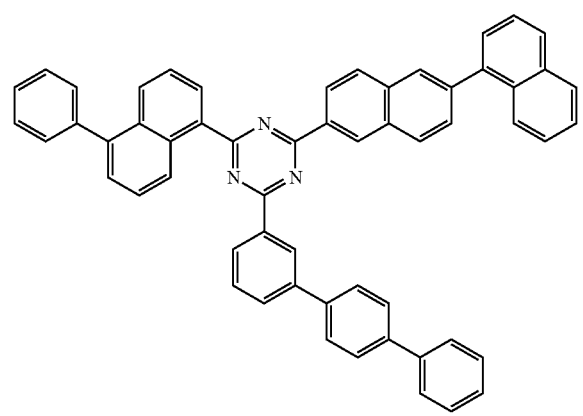
P-54
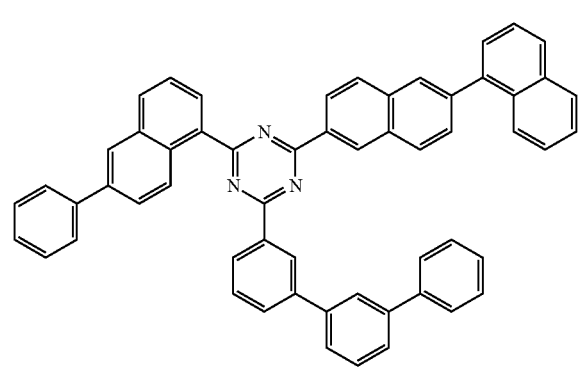
P-55
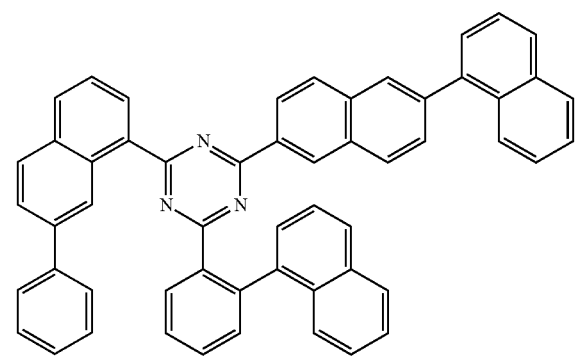
P-56
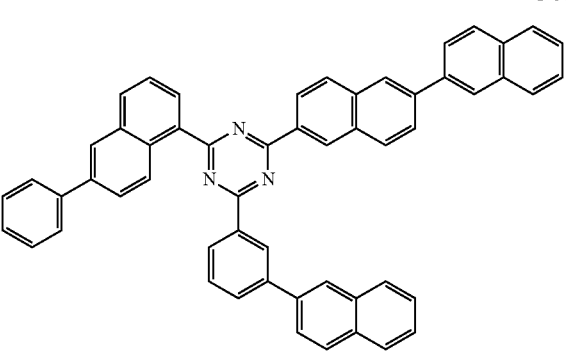
P-57
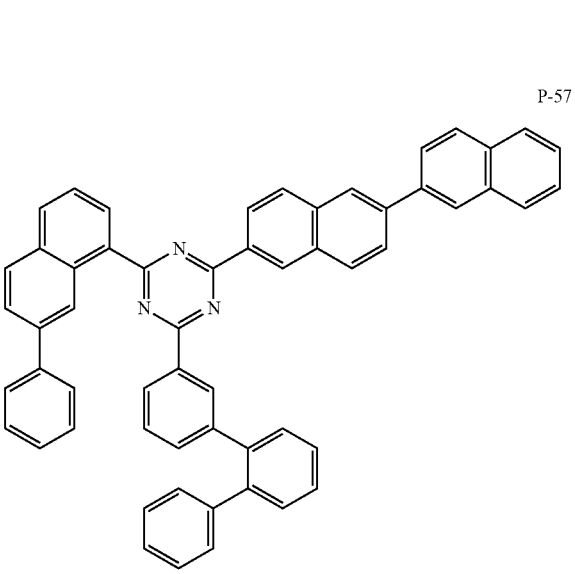
P-58
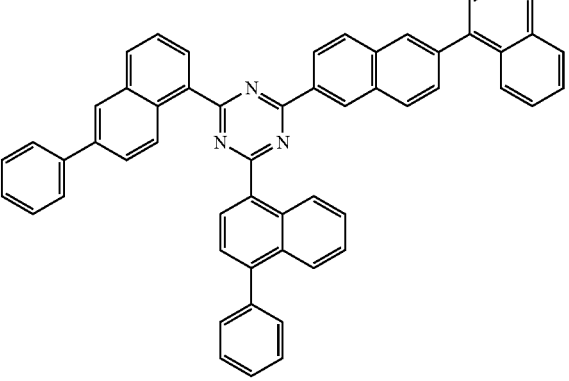

P-59
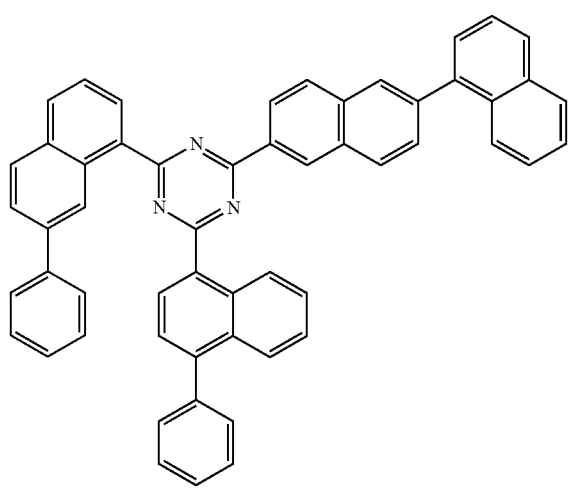
P-60
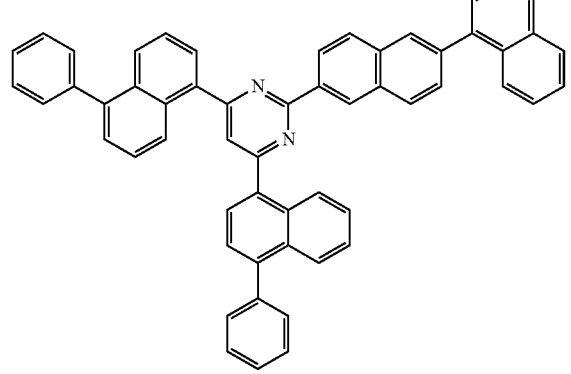
P-61
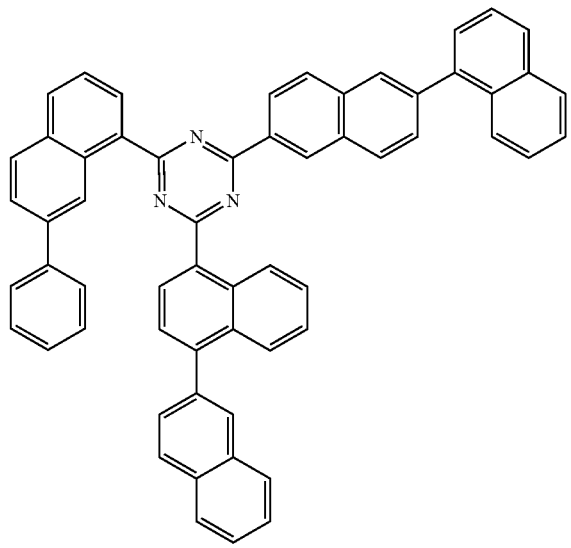
P-62
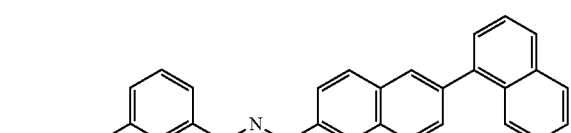
P-63
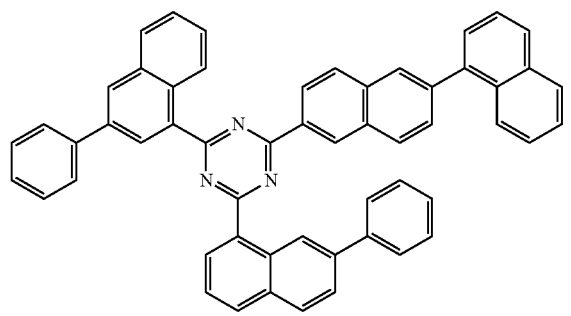
P-64
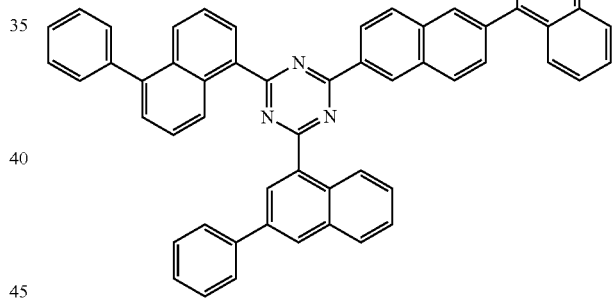
P-65
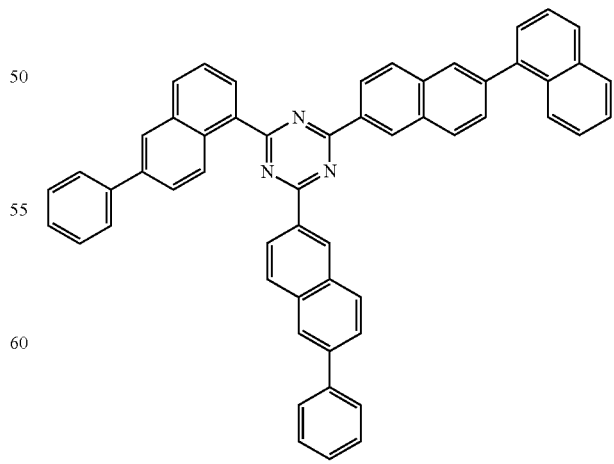

P-66
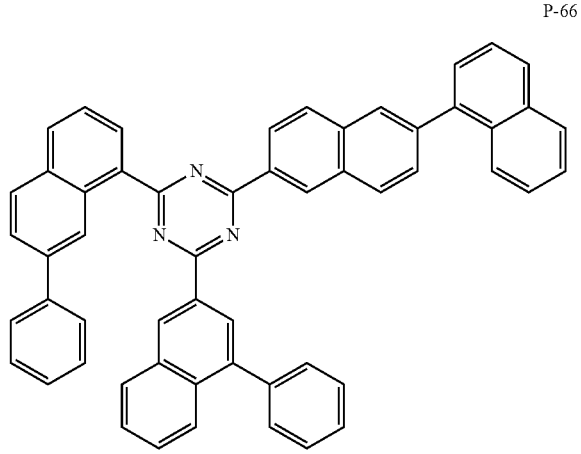
P-67
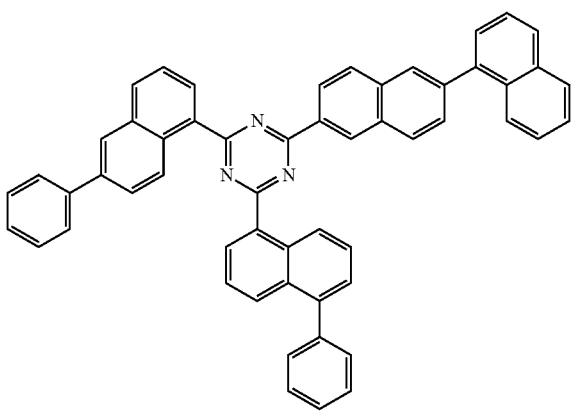
P-68
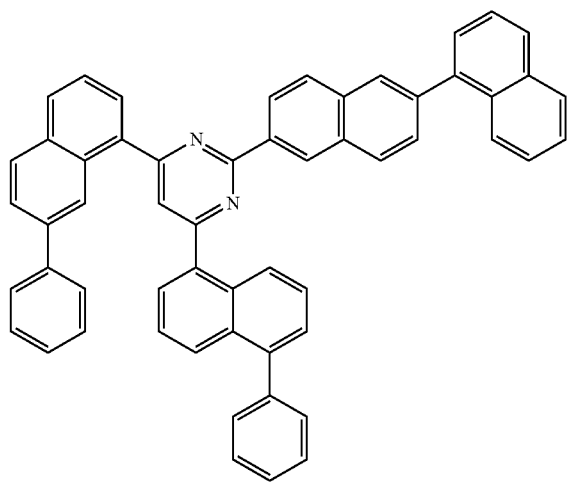
P-69
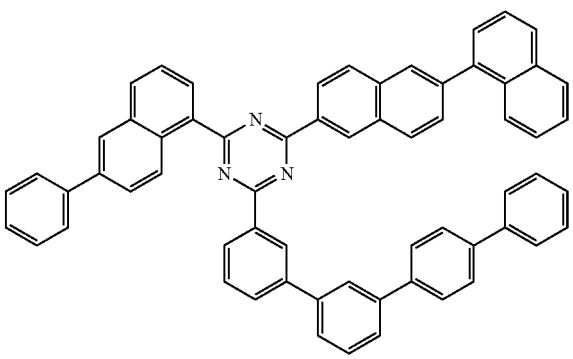
P-70
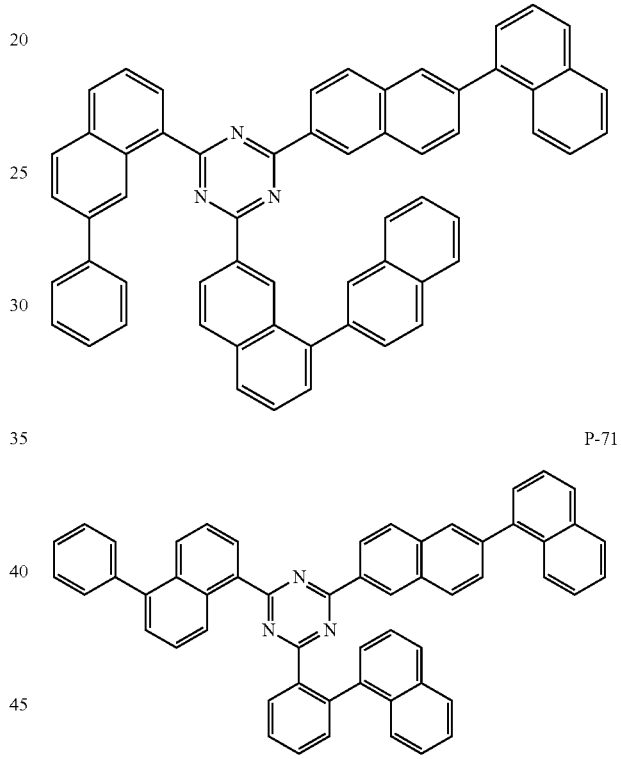
P-71
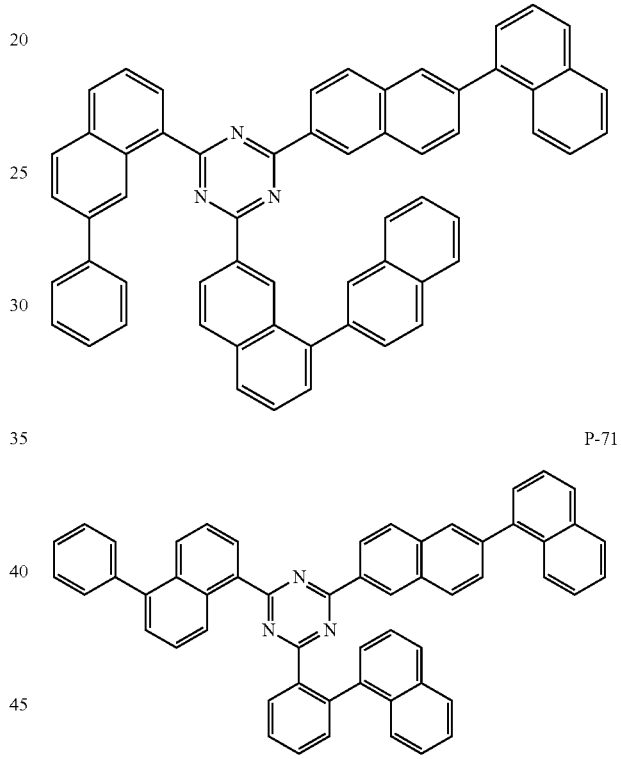
P-72
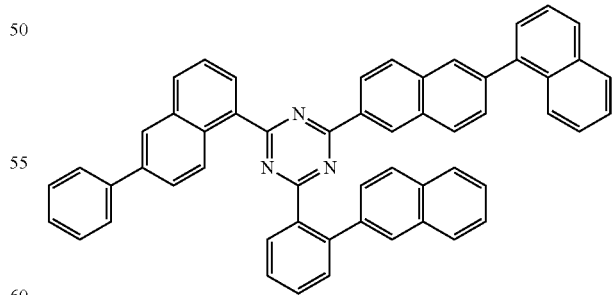

P-73
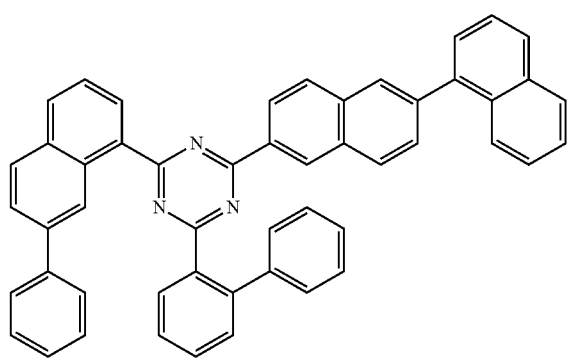
P-77
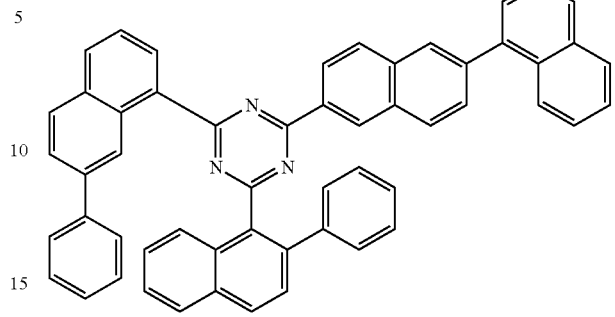
P-74
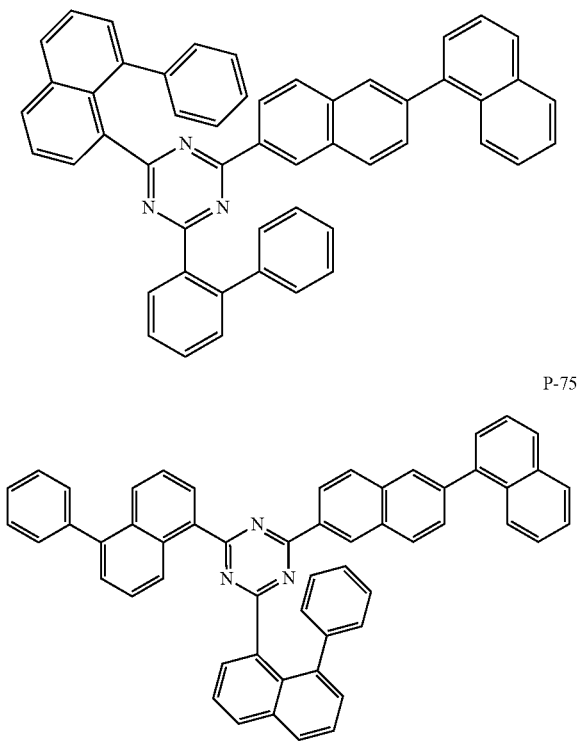
P-78
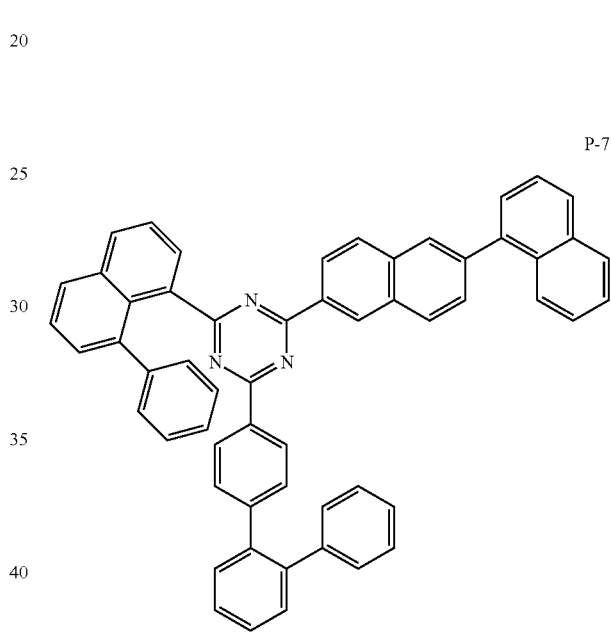
P-75
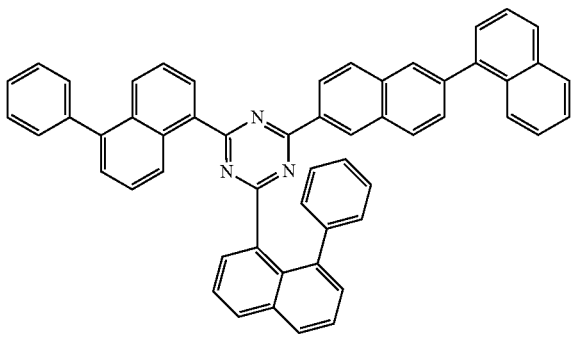
P-76
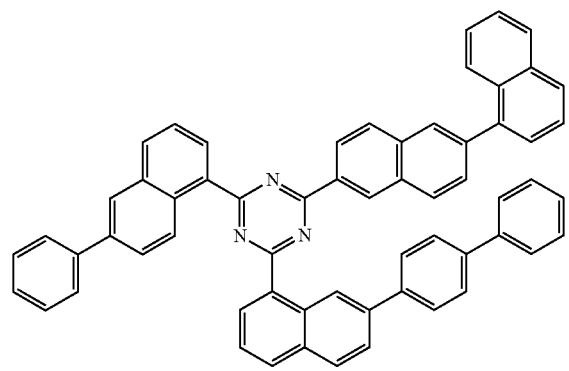
P-79
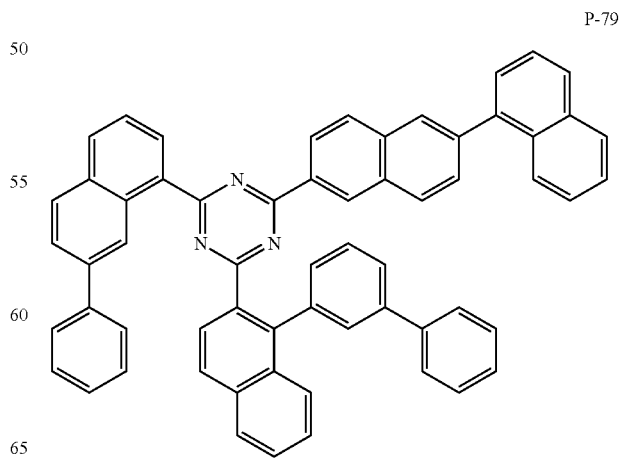

-continued
P-80
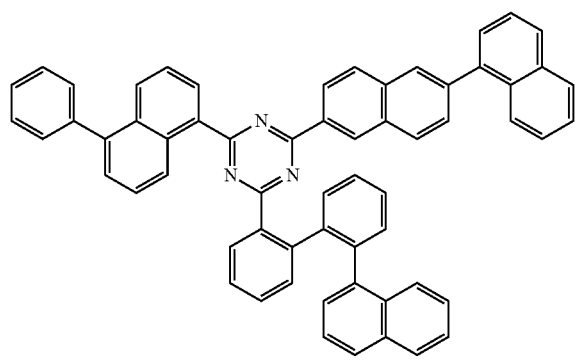
P-81
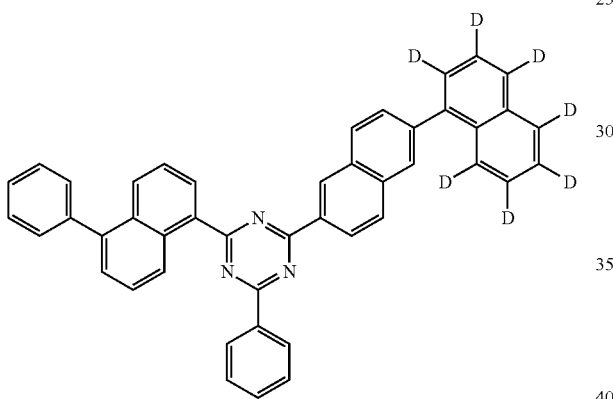
P-82
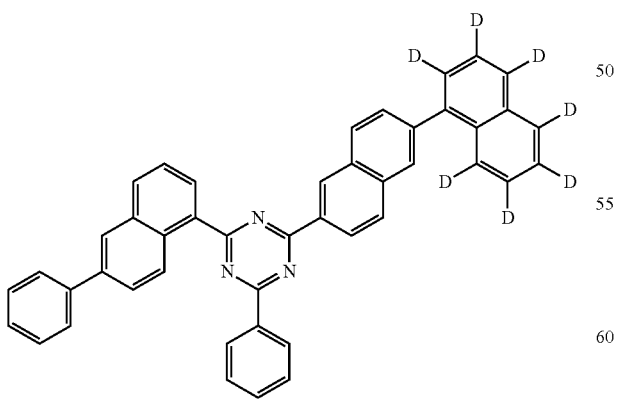
-continued
P-83
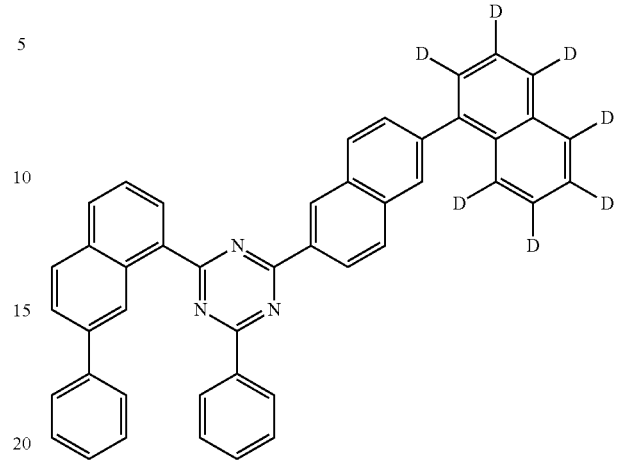
P-84
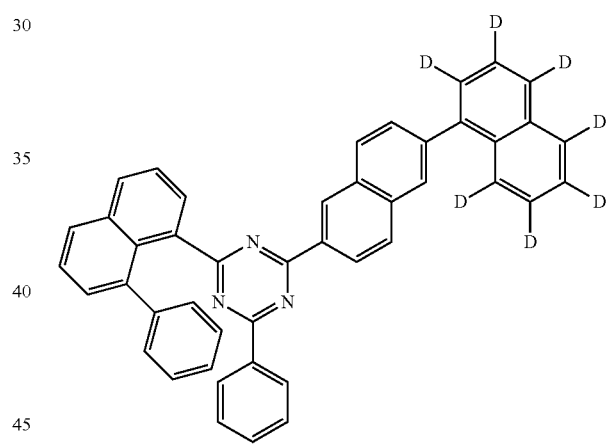
P-85
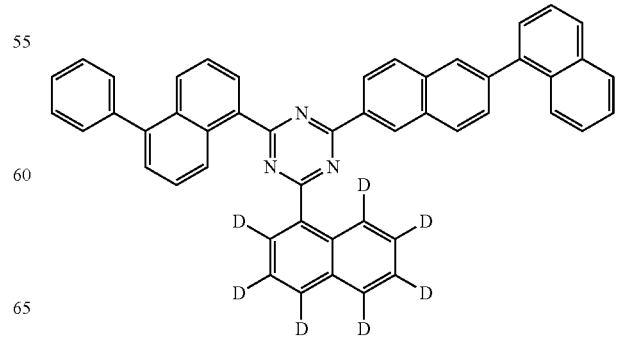

P-86
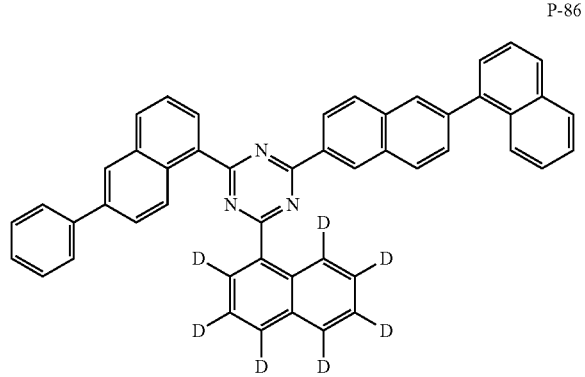
P-87
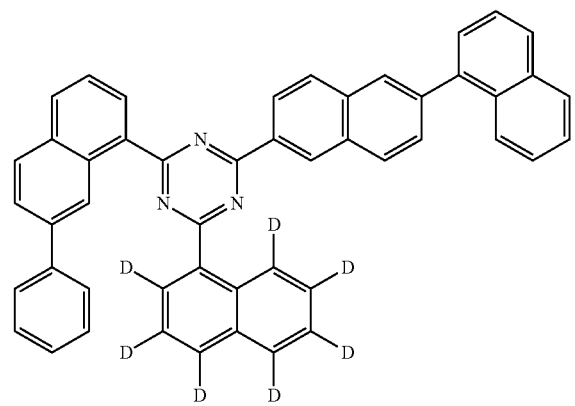
P-88
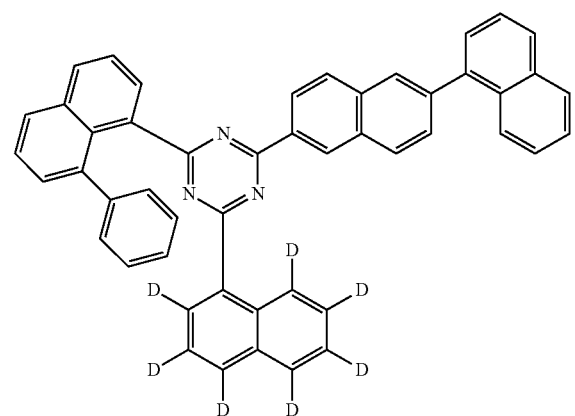
P-89
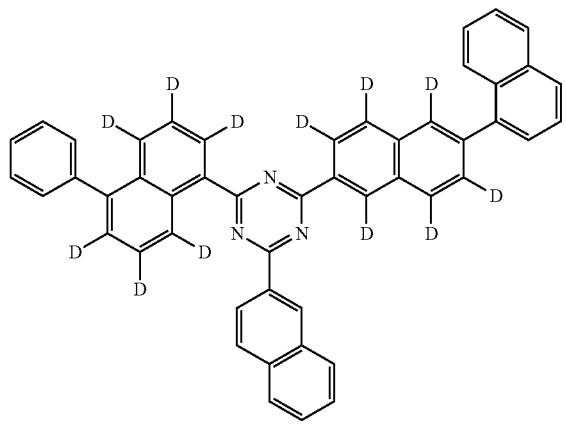
P-90
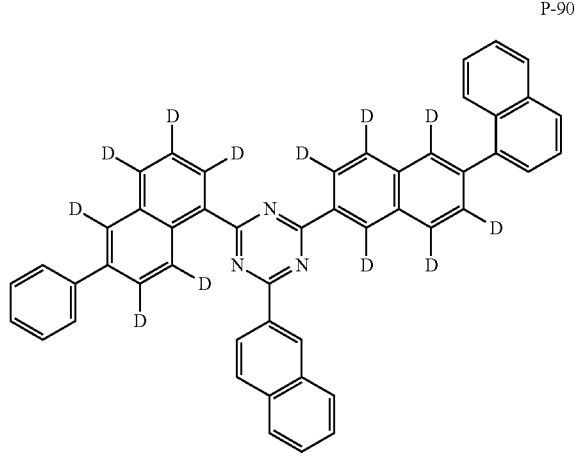
P-91
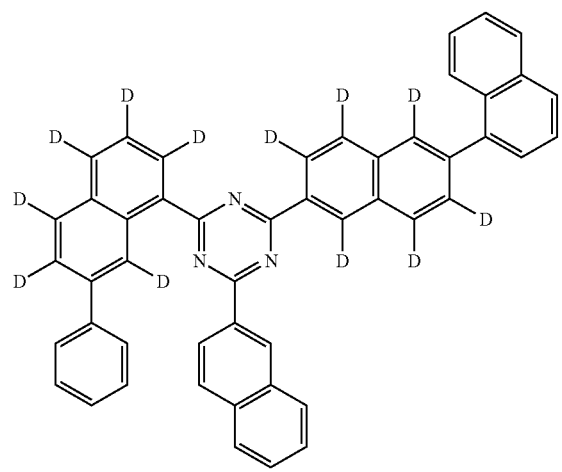

P-92
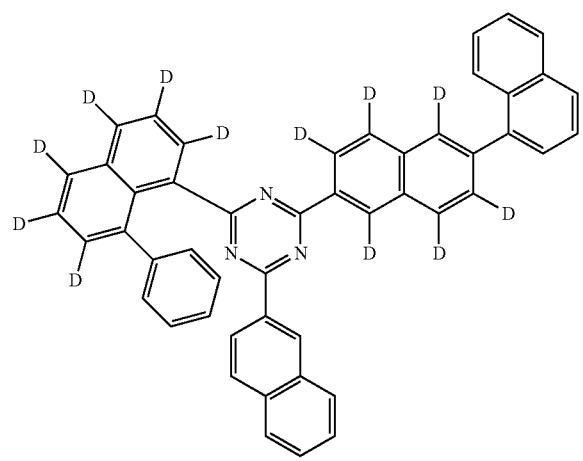
P-95
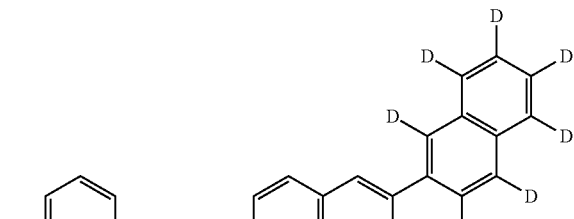
P-93
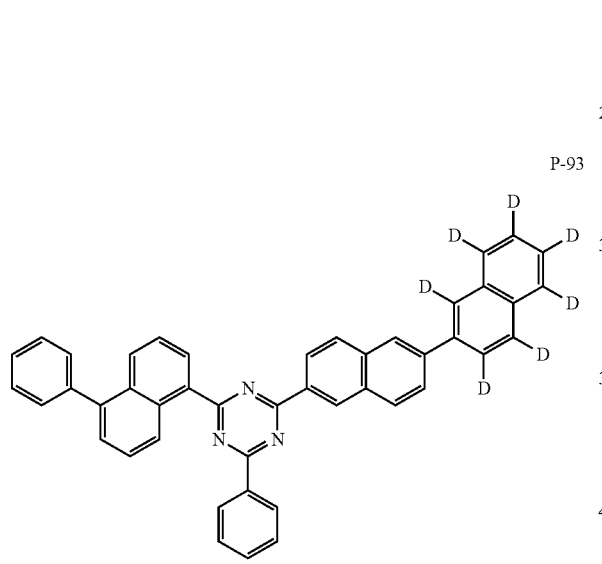
P-96
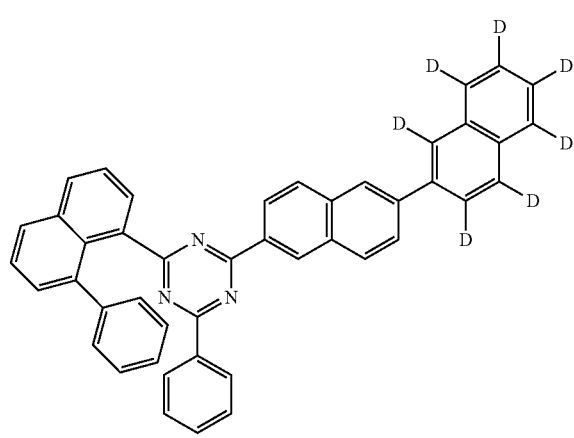
P-94
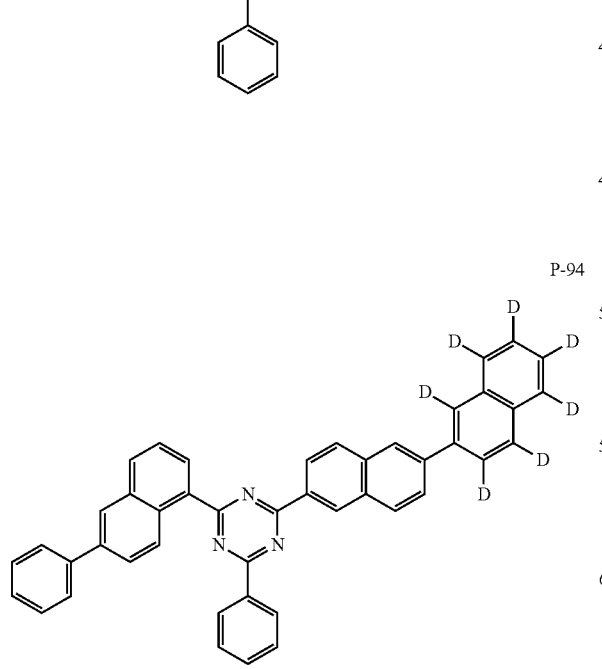
P-97
P-98
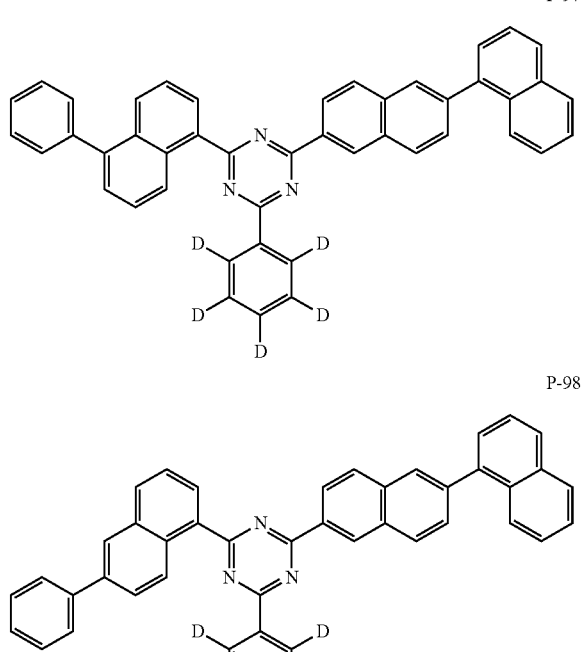

P-99
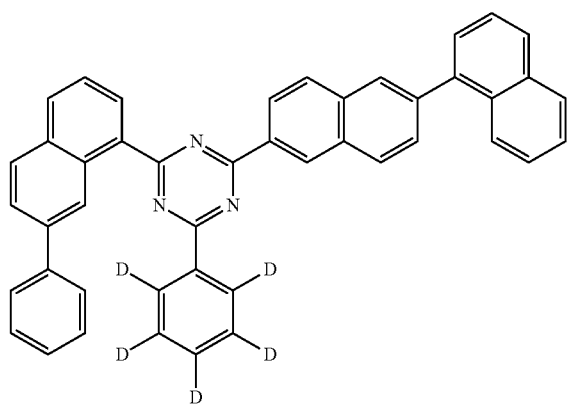
P-100
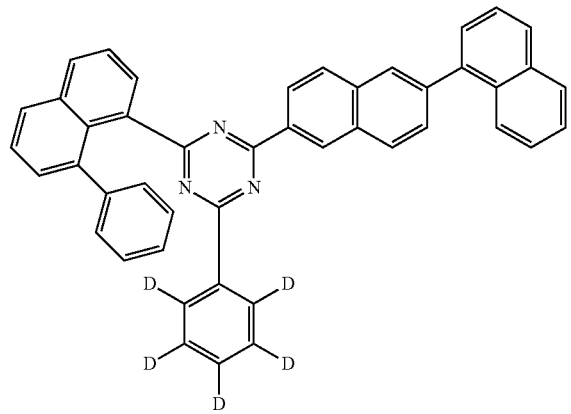
P-101
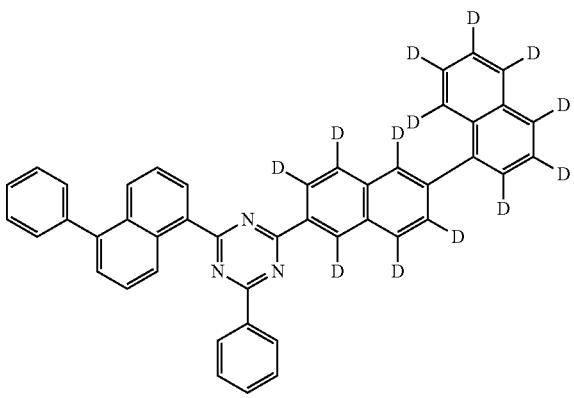
P-102
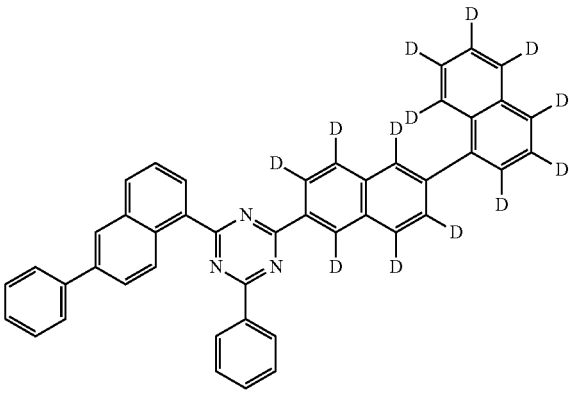
P-103
P-104
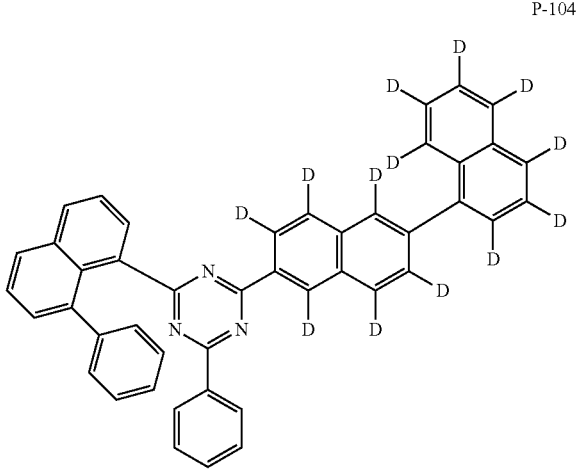

P-105
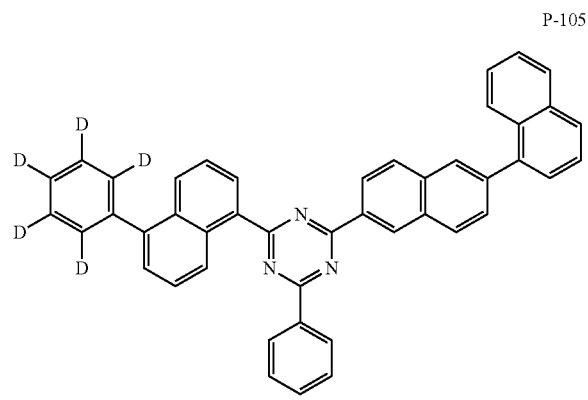
P-106
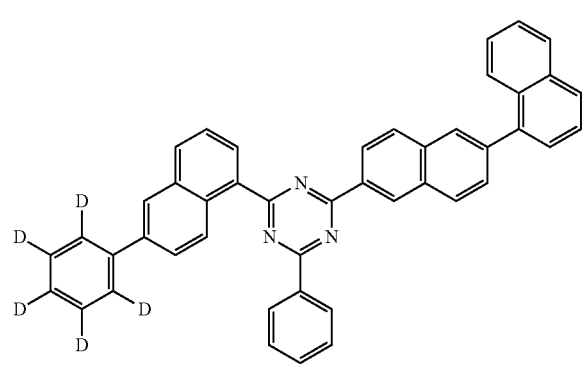
P-107
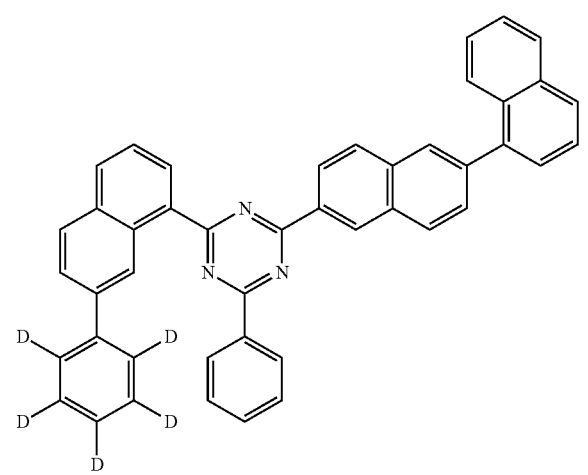
P-108
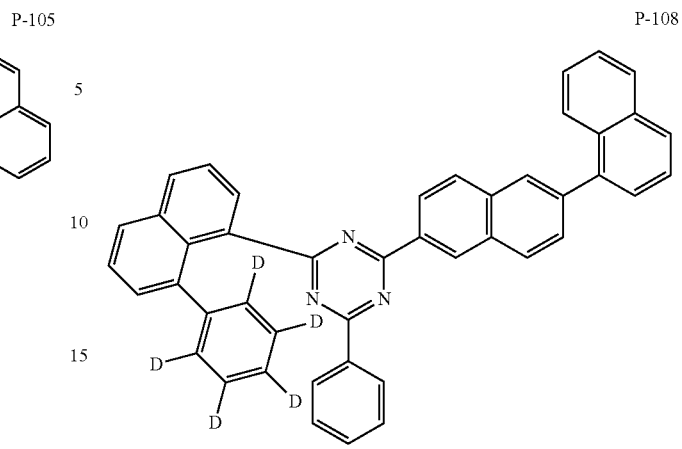
P-109
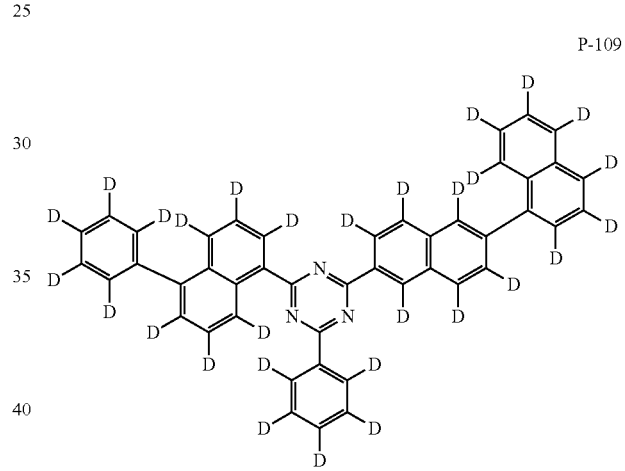
P-110

P-111
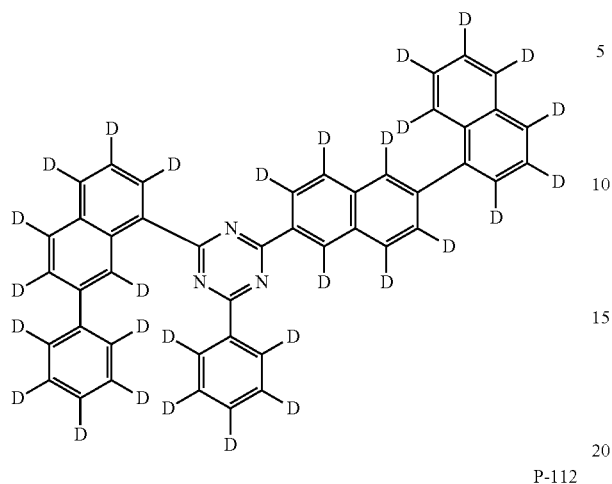
P-115
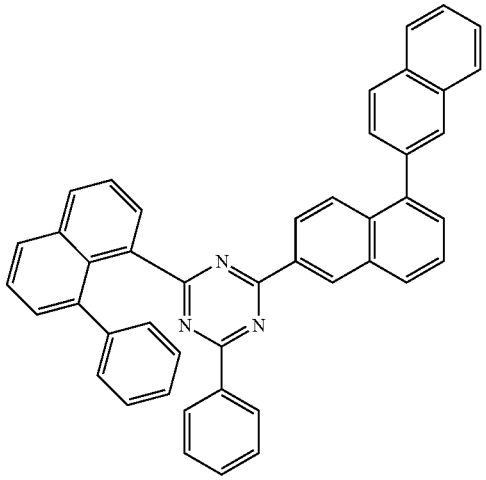
P-112
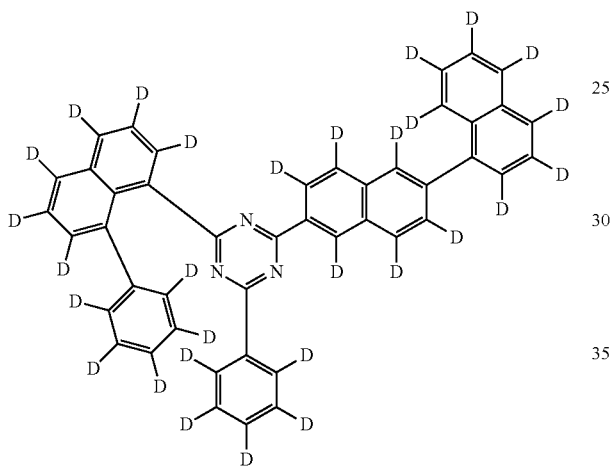
P-116
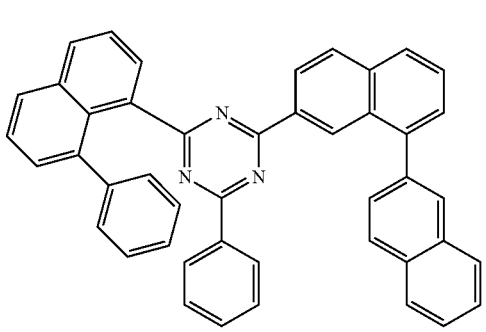
P-113
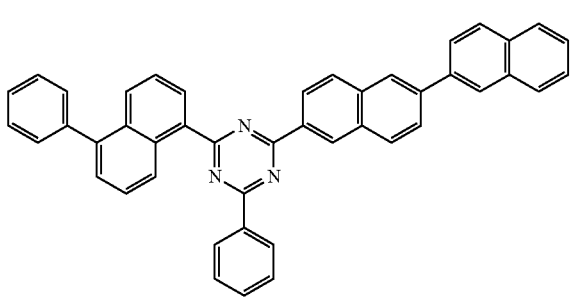
P-117
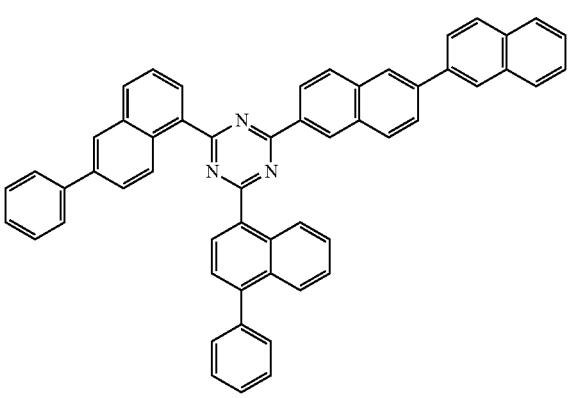
P-114
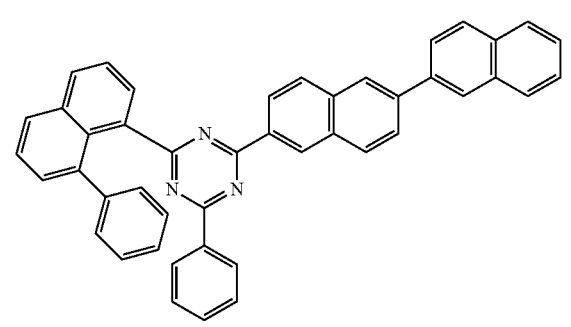
P-118
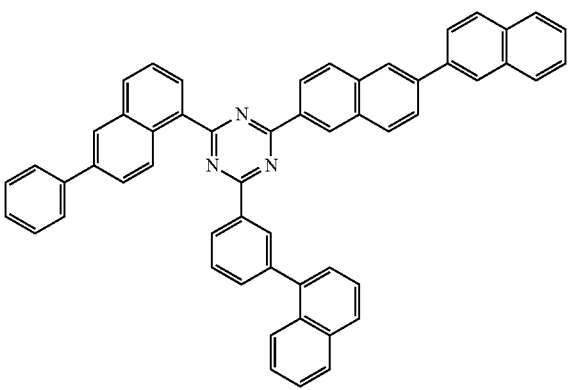

P-119
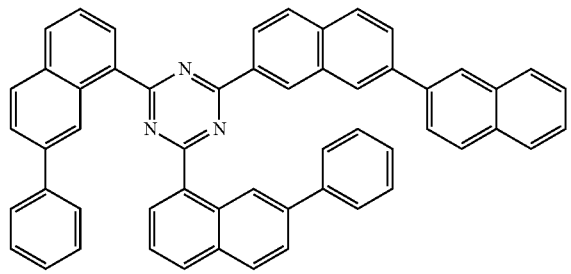
P-120
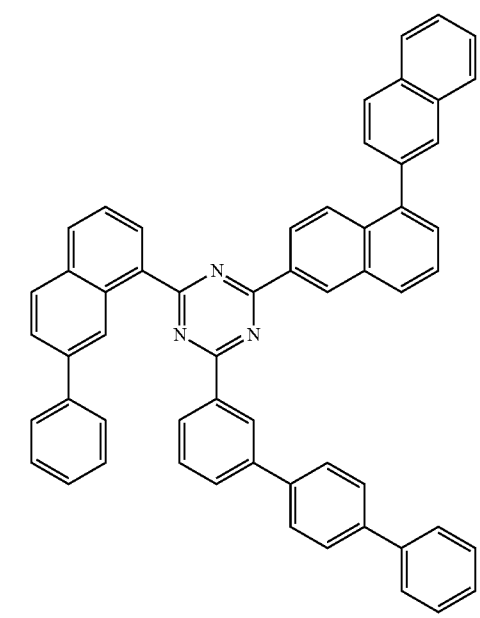
P-121
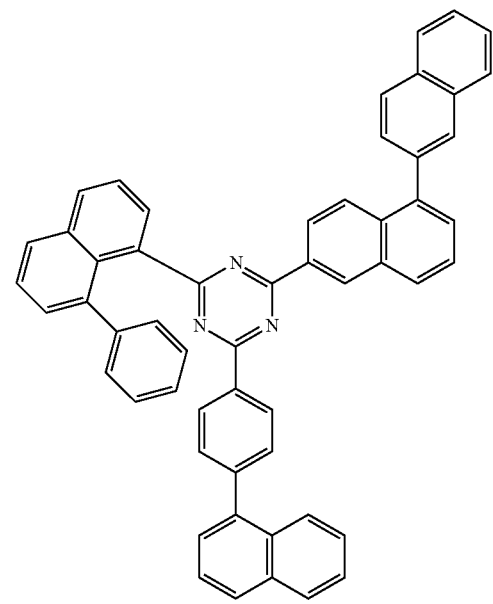
P-122
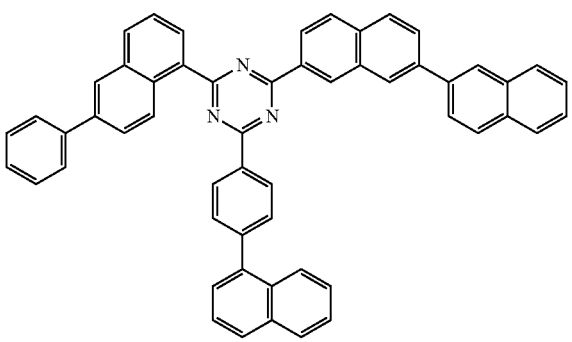
P-123
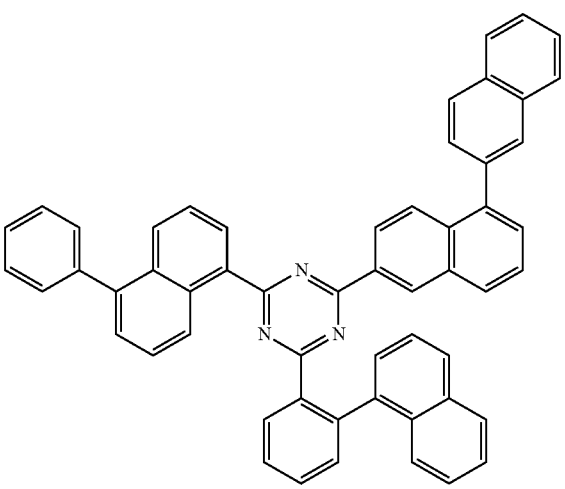
P-124
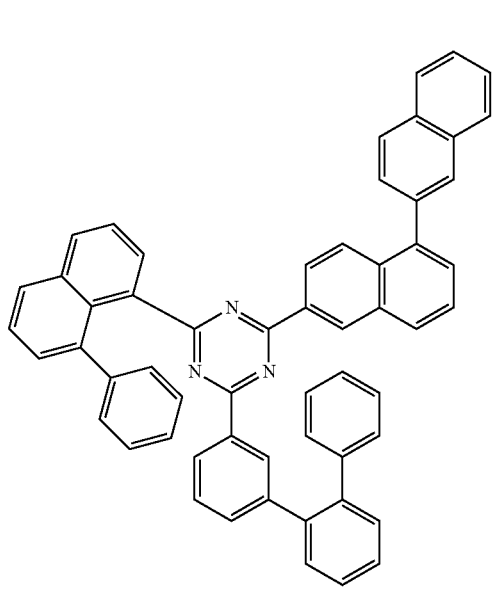

P-125
P-126
P-127
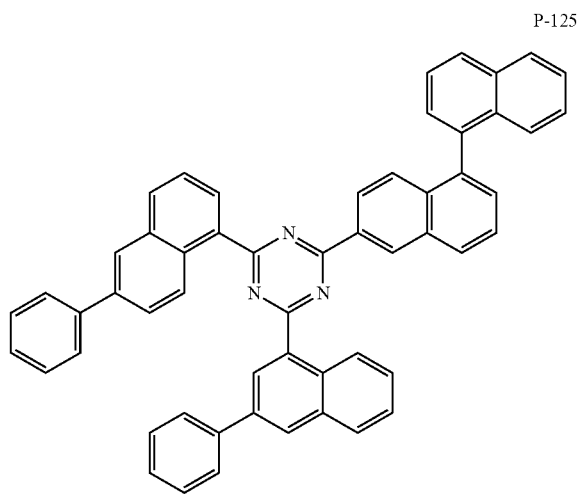
P-128
P-129
P-130
P-131
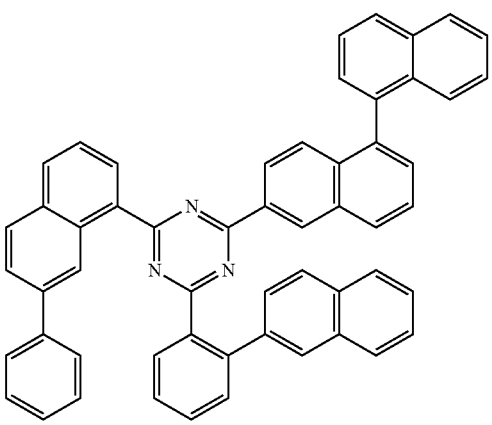
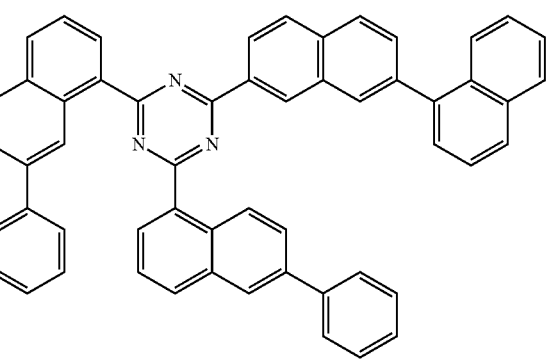
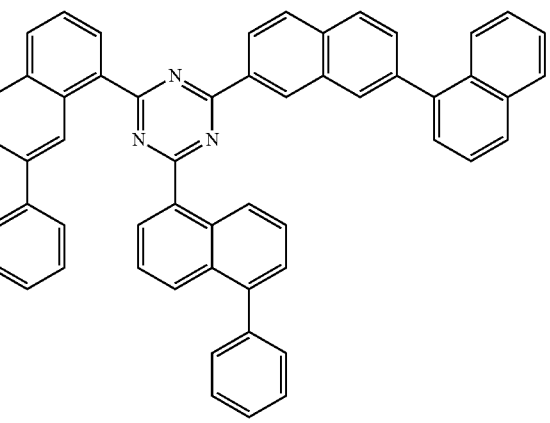
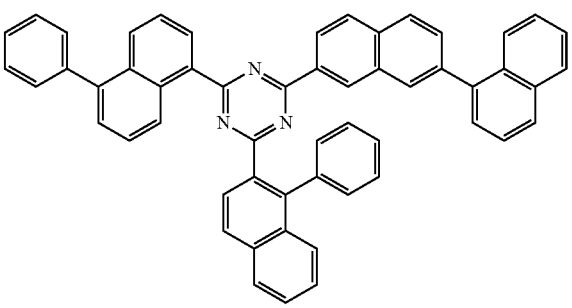

P-132
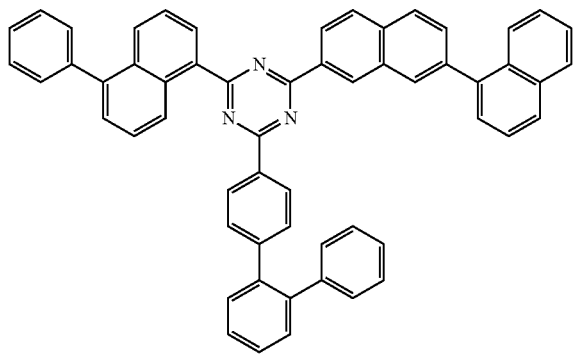

P-133
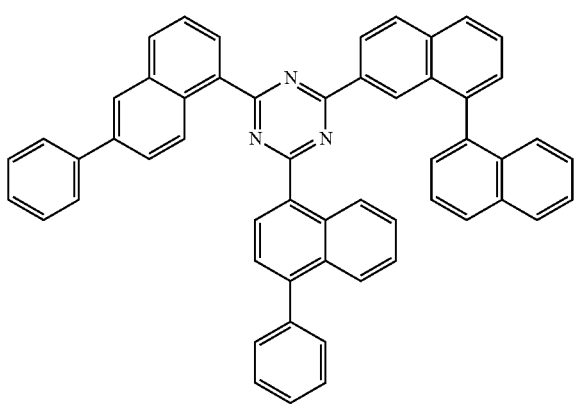

P-134
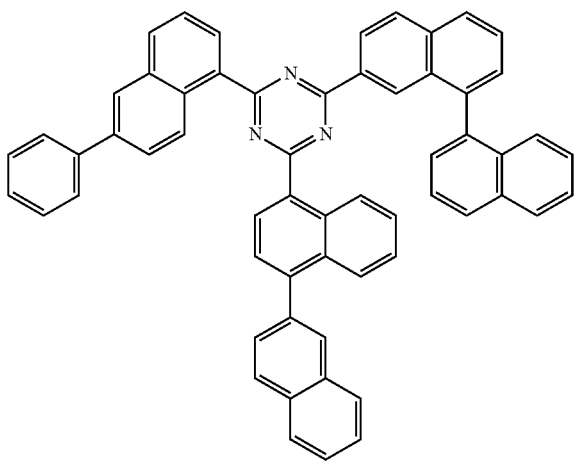

P-135
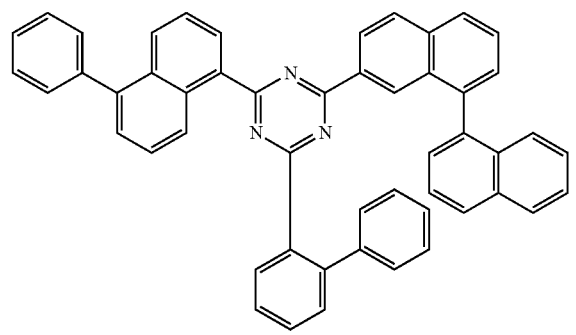

P-136
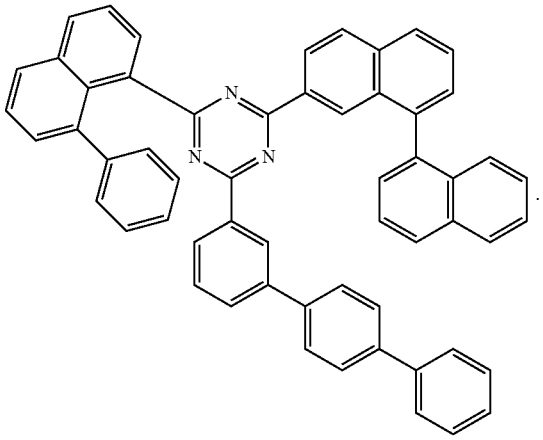

6. A composition for an organic electronic element comprising a compound of claim 1 and a compound represented by Formula 2 or 3:

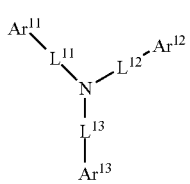
<Formula 2>

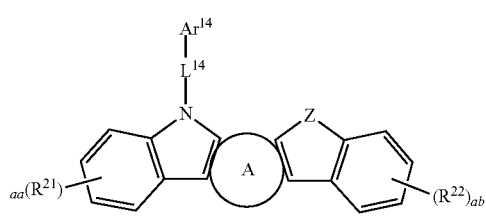
<Formula 3> wherein:
$L^{11}$, $L^{12}$, $L^{13}$ and $L^{14}$ are each independently selected from the group consisting of a single bond; a $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring, $Ar^{11}$, $Ar^{12}$ and $Ar^{13}$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, $Ar^{14}$ is selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^a$)($R^b$), wherein L' is selected from the group consisting of a single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring, Z is O, S, C(R$^{51}$)(R$^{52}$) or NR$^{53}$, wherein R$^{51}$, R$^{52}$, R$^{53}$, R$^a$ and R$^b$ are the same as the definition of Ar$^{11}$ or R$^{51}$ and R$^{52}$ can be bonded to each other to form a spiro, Ring A is an $C_6$~$C_{20}$ aryl group, R$^{21}$ and R$^{22}$ are each the same or different, and each independently selected from the group consisting of hydrogen; deuterium; a halogen; a cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, or an adjacent plurality of R$^{21}$ or plurality of R$^{22}$ may be bonded to each other to form a ring, aa and ab are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; a $C_3$-$C_{20}$ aliphatic ring; a $C_7$-$C_{20}$ arylalkyl group; a $C_8$-$C_{20}$ arylalkenyl group; a $C_7$-$C_{20}$ alkylaryl group; and -L'-N(R$^a$)(R$^b$), and hydrogen of these substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

7. The composition for an organic electronic element according to claim 6, wherein Formula 2 comprises a compound selected from compounds N-1 to N-128:

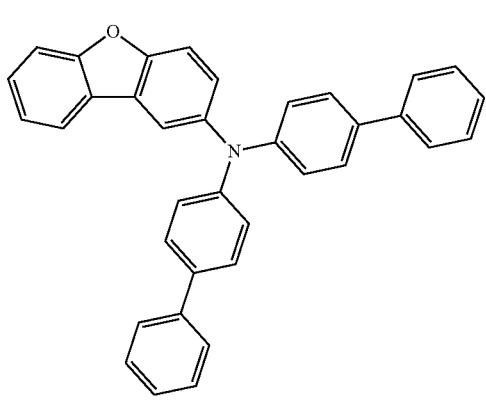

N-1

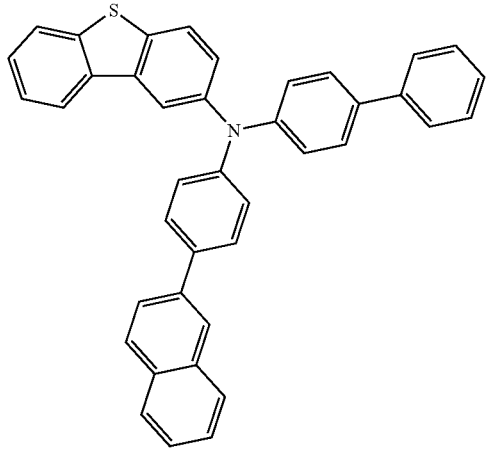

N-2

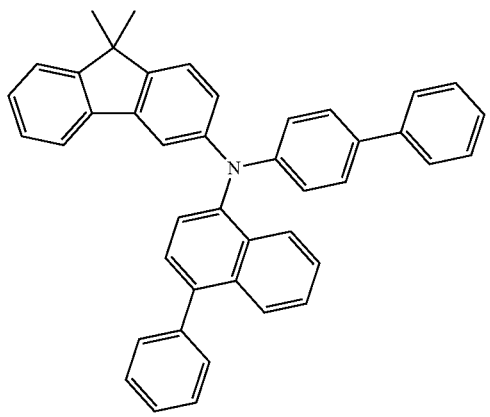

N-3

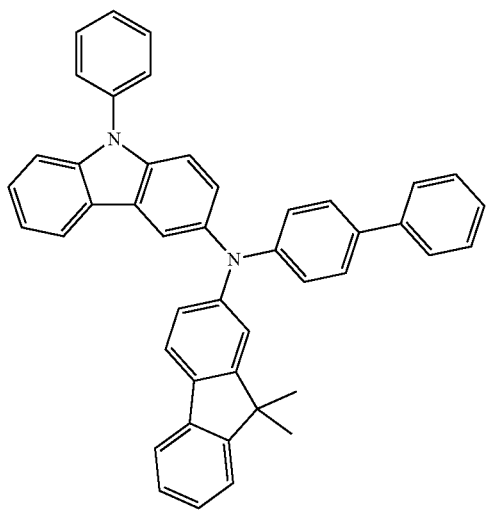

N-4

251
-continued
N-5
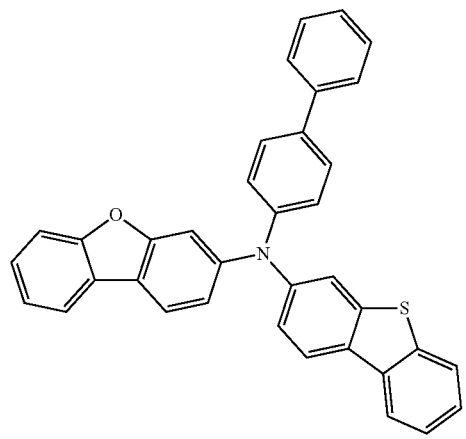
N-6
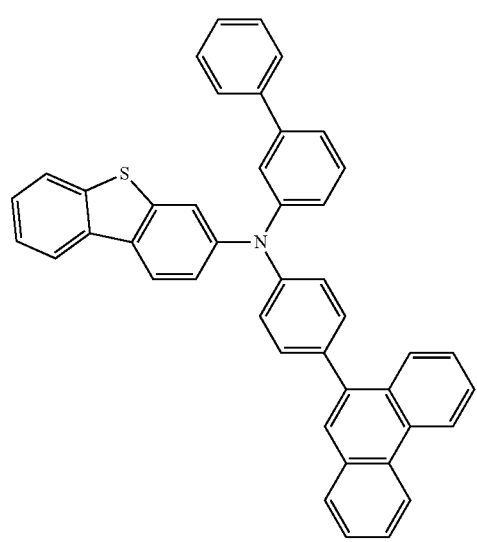
N-7
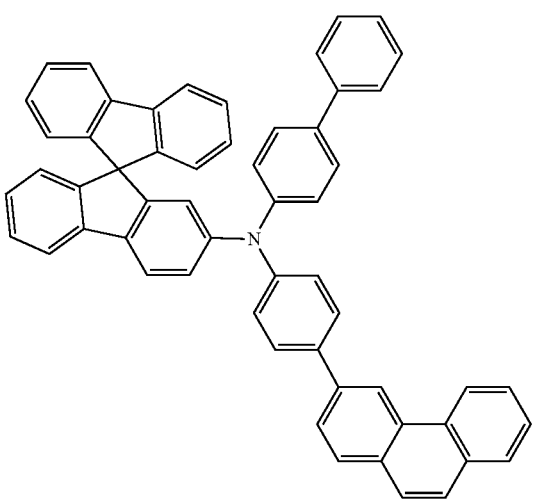
252
-continued
N-8
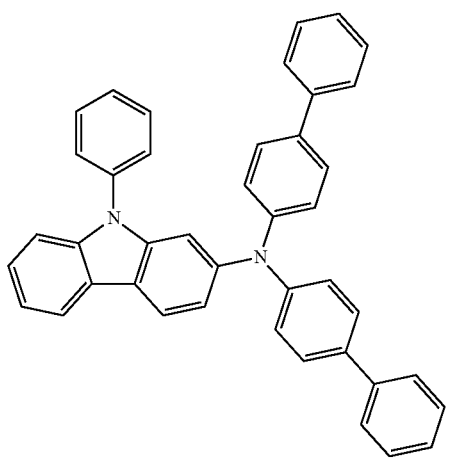
N-9
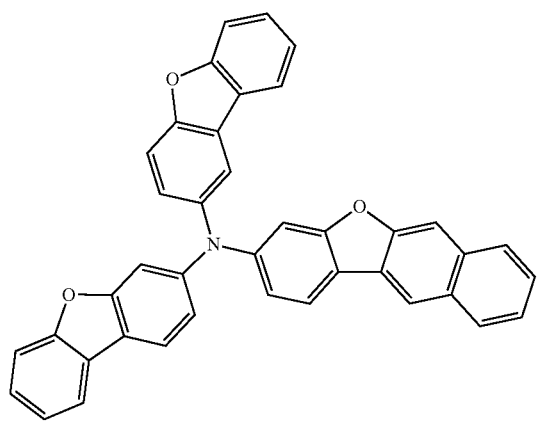
N-10
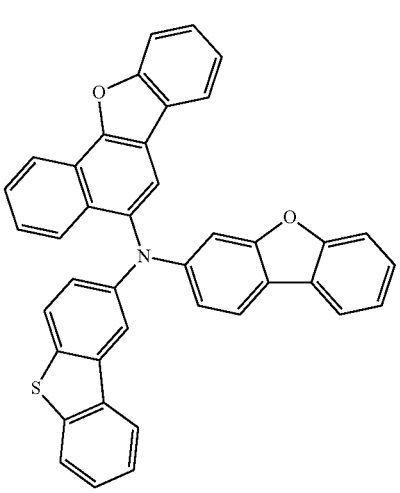

N-11
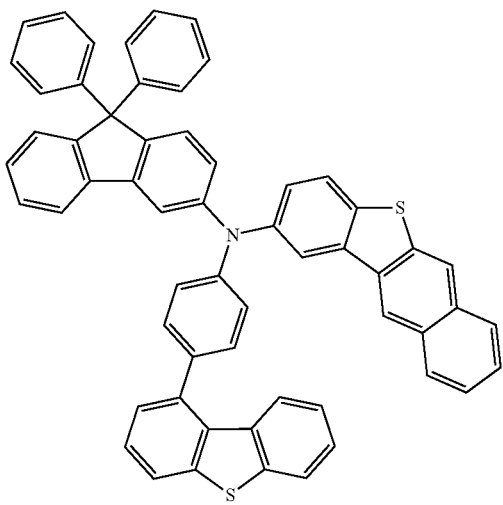
N-12
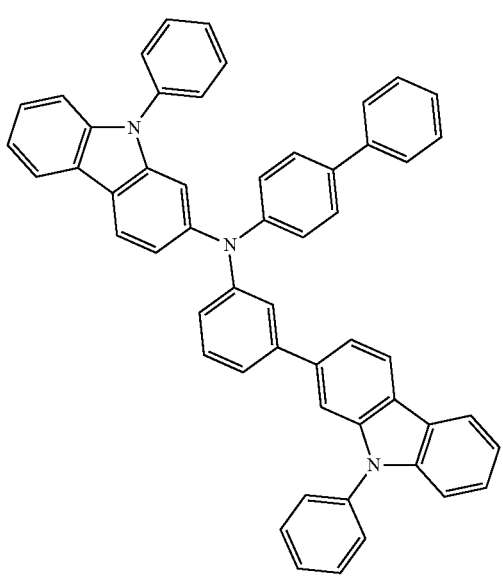
N-13
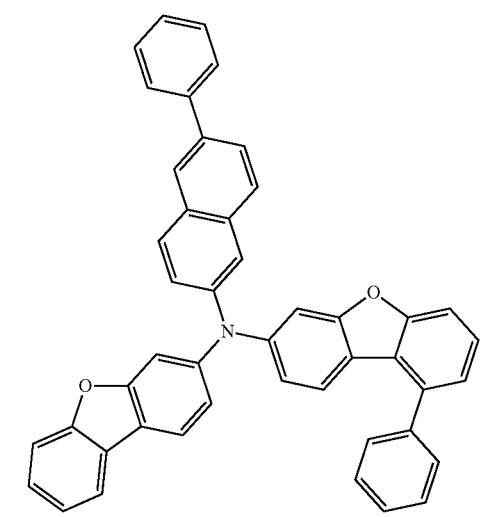
N-14
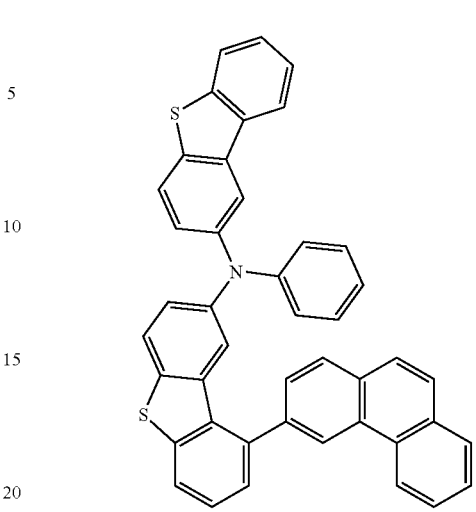
N-15
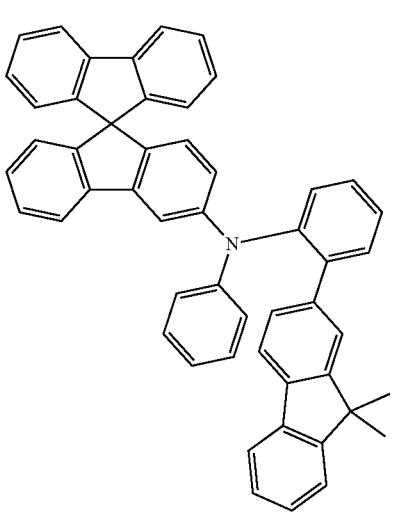
N-16
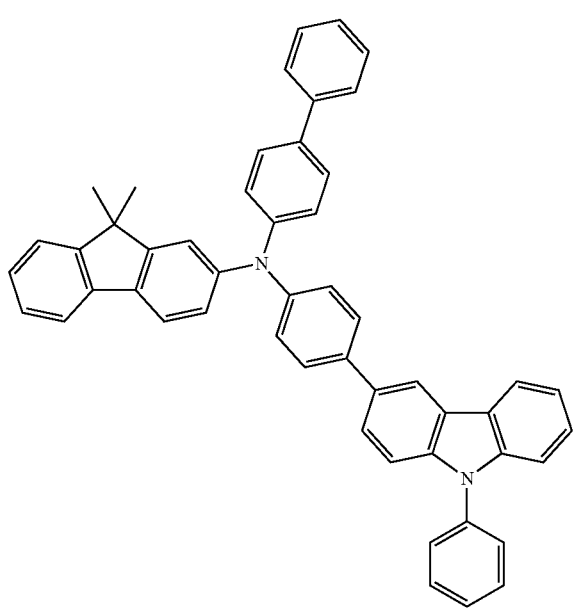

N-17
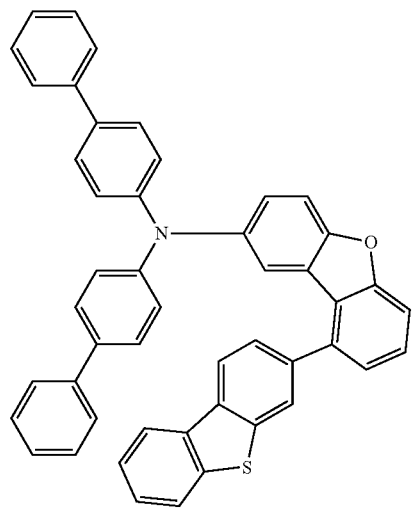
N-18
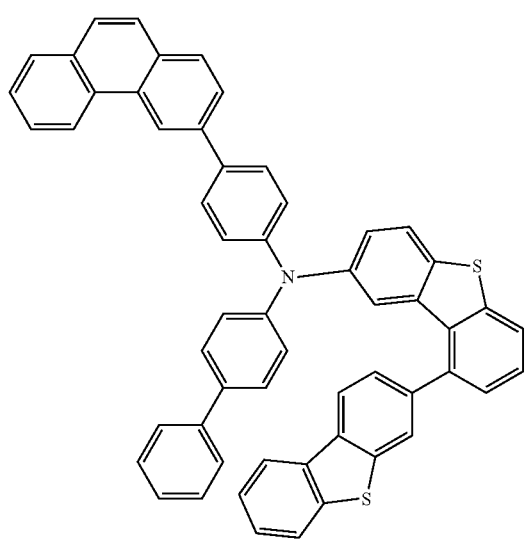
N-19
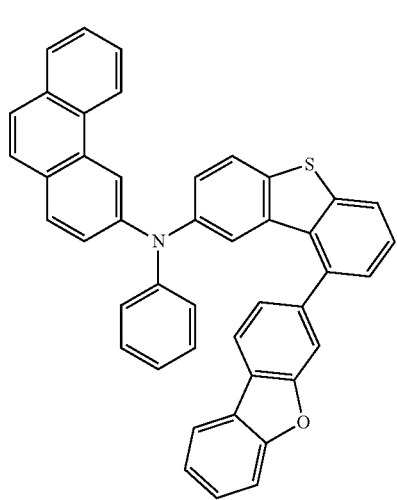
N-20
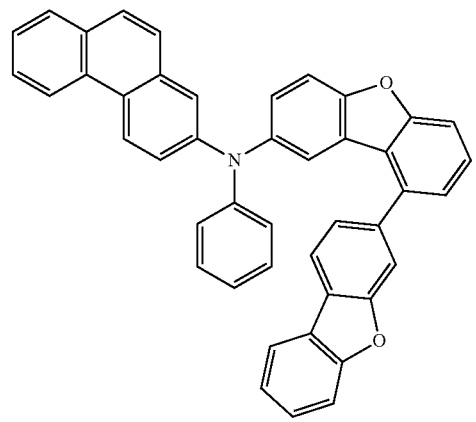
N-21
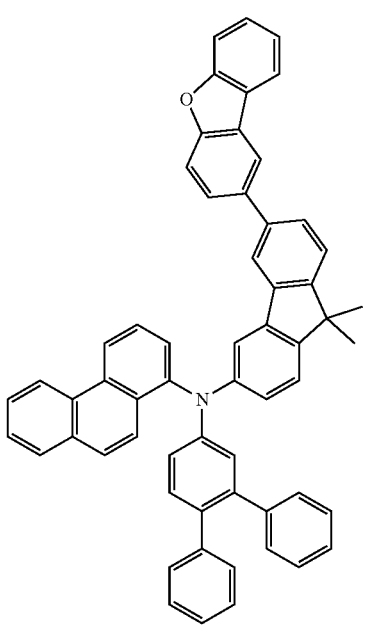
N-22
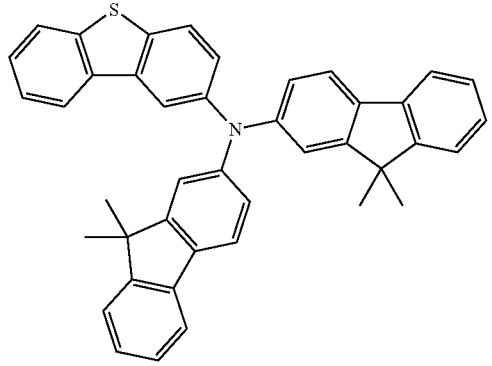

N-23
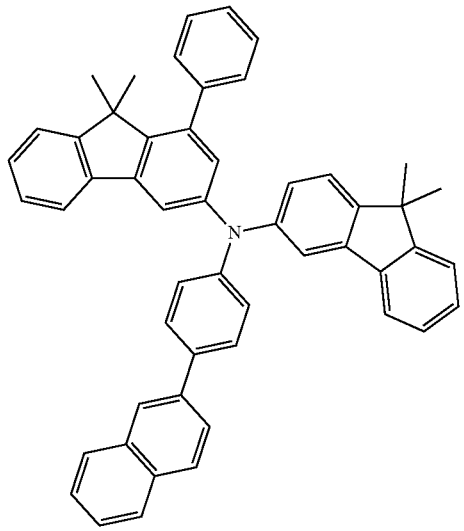
N-24
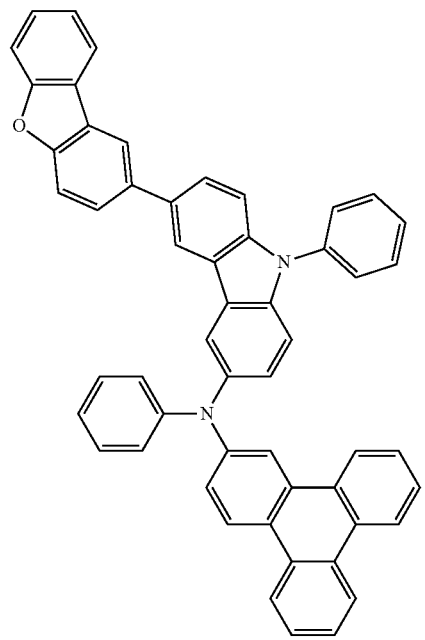
N-25
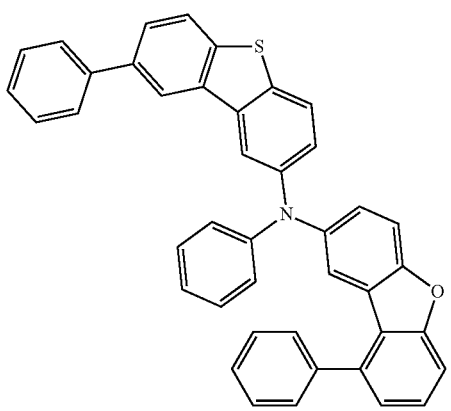
N-26
N-27
N-28
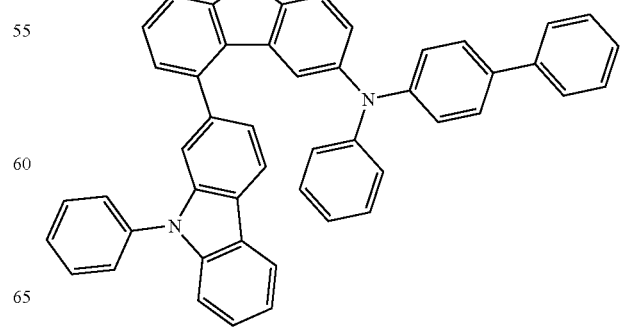

N-29
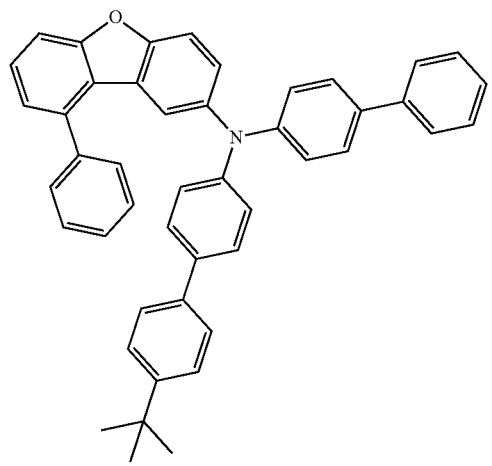
N-30
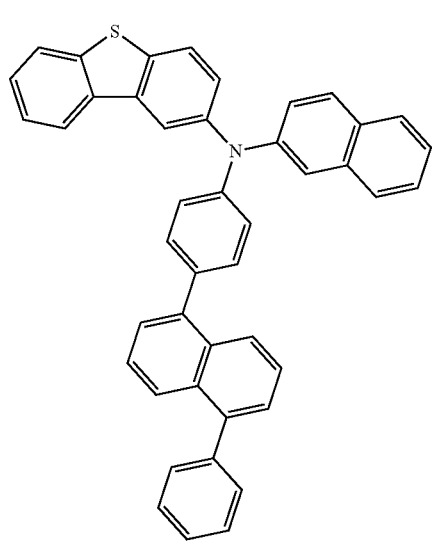
N-31
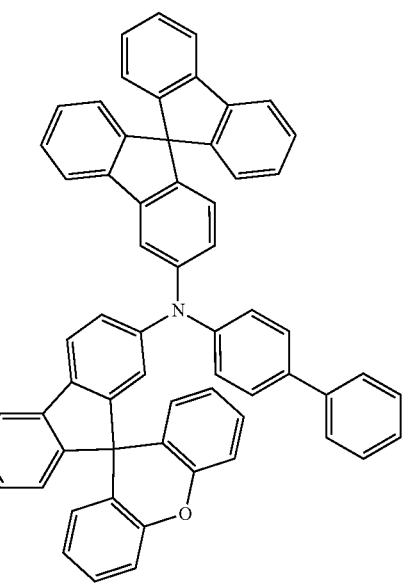
N-32
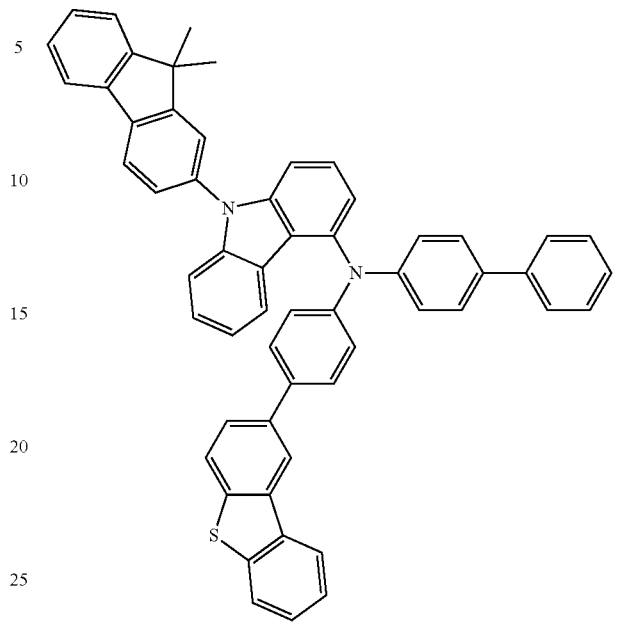
N-33
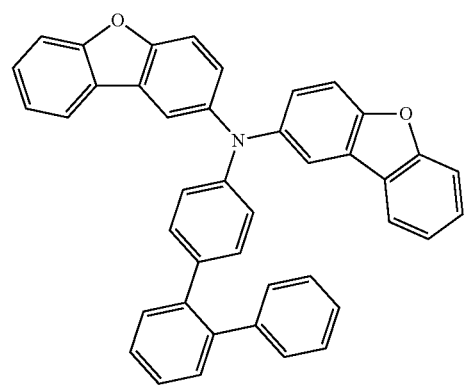
N-34
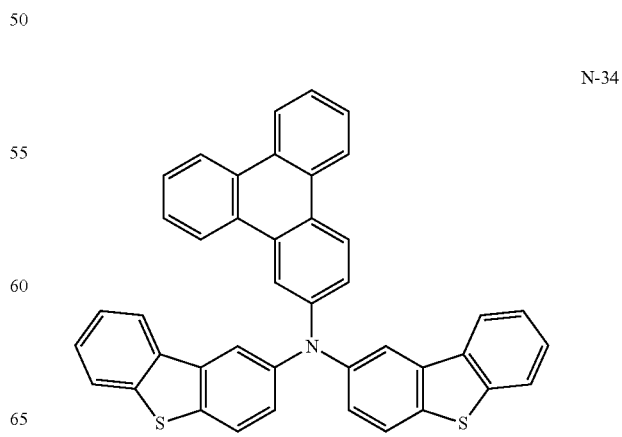

-continued
N-35
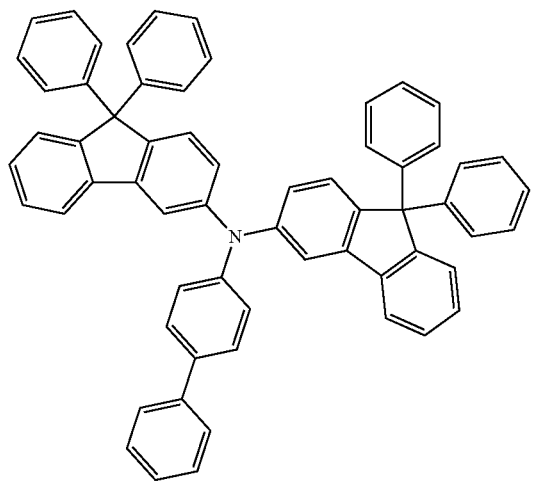
N-36
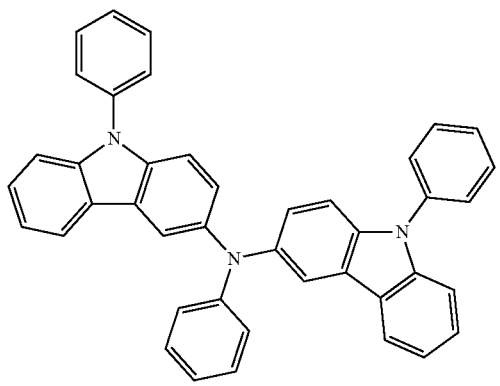
N-37
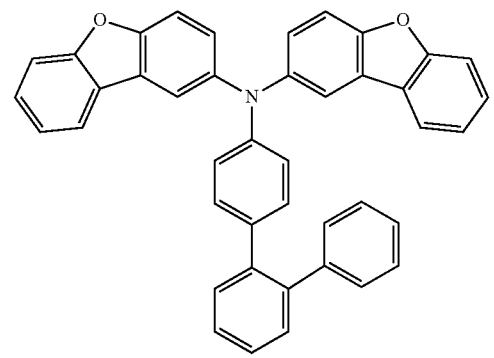
N-38
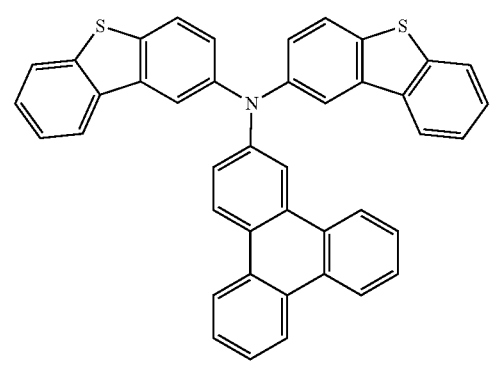
-continued
N-39
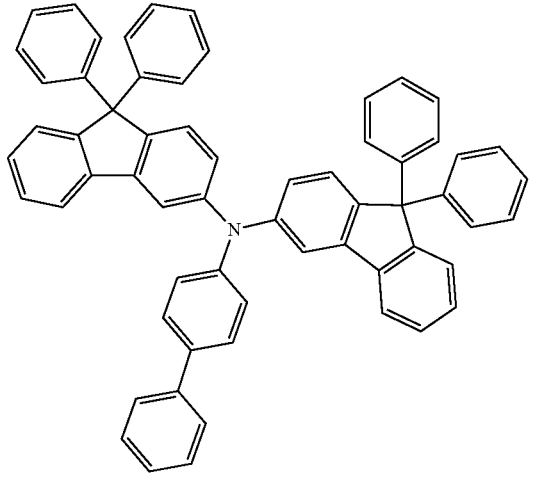
N-40
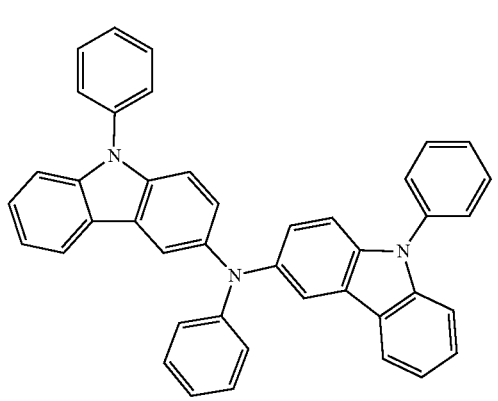
N-41
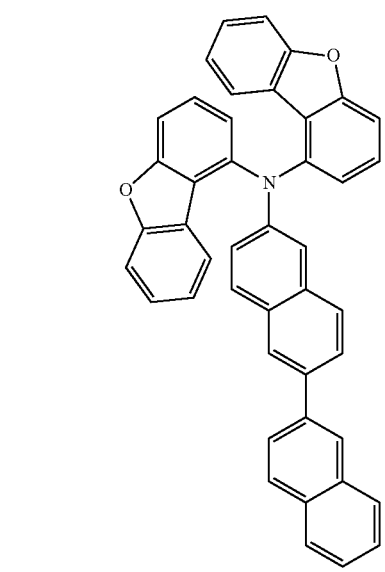

N-42
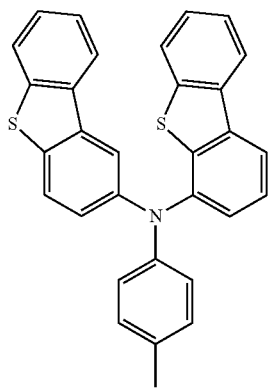
N-43
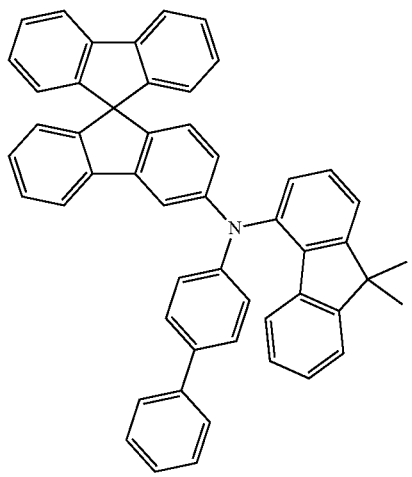
N-44
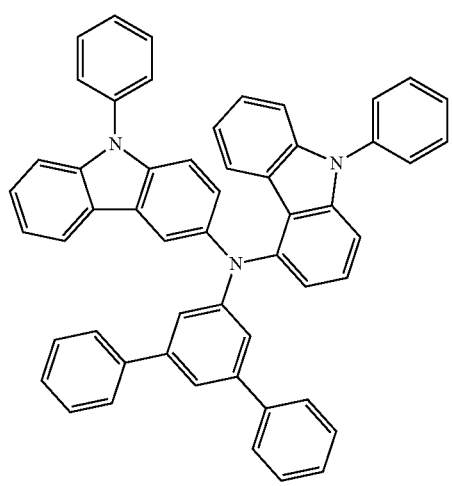
N-45
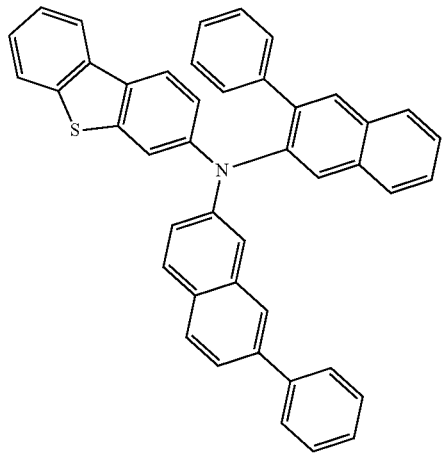
N-46
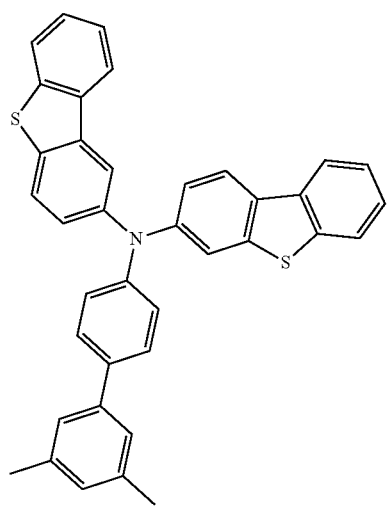
N-47
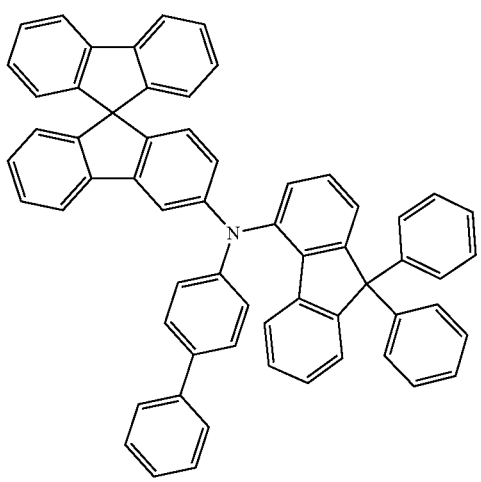

-continued
N-48
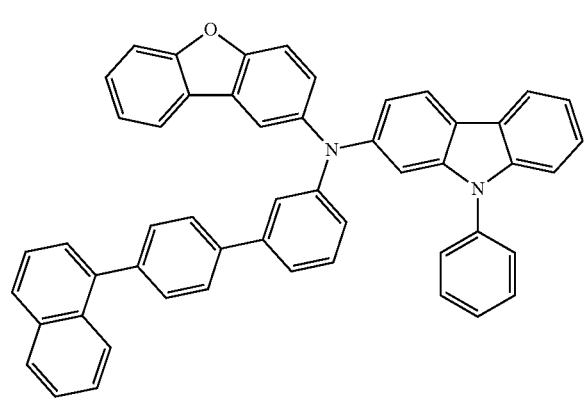
N-49
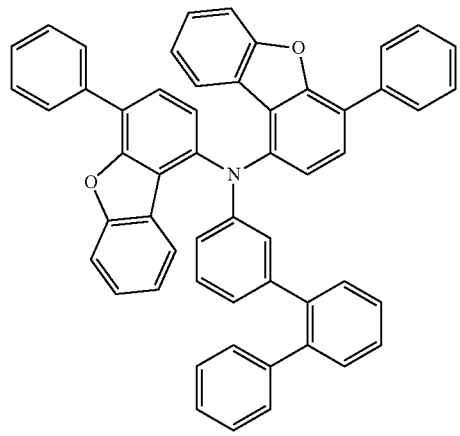
N-50
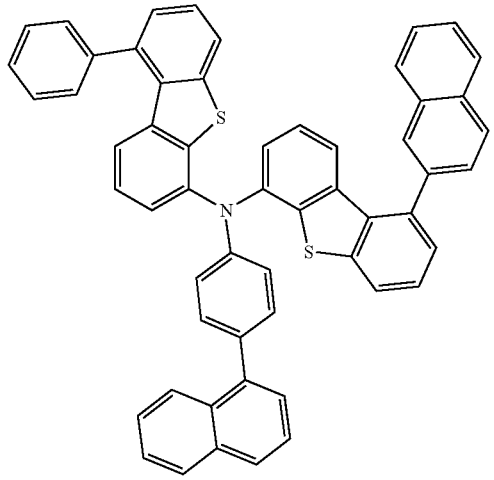
-continued
N-51
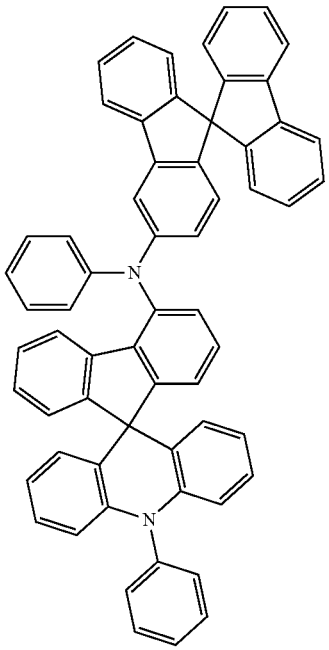
N-52
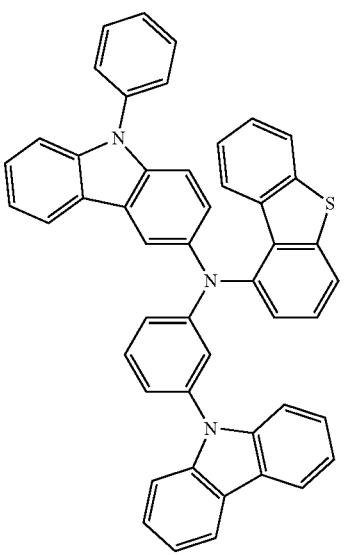
N-53
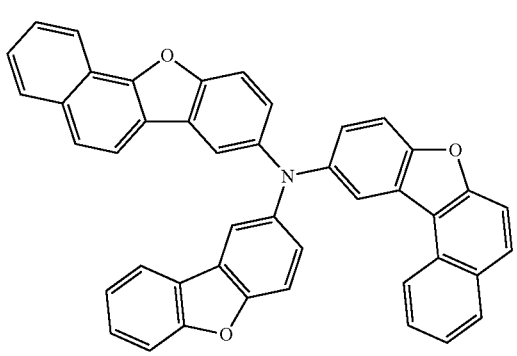

N-54
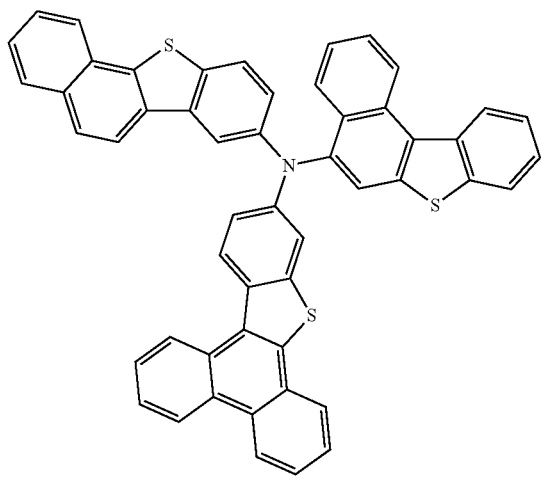
N-55
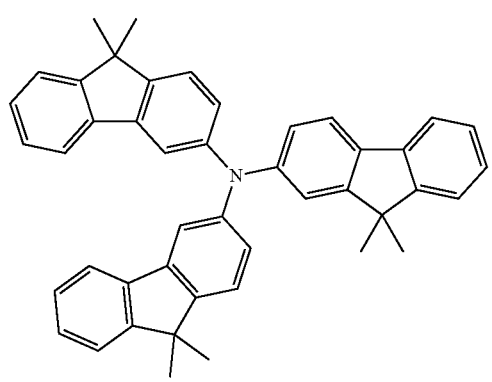
N-56
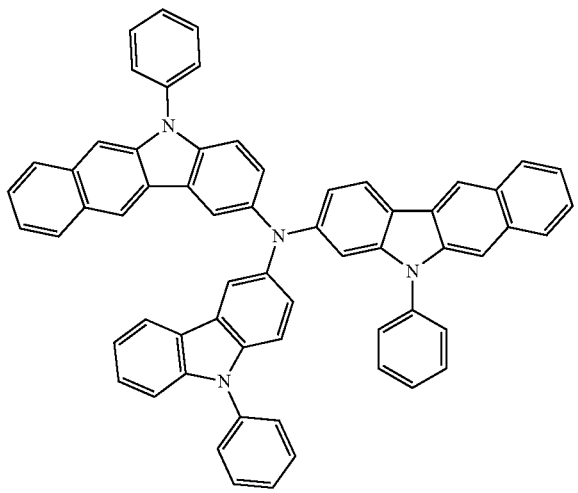
N-57
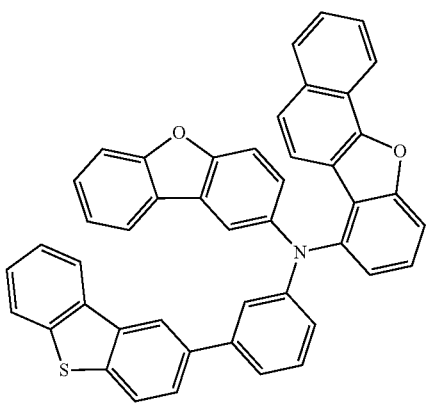
N-58
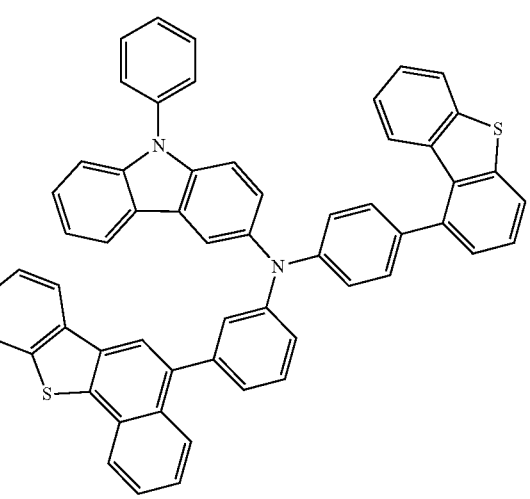
N-59
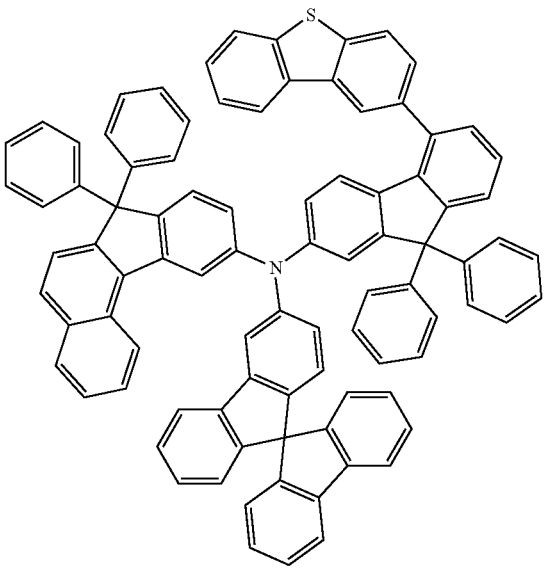

N-60
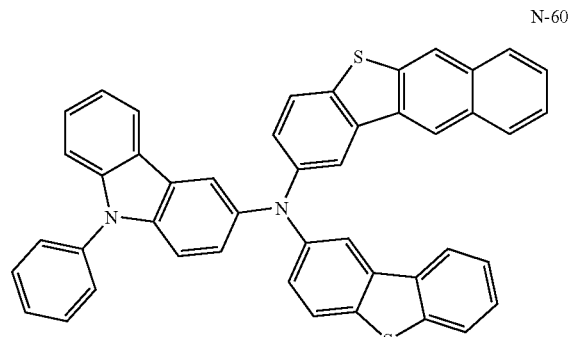
N-61
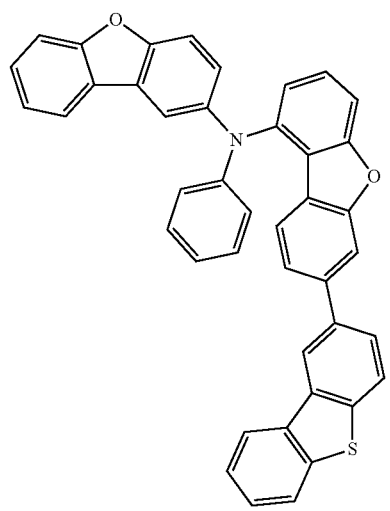
N-62
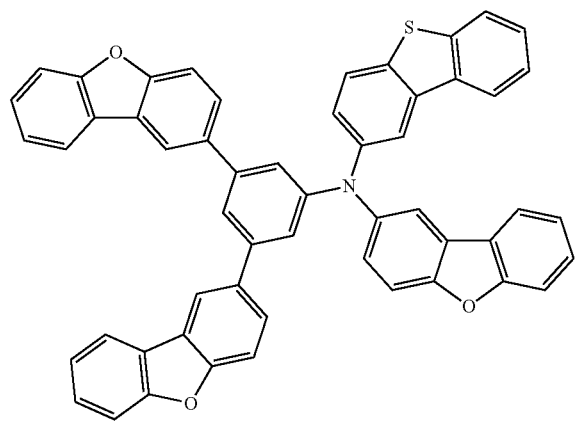
N-63
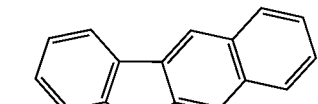
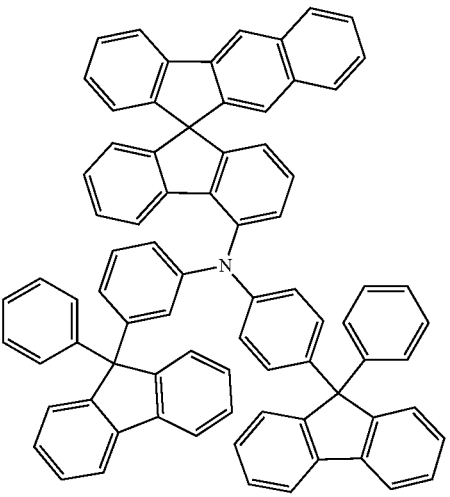
N-64
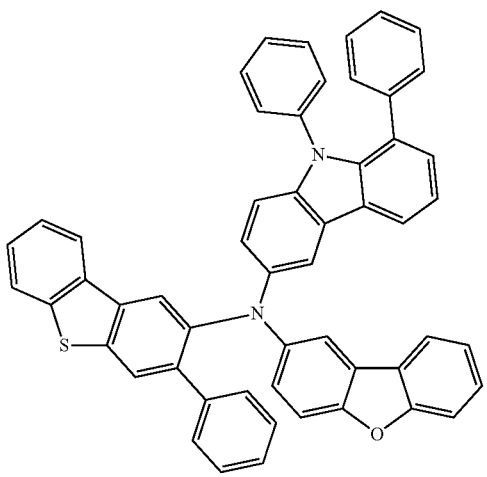
N-65
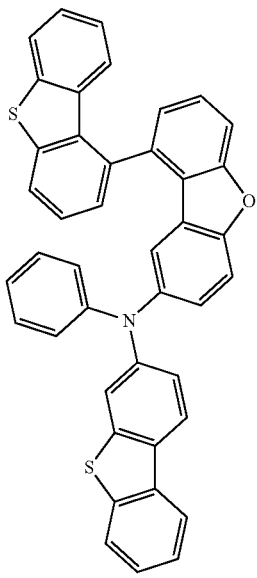

N-66
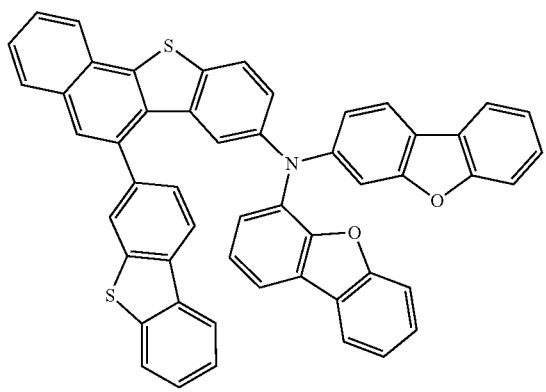
N-67
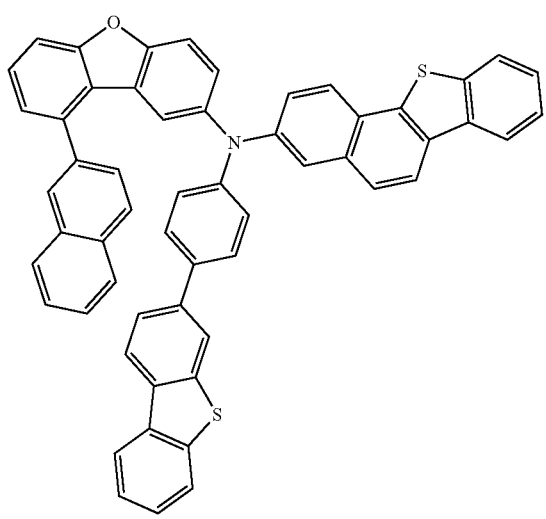
N-68
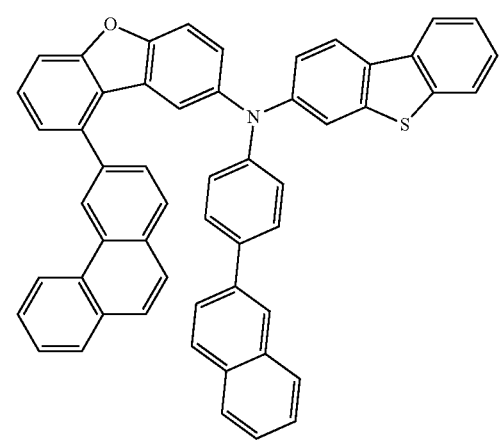
N-69
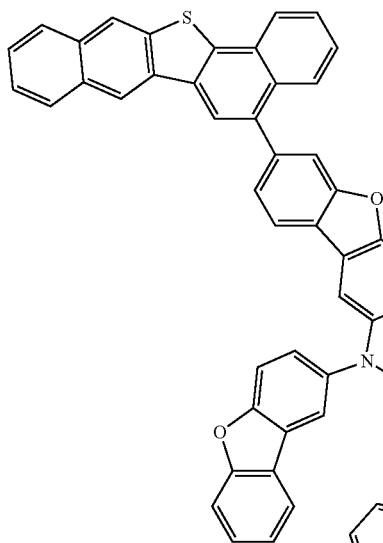
N-70
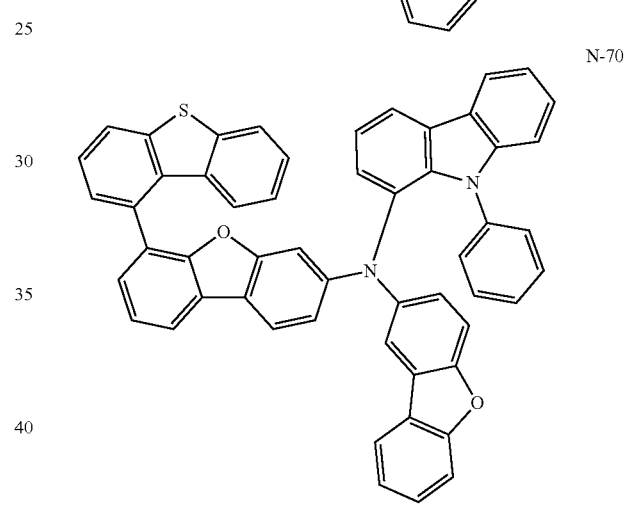
N-71
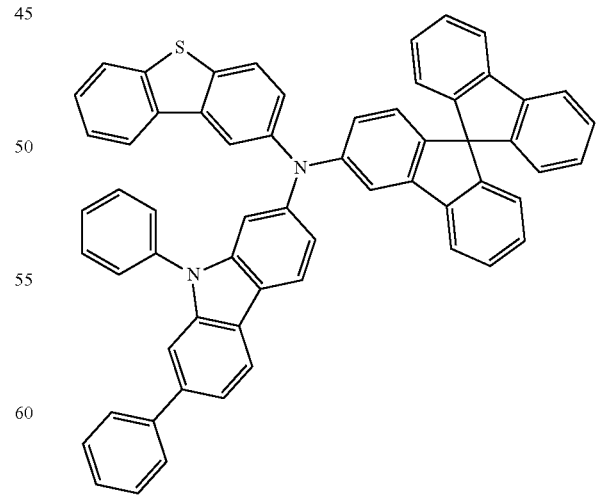

N-72
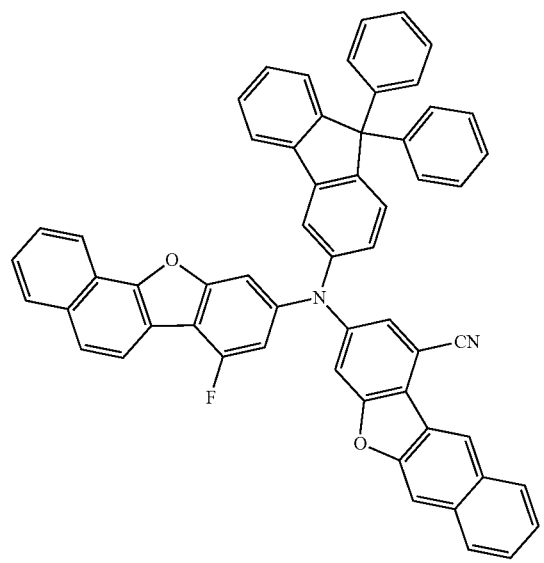
N-73
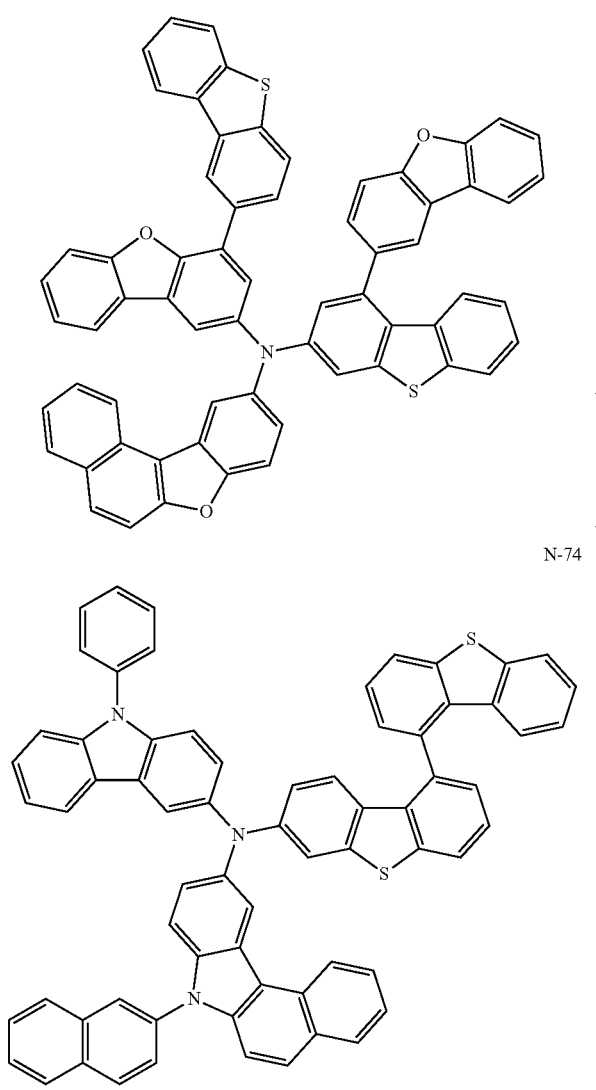
N-74
N-75
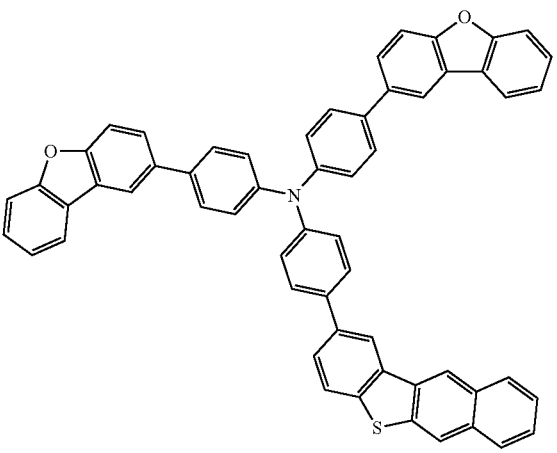
N-76
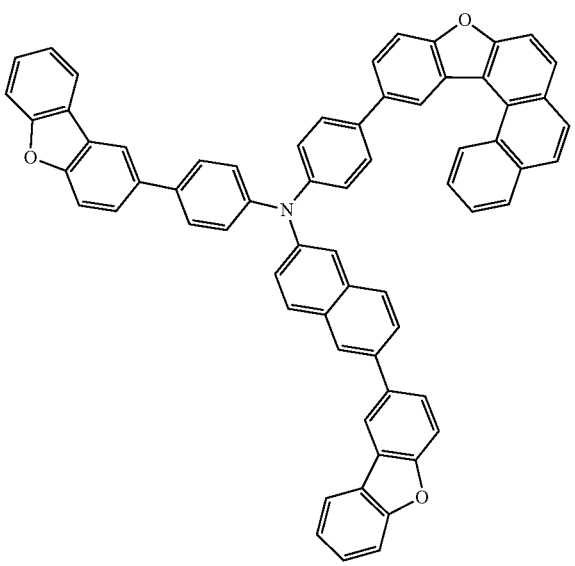
N-77
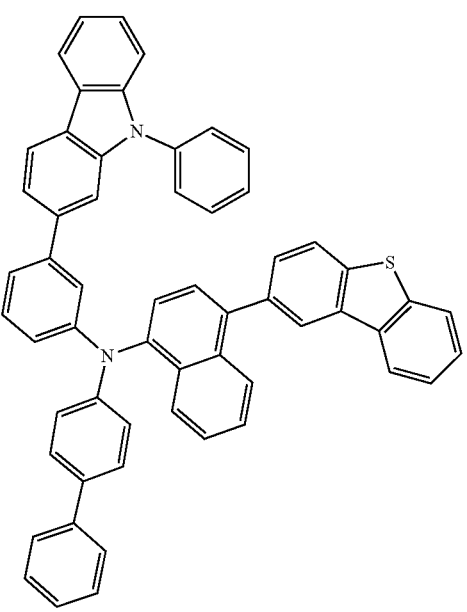

N-78
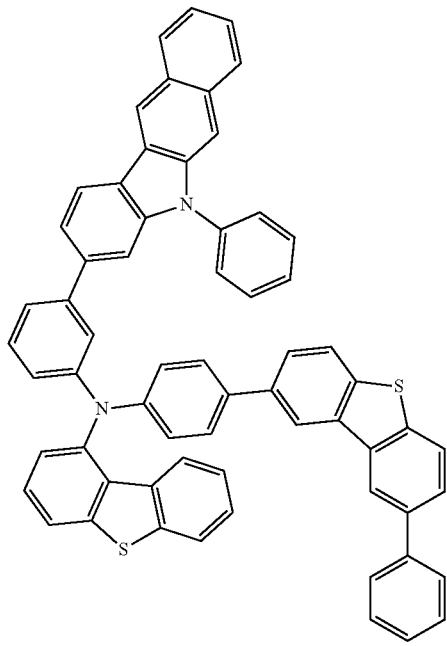
N-80
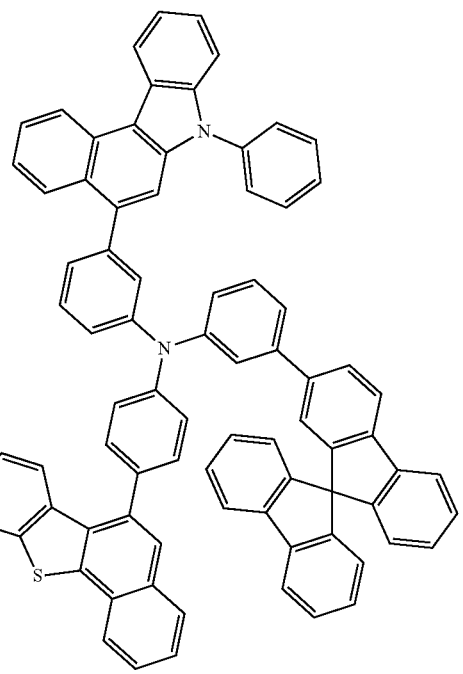
N-79
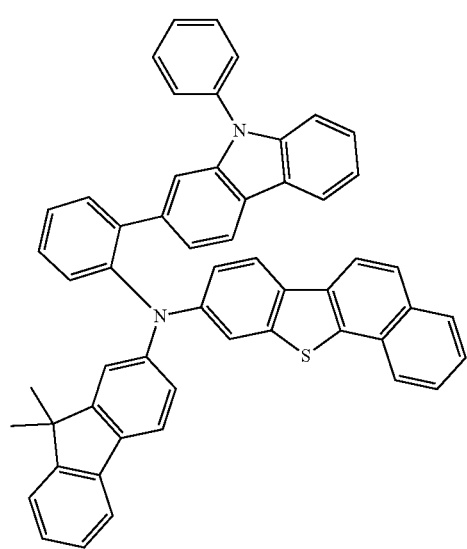
N-81
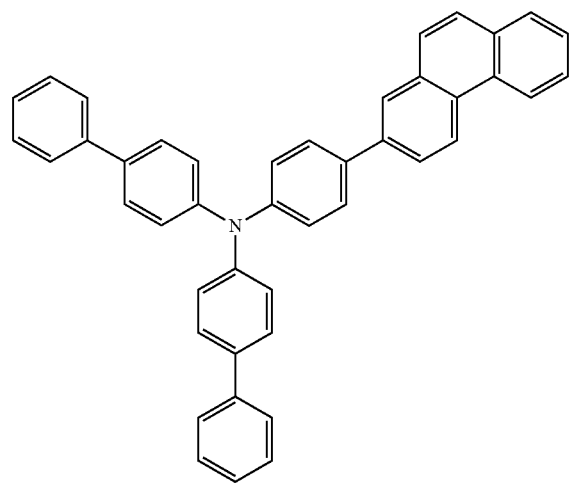

N-82
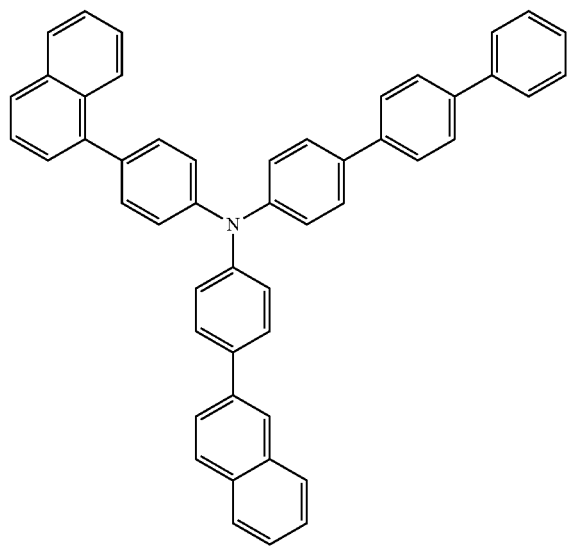
N-83
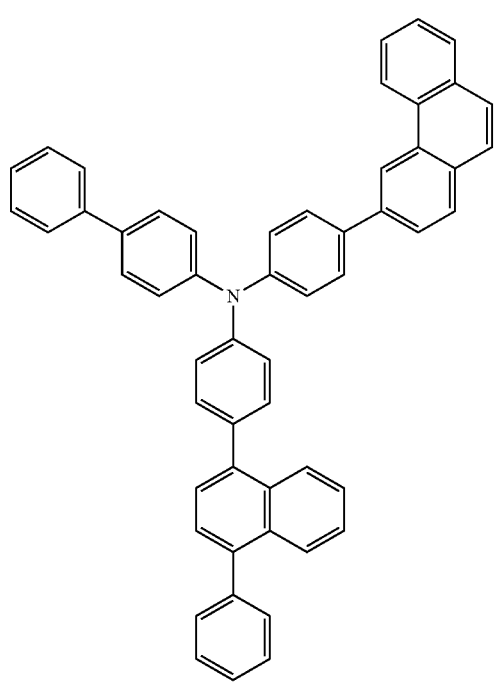
N-84
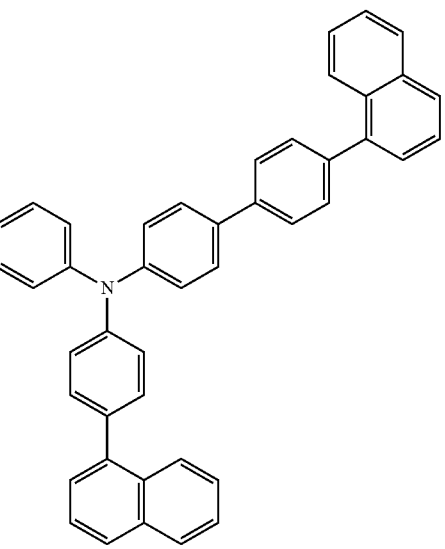
N-85
N-86
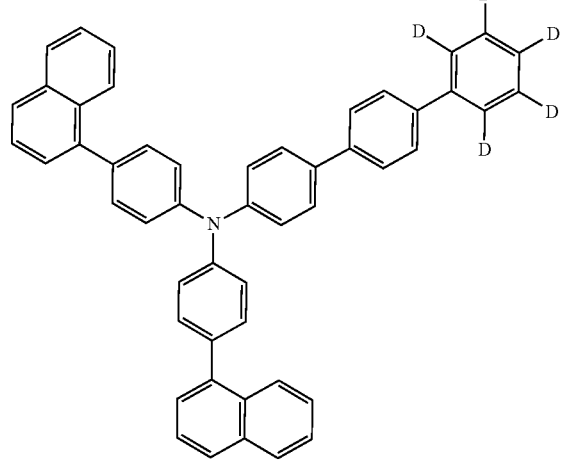

N-87
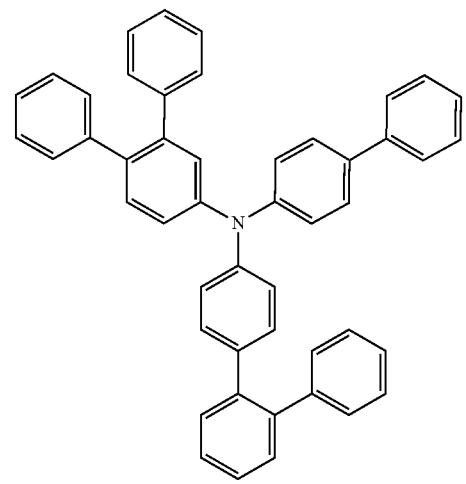
N-88
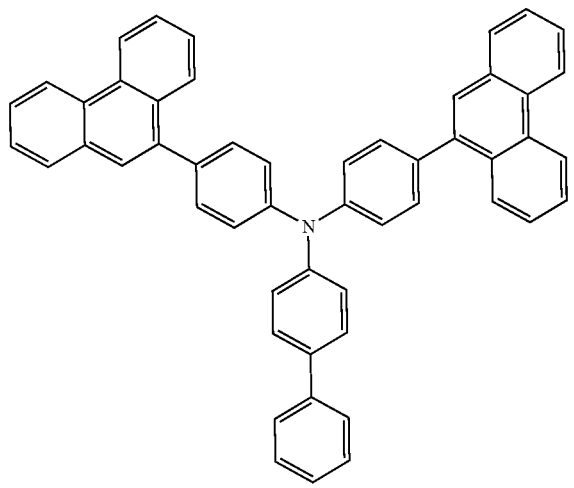
N-89
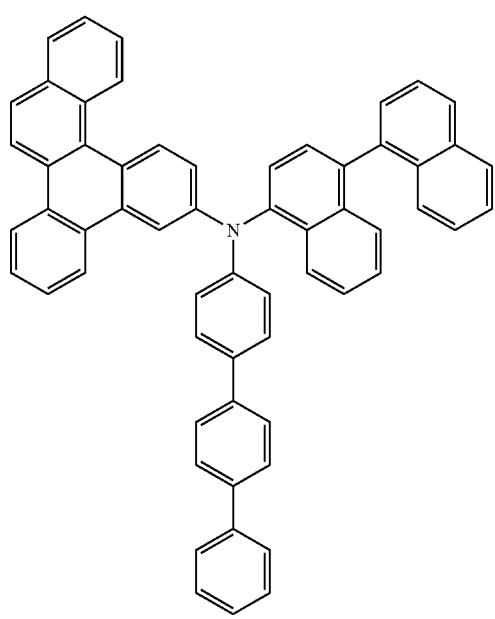
N-90
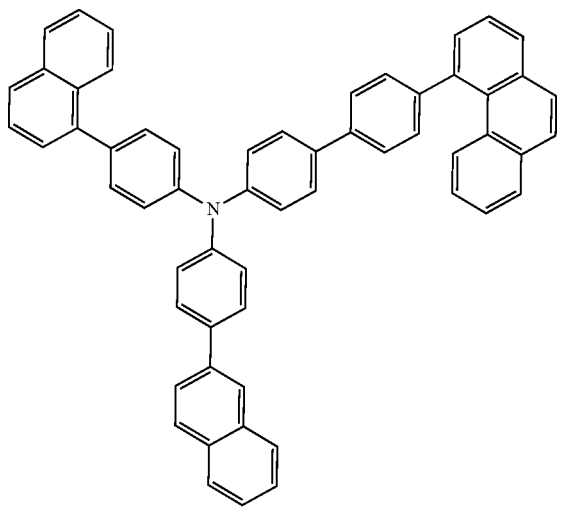
N-91
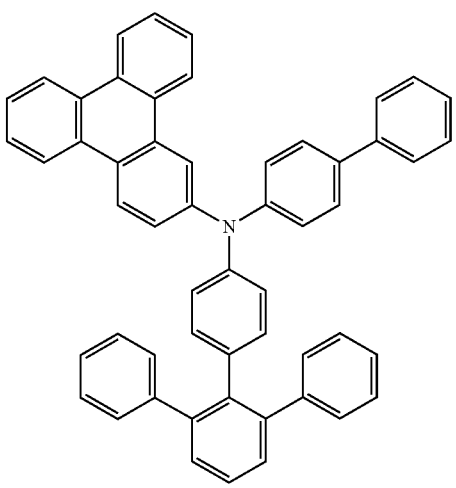
N-92
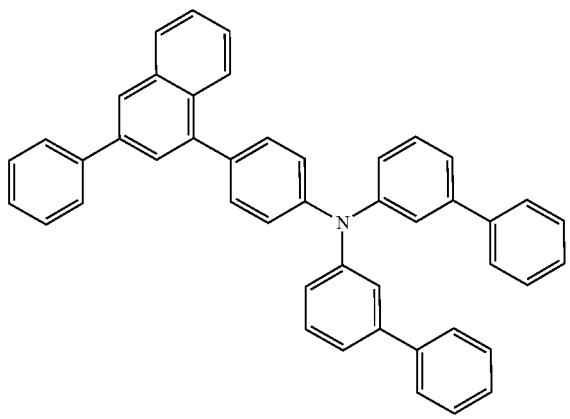

N-93
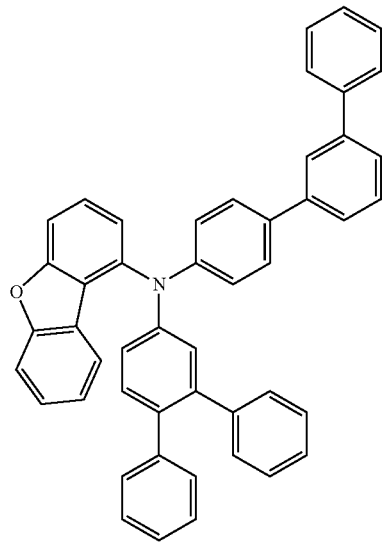
N-94
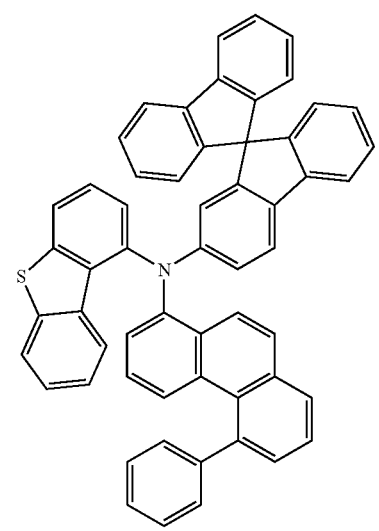
N-95
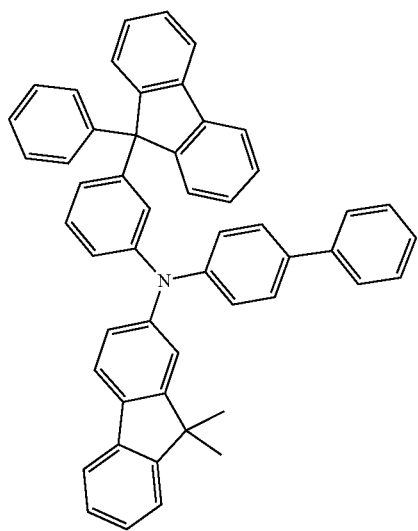
N-96
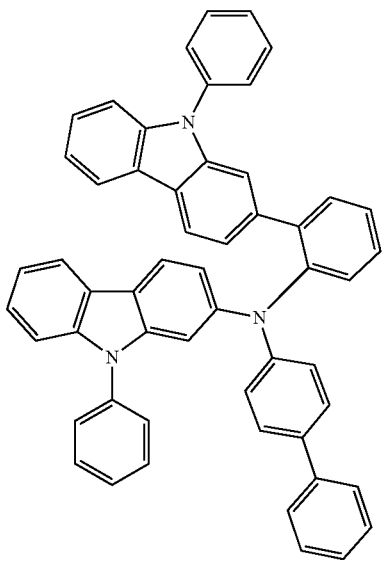
N-97
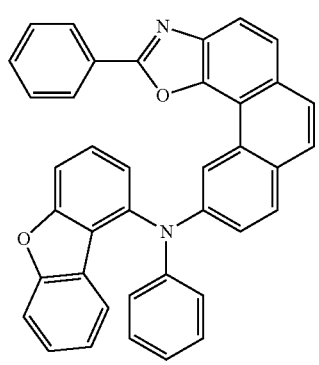
N-98
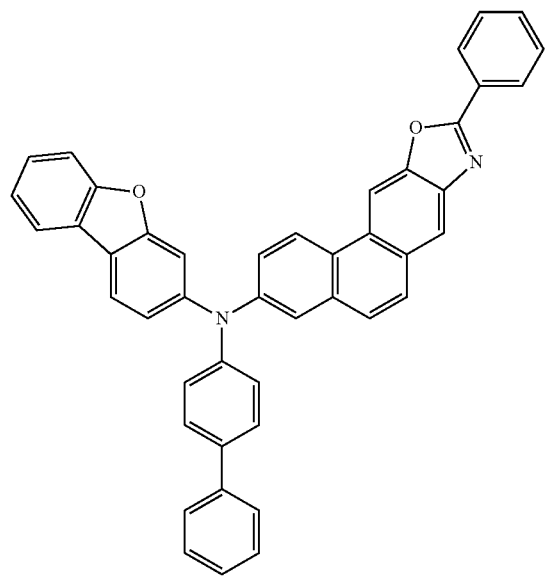

N-99
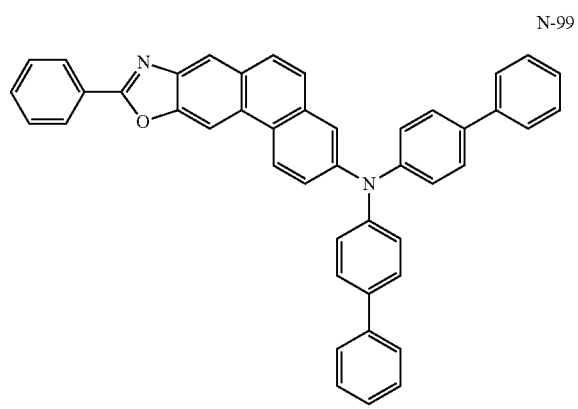
N-100
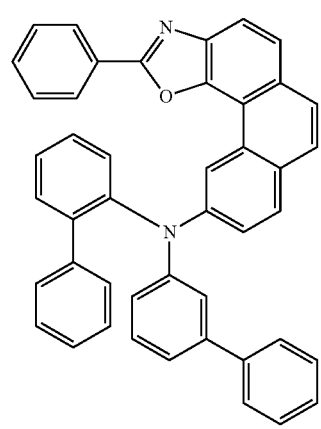
N-101
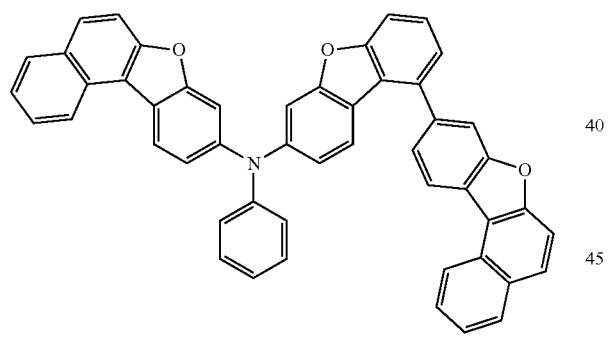
N-102
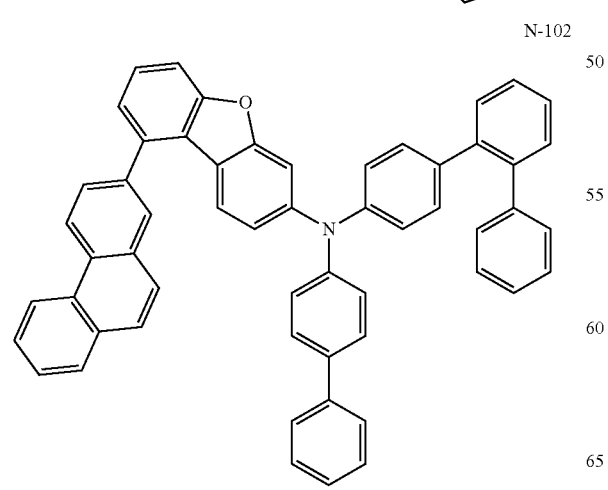
N-103
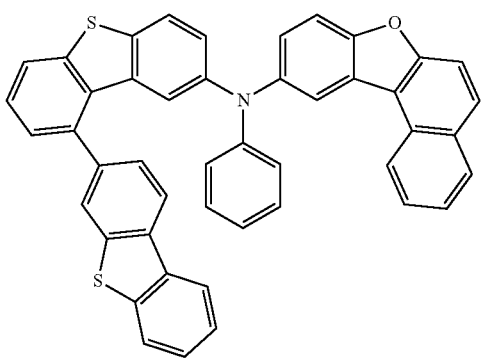
N-104
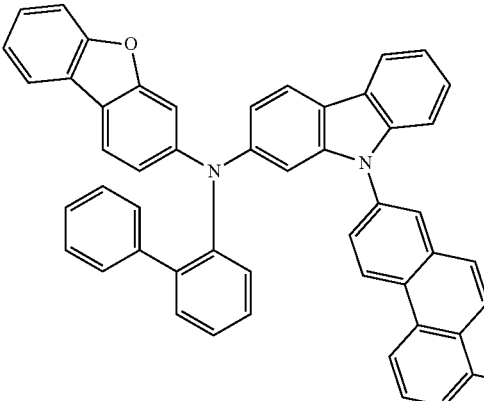
N-105
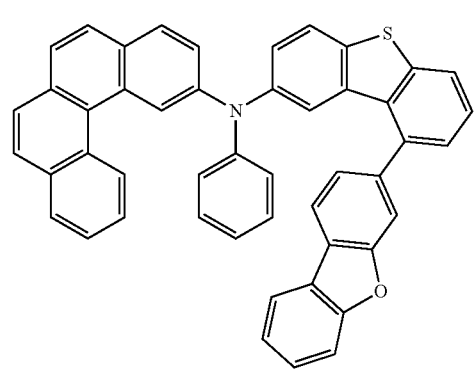

-continued
N-106
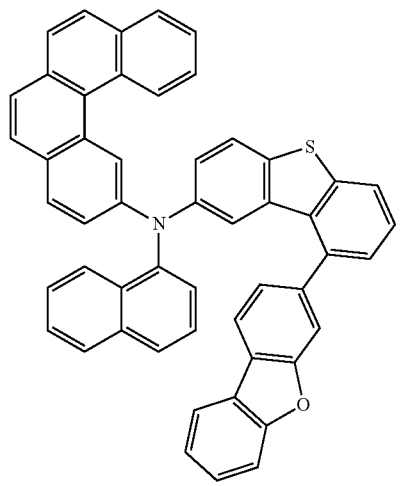
N-107
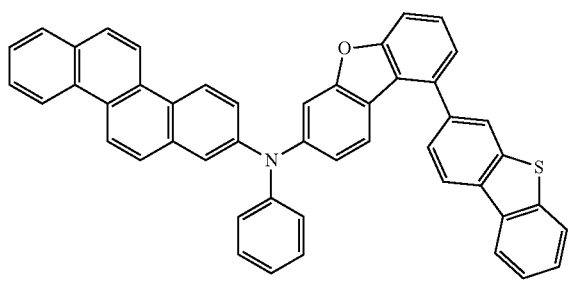
N-108
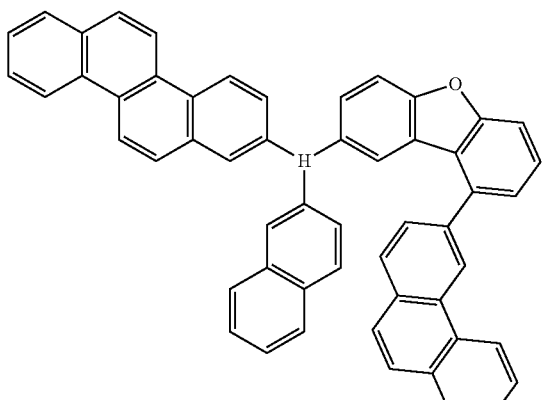
N-109
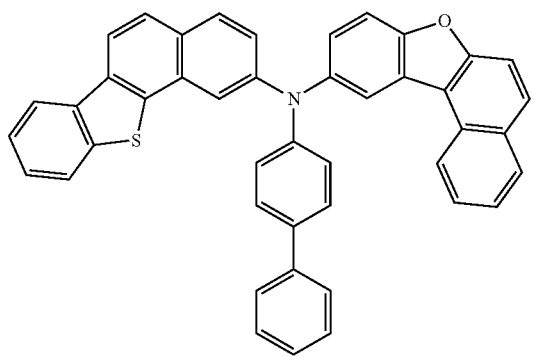
N-110
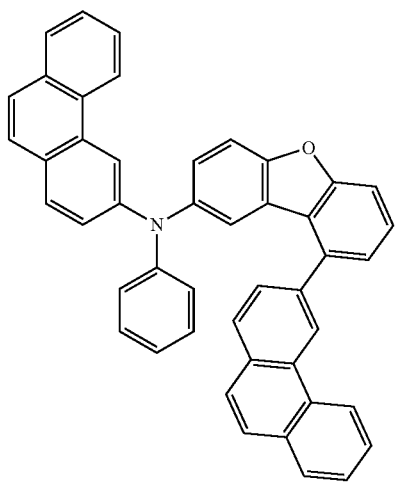
N-111
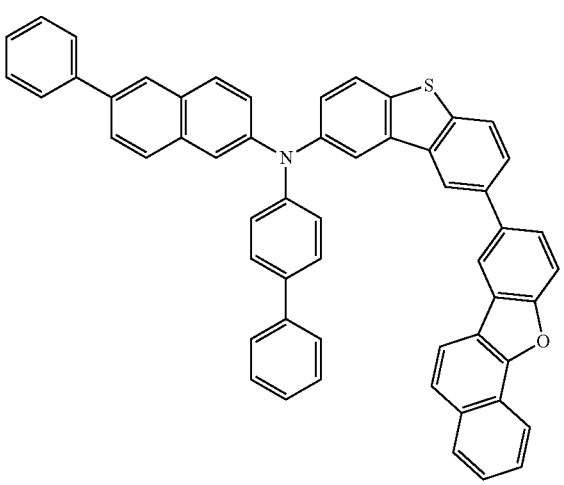
N-112
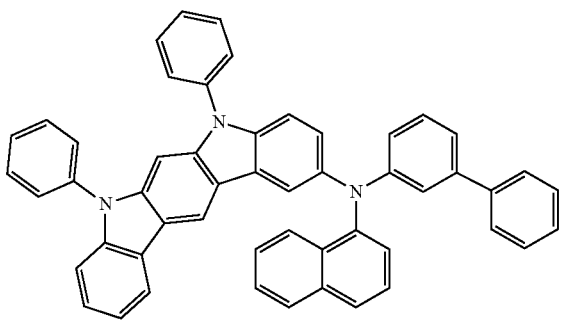

N-113
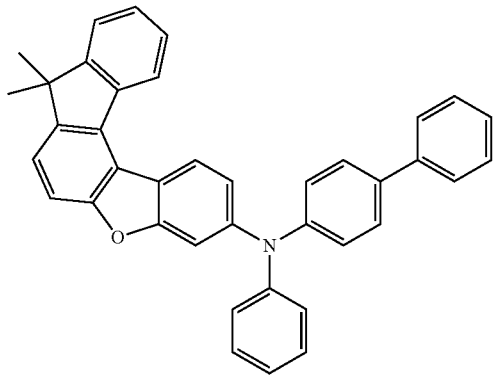
N-116
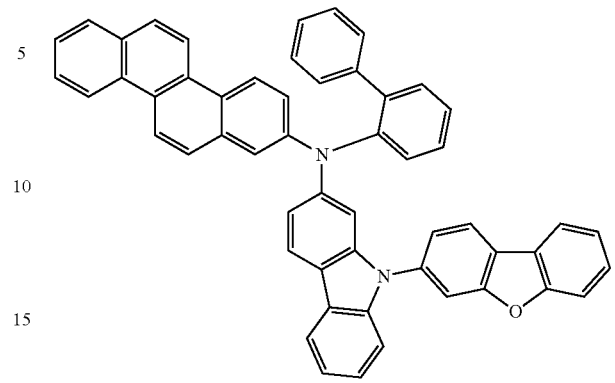
N-114
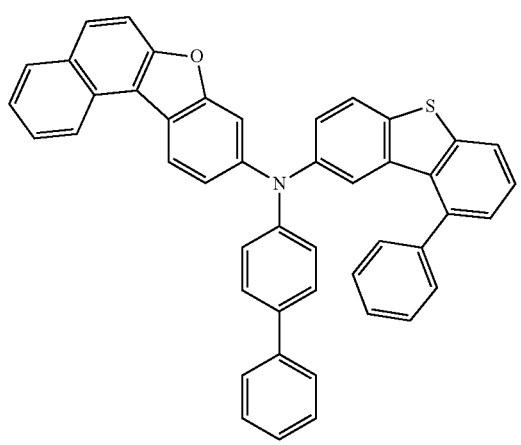
N-117
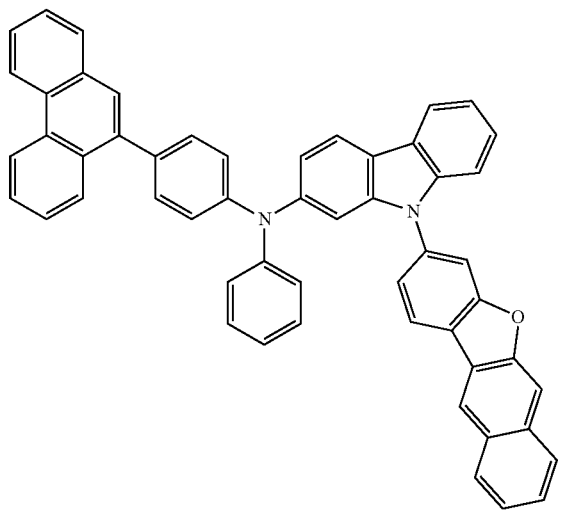
N-115
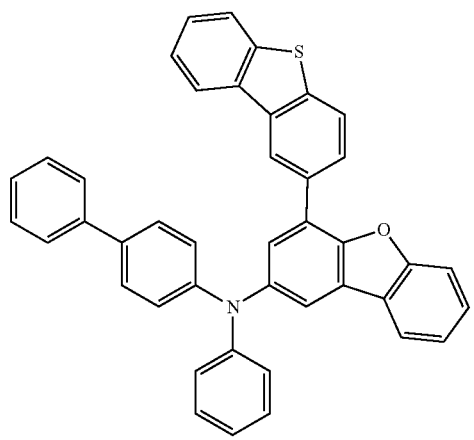
N-118
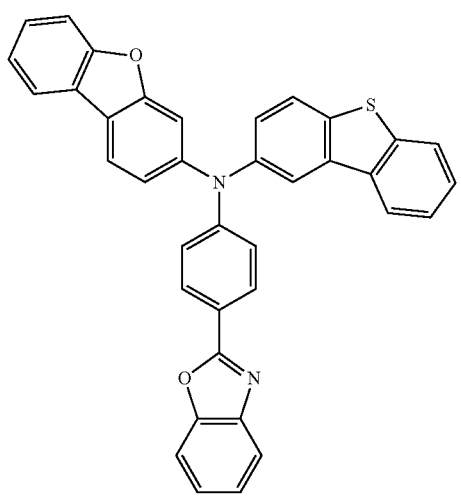

-continued
N-119
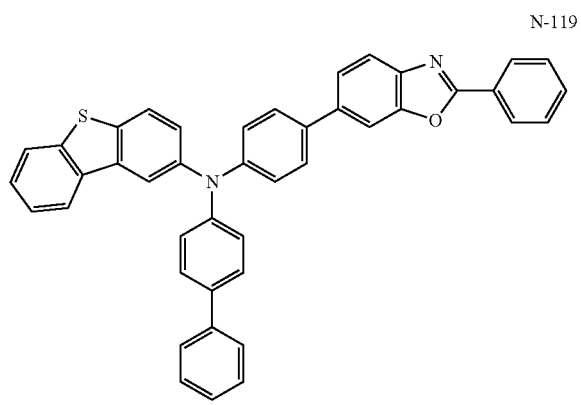
N-120
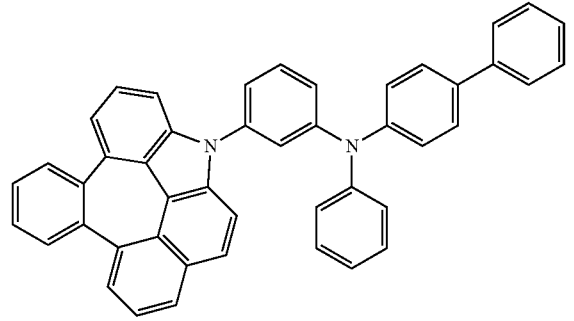
N-121
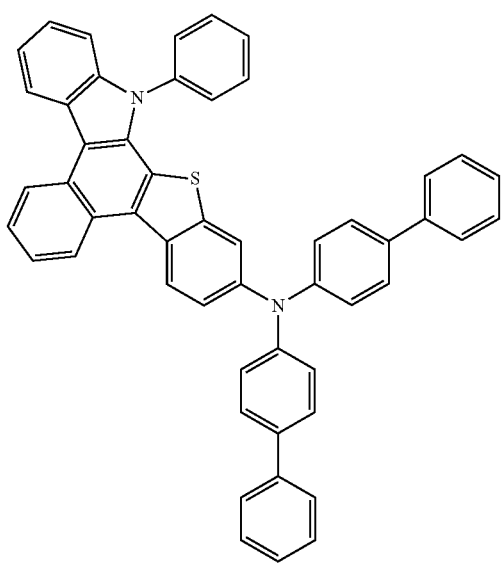
-continued
N-122
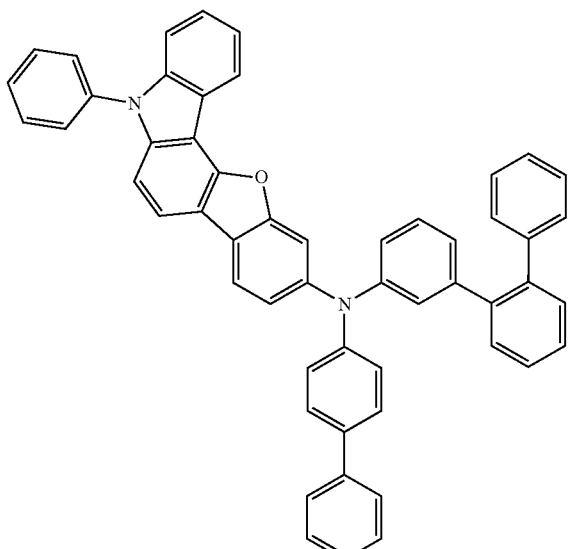
N-123
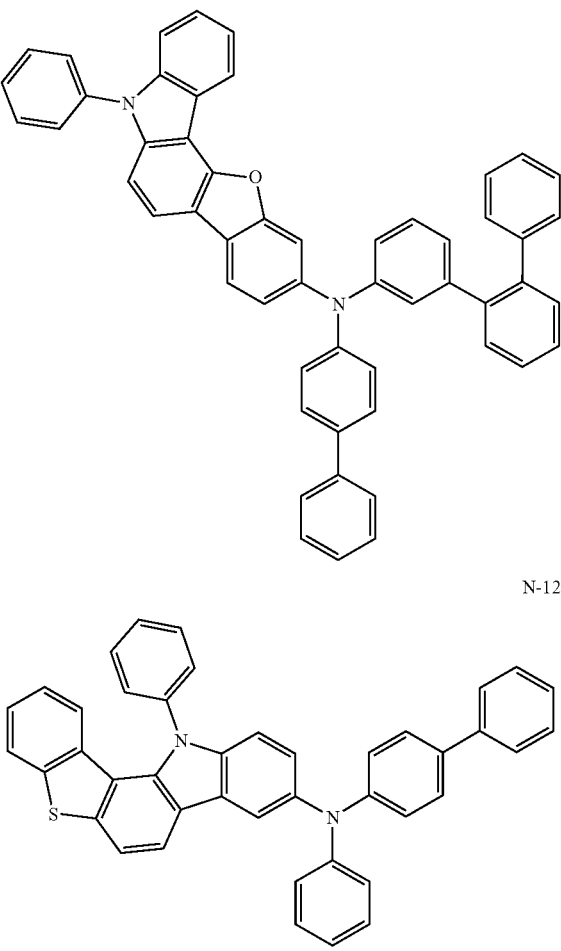
N-124
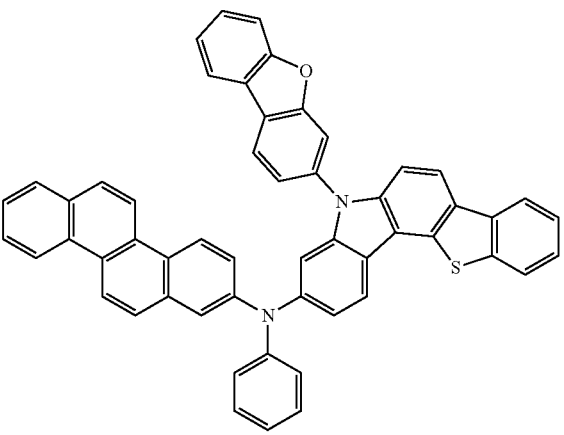

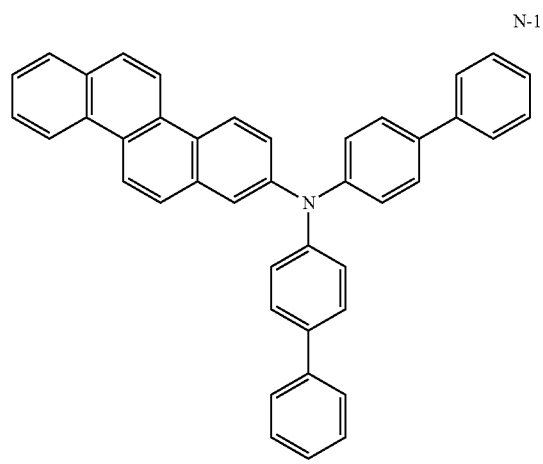
N-125
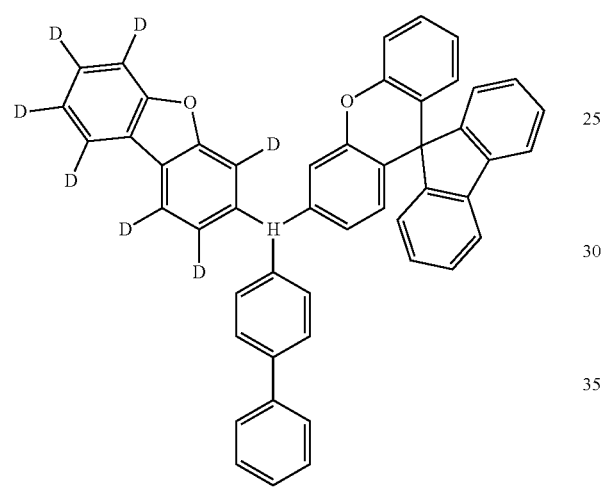
N-126
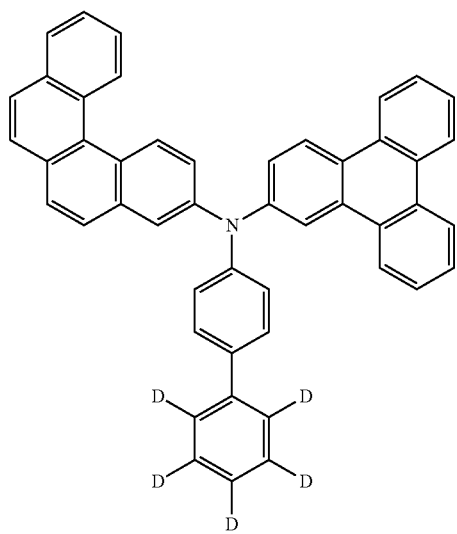
N-127
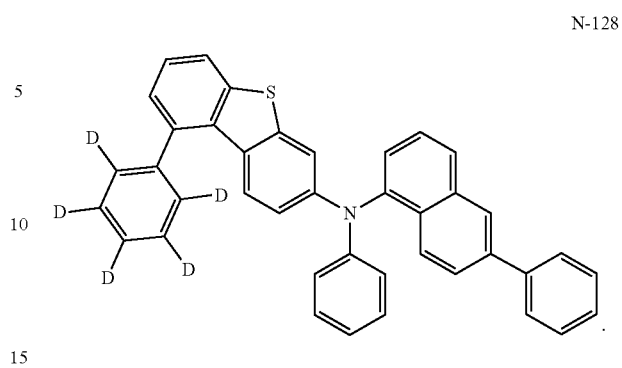
N-128
8. The composition for an organic electronic element according to claim 6, wherein Formula 3 comprises a compound selected by any one of the compounds S-1 to S-71, S-73 to S-99, and S-101 to S-120:
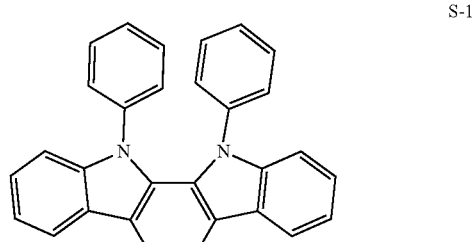
S-1
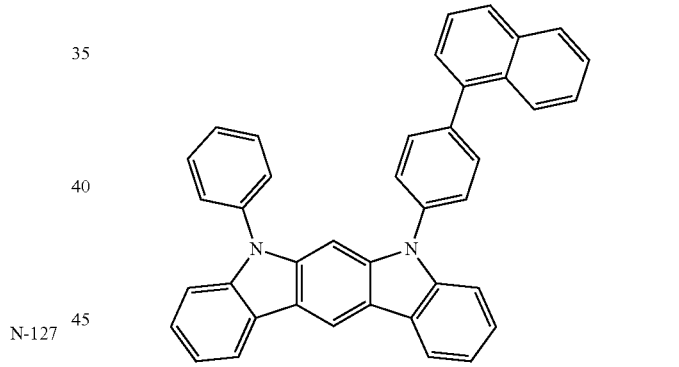
S-2
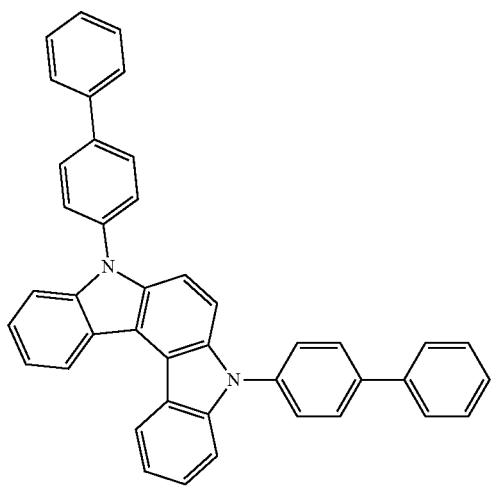
S-3

S-4
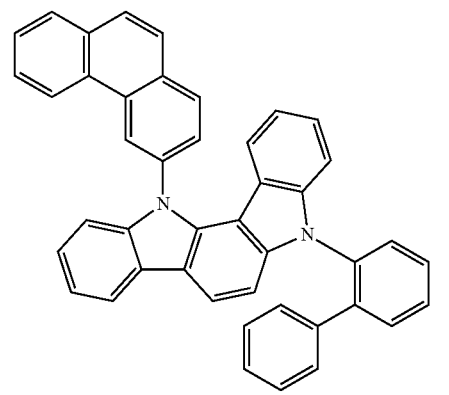
S-5
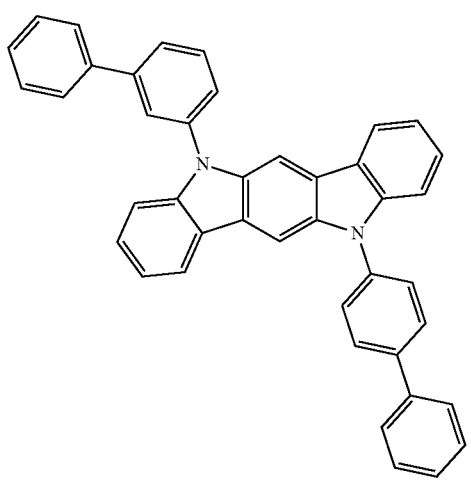
S-6
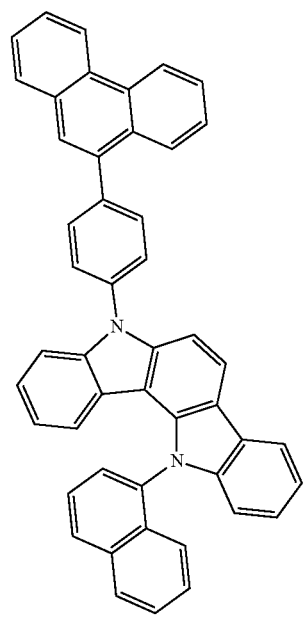
S-7
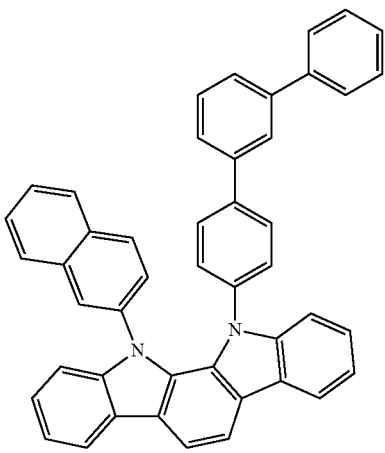
S-8
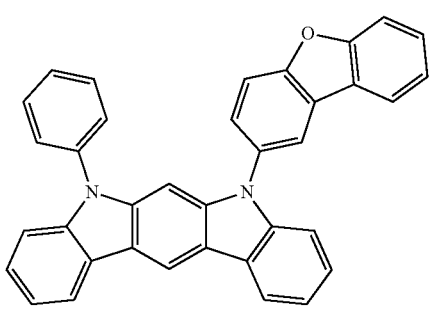
S-9
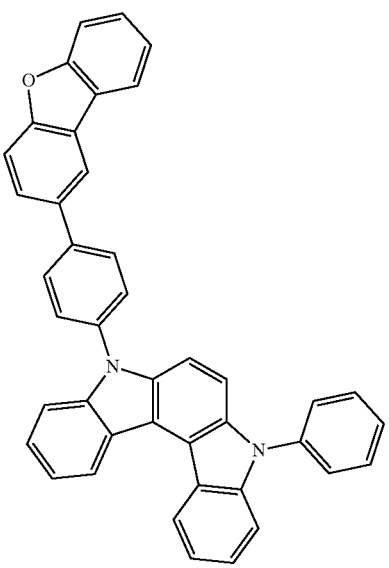

S-10
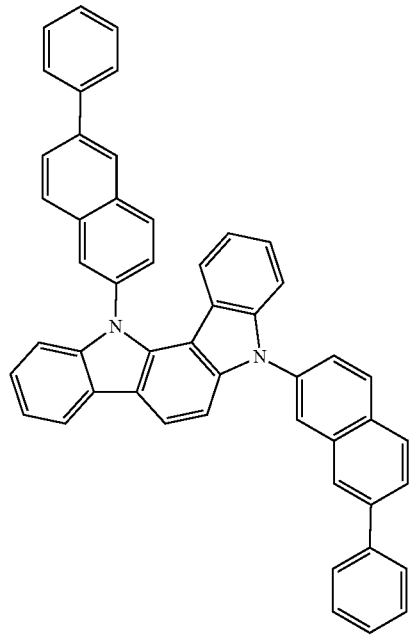
S-11
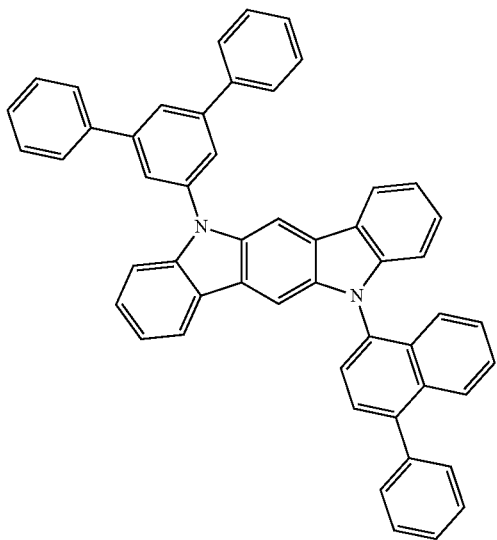
S-12
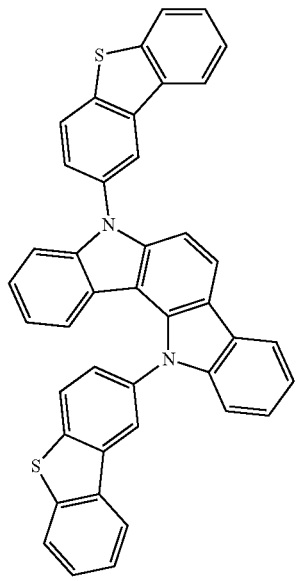
S-13
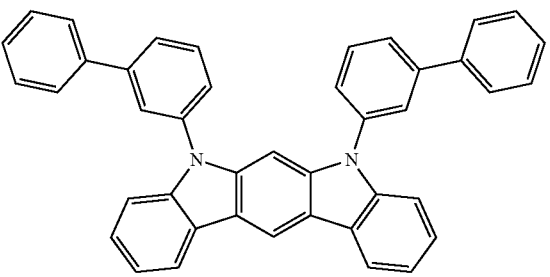
S-14
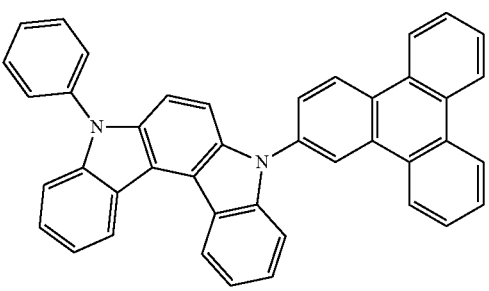
S-15

-continued
S-16
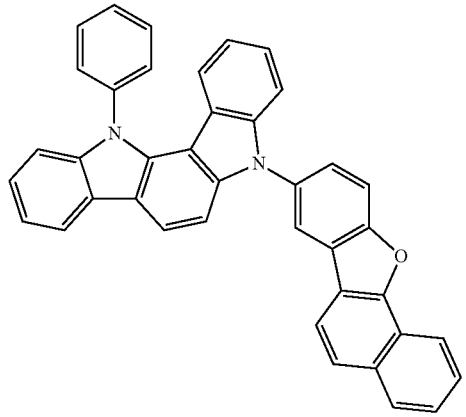
S-17
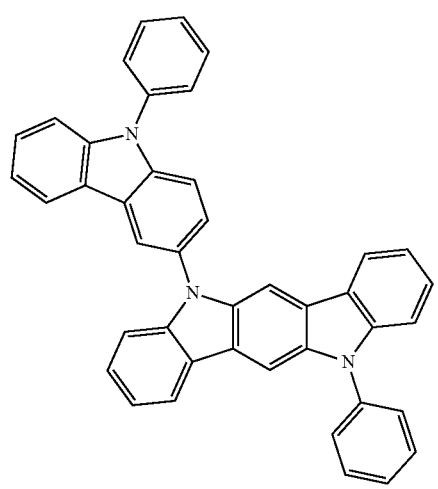
S-18
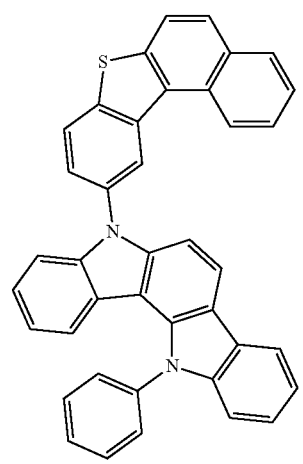
-continued
S-19
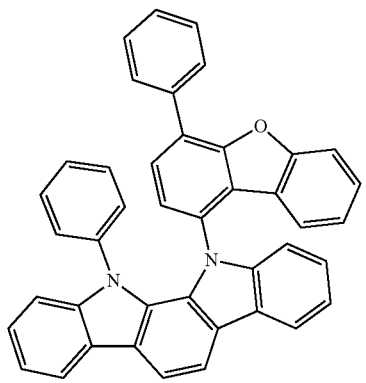
S-20
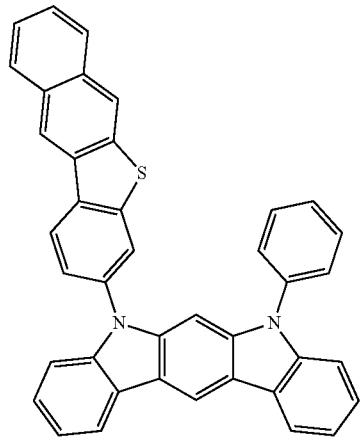
S-21
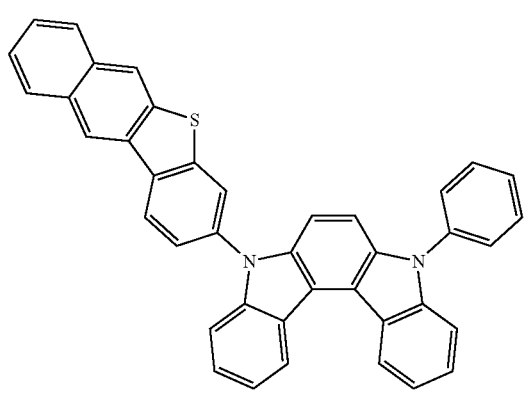

S-22
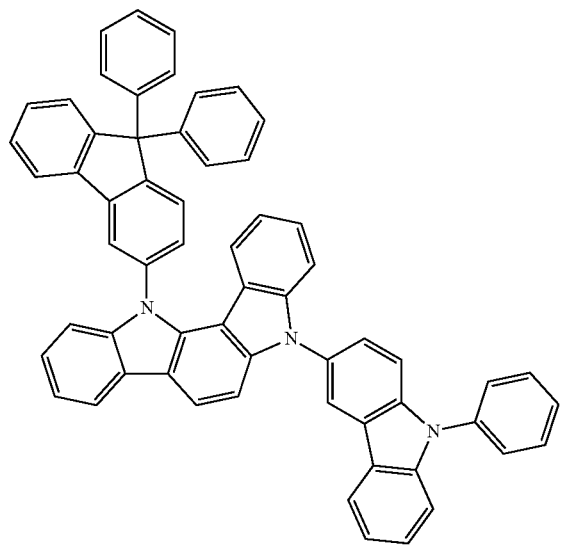
S-23
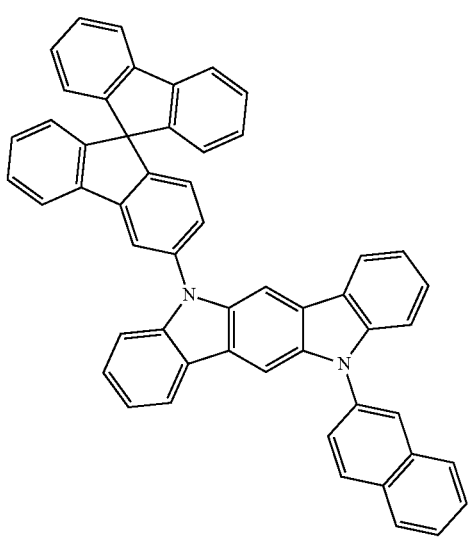
S-24
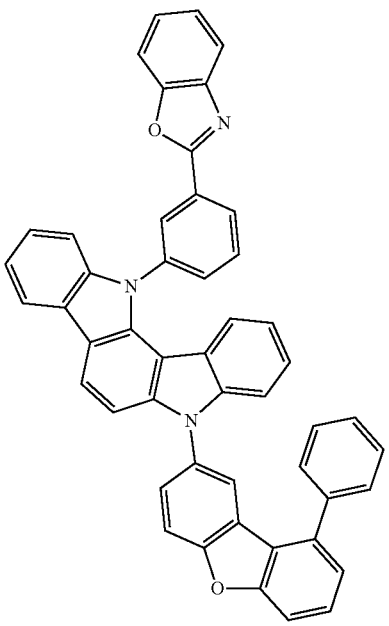
S-25
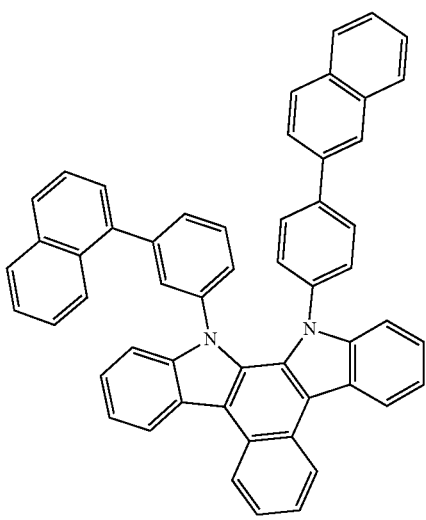
S-26
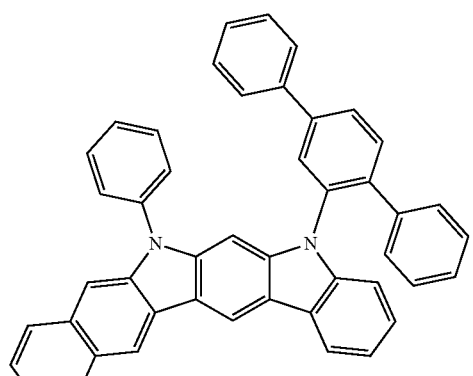

S-27
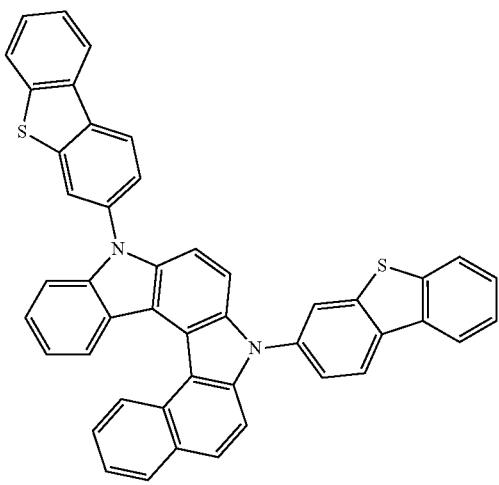
S-28
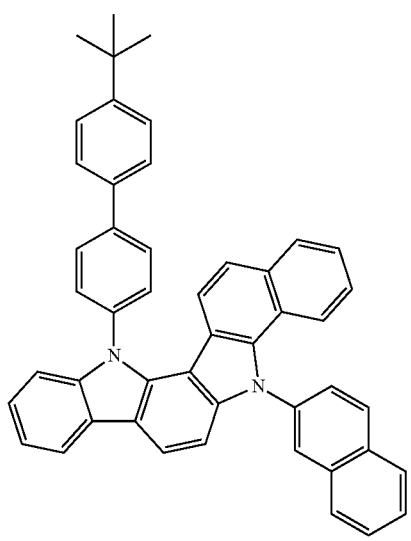
S-30
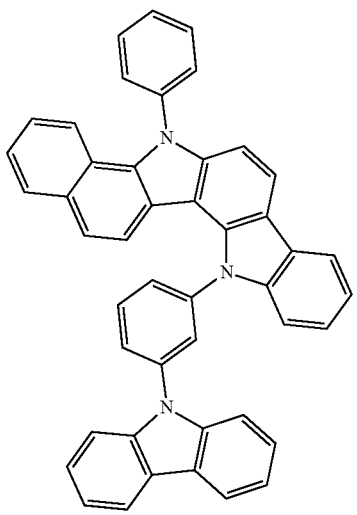
S-31
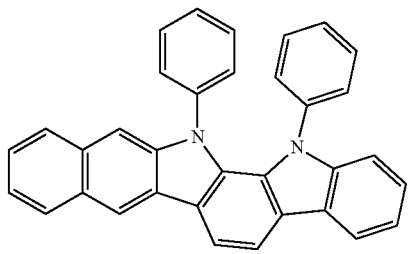
S-32
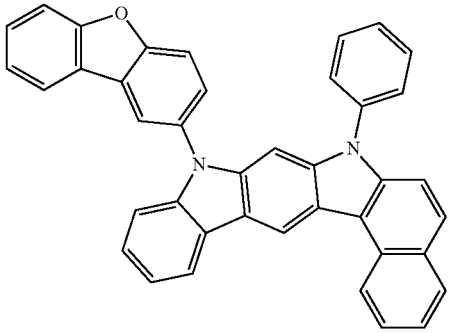
S-29
S-33
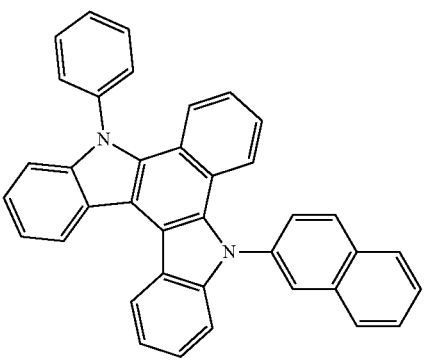

303
-continued
304
-continued
S-34
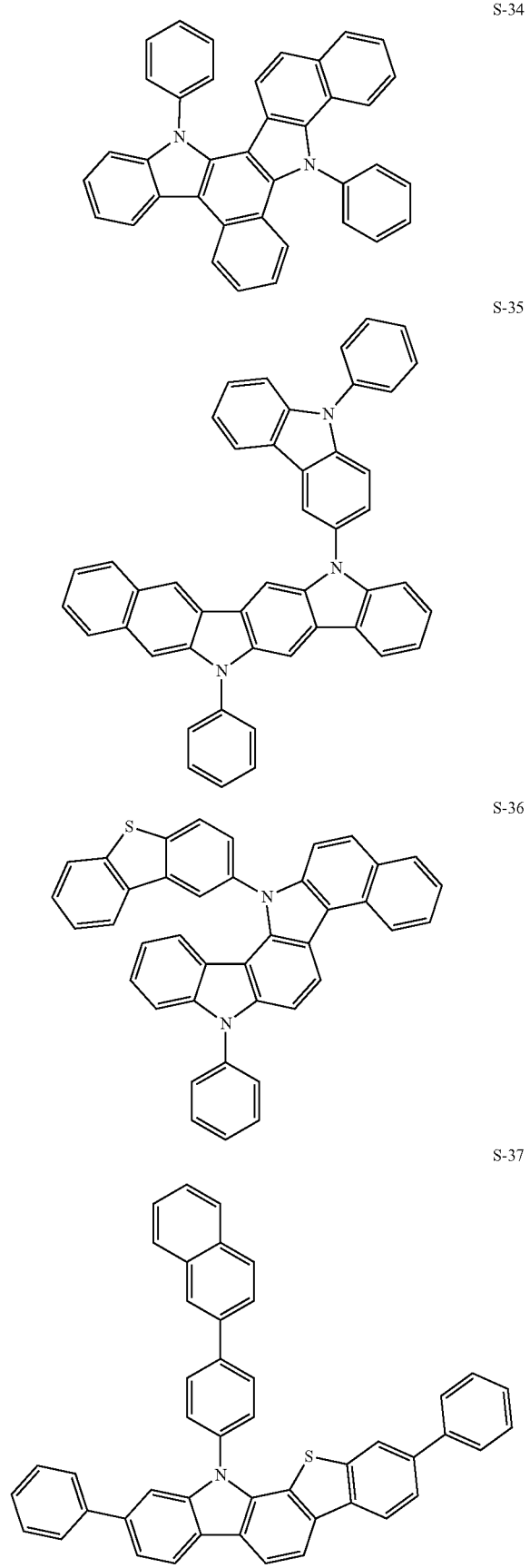
S-35
S-36
S-37
S-38
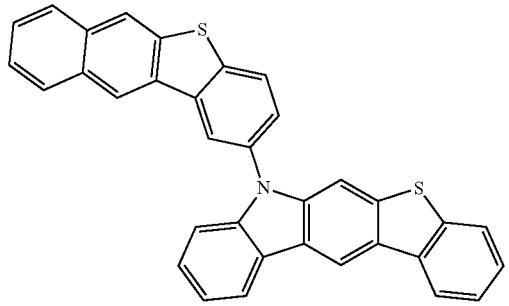
S-39
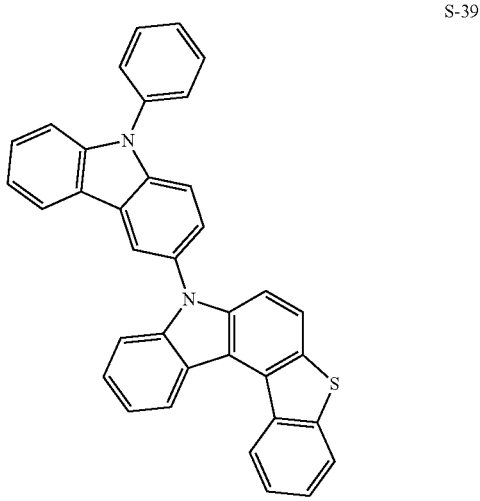
S-40
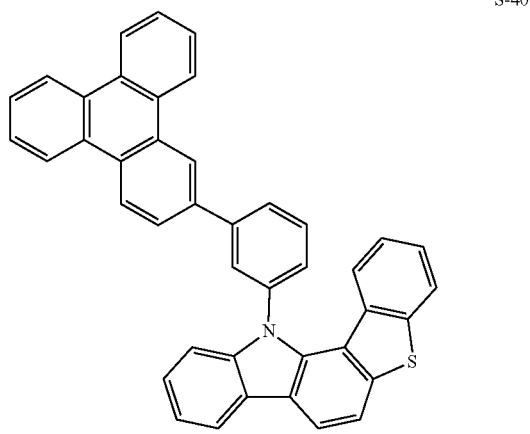

S-41
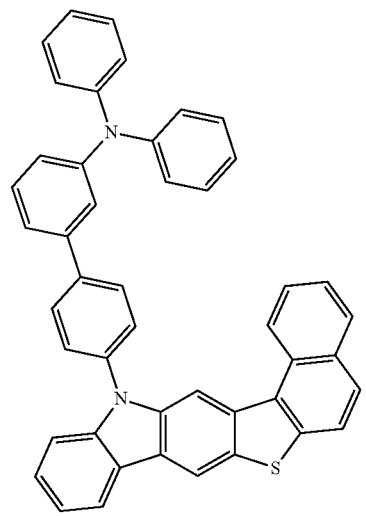
S-42
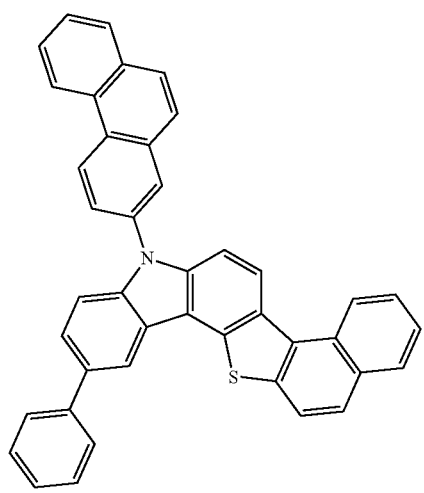
S-43
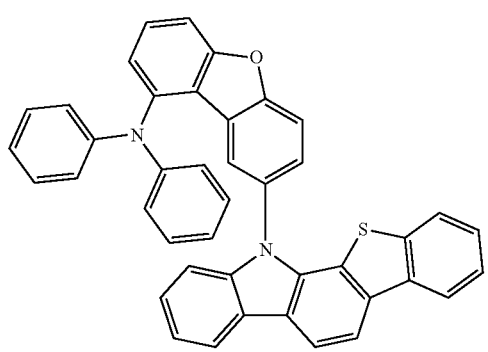
S-44
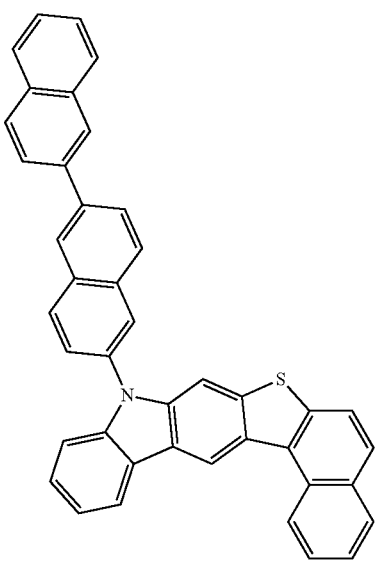
S-45
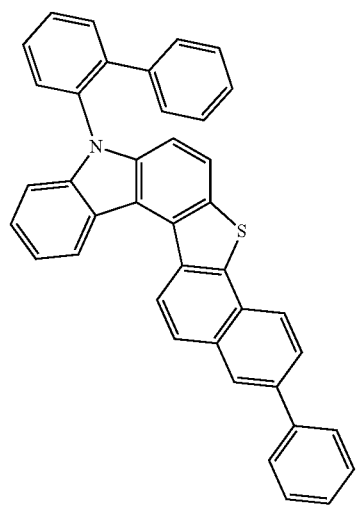
S-46
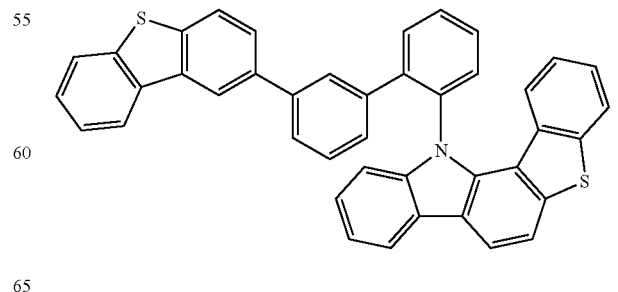

S-47
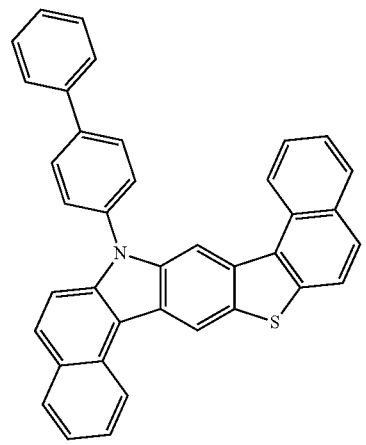
S-48
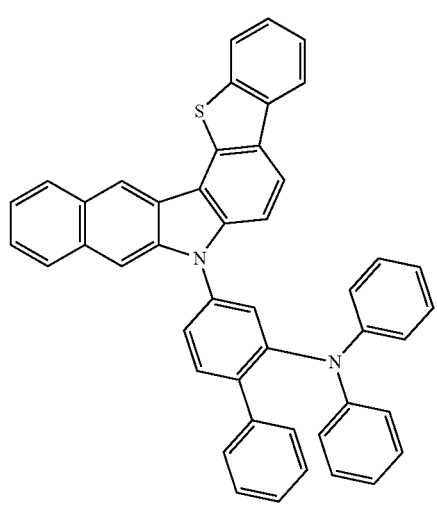
S-49
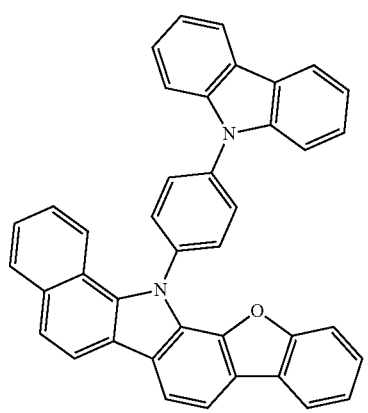
S-50
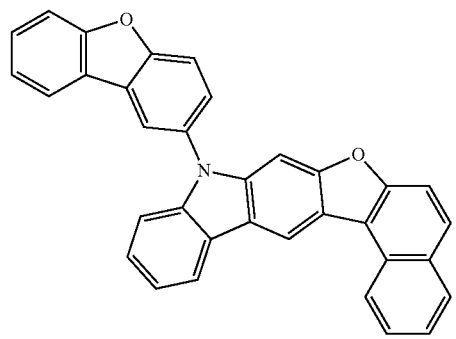
S-51
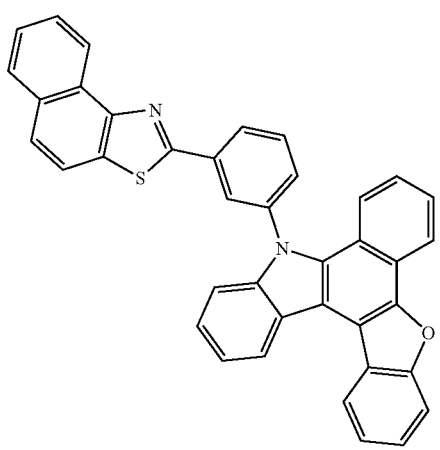
S-52
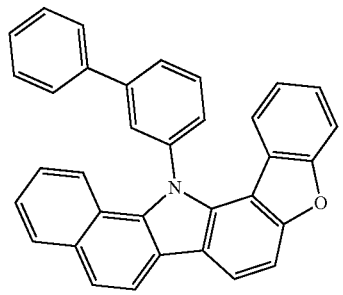
S-53
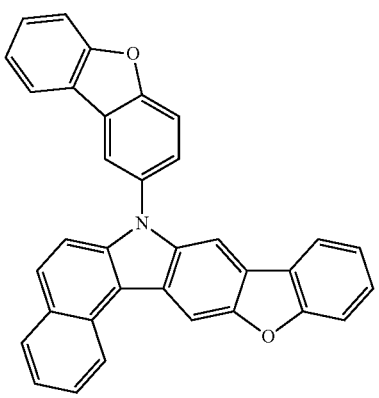

S-54
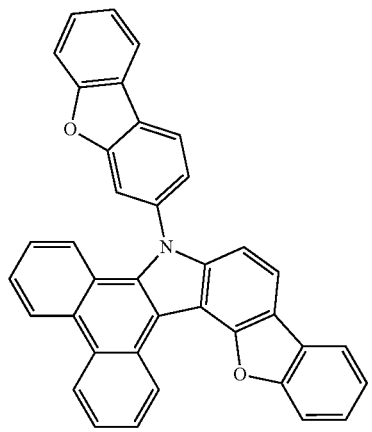
S-55
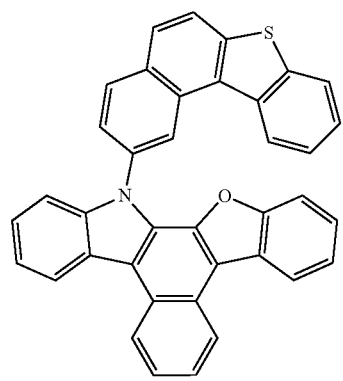
S-56
S-57
S-58
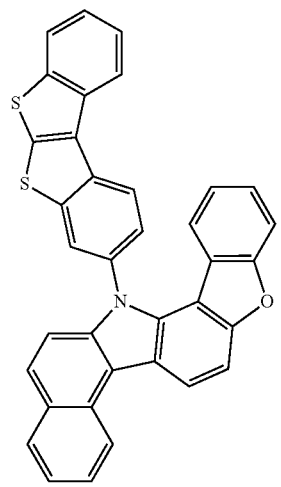
S-59
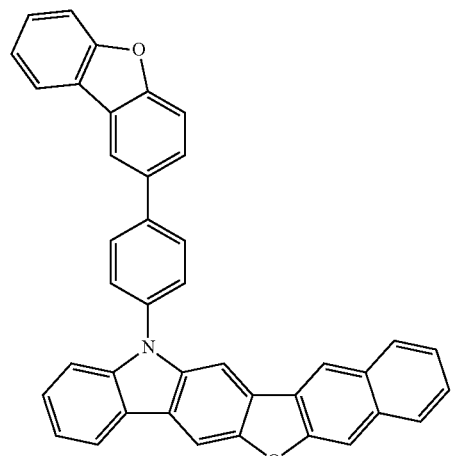
S-60
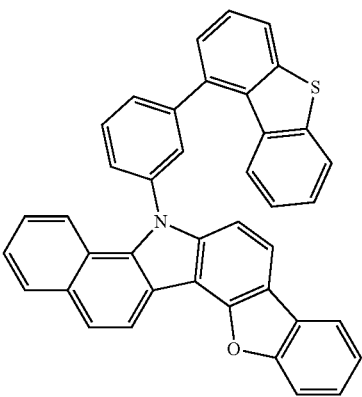

S-61
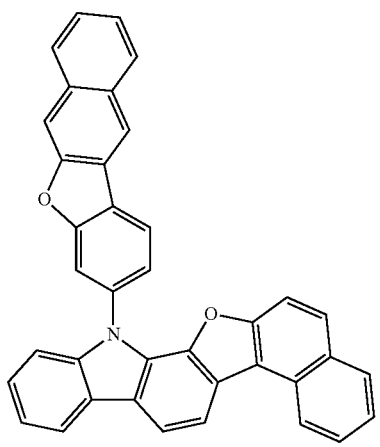
S-64
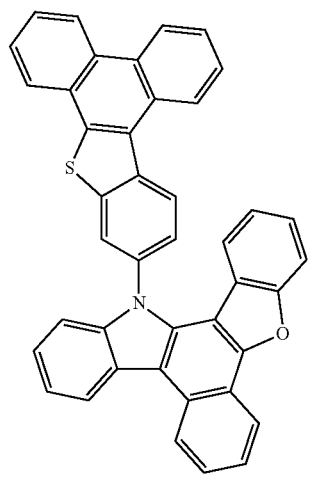
S-62
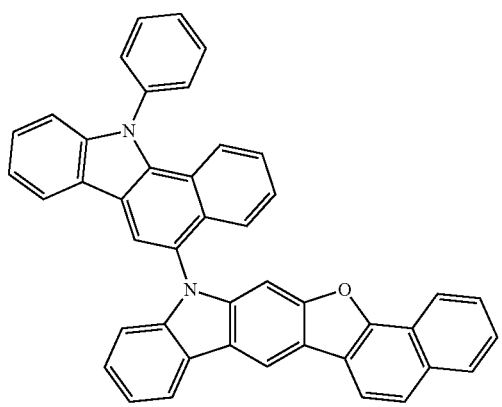
S-65
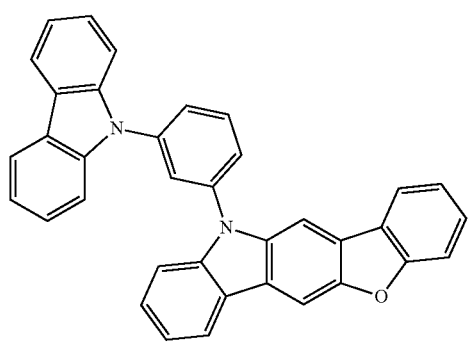
S-66
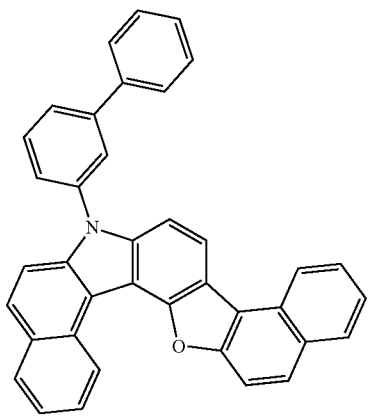
S-63
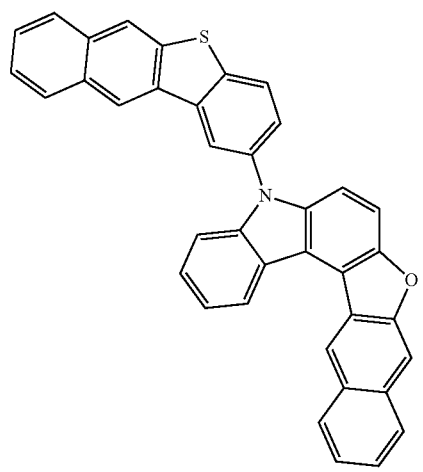
S-67
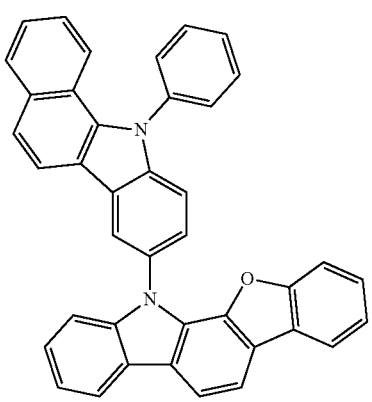

-continued
S-68
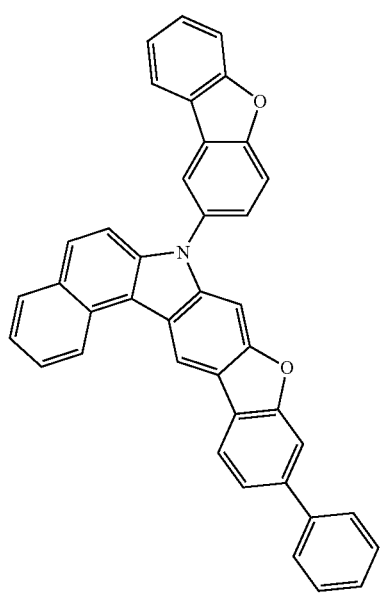
S-69
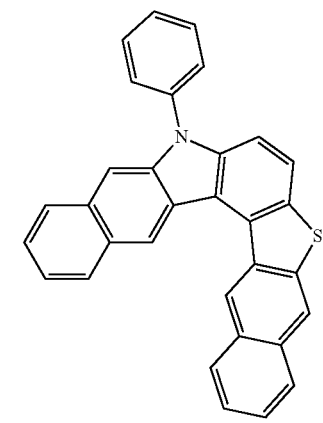
S-70
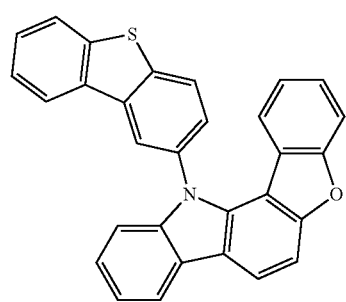
-continued
S-71
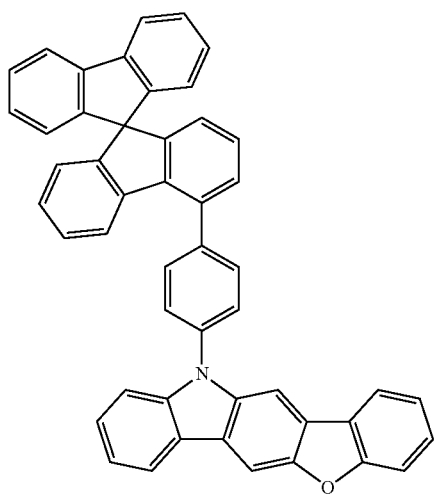
S-73
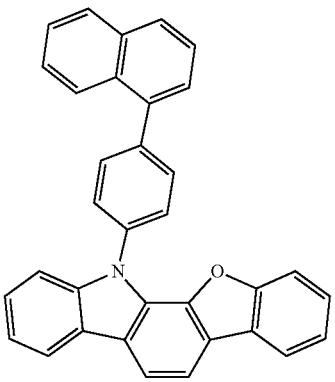
S-74
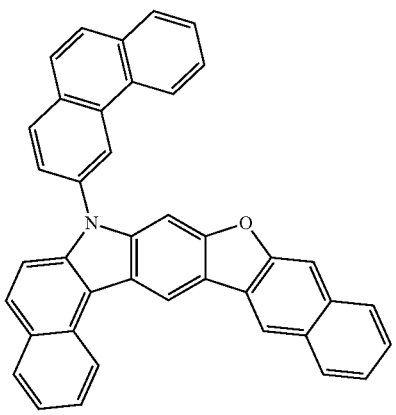
S-75
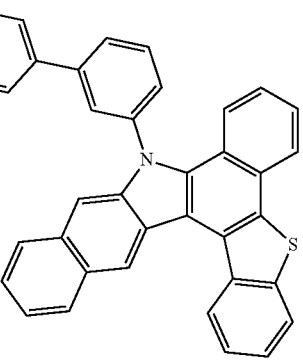

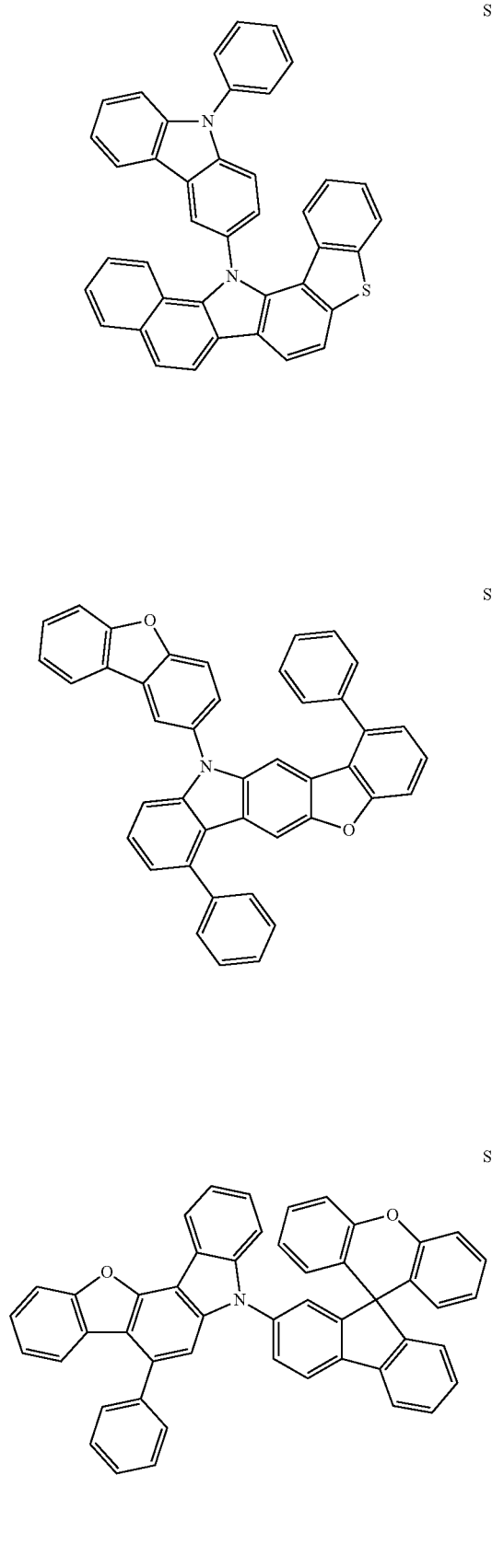
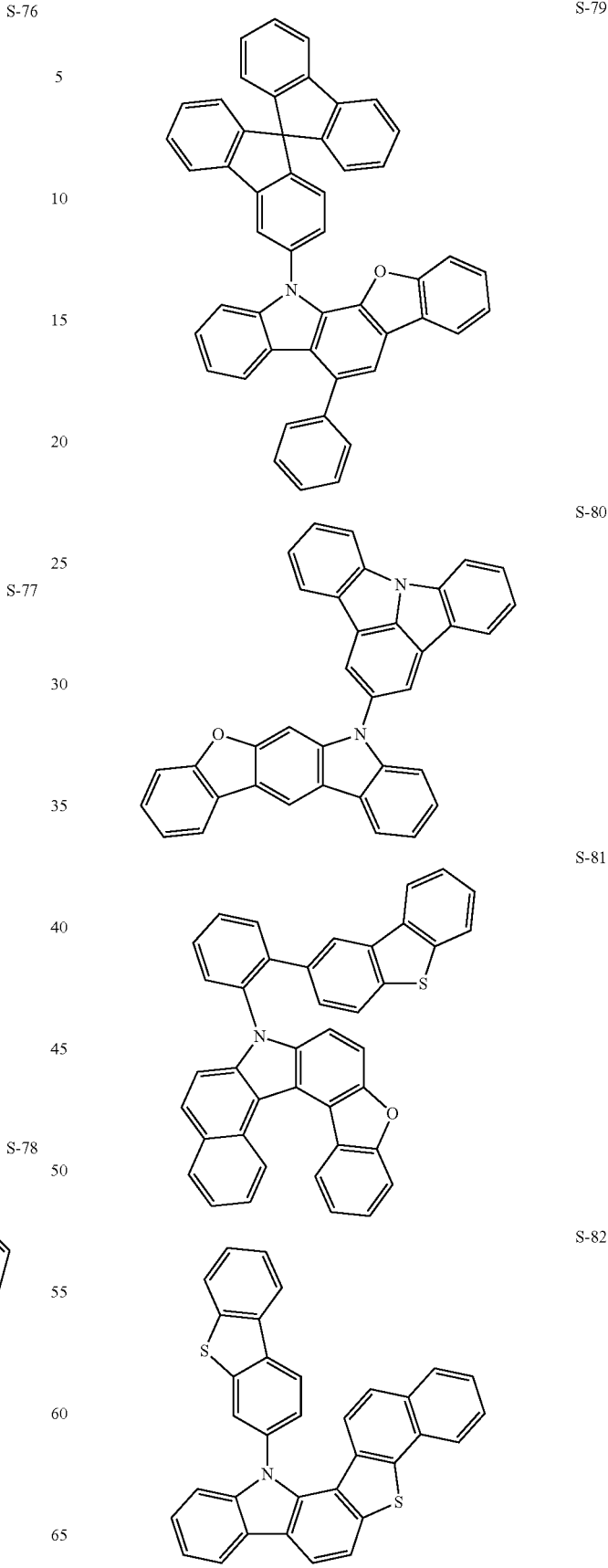

S-83
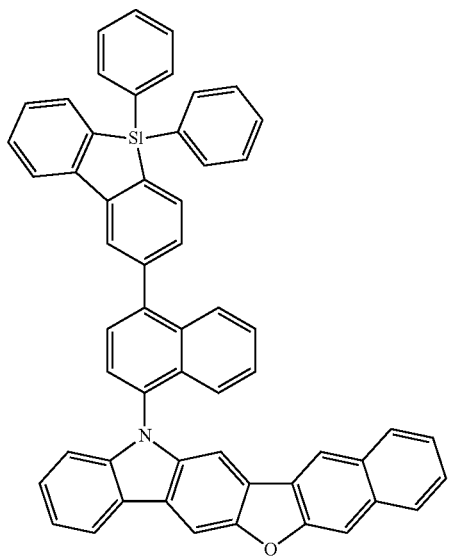
S-84
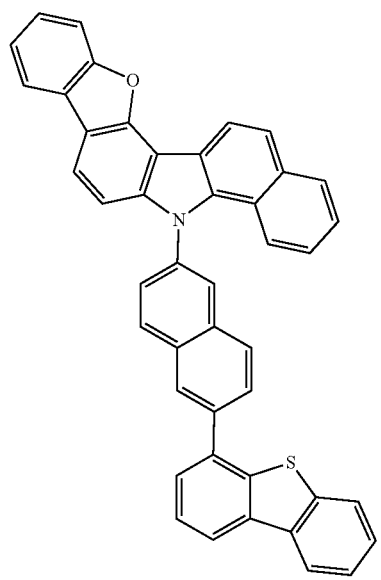
S-85
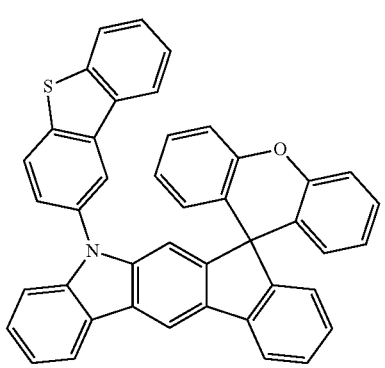
S-86
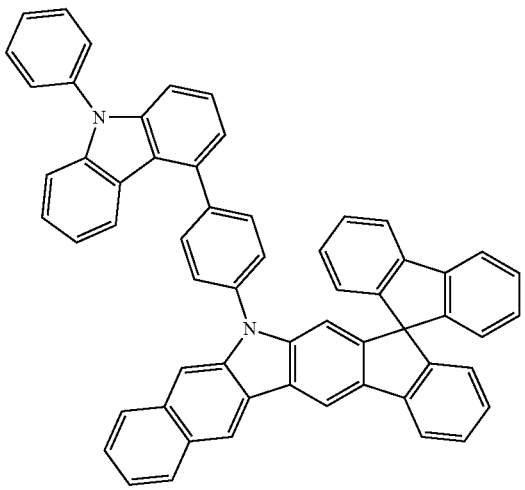
S-87
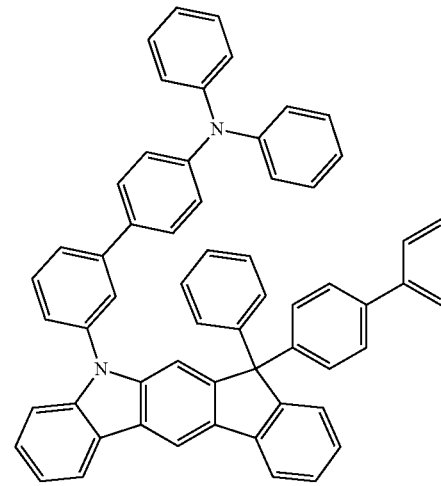
S-88
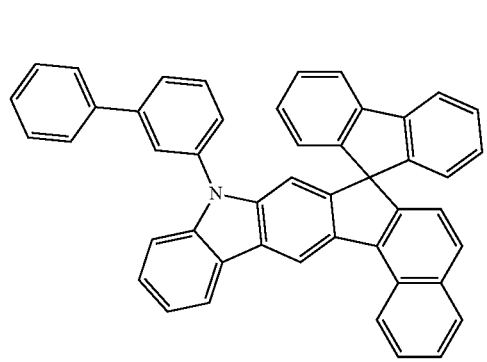

-continued
S-89
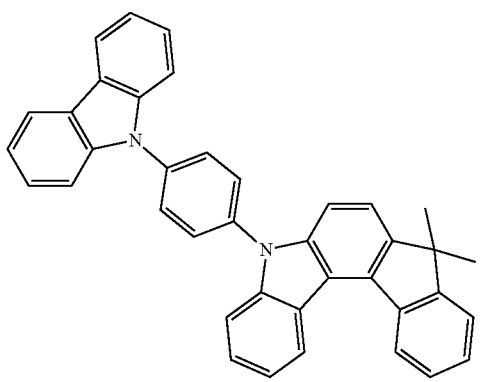
S-90
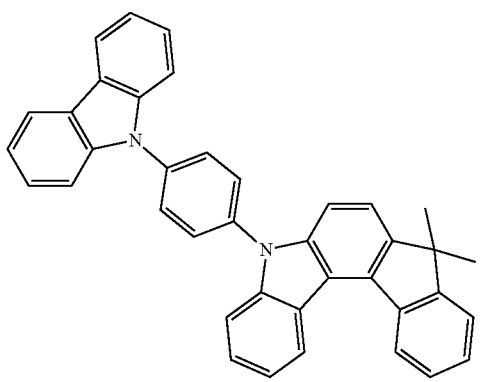
S-91
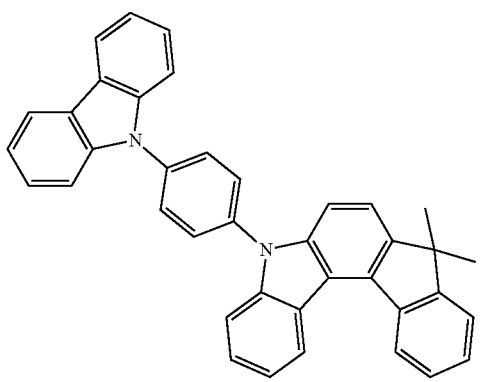
S-92
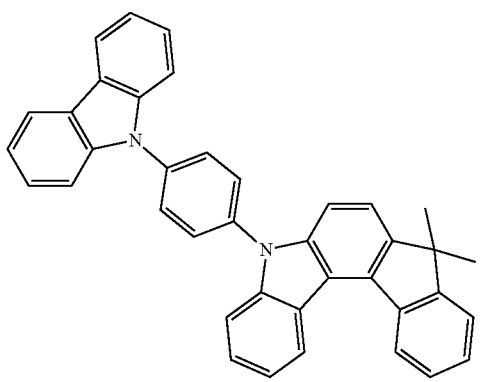
-continued
S-93
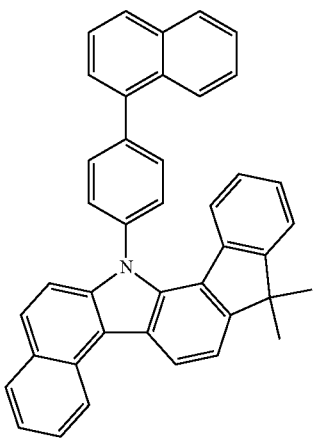
S-94
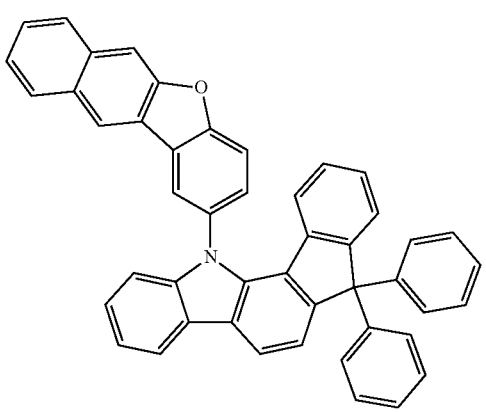
S-95
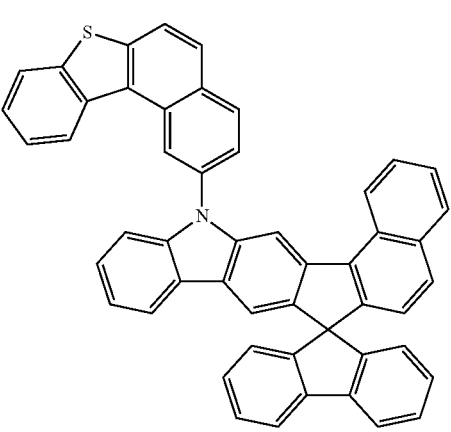

S-96
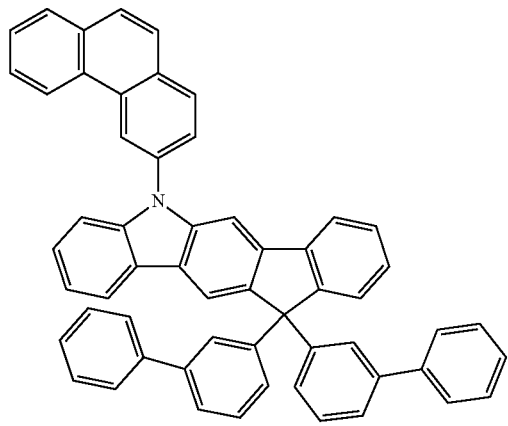
S-97
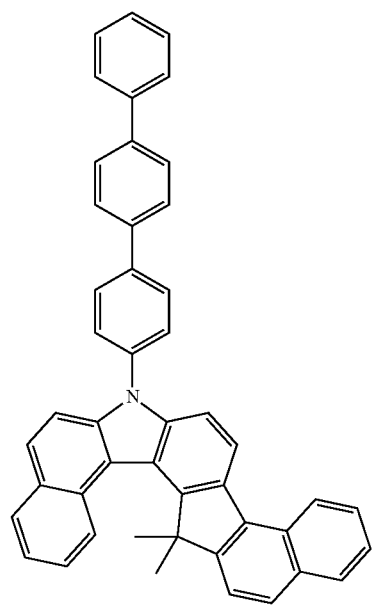
S-98
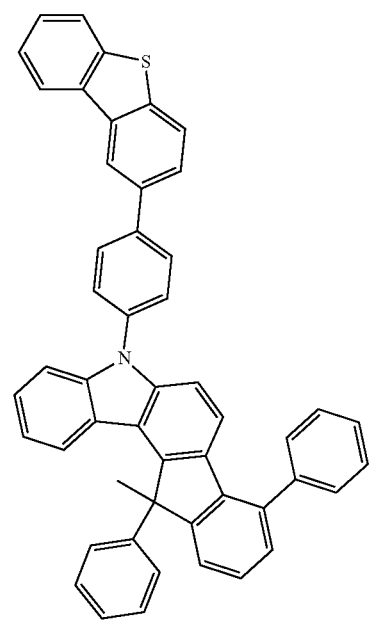
S-99
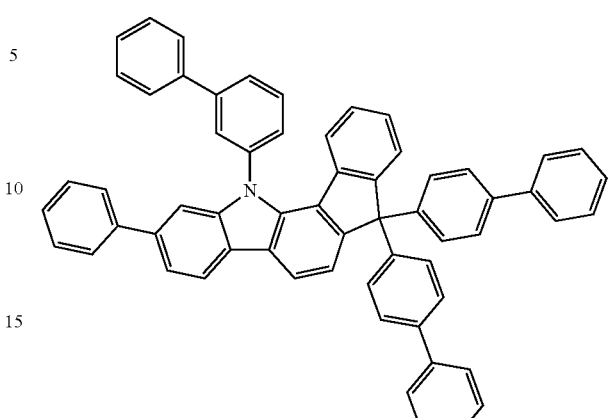
S-101
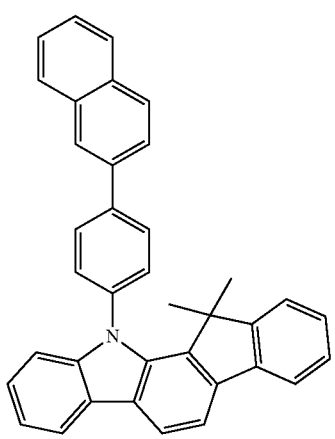
S-102
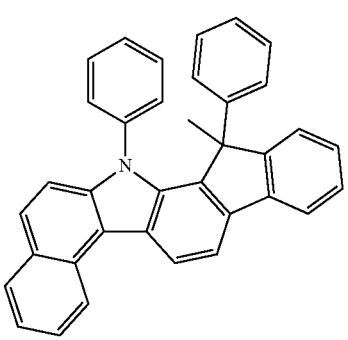
S-103
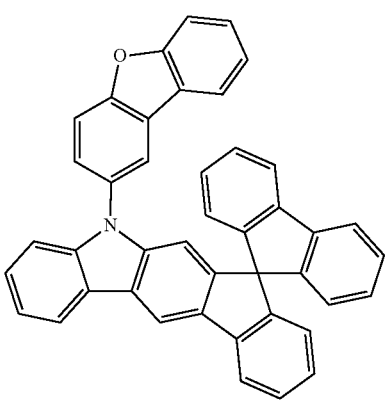

S-104
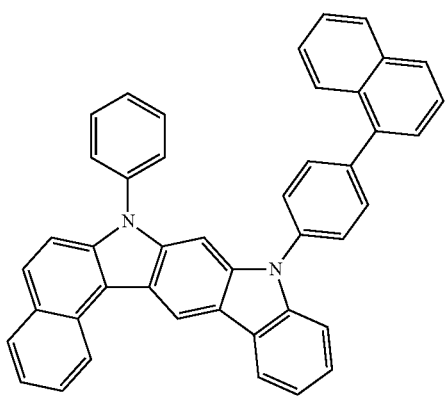
S-105
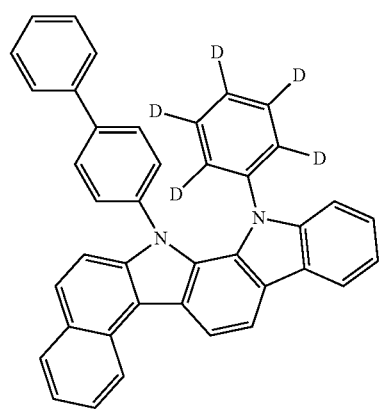
S-106
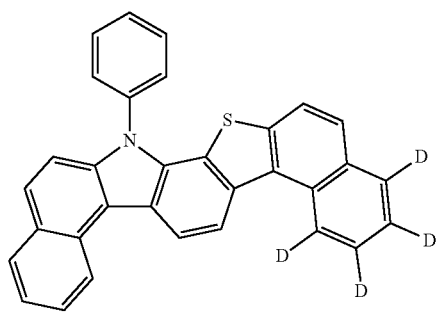
S-107
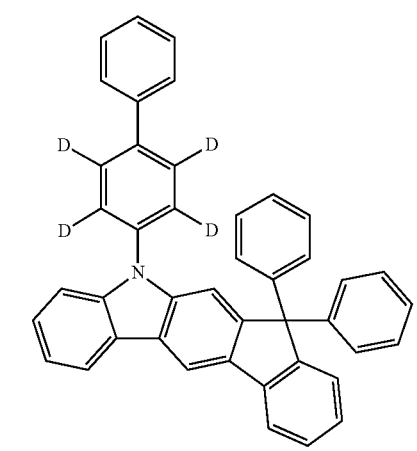
S-108
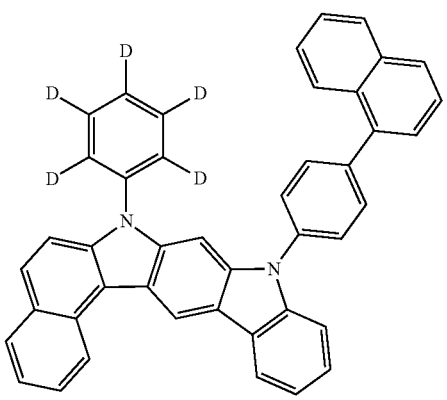
S-109
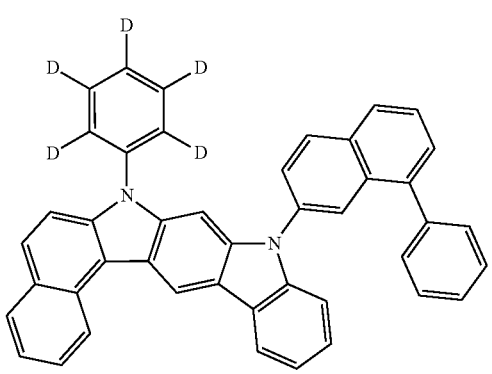
S-110
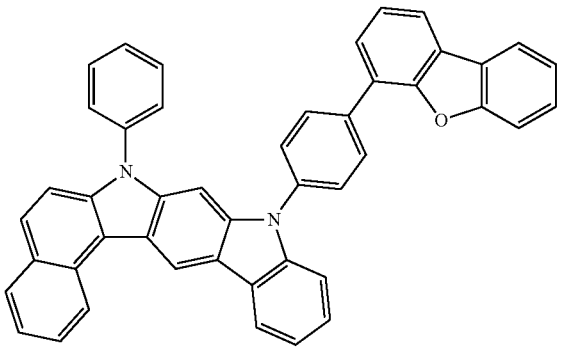
S-111
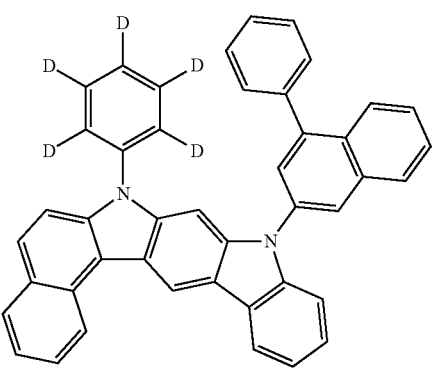

S-112
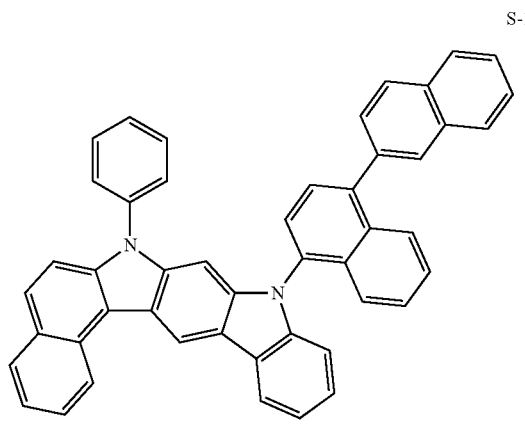
S-113
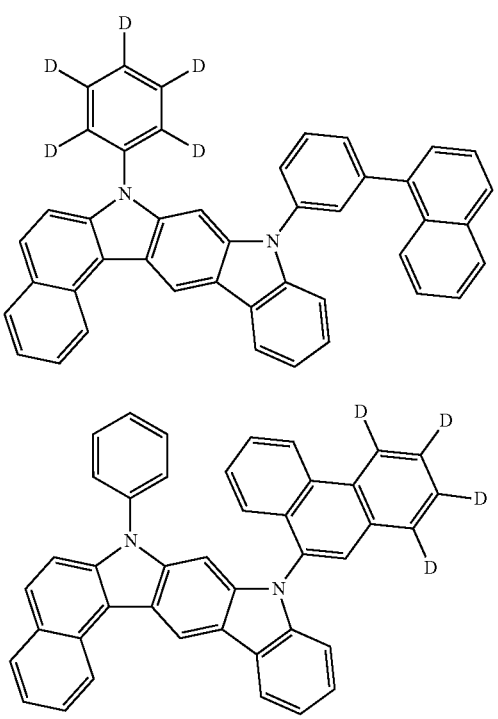
S-114
S-115
S-116
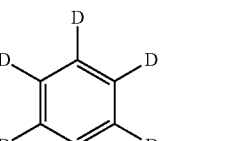
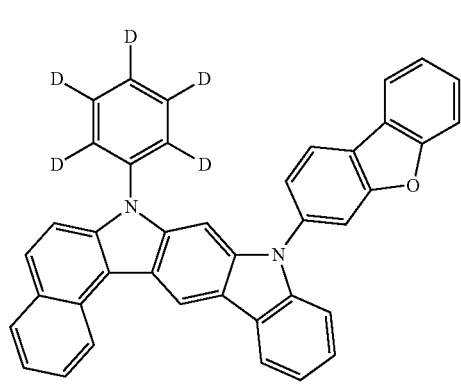
S-117
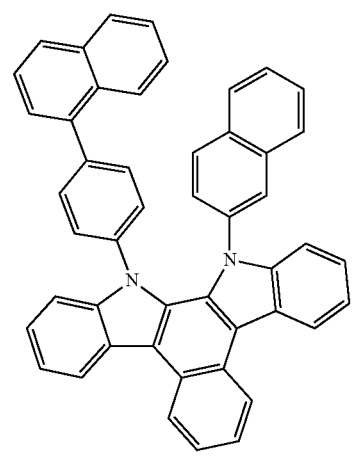
S-118
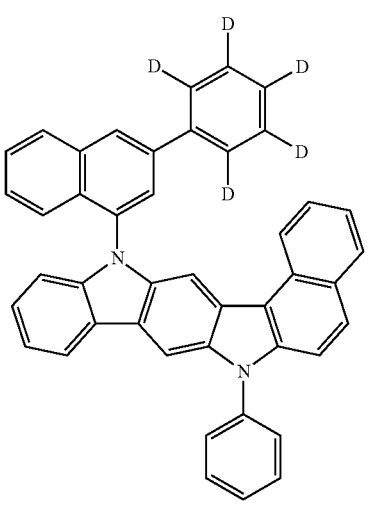
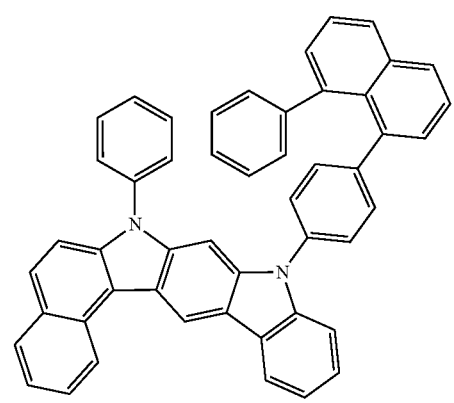

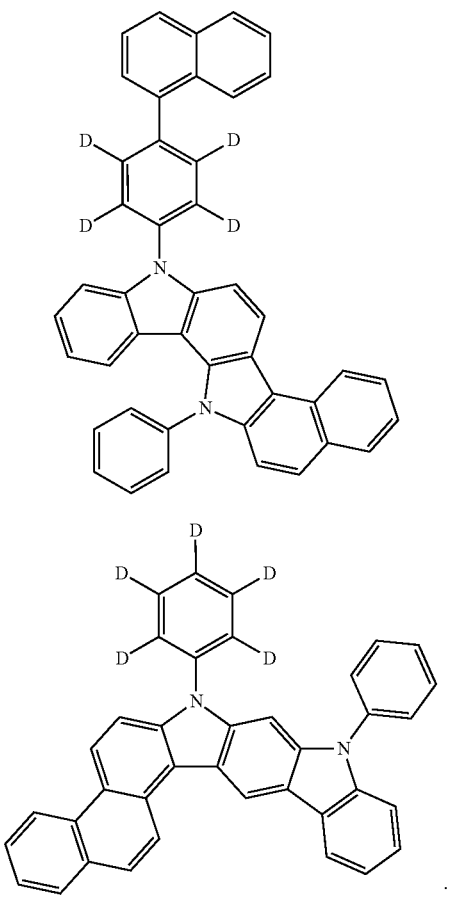

9. An organic electronic element comprising a first electrode; a second electrode; and an organic material layer formed between the first electrode and the second electrode, wherein the organic material layer comprises the compound of claim 1.

10. The organic electronic element according to claim 9, further comprising a light efficiency enhancing layer formed on at least one surface of the first electrode and the second electrode, the surface being opposite to the organic material layer.

11. The organic electronic element according to claim 9, wherein the organic material layer comprises 2 or more stacks comprising a hole transport layer, an emitting layer and an electron transport layer sequentially formed on the first electrode.

12. The organic electronic element according to claim 11, wherein the organic material layer further comprises a charge generation layer formed between the 2 or more stacks.

13. An electronic device comprising a display device comprising the organic electronic element of claim 9; and a control unit for driving the display device.

14. An electronic device according to claim 13, wherein the organic electronic element is at least one of an OLED, an organic solar cell, an organic photo conductor (OPC), organic transistor (organic TFT) and an element for monochromic or white illumination.

15. An organic electronic element comprising a first electrode; a second electrode; and an organic material layer formed between the first electrode and the second electrode, wherein the organic material layer comprises the composition for an organic electronic element of claim 6.

16. An electronic device comprising a display device comprising the organic electronic element of claim 15; and a control unit for driving the display device.

17. A method for reusing a compound of Formula 1 of claim 1 comprising:
recovering a crude organic light emitting material comprising the compound of Formula 1 from a deposition apparatus used in the process for depositing the organic emitting material to prepare an organic an organic light emitting device;
removing impurities from the crude organic light emitting material;
recovering the organic light emitting material after the impurities are removed; and
purifying the recovered organic light emitting material to have a purity of 99.9% or higher.

\* \* \* \* \*